US010611811B2

(12) United States Patent
Pulé et al.

(10) Patent No.: US 10,611,811 B2
(45) Date of Patent: *Apr. 7, 2020

(54) LIGAND

(71) Applicant: UCL BUSINESS LTD, London (GB)

(72) Inventors: Martin Pulé, London (GB); Kwee Yong, London (GB); Lydia Lee, London (GB); Neil Chaplin, London (GB); Ben Draper, London (GB)

(73) Assignee: UCL BUSINESS LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,660

(22) Filed: May 26, 2017

(65) Prior Publication Data
US 2017/0334964 A1 Nov. 23, 2017

Related U.S. Application Data

(63) Continuation of application No. 15/121,644, filed as application No. PCT/GB2015/050557 on Feb. 26, 2015.

(30) Foreign Application Priority Data

| Feb. 27, 2014 | (GB) | 1403479.7 |
| Feb. 27, 2014 | (GB) | 1403481.3 |
| Jun. 2, 2014 | (GB) | 1409759.6 |
| Jun. 2, 2014 | (GB) | 1409761.2 |

(51) Int. Cl.
C07K 14/705 (2006.01)
C07K 14/525 (2006.01)
C07K 14/725 (2006.01)
A61K 35/17 (2015.01)
C12N 15/85 (2006.01)
G01N 33/574 (2006.01)

(52) U.S. Cl.
CPC ............ C07K 14/525 (2013.01); A61K 35/17 (2013.01); C07K 14/7051 (2013.01); C12N 15/85 (2013.01); G01N 33/57407 (2013.01); C07K 2319/00 (2013.01); C07K 2319/03 (2013.01); C07K 2319/30 (2013.01); C07K 2319/70 (2013.01); G01N 2333/70575 (2013.01); G01N 2800/22 (2013.01)

(58) Field of Classification Search
None
See application file for complete search history.

(56) References Cited

U.S. PATENT DOCUMENTS

| 6,562,579 B1 * | 5/2003 | Yu ........................ C07H 21/04 435/7.1 |
| 7,381,803 B1 | 6/2008 | Weiner et al. |
| 8,003,335 B2 * | 8/2011 | Gottenberg .......... G01N 33/564 435/7.1 |

| 2005/0003480 A1 * | 1/2005 | Desjarlais ............ C07K 14/525 435/69.1 |
| 2006/0014248 A1 | 1/2006 | Marshall et al. |
| 2013/0156770 A1 | 6/2013 | Kufer et al. |
| 2016/0237139 A1 | 8/2016 | Pule et al. |
| 2016/0362467 A1 | 12/2016 | Pule et al. |

FOREIGN PATENT DOCUMENTS

| WO | WO-2001/060397 A1 | 8/2001 |
| WO | WO-02/066516 A2 | 8/2002 |
| WO | WO-2004/020593 A2 | 3/2004 |
| WO | WO-2004/089982 A2 | 10/2004 |
| WO | WO-2008/003115 A1 | 1/2008 |
| WO | WO-2008/045437 A2 | 4/2008 |
| WO | WO-2012/163805 A1 | 12/2012 |
| WO | WO-2013/072406 A1 | 5/2013 |
| WO | WO-2013/154760 A1 | 10/2013 |
| WO | WO-2015/052536 A1 | 4/2015 |
| WO | WO-2015/052538 A1 | 4/2015 |
| WO | WO-2015/128653 A2 | 9/2015 |
| WO | WO-2018/087557 A1 | 5/2018 |

OTHER PUBLICATIONS

Ingold, K. et al., 2005, J. Exp. Med., vol. 201: pp. 1375-1383.*
Hombach et al., Adoptive immunotherapy with genetically engineered T cells: modification of the IgG1 Fc 'spacer' domain in the extracellular moiety of chimeric antigen receptors avoids 'off-target' activation and unintended initiation of an innate immune response. Gene Ther. 17: 1206-13 (2010).
Kimberley et al., The design and characterization of receptor-selective APRIL variants. J. Biol. Chem. 287(44): 37434-46 (2012).
Kimberley et al., The proteoglycan (heparan sulfate proteoglycan) binding domain of APRIL serves as a platform for ligand multimerization and cross-linking. FASEB J. 23: 1584-95 (2009).
Maus et al., Zoom Zoom: Racing CARs for multiple myeloma. Clin. Cancer Res. 19(8): 1917-9 (2013).
Patel et al., Engineering an APRIL-specific B cell maturation antigen. J. Biol. Chem. 279(16): 16727-35 (2004).
Pule et al., A chimeric T cell antigen receptor that augments cytokine release and supports clonal expansion of primary human T cells. Molec. Ther. 12(5): 933-41 (2005).
UniParc Accession No. UPI000333A0DD, PREDICTED: tumor necrosis factor ligand superfamily member 13-like isoform X2 [Echinops telfairi], dated May 30, 2013.
UniParc Accession No. UPI000333ABF8, PREDICTED: tumor necrosis factor ligand superfamily member 13-like isoform X1 [Echinops telfairi], dated May 30, 2013.

(Continued)

Primary Examiner — Michael D Burkhart
(74) Attorney, Agent, or Firm — Marshall, Gerstein & Borun LLP

(57) ABSTRACT

The present invention provides a variant proliferation-inducing ligand (APRIL), which has a higher binding affinity to BCMA than wild-type APRIL; and/or altered binding kinetics compared with wild-type APRIL, and/or a higher BCMA:TACI (transmembrane activator and calcium modulator and cyclophilin ligand interactor) binding ratio than wild-type APRIL and which comprises mutations at one or more of the following positions: A125, V174, T175, M200, P201, S202, H203, D205 and R206.

15 Claims, 61 Drawing Sheets
Specification includes a Sequence Listing.

(56) References Cited

OTHER PUBLICATIONS

UniProt Accession No. C9JF68, SubName: Full=Tumor necrosis factor ligand superfamily member 13, Flag,: Fragment, dated Nov. 3, 2009.

Beitinjaneh et al., Durable responses after donor lymphocyte infusion for patients with residual multiple myeloma following non-myeloablative allogeneic stem cell transplant, Leuk. Lymphoma, 53(8):1525-9 (Aug. 2012).

Carpenter et al., B-cell maturation antigen is a promising target for adoptive T-cell therapy of multiple myeloma, Clin. Cancer Res., 19(8):2048-60 (2013).

Gorgun et al., Tumor-promoting immune-suppressive myeloid-derived suppressor cells in the multiple myeloma microenvironment in humans, Blood, 121(15):2975-87 (Apr. 2013).

Guan et al., The construction and characterization of a bifunctional EGFP/sAPRIL fusion protein. Appl. Microbiol. Biotechnol. 73(5): 1114-22 (2006).

Gutiérrez-González et al., Evaluation of the potential therapeutic benefits of macrophage reprogramming in multiple myeloma, Blood, 128(18):2241-52 (Nov. 2016).

Hymowitz et al., Structures of APRIL-receptor complexes: like BCMA, TACI employs only a single cysteine-rich domain for high affinity ligand binding, J. Biol. Chem., 280(8):7218-27 (Feb. 2005).

Kalos et al., Adoptive T cell transfer for cancer immunotherapy in the era of synthetic biology. Immunity, 39(1): 49-60 (2013).

Kawano et al., Targeting the bone marrow microenvironment in multiple myeloma, Immunol. Rev., 263:160-72 (Jan. 2015).

Krumbholz et al., B cells and antibodies in multiple sclerosis pathogenesis and therapy, Nat. Rev. Neurol., 8(11):613-23 (Nov. 2012).

Lee et al., An APRIL-based chimeric antigen receptor for dual targeting of BCMA and TACI in multiple myeloma, Blood, 131(7):746-58 (Feb. 2018).

Lee et al., Designing APRIL-based therapeutics for targeting BCMA in multiple myeloma. American Society of Gene and Cell Therapy 17th Annual Meeting: Simultaneous Oral Abstract Sessions in Cancer-Targeted Gene & Cell Therapy. http://www.abstracts2view.com/asgct/view.php?nu=ASGCT14L1_272, May 22, 2014.

Lee et al., Designing APRIL-based therapeutics for targeting BCMA in multiple myeloma. UK Myeloma Forum ASH 2013 Winning Abstracts (uploaded document created on Oct. 25, 2013, http://www.ukmf.org.uk/winners/ash-2013-new-orleans/, dated Jan. 5, 2015.

Suyani et al., Tumor-associated macrophages as a prognostic parameter in multiple myeloma, Ann. Hematol., 92(5):669-77 (2013).

Yu et al., APRIL and TALL-I and receptors BCMA and TACI: System for regulating humoral immunity. Nat. Immunol. 1(3): 252-6 (2000).

International Search Report and Written Opinion from International Application No. PCT/GB2015/050557 dated Sep. 11, 2015.

Matsushita et al., The role of BAFF in autoimmune diseases. *Jpn. J. Clin. Immunol.* 28(5): 333-342 (2005).

Pradet-Balade et al., An endogenous hybrid mRNA encodes TWE-PRIL, a functional cell surface TWEAK-APRIL fusion protein. *The Embo Journal* 21(21): 5711-5720 (2002).

Yong et al., Evaluation of Bcma as a therapeutic target in multiple myeloma using an antibody-drug conjugate,. *Blood* 122: 4447 (2013).

* cited by examiner

FIGURE 5A

METDTLLLWVLLLWVPGSTGSVLHLVPINATSKDDSDVTEVMWQPALRRGRGLQAQGYGVRIQDAGVYLLYSQ
VLFQDVTFTMGQVVSREGQGRQETLFRCIRSMPSHPDRAYNSCYSAGVFHLHQGDILSVIIPRARAKLNLSPH
GTFLGFVKL*SGGGSDP*TTTPAPRPPTPAPTIASQPLSLRPEACRPAAGGAVHTRGLDFACDIFWVLVVVGGVL
ACYSLLVTVAFIIFWVRSKRSRLLHSDYMNMTPRRPGPTRKHYQPYAPPRDFAAYRSRDQRLPPDAHKPPGGG
SFRTPIQEEQADAHSTLAKIRVKFSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDALHMQALPPR

FIGURE 5B

METDTLLLWVLLLWVPGSTGSVLHLVPINATSKDDSDVTEVMWQPALRRGRGLQAQGYGVRIQDAGVYLLYSQ
VLFQDVTFTMGQVVSREGQGRQETLFRCIRSMPSHPDRAYNSCYSAGVFHLHQGDILSVIIPRARAKLNLSPH
GTFLGFVKL*SGGGSDP*AEPKSPDKTHTCPPCPKDPKFWVLVVVGGVLACYSLLVTVAFIIFWVRSKRSRLLHS
DYMNMTPRRPGPTRKHYQPYAPPRDFAAYRSRDQRLPPDAHKPPGGGSFRTPIQEEQADAHSTLAKIRVKFSR
SADAPAYQQGQNQLYNELNLGRREEYDVLDKRRGRDPEMGGKPRRKNPQEGLYNELQKDKMAEAYSEIGMKGE
RRRGKGHDGLYQGLSTATKDTYDALHMQALPPR

FIGURE 5C

METDTLLLWVLLLWVPGSTGSVLHLVPINATSKDDSDVTEVMWQPALRRGRGLQAQGYGVRIQDAGVYLLYSQ
VLFQDVTFTMGQVVSREGQGRQETLFRCIRSMPSHPDRAYNSCYSAGVFHLHQGDILSVIIPRARAKLNLSPH
GTFLGFVKL*SGGGSDP*AEPKSPDKTHTCPPCPAPPVAGPSVFLFPPKPKDTLMIARTPEVTCVVVDVSHEDPE
VKFNWYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGKKDPKFWVLVVVGGVLACYSLLVTVAFIIFWVRSKRSRLLHSDYM
NMTPRRPGPTRKHYQPYAPPRDFAAYRSRDQRLPPDAHKPPGGGSFRTPIQEEQADAHSTLAKIRVKFSRSAD
APAYQQGQNQLYNELNLGRREEYDVLDKRRGRDPEMGGKPRRKNPQEGLYNELQKDKMAEAYSEIGMKGERRR
GKGHDGLYQGLSTATKDTYDALHMQALPPR

| Signal Peptide | Efficient signal peptide |
| --- | --- |
| dAPRIL | Truncated APRIL |
| Spacer | Either hinge-CH2CH3 of human IgG1, human CD8α stalk and human IgG1 hinge |
| TM and endodomain | Compound endodomain comprising of the CD28TM domain, CD28 endodomain and OX40 and CD3-Zeta endodomains |

APRIL CAR mediated target cell kill by Chromium Release

IFNG Release at D+1

APRIL CAR expressing T cells at D+7

FIGURE 19A

MGTSLLCWMALCLLGADHADG░░░░░░░░░░░░░░░░░VLHLVPINATSKDDSDVTEVMWQPALRRGRGLQ
AQGYGVRIQDAGVYLLYSQVLFQDVTFTMGQVVSREGQGRQETLFRCIRSMPSHPDRAYNSCYSAGVFHLHQG
DILSVIIPRARAKLNLSPHGTFLGFVKL*SGGGSD*AEPKSPDKTHTCPPCPAPPVAGPSVFLFPPKPKDTLMI
ARTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGKKDPKFWVLVVVGGVLACYSLLVTVA
FIIFWVRSKRSRLLHSDYMNMTPRRPGPTRKHYQPYAPPRDFAAYRSRDQRLPPDAHKPPGGGSFRTPIQEEQ
ADAHSTLAKIRVKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR

FIGURE 19B

MGTSLLCWMALCLLGADHADG░░░░░░░░░░░░░░░░░VLHLVPINATSKDDSDVTEVMWQPALRRGRGLQ
AQGYGVRIQDAGVYLLYSQVLFQDVTFTMGQVVSREGQGRQETLFRCIRSMPSHPDRAYNSCYSAGVFHLHQG
DILSVIIPRARAKLNLSPHGTFLGFVKL*SGGGSD*TTTPAPRPPTPAPTIASQPLSLRPEACRPAAGGAVHTR
GLDFACDIFWVLVVVGGVLACYSLLVTVAFIIFWVRSKRSRLLHSDYMNMTPRRPGPTRKHYQPYAPPRDFAA
YRSRDQRLPPDAHKPPGGGSFRTPIQEEQADAHSTLAKIRVKFSRSADAPAYQQGQNQLYNELNLGRREEYDV
LDKRRGRDPEMGGKPRRKNPQEGLYNELQKDKMAEAYSEIGMKGERRRGKGHDGLYQGLSTATKDTYDALHMQ
ALPPR

FIGURE 19C

MGTSLLCWMALCLLGADHADG░░░░░░░░░░░░░░░░░VLHLVPINATSKDDSDVTEVMWQPALRRGRGLQ
AQGYGVRIQDAGVYLLYSQVLFQDVTFTMGQVVSREGQGRQETLFRCIRSMPSHPDRAYNSCYSAGVFHLHQG
DILSVIIPRARAKLNLSPHGTFLGFVKL*SGGGSD*AEPKSPDKTHTCPPCPKDPKFWVLVVVGGVLACYSLLV
TVAFIIFWVRSKRSRLLHSDYMNMTPRRPGPTRKHYQPYAPPRDFAAYRSRDQRLPPDAHKPPGGGSFRTPIQ
EEQADAHSTLAKIRVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR

| Signal Peptide | Efficient signal peptide |
| --- | --- |
| tag and linker | Epitope tag and linker (will be removed for production version, here for Western blotting etc). |
| dAPRIL | Truncated APRIL |
| spacer | Either hinge-CH2CH3 of human IgG1, human CD8α stalk and human IgG1 hinge |
| TM and endodomain | Compound endodomain comprising of the CD28TM domain, CD28 endodomain and OX40 and CD3-Zeta endodomains |

| | | |
|---|---|---|
| M200X | 491 | gccggagggccagggcagacaggagaccctgttccggtgcatccggagcnnnccagccaccccgacag |
| M200C (2) | 403 | gccggagggccagggcagacaggagaccctgttccggtgcatccggagctgtccagccaccccgacag |
| M200L (3) | 401 | gccggagggccagggcagacaggagaccctgttccggtgcatccggagcttgccagccaccccgacag |
| M200S (10) | 405 | gccggagggccagggcagacaggagaccctgttccggtgcatccggagcagaccagccaccccgacag |
| M200* (15) | 406 | gccggagggccagggcagacaggagaccctgttccggtgcatccggagctgaccagccaccccgacag |
| M200A (33) | 403 | gccggagggccagggcagacaggagaccctgttccggtgcatccggagcgcgccagccaccccgacag |
| M200G (34) | 402 | gccggagggccagggcagacaggagaccctgttccggtgcatccggagcggtccagccaccccgacag |
| M200N (45) | 405 | gccggagggccagggcagacaggagaccctgttccggtgcatccggagcaatccagccaccccgacag |
| | | |
| P201X | 491 | gccggagggccagggcagacaggagaccctgttccggtgcatccggagcatgnnnagccaccccgacag |
| P201G-4_406.seq | 408 | gccggagggccagggcagacaggagaccctgttccggtgcatccggagcatgggcagccaccccgacag |
| P201A-18_406.seq | 405 | gccggagggccagggcagacaggagaccctgttccggtgcatccgcagcatggctagccaccccgacag |
| P201V-38_406.seq | 406 | gccggagggccagggcagacaggagaccctgttccggtgcatccggagcatggttagccaccccgacag |
| P201W-46_406.seq | 405 | gccggagggccagggcagacaggagaccctgttccggtgcatccgcagcatgtggagccaccccgacag |
| P201R-28_406.seq | 406 | gccggagggccagggcagacaggagaccctgttccggtgcatccgcagcatgcgaagccaccccgacag |
| P201Y-44_406.seq | 406 | gccggagggccagggcagacaggagaccctgttccggtgcatccgcagcatgtatagccaccccgacag |
| | | |
| S202X | 491 | gccggagggccagggcagacaggagaccctgttccggtgcatccggagcatgcccnnncccccgacag |
| S202G-5_406 | 409 | gccggagggccagggcagacaggagaccctgttccggtgcatccgcagcatgcccggtcaccccgacag |
| S202P-20_406 | 405 | gccggagggccagggcagacaggagaccctgttccggtgcatccgcagcatgcccccgcaccccgacag |
| S202F-22_406.seq | 401 | gccggagggccagggcagacaggagaccctgttccggtgcatccgcagcatgccctgcaccccgacag |
| S202V_H203N-26_4 | 398 | gccggagggccagggcagacaggagaccctgttccggtgcatccggagcatgcccgtgaacccccgacag |
| S202D-40_406.seq | 403 | gccggagggccagggcagacaggagaccctgttccggtgcatccggagcatgcccgatcaccccgacag |
| | | |
| T175X | 421 | gctggcgtgtacctgctgtactcccaggtgctgttccaggacgtgnnnttcacaatgggccaggtggtga |
| T175G_S202G-4_40 | 337 | gctggcgtgtacctgctgtactcccaggtgctgttccaggacgtgggattcacaatgggccaggtggtga |
| T175G_S202V-6_40 | 337 | gctggcgtgtacctgctgtactcccaggtgctgttccaggacgtgggttcacaatgggccaggtggtga |
| T175H-11_406.seq | 335 | gctggcgtgtacctgctgtactcccaggtgctgttccaggacgtgcatttcacaatgggccaggtggtga |
| T175P-15_406.seq | 336 | gctggcgtgtacctgctgtactcccaggtgctgttccaggacgtgcctttcacaatgggccaggtggtga |
| T175S-16_406.seq | 335 | gctggcgtgtacctgctgtactcccaggtgctgttccaggacgtgtcgttcacaatgggccaggtggtga |
| T175G-19_406.seq | 334 | gctggcgtgtacctgctgtactcccaggtgctgttccaggacgtgggtttcacaatgggccaggtggtga |
| T175A_S202E-24_4 | 333 | gctggcgtgtacctgctgtactcccaggtgctgttccaggacgtggcattcacaatgggccaggtggtga |
| T175S_S202G-25_4 | 336 | gctggcgtgtacctgctgtactcccaggtgctgttccaggacgtgtctttcacaatgggccaggtggtga |
| | | |
| T175X | 491 | gccggagggccacggcagacaggagaccctgttccggtgcatccggagcatgcccagccaccccgacag |
| T175G_S202G-4_40 | 407 | gccggagggccagggcagacaggagaccctgttccggtgcatccggagcatgcccggcaccccgacag |
| T175G_S202V-6_40 | 407 | gccggagggccagggcagacaggagaccctgttccggtgcatccggagcatgccctgcaccccgacag |
| T175H-11_406.seq | 405 | gccggagggccacggcagacaggagaccctgttccggtgcatccggagcatgcccagcaccccgacag |
| T175P-15_406.seq | 406 | gccggagggccagggcagacaggagaccctgttccggtgcatccggagcatgcccagcaccccgacag |
| T175S-16_406.seq | 405 | gccggagggccacggcagacaggagaccctgttccggtgcatccggagcatgcccagtcaccccgacag |
| T175G-19_406.seq | 404 | gccggagggccagggcagacaggagaccctgttccggtgcatccggagcatgcccgcaccccgacag |
| T175A_S202E-24_4 | 403 | gccggagggccagcgcagacaggagaccctgttccggtgcatccggagcatgcccagcaccccgacag |
| T175S_S202G-25_4 | 406 | gccggagggccacggcagacaggagaccctgttccggtgcatccggagcatgcccggtcaccccgacag |

FIGURE 21A

| | | |
|---|---|---|
| V174X | 421 | gctggcgtgtacctgctgtactcccaggtgctgttccaggacnnnaccttcacaatggcccaggtggtga |
| V174T_S202V-1_40 | 338 | gctggcgtgtacctgctgtactcccaggtgctgttccaggacacaaccttcacaatggcccaggtggtga |
| V174G-4_406.seq | 339 | gctggcgtgtacctgctgtactcccaggtgctgttccaggacgggaccttcacaatggcccaggtggtga |
| V174G_S202E-7_40 | 337 | gctggcgtgtacctgctgtactcccaggtgctgttccaggacgggaccttcacaatggcccaggtggtga |
| V174G_S202A-10_4 | 335 | gctggcgtgtacctgctgtactcccaggtgctgttccaggacgggaccttcacaatggcccaggtggtga |
| V174G_S202G-15_4 | 334 | gctggcgtgtacctgctgtactcccaggtgctgttccaggacgggaccttcacaatggcccaggtggtga |
| V174H_S202G-31_4 | 337 | gctggcgtgtacctgctgtactcccaggtgctgttccaggacacaaccttcacaatggcccaggtggtga |
| V174E_S202Y-41_4 | 332 | gctggcgtgtacctgctgtactcccaggtgctgttccaggacgagaccttcacaatggcccaggtggtga |

| | | |
|---|---|---|
| V174X | 491 | gccgggagggccagggcagacaggagaccctgttccggtgcatccggagcatgcccnnncaccccgacag |
| V174T_S202V-1_40 | 408 | gccgggagggccagggcagacaggagaccctgttccggtgcatccggagcatgccctccaccccgacag |
| V174G-4_406.seq | 409 | gccgggagggccagggcagacaggagaccctgttccggtgcatccggagcatgcccagccaccccgacag |
| V174G_S202E-7_40 | 407 | gccgggagggccagggcagacaggagaccctgttccggtgcatccggagcatgcccgagcaccccgacag |
| V174G_S202A-10_4 | 405 | gccgggagggccagggcagacaggagaccctgttccggtgcatccggagcatgcccgcgcaccccgacag |
| V174G_S202G-15_4 | 404 | gccgggagggccagggcagacaggagaccctgttccggtgcatccggagcatgcccggtcaccccgacag |
| V174H_S202G-31_4 | 407 | gccgggagggccagggcagacaggagaccctgttccggtgcatccggagcatgccctttcaccccgacag |
| V174E_S202Y-41_4 | 402 | gccgggagggccagggcagacaggagaccctgttccggtgcatccggagcatgcccgtacaccccgacag |

| | | |
|---|---|---|
| D205X_R206X | 541 | atgcccagccaccccnnnnnn-gcctacaacagctgctacagcgctggcgtgtttcacct |
| D205P-1_406.seq | 448 | atgcccagccacccccccaga-gcctacaacagctgctacagcgctggcgtgtttcacct |
| D205R_R206G-27_4 | 452 | atgcccagccaccccgcgga-gcctacaacagctgctacagcgctggcgtgtttcacct |
| D205P_R206K-33_4 | 454 | atgcccagccacccccaaaa-gcctacaacagctgctacagcgctggcgtgtttcacct |
| D205P_R206N-35_4 | 455 | atgcccagccacccccccaac-gcctacaacagctgctacagcgctggcgtgtttcacct |
| D205P_R206I-44_4 | 457 | atgcccagccacccccctata-gcctacaacagctgctacagcgctggcgtgtttcacct |
| D205S_R206H-4_40 | 454 | atgcccagccaccccctcccac-gcctacaacagctgctacagcgctggcgtgtttcacct |
| D205Y_R206stop-1 | 453 | atgcccagccaccccactga-gcctacaacagctgctacagcgctggcgtgtttcacct |
| D205+C-12_406 | 457 | atgcccagccaccccgacaga-gcctacaacagctgctacagcgctggcgtgtttcacct |
| D205H_R206L-16_4 | 456 | atgcccagccaccccatctc-gcctacaacagctgctacagcgctggcgtgtttcacct |
| D205S_R206P-22_4 | 457 | atgcccagccaccccctcccca-gcctacaacagctgctacagcgctggcgtgtttcacct |

| | | |
|---|---|---|
| A125X | 281 | gaggcggcagcgtgctgcacctggtgcccatcaacnnnaccagcaaggacgactctgatgtgaccgaggt |
| A125T-5_406 | 191 | gagccggcagcgtgctgcacctggtgcccatcaacacgaccagcaaggacgactctgatgtgacccaggt |

FIGURE 21B

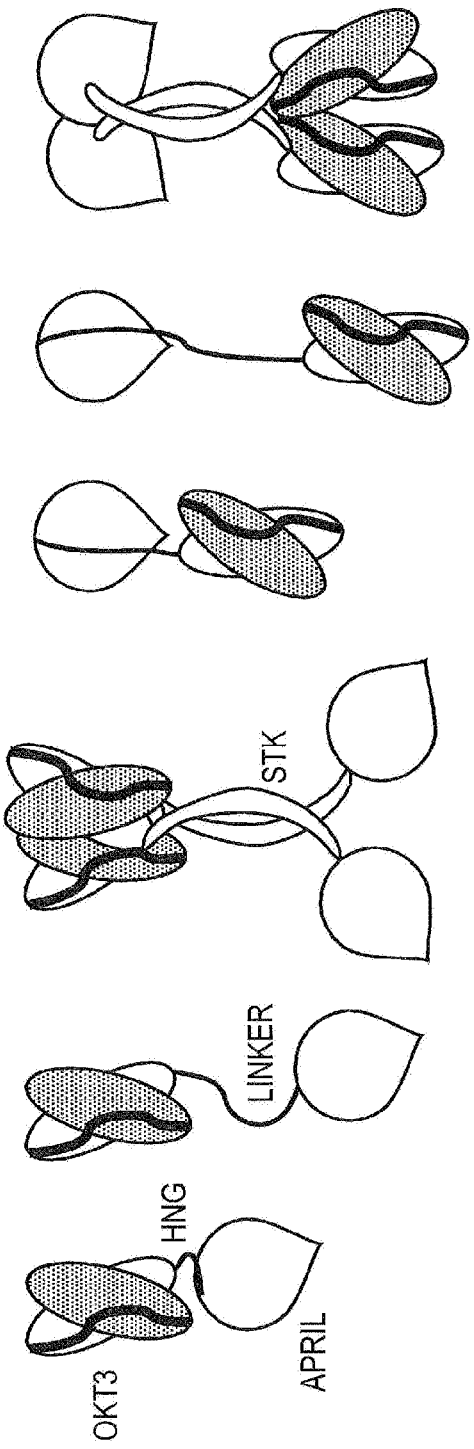

FIGURE 30A

METDTLLLWVLLLWVPGSTGQVQLQQSGAELARPGASVKMSCKASGYTFTRYTMHWVKQRPGQGLEWIGYINPSRGYTNYNQKFKDKATI
TTDKSSSTAYMQLSSLTSEDSAVYYCARYYDDHYCLDYWGQGTTLTVSSSGGGGSGGGGSGGGGSQIVLTQSPAIMSASPGEKVTMTCSA
SSSVSYMNWYQQKSGTSPKRWIYDTSKLASGVPAHFRGSGSGTSYSLTISGMEAEDAATYYCQQWSSNPFTFGSGTKLEINRSDPAEPKS
PDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKSGGGGSVLHLVPINATSKDDSDVTEVMWQPALRRGRGLQAQGYGVRIQDAGVYLLYSQVLFQDVTFTMGQVVSRE
GQGRQETLFRCIRSMPSHPDRAYNSCYSAGVFHLHQGDILSVIIPRARAKLNLSPHGTFLGFVKL

| | |
|---|---|
| Signal peptide | Compact highly efficient signal peptide with predicted ~95% cleavage after the terminal glycine. |
| OKT3 scFv | Single-chain variable fragment from OKT3. The heavy and light chain variable regions have been isolated from native signal peptide and constant regions and linked together with a SGGGGS3 linker. |
| SDP linker | This is another linker motif we use to introduce a chain-break (separate two distinct domains but allows orientation in different angles). Also conveniently codes for a BamHI restriction site |
| IgG1 hinge | The human IgG1 hinge sequence. |
| SGGGGS linker | Serine-glycine linker to connect the carboxy-terminus onto truncated APRIL. |
| dAPRIL | APRIL truncated as discussed above after Ingold[1] |

FIGURE 30B

METDTLLLWVLLLWVPGSTGQVQLQQSGAELARPGASVKMSCKASGYTFTRYTMHWVKQRPGQGLEWIGYINPSRGYTNYNQKFKDKATI
TTDKSSSTAYMQLSSLTSEDSAVYYCARYYDDHYCLDYWGQGTTLTVSSSGGGGSGGGGSGGGGSQIVLTQSPAIMSASPGEKVTMTCSA
SSSVSYMNWYQQKSGTSPKRWIYDTSKLASGVPAHFRGSGSGTSYSLTISGMEAEDAATYYCQQWSSNPFTFGSGTKLEINRSDPAEPKS
PDPKPTTTPAPRPPTPAPTIASQPLSLRPEACRPAAGGAVHTRGLDFACDSGGGGSVLHLVPINATSKDDSDVTEVMWQPALRRGRGLQAQGYGVRIQDA
GVYLLYSQVLFQDVTFTMGQVVSREGQGRQETLFRCIRSMPSHPDRAYNSCYSAGVFHLHQGDILSVIIPRARAKLNLSPHGTFLGFVKL

| | |
|---|---|
| Signal peptide | Signal peptide as per APRILiTE#03 |
| OKT3 scFv | Single-chain variable fragment from OKT3 in heavy light orientation |
| SDP linker | Linker motif we use to introduce a chain-break. Also conveniently codes for a BamHI restriction site |
| CD8α stalk | The stalk structure for CD8α |
| SGGGGS linker | Serine-glycine linker to connect the carboxy-terminus onto truncated APRIL. |
| dAPRIL | APRIL truncated as discussed above. |

FIGURE 30C

MGTSLLCWMALCLLGADHADGVLHLVPINATSKDDSDVTEVMWQPALRRGRGLQAQGYGVRIQDAGVYLLYSQVLFQDVTFTMGQVVSRE
GQGRQETLFRCIRSMPSHPDRAYNSCYSAGVFHLHQGDILSVIIPRARAKLNLSPHGTFLGFVKLSGGGSDPAEPKSPDPKPTTTPAPRPPTPAPTIASQ
PLSLRPEACRPAAGGAVHTRGLDFACDSGGGGSQVQLQQSGAELARPGASVKMSCKASGYTFTRYTMHWVKQRPGQGLEWIGYINPSRGY
TNYNQKFKDKATLTTDKSSSTAYMQLSSLTSEDSAVYYCARYYDDHYCLDYWGQGTTLTVSSSGGGGSGGGGSGGGGSQIVLTQSPAIMS
ASPGEKVTMTCSASSSVSYMNWYQQKSGTSPKRWIYDTSKLASGVPAHFRGSGSGTSYSLTISGMEAEDAATYYCQQWSSNPFTFGSGTK
LEINRS

| | |
|---|---|
| Signal peptide | Compact highly efficient signal peptide with predicted ~95% cleavage after the terminal glycine. A highly efficient signal peptide is needed to |
| dAPRIL | APRIL truncated |
| SGGGSDP | Flexible linker and chain break |
| CD8α stalk | The stalk structure for CD8α |
| linker | Serine-glycine linker to connect the carboxy-terminus onto truncated APRIL. |
| OKT3 scFv | Single-chain variable fragment from OKT3 |

SEQUENCE LISTING

```
<160> NUMBER OF SEQ ID NOS: 152

<210> SEQ ID NO 1
<211> LENGTH: 250
<212> TYPE: PRT
<213> ORGANISM: Homo sapiens

<400> SEQUENCE: 1

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125
```

```
Asp Asp Ser Asp Val Thr Glu Val Met Trp Gln Pro Ala Leu Arg Arg
        130                 135                 140
Gly Arg Gly Leu Gln Ala Gln Gly Tyr Gly Val Arg Ile Gln Asp Ala
145                 150                 155                 160
Gly Val Tyr Leu Leu Tyr Ser Gln Val Leu Phe Gln Asp Val Thr Phe
                165                 170                 175
Thr Met Gly Gln Val Val Ser Arg Glu Gly Gln Gly Arg Gln Glu Thr
            180                 185                 190
Leu Phe Arg Cys Ile Arg Ser Met Pro Ser His Pro Asp Arg Ala Tyr
        195                 200                 205
Asn Ser Cys Tyr Ser Ala Gly Val Phe His Leu His Gln Gly Asp Ile
        210                 215                 220
Leu Ser Val Ile Ile Pro Arg Ala Arg Ala Lys Leu Asn Leu Ser Pro
225                 230                 235                 240
His Gly Thr Phe Leu Gly Phe Val Lys Leu
                245                 250

<210> SEQ ID NO 2
<211> LENGTH: 134
<212> TYPE: PRT
<213> ORGANISM: Homo sapiens

<400> SEQUENCE: 2

Val Leu His Leu Val Pro Ile Asn Ala Thr Ser Lys Asp Asp Ser Asp
1               5                   10                  15
Val Thr Glu Val Met Trp Gln Pro Ala Leu Arg Arg Gly Arg Gly Leu
            20                  25                  30
Gln Ala Gln Gly Tyr Gly Val Arg Ile Gln Asp Ala Gly Val Tyr Leu
        35                  40                  45
Leu Tyr Ser Gln Val Leu Phe Gln Asp Val Thr Phe Thr Met Gly Gln
    50                  55                  60
Val Val Ser Arg Glu Gly Gln Gly Arg Gln Glu Thr Leu Phe Arg Cys
65                  70                  75                  80
Ile Arg Ser Met Pro Ser His Pro Asp Arg Ala Tyr Asn Ser Cys Tyr
                85                  90                  95
Ser Ala Gly Val Phe His Leu His Gln Gly Asp Ile Leu Ser Val Ile
            100                 105                 110
Ile Pro Arg Ala Arg Ala Lys Leu Asn Leu Ser Pro His Gly Thr Phe
        115                 120                 125
Leu Gly Phe Val Lys Leu
    130

<210> SEQ ID NO 3
<211> LENGTH: 134
<212> TYPE: PRT
<213> ORGANISM: Artificial Sequence
<220> FEATURE:
<223> OTHER INFORMATION: Variant APRIL (a proliferation-inducing ligand)
      sequence

<400> SEQUENCE: 3

Val Leu His Leu Val Pro Ile Asn Thr Thr Ser Lys Asp Asp Ser Asp
1               5                   10                  15
Val Thr Glu Val Met Trp Gln Pro Ala Leu Arg Arg Gly Arg Gly Leu
            20                  25                  30
Gln Ala Gln Gly Tyr Gly Val Arg Ile Gln Asp Ala Gly Val Tyr Leu
        35                  40                  45
```

```
Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
        115                 120                 125

Leu Gly Phe Val Lys Leu
        130

<210> SEQ ID NO 4
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 4

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Thr Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
        115                 120                 125

Leu Gly Phe Val Lys Leu
        130

<210> SEQ ID NO 5
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 5

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Gly Thr Phe Thr Met Gly Gln
    50                  55                  60

Val Val Ser Arg Glu Gly Gln Gly Arg Gln Glu Thr Leu Phe Arg Cys
```

```
                65                  70                  75                  80
Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 6
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 6

Val Leu His Leu Val Pro Ile Asn Ala Thr Ser Lys Asp Asp Ser Asp
1               5                  10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val His Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 7
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 7

Val Leu His Leu Val Pro Ile Asn Ala Thr Ser Lys Asp Asp Ser Asp
1               5                  10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ser Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95
```

```
Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 8
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 8

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Gly Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 9
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 9

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Cys Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125
```

```
Leu Gly Phe Val Lys Leu
        130

<210> SEQ ID NO 10
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 10

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Leu Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
        130

<210> SEQ ID NO 11
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 11

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
        130
```

```
<210> SEQ ID NO 12
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 12

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Ser Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 13
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 13

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Ala Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 14
<211> LENGTH: 134
<212> TYPE: PRT
<213> ORGANISM: Artificial Sequence
<220> FEATURE:
```

<223> OTHER INFORMATION: Variant APRIL sequence

<400> SEQUENCE: 14

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Asn Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 15
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 15

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Val Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 16
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 16

Val Leu His Leu Val Pro Ile Asn Ala Thr Ser Lys Asp Asp Ser Asp

```
                1               5                   10                  15
Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Ala Ser His Pro Asp Arg Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
        130

<210> SEQ ID NO 17
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 17

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Gly Ser His Pro Asp Arg Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
        130

<210> SEQ ID NO 18
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 18

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30
```

```
Gln Ala Gln Gly Tyr Gly Val Arg Ile Gln Asp Ala Gly Val Tyr Leu
            35                  40                  45

Leu Tyr Ser Gln Val Leu Phe Gln Asp Val Thr Phe Thr Met Gly Gln
 50                  55                  60

Val Val Ser Arg Glu Gly Gln Gly Arg Gln Glu Thr Leu Phe Arg Cys
 65                  70                  75                  80

Ile Arg Ser Met Tyr Ser His Pro Asp Arg Ala Tyr Asn Ser Cys Tyr
                 85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
            130

<210> SEQ ID NO 19
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 19

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Thr Phe Thr Met Gly Gln
 50                  55                  60

Val Val Ser Arg Glu Gly Gln Gly Arg Gln Glu Thr Leu Phe Arg Cys
 65                  70                  75                  80

Ile Arg Ser Met Arg Ser His Pro Asp Arg Ala Tyr Asn Ser Cys Tyr
                 85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
            130

<210> SEQ ID NO 20
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 20

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Thr Phe Thr Met Gly Gln
 50                  55                  60
```

```
Val Val Ser Arg Glu Gly Gln Gly Arg Gln Glu Thr Leu Phe Arg Cys
65                  70                  75                  80

Ile Arg Ser Met Trp Ser His Pro Asp Arg Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
        130
```

<210> SEQ ID NO 21
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 21

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Gly His Pro Asp Arg Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
        130
```

<210> SEQ ID NO 22
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 22

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Phe His Pro Asp Arg Ala Tyr Asn Ser Cys Tyr
```

```
                    85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
            130

<210> SEQ ID NO 23
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 23

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Asp His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
            130

<210> SEQ ID NO 24
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 24

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Val His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110
```

```
Ile Pro Arg Ala Arg Ala Lys Leu Asn Leu Ser Pro His Gly Thr Phe
            115                 120                 125

Leu Gly Phe Val Lys Leu
        130

<210> SEQ ID NO 25
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 25

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Pro His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
        130

<210> SEQ ID NO 26
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 26

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
        130
```

<210> SEQ ID NO 27
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 27

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Thr Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 28
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 28

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Thr Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 29
<211> LENGTH: 134
<212> TYPE: PRT

<213> ORGANISM: Artificial Sequence
<220> FEATURE:
<223> OTHER INFORMATION: Variant APRIL sequence

<400> SEQUENCE: 29

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Ser Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Gly His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 30
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 30

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Thr Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Val His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 31
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 31

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Gly Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Gly His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 32
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 32

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Gly Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Glu His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 33
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 33

```
Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
```

```
                    20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Gly Thr Phe Thr Met Gly Gln
        50                  55                  60

Val Val Ser Arg Glu Gly Gln Gly Arg Gln Glu Thr Leu Phe Arg Cys
 65                  70                  75                  80

Ile Arg Ser Met Pro Ala His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
        130

<210> SEQ ID NO 34
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 34

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Gly Thr Phe Thr Met Gly Gln
        50                  55                  60

Val Val Ser Arg Glu Gly Gln Gly Arg Gln Glu Thr Leu Phe Arg Cys
 65                  70                  75                  80

Ile Arg Ser Met Pro Gly His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
        130

<210> SEQ ID NO 35
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 35

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45
```

```
Leu Tyr Ser Gln Val Leu Phe Gln Asp Glu Thr Phe Thr Met Gly Gln
        50                  55                  60

Val Val Ser Arg Glu Gly Gln Gly Arg Gln Glu Thr Leu Phe Arg Cys
 65                  70                  75                  80

Ile Arg Ser Met Pro Tyr His Pro Asp Arg Ala Tyr Asn Ser Cys Tyr
                85                  90                  95

Ser Ala Gly Val Phe His Leu His Gln Gly Asp Ile Leu Ser Val Ile
               100                 105                 110

Ile Pro Arg Ala Arg Ala Lys Leu Asn Leu Ser Pro His Gly Thr Phe
               115                 120                 125

Leu Gly Phe Val Lys Leu
        130

<210> SEQ ID NO 36
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 36

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Ala Phe Thr Met Gly Gln
        50                  55                  60

Val Val Ser Arg Glu Gly Gln Gly Arg Gln Glu Thr Leu Phe Arg Cys
 65                  70                  75                  80

Ile Arg Ser Met Pro Glu His Pro Asp Arg Ala Tyr Asn Ser Cys Tyr
                85                  90                  95

Ser Ala Gly Val Phe His Leu His Gln Gly Asp Ile Leu Ser Val Ile
               100                 105                 110

Ile Pro Arg Ala Arg Ala Lys Leu Asn Leu Ser Pro His Gly Thr Phe
               115                 120                 125

Leu Gly Phe Val Lys Leu
        130

<210> SEQ ID NO 37
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 37

Val Leu His Leu Val Pro Ile Asn Ala Thr Ser Lys Asp Asp Ser Asp
 1               5                  10                  15

Val Thr Glu Val Met Trp Gln Pro Ala Leu Arg Arg Gly Arg Gly Leu
                20                  25                  30

Gln Ala Gln Gly Tyr Gly Val Arg Ile Gln Asp Ala Gly Val Tyr Leu
            35                  40                  45

Leu Tyr Ser Gln Val Leu Phe Gln Asp Val Gly Phe Thr Met Gly Gln
        50                  55                  60

Val Val Ser Arg Glu Gly Gln Gly Arg Gln Glu Thr Leu Phe Arg Cys
 65                  70                  75                  80
```

```
Ile Arg Ser Met Pro Gly His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 38
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 38

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Gly Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Val His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 39
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 39

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Pro His Pro Asp Arg Ala Tyr Asn Ser Cys Tyr
                85                  90                  95

Ser Ala Gly Val Phe His Leu His Gln Gly Asp Ile Leu Ser Val Ile
```

```
                100                 105                 110

Ile Pro Arg Ala Arg Ala Lys Leu Asn Leu Ser Pro His Gly Thr Phe
            115                 120                 125

Leu Gly Phe Val Lys Leu
        130

<210> SEQ ID NO 40
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 40

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
        130

<210> SEQ ID NO 41
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 41

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ser Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Gly His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125
```

```
Leu Gly Phe Val Lys Leu
    130

<210> SEQ ID NO 42
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 42

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Val Asn Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 43
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 43

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro His Leu Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 44
```

<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 44

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Pro Lys Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 45
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 45

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Pro Asn Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 46
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 46

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Ser Pro Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 47
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 47

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Arg Gly Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 48
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 48

Val Leu His Leu Val Pro Ile Asn Ala Thr Ser Lys Asp Asp Ser Asp
1               5                   10                  15

```
Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
50                  55                  60

Val Val Ser Arg Glu Gly Gln Gly Arg Gln Glu Thr Leu Phe Arg Cys
65                  70                  75                  80

Ile Arg Ser Met Pro Ser His Pro Pro Ile Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
    130

<210> SEQ ID NO 49
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 49

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
50                  55                  60

Val Val Ser Arg Glu Gly Gln Gly Arg Gln Glu Thr Leu Phe Arg Cys
65                  70                  75                  80

Ile Arg Ser Met Pro Ser His Pro Ser His Ala Tyr Asn Ser Cys Tyr
                85                  90                  95

Ser Ala Gly Val Phe His Leu His Gln Gly Asp Ile Leu Ser Val Ile
                100                 105                 110

Ile Pro Arg Ala Arg Ala Lys Leu Asn Leu Ser Pro His Gly Thr Phe
            115                 120                 125

Leu Gly Phe Val Lys Leu
    130

<210> SEQ ID NO 50
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 50

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
```

```
            35                  40                  45
Leu Tyr Ser Gln Val Leu Phe Gln Asp Thr Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Glu His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 51
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 51

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Thr Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 52
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 52

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ala Phe Thr Met Gly Gln
    50                  55                  60
```

Val Val Ser Arg Glu Gly Gln Gly Arg Gln Glu Thr Leu Phe Arg Cys
65                  70                  75                  80

Ile Arg Ser Met Pro Ser His Pro Pro Asn Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 53
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 53

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Ser His Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 54
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 54

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Ser His Pro Pro Asn Ala Tyr Asn Ser Cys Tyr
                85                  90                  95

```
Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
            130

<210> SEQ ID NO 55
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 55

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Ser His Pro Ser His Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
            115                 120                 125

Leu Gly Phe Val Lys Leu
            130

<210> SEQ ID NO 56
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 56

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Thr Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Gly Pro Glu His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
```

```
                            115                 120                 125
Leu Gly Phe Val Lys Leu
    130

<210> SEQ ID NO 57
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 57

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Glu His Pro Asn Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 58
<211> LENGTH: 134
<212> TYPE: PRT
<213> ORGANISM: Artificial Sequence
<220> FEATURE:
<223> OTHER INFORMATION: Variant APRIL sequence

<400> SEQUENCE: 58

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Ala Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Glu His Pro Asp His Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130
```

<210> SEQ ID NO 59
<211> LENGTH: 13
<212> TYPE: PRT
<213> ORGANISM: Artificial Sequence
<220> FEATURE:
<223> OTHER INFORMATION: Heavy chain CDR1

<400> SEQUENCE: 59

Lys Ala Ser Gly Tyr Thr Phe Thr Arg Tyr Thr Met His
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Heavy chain CDR2

<400> SEQUENCE: 60

Ile Asn Pro Ser Arg Gly Tyr Thr Asn Tyr Asn Gln Lys Phe Lys Asp
1               5                   10                  15

<210> SEQ ID NO 61
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 61

Tyr Tyr Asp Asp His Tyr Cys Leu Asp Tyr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Light chain CDR1

<400> SEQUENCE: 62

Ser Ala Ser Ser Ser Val Ser Tyr Met Asn
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Light chain CDR2

<400> SEQUENCE: 63

Arg Trp Ile Tyr Asp Thr Ser Lys Leu Ala Ser
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Light chain CDR3

<400> SEQUENCE: 64

Gln Gln Trp Ser Ser Asn Pro Phe Thr
1               5

```
<210> SEQ ID NO 65
<211> LENGTH: 242
<212> TYPE: PRT
<213> ORGANISM: Artificial Sequence
<220> FEATURE:
<223> OTHER INFORMATION: scFv sequence

<400> SEQUENCE: 65
```

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly
        115                 120                 125

Gly Ser Gly Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
    210                 215                 220

Trp Ser Ser Asn Pro Phe Thr Phe Gly Ser Gly Thr Lys Leu Glu Ile
225                 230                 235                 240

Asn Arg

```
<210> SEQ ID NO 66
<211> LENGTH: 425
<212> TYPE: PRT
<213> ORGANISM: Artificial Sequence
<220> FEATURE:
<223> OTHER INFORMATION: Sequence of bi-specific molecule

<400> SEQUENCE: 66
```

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Arg Tyr Thr Met His Trp Val Lys Gln Arg Pro Gly Gln Gly
    50                  55                  60

Leu Glu Trp Ile Gly Tyr Ile Asn Pro Ser Arg Gly Tyr Thr Asn Tyr

```
             65                  70                  75                  80
Asn Gln Lys Phe Lys Asp Lys Ala Thr Leu Thr Thr Asp Lys Ser Ser
                 85                  90                  95

Ser Thr Ala Tyr Met Gln Leu Ser Ser Leu Thr Ser Glu Asp Ser Ala
                100                 105                 110

Val Tyr Tyr Cys Ala Arg Tyr Tyr Asp Asp His Tyr Cys Leu Asp Tyr
                115                 120                 125

Trp Gly Gln Gly Thr Thr Leu Thr Val Ser Ser Gly Gly Gly Gly
130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met Asn Trp Tyr Gln Gln
                180                 185                 190

Lys Ser Gly Thr Ser Pro Lys Arg Trp Ile Tyr Asp Thr Ser Lys Leu
                195                 200                 205

Ala Ser Gly Val Pro Ala His Phe Arg Gly Ser Gly Ser Gly Thr Ser
                210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ser Asp Pro Ala Glu Pro Lys Ser Pro Asp
                260                 265                 270

Lys Thr His Thr Cys Pro Pro Cys Pro Lys Asp Pro Lys Ser Gly Gly
                275                 280                 285

Gly Gly Ser Val Leu His Leu Val Pro Ile Asn Ala Thr Ser Lys Asp
                290                 295                 300

Asp Ser Asp Val Thr Glu Val Met Trp Gln Pro Ala Leu Arg Arg Gly
305                 310                 315                 320

Arg Gly Leu Gln Ala Gln Gly Tyr Gly Val Arg Ile Gln Asp Ala Gly
                325                 330                 335

Val Tyr Leu Leu Tyr Ser Gln Val Leu Phe Gln Asp Val Thr Phe Thr
                340                 345                 350

Met Gly Gln Val Val Ser Arg Glu Gly Gln Gly Arg Gln Glu Thr Leu
                355                 360                 365

Phe Arg Cys Ile Arg Ser Met Pro Ser His Pro Asp Arg Ala Tyr Asn
370                 375                 380

Ser Cys Tyr Ser Ala Gly Val Phe His Leu His Gln Gly Asp Ile Leu
385                 390                 395                 400

Ser Val Ile Ile Pro Arg Ala Arg Ala Lys Leu Asn Leu Ser Pro His
                405                 410                 415

Gly Thr Phe Leu Gly Phe Val Lys Leu
                420                 425

<210> SEQ ID NO 67
<211> LENGTH: 450
<212> TYPE: PRT
<213> ORGANISM: Artificial Sequence
<220> FEATURE:
<223> OTHER INFORMATION: Sequence of bi-specific molecule

<400> SEQUENCE: 67

Met Glu Thr Asp Thr Leu Leu Leu Trp Val Leu Leu Leu Trp Val Pro
```

```
   1               5                   10                  15
Gly Ser Thr Gly Gln Val Gln Leu Gln Gln Ser Gly Ala Glu Leu Ala
                20                  25                  30

Arg Pro Gly Ala Ser Val Lys Met Ser Cys Lys Ala Ser Gly Tyr Thr
                35                  40                  45

Phe Thr Arg Tyr Thr Met His Trp Val Lys Gln Arg Pro Gly Gln Gly
                50                  55                  60

Leu Glu Trp Ile Gly Tyr Ile Asn Pro Ser Arg Gly Tyr Thr Asn Tyr
 65                 70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
                100                 105                 110

Val Tyr Tyr Cys Ala Arg Tyr Tyr Asp Asp His Tyr Cys Leu Asp Tyr
                115                 120                 125

Trp Gly Gln Gly Thr Thr Leu Thr Val Ser Ser Gly Gly Gly Gly
                130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met Asn Trp Tyr Gln Gln
                180                 185                 190

Lys Ser Gly Thr Ser Pro Lys Arg Trp Ile Tyr Asp Thr Ser Lys Leu
                195                 200                 205

Ala Ser Gly Val Pro Ala His Phe Arg Gly Ser Gly Ser Gly Thr Ser
                210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ser Asp Pro Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
                290                 295                 300

Leu Asp Phe Ala Cys Asp Ser Gly Gly Gly Ser Val Leu His Leu
305                 310                 315                 320

Val Pro Ile Asn Ala Thr Ser Lys Asp Asp Ser Asp Val Thr Glu Val
                325                 330                 335

Met Trp Gln Pro Ala Leu Arg Arg Gly Arg Gly Leu Gln Ala Gln Gly
                340                 345                 350

Tyr Gly Val Arg Ile Gln Asp Ala Gly Val Tyr Leu Leu Tyr Ser Gln
                355                 360                 365

Val Leu Phe Gln Asp Val Thr Phe Thr Met Gly Gln Val Val Ser Arg
                370                 375                 380

Glu Gly Gln Gly Arg Gln Glu Thr Leu Phe Arg Cys Ile Arg Ser Met
385                 390                 395                 400

Pro Ser His Pro Asp Arg Ala Tyr Asn Ser Cys Tyr Ser Ala Gly Val
                405                 410                 415

Phe His Leu His Gln Gly Asp Ile Leu Ser Val Ile Ile Pro Arg Ala
                420                 425                 430
```

Arg Ala Lys Leu Asn Leu Ser Pro His Gly Thr Phe Leu Gly Phe Val
        435                 440                 445

Lys Leu
    450

<210> SEQ ID NO 68
<211> LENGTH: 456
<212> TYPE: PRT
<213> ORGANISM: Artificial Sequence
<220> FEATURE:
<223> OTHER INFORMATION: Sequence of bi-specific molecule

<400> SEQUENCE: 68

Met Gly Thr Ser Leu Leu Cys Trp Met Ala Leu Cys Leu Leu Gly Ala
1               5                   10                  15

Asp His Ala Asp Gly Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Pro Thr Pro Ala Pro Thr
                165                 170                 175

Ile Ala Ser Gln Pro Leu Ser Leu Arg Pro Glu Ala Cys Arg Pro Ala
            180                 185                 190

Ala Gly Gly Ala Val His Thr Arg Gly Leu Asp Phe Ala Cys Asp Ser
        195                 200                 205

Gly Gly Gly Gly Ser Gln Val Gln Leu Gln Gln Ser Gly Ala Glu Leu
    210                 215                 220

Ala Arg Pro Gly Ala Ser Val Lys Met Ser Cys Lys Ala Ser Gly Tyr
225                 230                 235                 240

Thr Phe Thr Arg Tyr Thr Met His Trp Val Lys Gln Arg Pro Gly Gln
                245                 250                 255

Gly Leu Glu Trp Ile Gly Tyr Ile Asn Pro Ser Arg Gly Tyr Thr Asn
            260                 265                 270

Tyr Asn Gln Lys Phe Lys Asp Lys Ala Thr Leu Thr Thr Asp Lys Ser
        275                 280                 285

Ser Ser Thr Ala Tyr Met Gln Leu Ser Ser Leu Thr Ser Glu Asp Ser
    290                 295                 300

Ala Val Tyr Tyr Cys Ala Arg Tyr Tyr Asp Asp His Tyr Cys Leu Asp
305                 310                 315                 320

Tyr Trp Gly Gln Gly Thr Thr Leu Thr Val Ser Ser Gly Gly Gly Gly
                325                 330                 335

-continued

Gly Ser Gly Gly Gly Ser Gly Gly Gly Ser Gln Ile Val Leu
                340                 345                 350

Thr Gln Ser Pro Ala Ile Met Ser Ala Ser Pro Gly Glu Lys Val Thr
            355                 360                 365

Met Thr Cys Ser Ala Ser Ser Val Ser Tyr Met Asn Trp Tyr Gln
    370                 375                 380

Gln Lys Ser Gly Thr Ser Pro Lys Arg Trp Ile Tyr Asp Thr Ser Lys
385                 390                 395                 400

Leu Ala Ser Gly Val Pro Ala His Phe Arg Gly Ser Gly Ser Gly Thr
                405                 410                 415

Ser Tyr Ser Leu Thr Ile Ser Gly Met Glu Ala Glu Asp Ala Ala Thr
            420                 425                 430

Tyr Tyr Cys Gln Gln Trp Ser Ser Asn Pro Phe Thr Phe Gly Ser Gly
                435                 440                 445

Thr Lys Leu Glu Ile Asn Arg Ser
    450                 455

<210> SEQ ID NO 69
<211> LENGTH: 20
<212> TYPE: PRT
<213> ORGANISM: Artificial Sequence
<220> FEATURE:
<223> OTHER INFORMATION: Signal peptide

<400> SEQUENCE: 69

Met Glu Thr Asp Thr Leu Leu Leu Trp Val Leu Leu Leu Trp Val Pro
1               5                   10                  15

Gly Ser Thr Gly
            20

<210> SEQ ID NO 70
<211> LENGTH: 21
<212> TYPE: PRT
<213> ORGANISM: Artificial Sequence
<220> FEATURE:
<223> OTHER INFORMATION: Signal peptide

<400> SEQUENCE: 70

Met Gly Thr Ser Leu Leu Cys Trp Met Ala Leu Cys Leu Leu Gly Ala
1               5                   10                  15

Asp His Ala Asp Gly
            20

<210> SEQ ID NO 71
<211> LENGTH: 26
<212> TYPE: PRT
<213> ORGANISM: Artificial Sequence
<220> FEATURE:
<223> OTHER INFORMATION: Spacer sequence (IgG1 hinge)

<400> SEQUENCE: 71

Ala Glu Pro Lys Ser Pro Asp Lys Thr His Thr Cys Pro Pro Cys Pro
1               5                   10                  15

Lys Asp Pro Lys Ser Gly Gly Gly Gly Ser
            20                  25

<210> SEQ ID NO 72
<211> LENGTH: 45
<212> TYPE: PRT
<213> ORGANISM: Artificial Sequence
<220> FEATURE:

<223> OTHER INFORMATION: Spacer sequence (CD8 stalk)

<400> SEQUENCE: 72

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 73
<211> LENGTH: 7
<212> TYPE: PRT
<213> ORGANISM: Artificial Sequence
<220> FEATURE:
<223> OTHER INFORMATION: Linker

<400> SEQUENCE: 73

Ser Gly Gly Gly Ser Asp Pro
1               5

<210> SEQ ID NO 74
<211> LENGTH: 6
<212> TYPE: PRT
<213> ORGANISM: Artificial Sequence
<220> FEATURE:
<223> OTHER INFORMATION: Linker

<400> SEQUENCE: 74

Ser Gly Gly Gly Gly Ser
1               5

<210> SEQ ID NO 75
<211> LENGTH: 614
<212> TYPE: PRT
<213> ORGANISM: Artificial Sequence
<220> FEATURE:
<223> OTHER INFORMATION: Chimeric antigen receptor (CAR)
      dAPRIL-HCH2CH3pvaa-CD28OXZ

<400> SEQUENCE: 75

Met Glu Thr Asp Thr Leu Leu Leu Trp Val Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

-continued

```
Asp Pro Ala Glu Pro Lys Ser Pro Asp Lys Thr His Thr Cys Pro Pro
                165                 170                 175
Cys Pro Ala Pro Pro Val Ala Gly Pro Ser Val Phe Leu Phe Pro Pro
            180                 185                 190
Lys Pro Lys Asp Thr Leu Met Ile Ala Arg Thr Pro Glu Val Thr Cys
        195                 200                 205
Val Val Val Asp Val Ser His Glu Asp Pro Glu Val Lys Phe Asn Trp
210                 215                 220
Tyr Val Asp Gly Val Glu Val His Asn Ala Lys Thr Lys Pro Arg Glu
225                 230                 235                 240
Glu Gln Tyr Asn Ser Thr Tyr Arg Val Val Ser Val Leu Thr Val Leu
                245                 250                 255
His Gln Asp Trp Leu Asn Gly Lys Glu Tyr Lys Cys Lys Val Ser Asn
            260                 265                 270
Lys Ala Leu Pro Ala Pro Ile Glu Lys Thr Ile Ser Lys Ala Lys Gly
        275                 280                 285
Gln Pro Arg Glu Pro Gln Val Tyr Thr Leu Pro Pro Ser Arg Asp Glu
290                 295                 300
Leu Thr Lys Asn Gln Val Ser Leu Thr Cys Leu Val Lys Gly Phe Tyr
305                 310                 315                 320
Pro Ser Asp Ile Ala Val Glu Trp Glu Ser Asn Gly Gln Pro Glu Asn
                325                 330                 335
Asn Tyr Lys Thr Thr Pro Pro Val Leu Asp Ser Asp Gly Ser Phe Phe
            340                 345                 350
Leu Tyr Ser Lys Leu Thr Val Asp Lys Ser Arg Trp Gln Gln Gly Asn
        355                 360                 365
Val Phe Ser Cys Ser Val Met His Glu Ala Leu His Asn His Tyr Thr
370                 375                 380
Gln Lys Ser Leu Ser Leu Ser Pro Gly Lys Lys Asp Pro Lys Phe Trp
385                 390                 395                 400
Val Leu Val Val Val Gly Gly Val Leu Ala Cys Tyr Ser Leu Leu Val
                405                 410                 415
Thr Val Ala Phe Ile Ile Phe Trp Val Arg Ser Lys Arg Ser Arg Leu
            420                 425                 430
Leu His Ser Asp Tyr Met Asn Met Thr Pro Arg Arg Pro Gly Pro Thr
        435                 440                 445
Arg Lys His Tyr Gln Pro Tyr Ala Pro Pro Arg Asp Phe Ala Ala Tyr
450                 455                 460
Arg Ser Arg Asp Gln Arg Leu Pro Pro Asp Ala His Lys Pro Pro Gly
465                 470                 475                 480
Gly Gly Ser Phe Arg Thr Pro Ile Gln Glu Glu Gln Ala Asp Ala His
                485                 490                 495
Ser Thr Leu Ala Lys Ile Arg Val Lys Phe Ser Arg Ser Ala Asp Ala
            500                 505                 510
Pro Ala Tyr Gln Gln Gly Gln Asn Gln Leu Tyr Asn Glu Leu Asn Leu
        515                 520                 525
Gly Arg Arg Glu Glu Tyr Asp Val Leu Asp Lys Arg Arg Gly Arg Asp
530                 535                 540
Pro Glu Met Gly Gly Lys Pro Arg Arg Lys Asn Pro Gln Glu Gly Leu
545                 550                 555                 560
Tyr Asn Glu Leu Gln Lys Asp Lys Met Ala Glu Ala Tyr Ser Glu Ile
                565                 570                 575
```

```
Gly Met Lys Gly Glu Arg Arg Gly Lys Gly His Asp Gly Leu Tyr
            580                 585                 590

Gln Gly Leu Ser Thr Ala Thr Lys Asp Thr Tyr Asp Ala Leu His Met
        595                 600                 605

Gln Ala Leu Pro Pro Arg
    610

<210> SEQ ID NO 76
<211> LENGTH: 424
<212> TYPE: PRT
<213> ORGANISM: Artificial Sequence
<220> FEATURE:
<223> OTHER INFORMATION: Chimeric antigen receptor (CAR)
      dAPRIL-CD8STK-CD28OXZ

<400> SEQUENCE: 76

Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Pro Thr Pro Ala Pro Thr
                165                 170                 175

Ile Ala Ser Gln Pro Leu Ser Leu Arg Pro Glu Ala Cys Arg Pro Ala
            180                 185                 190

Ala Gly Gly Ala Val His Thr Arg Gly Leu Asp Phe Ala Cys Asp Ile
        195                 200                 205

Phe Trp Val Leu Val Val Val Gly Gly Val Leu Ala Cys Tyr Ser Leu
    210                 215                 220

Leu Val Thr Val Ala Phe Ile Ile Phe Trp Val Arg Ser Lys Arg Ser
225                 230                 235                 240

Arg Leu Leu His Ser Asp Tyr Met Asn Met Thr Pro Arg Arg Pro Gly
                245                 250                 255

Pro Thr Arg Lys His Tyr Gln Pro Tyr Ala Pro Pro Arg Asp Phe Ala
            260                 265                 270

Ala Tyr Arg Ser Arg Asp Gln Arg Leu Pro Pro Asp Ala His Lys Pro
        275                 280                 285

Pro Gly Gly Gly Ser Phe Arg Thr Pro Ile Gln Glu Glu Gln Ala Asp
    290                 295                 300

Ala His Ser Thr Leu Ala Lys Ile Arg Val Lys Phe Ser Arg Ser Ala
305                 310                 315                 320
```

```
Asp Ala Pro Ala Tyr Gln Gln Gly Gln Asn Gln Leu Tyr Asn Glu Leu
            325                 330                 335

Asn Leu Gly Arg Arg Glu Glu Tyr Asp Val Leu Asp Lys Arg Arg Gly
            340                 345                 350

Arg Asp Pro Glu Met Gly Gly Lys Pro Arg Arg Lys Asn Pro Gln Glu
            355                 360                 365

Gly Leu Tyr Asn Glu Leu Gln Lys Asp Lys Met Ala Glu Ala Tyr Ser
        370                 375                 380

Glu Ile Gly Met Lys Gly Glu Arg Arg Arg Gly Lys Gly His Asp Gly
385                 390                 395                 400

Leu Tyr Gln Gly Leu Ser Thr Ala Thr Lys Asp Thr Tyr Asp Ala Leu
                405                 410                 415

His Met Gln Ala Leu Pro Pro Arg
            420
```

<210> SEQ ID NO 77
<211> LENGTH: 398
<212> TYPE: PRT
<213> ORGANISM: Artificial Sequence
<220> FEATURE:
<223> OTHER INFORMATION: Chimeric antigen receptor (CAR)
      dAPRIL-HNG-CD28OXZ

<400> SEQUENCE: 77

```
Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Lys Asp Pro Lys Phe Trp Val Leu Val Val Val Gly Gly Val
            180                 185                 190

Leu Ala Cys Tyr Ser Leu Leu Val Thr Val Ala Phe Ile Ile Phe Trp
        195                 200                 205

Val Arg Ser Lys Arg Ser Arg Leu Leu His Ser Asp Tyr Met Asn Met
    210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser Arg Asp Gln Arg Leu Pro
```

```
                    245                 250                 255
Pro Asp Ala His Lys Pro Pro Gly Gly Gly Ser Phe Arg Thr Pro Ile
                260                 265                 270

Gln Glu Glu Gln Ala Asp Ala His Ser Thr Leu Ala Lys Ile Arg Val
            275                 280                 285

Lys Phe Ser Arg Ser Ala Asp Ala Pro Ala Tyr Gln Gln Gly Gln Asn
        290                 295                 300

Gln Leu Tyr Asn Glu Leu Asn Leu Gly Arg Arg Glu Glu Tyr Asp Val
305                 310                 315                 320

Leu Asp Lys Arg Arg Gly Arg Asp Pro Glu Met Gly Gly Lys Pro Arg
                325                 330                 335

Arg Lys Asn Pro Gln Glu Gly Leu Tyr Asn Glu Leu Gln Lys Asp Lys
                340                 345                 350

Met Ala Glu Ala Tyr Ser Glu Ile Gly Met Lys Gly Glu Arg Arg Arg
            355                 360                 365

Gly Lys Gly His Asp Gly Leu Tyr Gln Gly Leu Ser Thr Ala Thr Lys
        370                 375                 380

Asp Thr Tyr Asp Ala Leu His Met Gln Ala Leu Pro Pro Arg
385                 390                 395

<210> SEQ ID NO 78
<211> LENGTH: 633
<212> TYPE: PRT
<213> ORGANISM: Artificial Sequence
<220> FEATURE:
<223> OTHER INFORMATION: Chimeric antigen receptor (CAR)
      dAPRIL-HCH2CH3pvaa-CD28OXZ

<400> SEQUENCE: 78

Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
                20                  25                  30

Ser Thr Ser Gly Gly Gly Gly Ser Val Leu His Leu Val Pro Ile Asn
            35                  40                  45

Ala Thr Ser Lys Asp Asp Ser Asp Val Thr Glu Val Met Trp Gln Pro
        50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
                100                 105                 110

Arg Gln Glu Thr Leu Phe Arg Cys Ile Arg Ser Met Pro Ser His Pro
            115                 120                 125

Asp Arg Ala Tyr Asn Ser Cys Tyr Ser Ala Gly Val Phe His Leu His
        130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Ala Glu Pro Lys Ser Pro Asp Lys Thr His Thr
            180                 185                 190

Cys Pro Pro Cys Pro Ala Pro Pro Val Ala Gly Pro Ser Val Phe Leu
        195                 200                 205
```

```
Phe Pro Pro Lys Pro Lys Asp Thr Leu Met Ile Ala Arg Thr Pro Glu
    210             215                 220
Val Thr Cys Val Val Asp Val Ser His Glu Asp Pro Glu Val Lys
225             230                 235                 240
Phe Asn Trp Tyr Val Asp Gly Val Glu Val His Asn Ala Lys Thr Lys
                245                 250                 255
Pro Arg Glu Glu Gln Tyr Asn Ser Thr Tyr Arg Val Val Ser Val Leu
            260                 265                 270
Thr Val Leu His Gln Asp Trp Leu Asn Gly Lys Glu Tyr Lys Cys Lys
                275                 280                 285
Val Ser Asn Lys Ala Leu Pro Ala Pro Ile Glu Lys Thr Ile Ser Lys
290                 295                 300
Ala Lys Gly Gln Pro Arg Glu Pro Gln Val Tyr Thr Leu Pro Pro Ser
305                 310                 315                 320
Arg Asp Glu Leu Thr Lys Asn Gln Val Ser Leu Thr Cys Leu Val Lys
                325                 330                 335
Gly Phe Tyr Pro Ser Asp Ile Ala Val Glu Trp Glu Ser Asn Gly Gln
                340                 345                 350
Pro Glu Asn Asn Tyr Lys Thr Thr Pro Pro Val Leu Asp Ser Asp Gly
            355                 360                 365
Ser Phe Phe Leu Tyr Ser Lys Leu Thr Val Asp Lys Ser Arg Trp Gln
370                 375                 380
Gln Gly Asn Val Phe Ser Cys Ser Val Met His Glu Ala Leu His Asn
385                 390                 395                 400
His Tyr Thr Gln Lys Ser Leu Ser Leu Ser Pro Gly Lys Lys Asp Pro
                405                 410                 415
Lys Phe Trp Val Leu Val Val Val Gly Gly Val Leu Ala Cys Tyr Ser
                420                 425                 430
Leu Leu Val Thr Val Ala Phe Ile Ile Phe Trp Val Arg Ser Lys Arg
                435                 440                 445
Ser Arg Leu Leu His Ser Asp Tyr Met Asn Met Thr Pro Arg Arg Pro
            450                 455                 460
Gly Pro Thr Arg Lys His Tyr Gln Pro Tyr Ala Pro Pro Arg Asp Phe
465                 470                 475                 480
Ala Ala Tyr Arg Ser Arg Asp Gln Arg Leu Pro Pro Asp Ala His Lys
                485                 490                 495
Pro Pro Gly Gly Gly Ser Phe Arg Thr Pro Ile Gln Glu Glu Gln Ala
                500                 505                 510
Asp Ala His Ser Thr Leu Ala Lys Ile Arg Val Lys Phe Ser Arg Ser
            515                 520                 525
Ala Asp Ala Pro Ala Tyr Gln Gln Gly Gln Asn Gln Leu Tyr Asn Glu
530                 535                 540
Leu Asn Leu Gly Arg Arg Glu Glu Tyr Asp Val Leu Asp Lys Arg Arg
545                 550                 555                 560
Gly Arg Asp Pro Glu Met Gly Gly Lys Pro Arg Arg Lys Asn Pro Gln
                565                 570                 575
Glu Gly Leu Tyr Asn Glu Leu Gln Lys Asp Lys Met Ala Glu Ala Tyr
            580                 585                 590
Ser Glu Ile Gly Met Lys Gly Glu Arg Arg Arg Gly Lys Gly His Asp
                595                 600                 605
Gly Leu Tyr Gln Gly Leu Ser Thr Ala Thr Lys Asp Thr Tyr Asp Ala
            610                 615                 620
Leu His Met Gln Ala Leu Pro Pro Arg
```

```
                 625                 630

<210> SEQ ID NO 79
<211> LENGTH: 443
<212> TYPE: PRT
<213> ORGANISM: Artificial Sequence
<220> FEATURE:
<223> OTHER INFORMATION: Chimeric antigen receptor (CAR)
      dAPRIL-CD8STK-CD28OXZ

<400> SEQUENCE: 79

Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
                20                  25                  30

Ser Thr Ser Gly Gly Gly Gly Ser Val Leu His Leu Val Pro Ile Asn
            35                  40                  45

Ala Thr Ser Lys Asp Asp Ser Asp Val Thr Glu Val Met Trp Gln Pro
        50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
            100                 105                 110

Arg Gln Glu Thr Leu Phe Arg Cys Ile Arg Ser Met Pro Ser His Pro
        115                 120                 125

Asp Arg Ala Tyr Asn Ser Cys Tyr Ser Ala Gly Val Phe His Leu His
    130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Thr Thr Thr Pro Ala Pro Arg Pro Pro Thr Pro
            180                 185                 190

Ala Pro Thr Ile Ala Ser Gln Pro Leu Ser Leu Arg Pro Glu Ala Cys
        195                 200                 205

Arg Pro Ala Ala Gly Gly Ala Val His Thr Arg Gly Leu Asp Phe Ala
    210                 215                 220

Cys Asp Ile Phe Trp Val Leu Val Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Asp Gln Arg Leu Pro Pro Asp Ala
    290                 295                 300

His Lys Pro Pro Gly Gly Gly Ser Phe Arg Thr Pro Ile Gln Glu Glu
305                 310                 315                 320

Gln Ala Asp Ala His Ser Thr Leu Ala Lys Ile Arg Val Lys Phe Ser
                325                 330                 335

Arg Ser Ala Asp Ala Pro Ala Tyr Gln Gln Gly Gln Asn Gln Leu Tyr
            340                 345                 350
```

```
Asn Glu Leu Asn Leu Gly Arg Arg Glu Glu Tyr Asp Val Leu Asp Lys
            355                 360                 365

Arg Arg Gly Arg Asp Pro Glu Met Gly Gly Lys Pro Arg Arg Lys Asn
370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415

His Asp Gly Leu Tyr Gln Gly Leu Ser Thr Ala Thr Lys Asp Thr Tyr
            420                 425                 430

Asp Ala Leu His Met Gln Ala Leu Pro Pro Arg
            435                 440

<210> SEQ ID NO 80
<211> LENGTH: 417
<212> TYPE: PRT
<213> ORGANISM: Artificial Sequence
<220> FEATURE:
<223> OTHER INFORMATION: Chimeric antigen receptor (CAR)
      dAPRIL-HNG-CD28OXZ

<400> SEQUENCE: 80

Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
            20                  25                  30

Ser Thr Ser Gly Gly Gly Gly Ser Val Leu His Leu Val Pro Ile Asn
            35                  40                  45

Ala Thr Ser Lys Asp Asp Ser Asp Val Thr Glu Val Met Trp Gln Pro
50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
            100                 105                 110

Arg Gln Glu Thr Leu Phe Arg Cys Ile Arg Ser Met Pro Ser His Pro
            115                 120                 125

Asp Arg Ala Tyr Asn Ser Cys Tyr Ser Ala Gly Val Phe His Leu His
            130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Ala Glu Pro Lys Ser Pro Asp Lys Thr His Thr
            180                 185                 190

Cys Pro Pro Cys Pro Lys Asp Pro Lys Phe Trp Val Leu Val Val Val
            195                 200                 205

Gly Gly Val Leu Ala Cys Tyr Ser Leu Leu Val Thr Val Ala Phe Ile
            210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
                245                 250                 255

Pro Tyr Ala Pro Pro Arg Asp Phe Ala Ala Tyr Arg Ser Arg Asp Gln
            260                 265                 270
```

Arg Leu Pro Pro Asp Ala His Lys Pro Pro Gly Gly Ser Phe Arg
        275                 280                 285

Thr Pro Ile Gln Glu Glu Gln Ala Asp Ala His Ser Thr Leu Ala Lys
        290                 295                 300

Ile Arg Val Lys Phe Ser Arg Ser Ala Asp Ala Pro Ala Tyr Gln Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
                340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
        370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 81
<211> LENGTH: 1278
<212> TYPE: DNA
<213> ORGANISM: Artificial Sequence
<220> FEATURE:
<223> OTHER INFORMATION: Nucleic acid sequence encoding APRIL-BiTE
      (APRILiTE#01)

<400> SEQUENCE: 81
atggagaccg acaccctgct gctgtgggtg ctgctgctgt gggtgccagg cagcaccggc      60
caggtgcagc tgcagcagag cggagccgag ctggccagac caggcgccag cgtgaagatg     120
agctgcaagg ccagcggcta caccttcacc cggtacacca tgcactgggt gaagcagcgg     180
ccaggccagg gcctggagtg gatcggctac atcaacccca gcagaggcta caccaactac     240
aaccagaagt tcaaggacaa ggccaccctg accaccgaca gagcagcag caccgcctac     300 atgcagctga gcagcctgac cagcgaggac agcgccgtgt actactgcgc cagatactac     360
gacgaccact actgcctgga ctactgggc cagggcacca ccctgaccgt gagcagctct     420
ggcggaggcg gctctggcgg aggcggctct ggcggaggcg gcagccagat cgtgctgacc     480
cagagcccag ccatcatgag cgccagccca ggcgagaagg tgaccatgac ctgcagcgcc     540
agcagcagcg tgagctacat gaactggtac cagcagaaga gcggcaccag ccccaagcgg     600
tggatctacg acaccagcaa gctggccagc ggcgtgccag cccacttcag aggcagcggc     660
agcggcacca gctacagcct gaccatcagc ggcatggagg ccgaggatgc cgccacctac     720
tactgccagc agtggagcag caacccccttc accttcggca gcggcaccaa gctggagatc     780
aaccggtcgg atcccgccga gcccaaatct cctgacaaaa ctcacacatg cccaccgtgc     840
ccaaaagatc ccaaatctgg cggaggcggc agcgtgctgc acctggtgcc catcaacgcc     900
accagcaagg acgactctga tgtgaccgag gtgatgtggc agccagccct gagacgggc      960 agaggcctgc aggcccaggg ctacggcgtg agaatccagg acgctggcgt gtacctgctg    1020
tactcccagg tgctgttcca ggacgtgacc ttcacaatgg ccaggtggt gagcggagag    1080 ggccagggca gacaggagac cctgttccgg tgcatccgga gcatgccag ccaccccgac    1140

| | |
|---|---|
| agagcctaca acagctgcta cagcgctggc gtgtttcacc tgcaccaggg cgacatcctg | 1200 |
| agcgtgatca tccccagagc cagagccaag ctgaacctgt ccccccacgg cacctttctg | 1260 |
| ggcttcgtga agctgtga | 1278 |

<210> SEQ ID NO 82
<211> LENGTH: 1353
<212> TYPE: DNA
<213> ORGANISM: Artificial Sequence
<220> FEATURE:
<223> OTHER INFORMATION: Nucleic acid sequence encoding APRIL-BiTE (APRILiTE#03)

<400> SEQUENCE: 82

| | |
|---|---|
| atggagaccg acaccctgct gctgtgggtg ctgctgctgt gggtgccagg cagcaccggc | 60 |
| caggtgcagc tgcagcagag cggagccgag ctggccagac aggcgccag cgtgaagatg | 120 |
| agctgcaagg ccagcggcta caccttcacc cggtacacca tgcactgggt gaagcagcgg | 180 |
| ccaggccagg gcctggagtg gatcggctac atcaaccca gcagaggcta caccaactac | 240 |
| aaccagaagt tcaaggacaa ggccaccctg accaccgaca gagcagcag caccgcctac | 300 |
| atgcagctga gcagcctgac cagcgaggac agcgccgtgt actactgcgc cagatactac | 360 |
| gacgaccact actgcctgga ctactggggc cagggcacca ccctgaccgt gagcagctct | 420 |
| ggcggaggcg gctctggcgg aggcggctct ggcggaggcg gcagccagat cgtgctgacc | 480 |
| cagagcccag ccatcatgag cgccagccca ggcgagaagg tgaccatgac ctgcagcgcc | 540 |
| agcagcagcg tgagctacat gaactggtac cagcagaaga gcggcaccag ccccaagcgg | 600 |
| tggatctacg acaccagcaa gctggccagc ggcgtgccag cccacttcag aggcagcggc | 660 |
| agcggcacca gctacagcct gaccatcagc ggcatggagg ccgaggatgc cgccacctac | 720 |
| tactgccagc agtggagcag caacccettc accttcggca gcggcaccaa gctggagatc | 780 |
| aaccggtcgg atcccaccac gacgccagcg ccgcgaccac caacaccggc gcccaccatc | 840 |
| gcgtcgcagc ccctgtccct gcgcccagag gcgtgccggc cagcggcggg gggcgcagtg | 900 |
| cacacgaggg ggctggactt cgcctgtgat tctggcggag gcggcagcgt gctgcacctg | 960 |
| gtgcccatca cgccaccag caaggacgac tctgatgtga ccgaggtgat gtggcagcca | 1020 |
| gccctgagac ggggcagagg cctgcaggcc cagggctacg gcgtgagaat ccaggacgct | 1080 |
| ggcgtgtacc tgctgtactc ccaggtgctg ttccaggacg tgaccttcac aatgggccag | 1140 |
| gtggtgagcc gggagggcca gggcagacag gagaccctgt tccggtgcat ccggagcatg | 1200 |
| cccagccacc ccgacagagc ctacaacagc tgctacagcg ctggcgtgtt tcacctgcac | 1260 |
| cagggcgaca tcctgagcgt gatcatcccc agagccagag ccaagctgaa cctgtccccc | 1320 |
| cacggcacct ttctgggctt cgtgaagctg tga | 1353 |

<210> SEQ ID NO 83
<211> LENGTH: 1371
<212> TYPE: DNA
<213> ORGANISM: Artificial Sequence
<220> FEATURE:
<223> OTHER INFORMATION: Nucleic acid sequence encoding APRIL-BiTE (APRILiTE#06)

<400> SEQUENCE: 83

| | |
|---|---|
| atgggcacct ccctgctgtg ctggatggcc ctgtgcctgc tgggagccga ccacgccgac | 60 |
| ggcgtgctgc acctggtgcc catcaacgcc accagcaagg acgactctga tgtgaccgag | 120 |
| gtgatgtggc agccagccct gagacggggc agaggcctgc aggcccaggg ctacggcgtg | 180 |

```
agaatccagg acgctggcgt gtacctgctg tactcccagg tgctgttcca ggacgtgacc      240
ttcacaatgg gccaggtggt gagccggag ggccagggca gacaggagac cctgttccgg       300
tgcatccgga gcatgcccag ccaccccgac agagcctaca acagctgcta cagcgctggc      360
gtgtttcacc tgcaccaggg cgacatcctg agcgtgatca tccccagagc cagagccaag      420
ctgaacctgt ccccccacgg caccttctg ggcttcgtga agctgtctgg aggcggctcg       480
gatcccacca cgacgccagc gccgcgacca ccaacaccgg cgcccaccat cgcgtcgcag      540 ccctgtccc tgcgcccaga ggcgtgccgg ccagcggcgg ggggcgcagt gcacacgagg       600
gggctggact tcgcctgtga tagcggtggc ggtggcagcc aggtgcagct gcagcagagc      660
ggagccgagc tggccagacc aggcgccagc gtgaagatga gctgcaaggc cagcggctac      720
accttcaccc ggtacaccat gcactgggtg aagcagcggc caggcaggg cctggagtgg       780 atcggctaca tcaaccccag cagaggctac accaactaca accagaagtt caaggacaag      840
gccaccctga ccaccgacaa gagcagcagc accgcctaca tgcagctgag cagcctgacc      900
agcgaggaca cgccgtgta ctactgcgcc agatactacg acgaccacta ctgcctggac       960
tactggggcc agggcaccac cctgaccgtg agcagctctg gcggaggcgg ctctggcgga     1020
ggcggctctg gcggaggcgg cagccagatc gtgctgaccc agagcccagc catcatgagc     1080
gccagcccag gcgagaaggt gaccatgacc tgcagcgcca gcagcagcgt gagctacatg     1140
aactggtacc agcagaagag cggcaccagc cccaagcggt ggatctacga caccagcaag     1200
ctggccagcg gcgtgccagc ccacttcaga ggcagcggca gcggcaccag ctacagcctg     1260
accatcagcg gcatggaggc cgaggatgcc gccacctact actgccagca gtggagcagc     1320
aaccccttca ccttcggcag cggcaccaag ctggagatca ccggtcgtg a               1371

<210> SEQ ID NO 84
<211> LENGTH: 1845
<212> TYPE: DNA
<213> ORGANISM: Artificial Sequence
<220> FEATURE:
<223> OTHER INFORMATION: Nucleic acid sequence encoding APRIL-CAR
      dAPRIL-HCH2CH3pvaa-CD28OXZ

<400> SEQUENCE: 84
atggagaccg acaccctgct gctgtgggtg ctgctgctgt gggtgccagg cagcaccggc       60
agcgtgctcc acctggtgcc catcaacgcc accagcaagg acgactctga tgtgaccgag      120
gtgatgtggc agccagccct gagacggggc agaggcctgc aggcccaggg ctacggcgtg      180
agaatccagg acgctggcgt gtacctgctg tactcccagg tgctgttcca ggacgtgacc      240
ttcacaatgg gccaggtggt gagccggag ggccagggca gacaggagac cctgttccgg       300
tgcatccgga gcatgcccag ccaccccgac agagcctaca acagctgcta cagcgctggc      360
gtgtttcacc tgcaccaggg cgacatcctg agcgtgatca tccccagagc cagagccaag      420
ctgaacctgt ccccccacgg caccttctg ggcttcgtga agctgtctgg aggcggctcg       480
gatcccgccg agcccaaatc tcctgacaaa actcacacat gcccaccgtg cccagcacct     540
cccgtggccg gcccgtcagt cttcctcttc cccccaaaac ccaaggacac cctcatgatc     600
gcccggaccc ctgaggtcac atgcgtggtg gtggacgtga gccacgaaga ccctgaggtc     660
aagttcaact ggtacgtgga cggcgtggag gtgcataatg ccaagacaaa gccgcgggag     720
gagcagtaca acagcacgta ccgtgtggtc agcgtcctca ccgtcctgca ccaggactgg     780
ctgaatggca aggagtacaa gtgcaaggtc tccaacaaag ccctcccagc ccccatcgag     840
```

```
aaaaccatct ccaaagccaa agggcagccc cgagaaccac aggtgtacac cctgccccca    900
tcccgggatg agctgaccaa gaaccaggtc agcctgacct gcctggtcaa aggcttctat    960
cccagcgaca tcgccgtgga gtgggagagc aatgggcaac cggagaacaa ctacaagacc   1020
acgcctcccg tgctggactc cgacggctcc ttcttcctct acagcaagct caccgtggac   1080
aagagcaggt ggcagcaggg gaacgtcttc tcatgctccg tgatgcatga ggctctgcac   1140
aaccactaca cgcagaagag cctctccctg tctccgggta aaaaagatcc caaattttgg   1200
gtgctggtgg tggttggtgg agtcctggct tgctatagct tgctagtaac agtggccttt   1260
attattttct gggtgaggag taagaggagc aggctcctgc acagtgacta catgaacatg   1320
actccccgcc gccccgggcc cacccgcaag cattaccagc cctatgcccc accacgcgac   1380
ttcgcagcct atcgctccag ggaccagagg ctgccccccg atgcccacaa gcccctgggg   1440
ggaggcagtt ccggacccc catccaagag gagcaggccg acgcccactc caccctggcc   1500
aagatcagag tgaagttcag caggagcgca gacgccccg cgtaccagca gggccagaac   1560
cagctctata cgagctcaa tctaggacga agagaggagt acgatgtttt ggacaagaga   1620
cgtggccggg accctgagat ggggggaaag ccgagaagga agaaccctca ggaaggcctg   1680
tacaatgaac tgcagaaaga taagatggcg gaggcctaca gtgagattgg gatgaaaggc   1740
gagcgccgga ggggcaaggg gcacgatggc ctttaccagg gtctcagtac agccaccaag   1800
gacacctacg acgcccttca catgcaggcc ctgcctcctc gctaa                  1845
```

<210> SEQ ID NO 85
<211> LENGTH: 1275
<212> TYPE: DNA
<213> ORGANISM: Artificial Sequence
<220> FEATURE:
<223> OTHER INFORMATION: Nucleic acid sequence encoding APRIL-CAR
      dAPRIL-CD8STK-CD28OXZ

<400> SEQUENCE: 85

```
atggagaccg acaccctgct gctgtgggtg ctgctgctgt gggtgccagg cagcaccggc     60
agcgtgctcc acctggtgcc catcaacgcc accagcaagg acgactctga tgtgaccgag    120
gtgatgtggc agccagccct gagacggggc agaggcctgc aggcccaggg ctacggcgtg    180
agaatccagg acgctggcgt gtacctgctg tactcccagg tgctgttcca ggacgtgacc    240
ttcacaatgg gccaggtggt gagccgggag ggccagggca cagggagac cctgttccgg    300 tgcatccgga gcatgcccag ccaccccgac agagcctaca cagctgcta cagcgctggc    360 gtgtttcacc tgcaccaggg cgacatcctg agcgtgatca tccccagagc cagagccaag    420
ctgaacctgt ccccccacgg caccttctg ggcttcgtga agctgtctgg aggcggctcg    480
gatcccacca cgacgccagc gccgcgacca ccaacaccgg cgccaccat cgcgtcgcag    540 cccctgtccc tgcgcccaga ggcgtgccgg ccagcggcgg ggggcgcagt gcacacgagg    600
gggctggact cgcctgtga tatcttttgg gtgctggtgg tggttggtgg agtcctggct    660
tgctatagct tgctagtaac agtggccttt attattttct gggtgaggag taagaggagc    720
aggctcctgc acagtgacta catgaacatg actccccgcc gccccgggcc cacccgcaag    780
cattaccagc cctatgcccc accacgcgac ttcgcagcct atcgctccag ggaccagagg    840
ctgccccccg atgcccacaa gcccctgggg ggaggcagtt ccggacccc catccaagag    900 gagcaggccg acgcccactc caccctggcc aagatcagag tgaagttcag caggagcgca    960 gacgccccg cgtaccagca gggccagaac cagctctata cgagctcaa tctaggacga   1020
```

```
agagaggagt acgatgtttt ggacaagaga cgtggccggg accctgagat ggggggaaag    1080
ccgagaagga agaaccctca ggaaggcctg tacaatgaac tgcagaaaga taagatggcg    1140
gaggcctaca gtgagattgg gatgaaaggc gagcgccgga ggggcaaggg cacgatggc     1200 ctttaccagg gtctcagtac agccaccaag gacacctacg acgcccttca catgcaggcc    1260
ctgcctcctc gctaa                                                     1275
```

<210> SEQ ID NO 86
<211> LENGTH: 1197
<212> TYPE: DNA
<213> ORGANISM: Artificial Sequence
<220> FEATURE:
<223> OTHER INFORMATION: Nucleic acid sequence encoding APRIL-CAR dAPRIL-HNG-CD28OXZ

<400> SEQUENCE: 86

```
atggagaccg acaccctgct gctgtgggtg ctgctgctgt gggtgccagg cagcaccggc     60
agcgtgctcc acctggtgcc catcaacgcc accagcaagg acgactctga tgtgaccgag    120
gtgatgtggc agccagccct gagacggggc agaggcctgc aggcccaggg ctacggcgtg    180
agaatccagg acgctggcgt gtacctgctg tactcccagg tgctgttcca ggacgtgacc    240
ttcacaatgg gccaggtggt gagccggag ggccagggca gaggagac cctgttccgg      300 tgcatccgga gcatgcccag ccaccccgac agagcctaca cagctgcta cagcgctggc    360 gtgtttcacc tgcaccaggg cgacatcctg agcgtgatca tccccagagc cagagccaag    420
ctgaacctgt cccccacgg caccttctgt ggcttcgtga gctgtctgg aggcggctcg     480 gatcccgccg agcccaaatc tcctgacaaa actcacacat gcccaccgtg cccaaaagat    540
cccaaatttt gggtgctggt ggtggttggt ggagtcctgg cttgctatag cttgctagta    600
acagtggcct ttattatttt ctgggtgagg agtaagagga gcaggctcct gcacagtgac    660
tacatgaaca tgactccccg ccgcccggg ccacccgca agcattacca gccctatgcc      720
ccaccacgcg acttcgcagc ctatcgctcc agggaccaga ggctgccccc cgatgcccac    780 aagcccctg ggggaggcag tttccggacc cccatccaag aggagcaggc cgacgcccac    840 tccacctg ccaagatcag agtgaagtc agcaggagcg cagacgcccc cgcgtaccag     900
cagggccaga accagctcta taacgagctc aatctaggac gaagagagga gtacgatgtt    960
ttggacaaga cgtggcccg ggaccctgag atgggggga agccgagaag gaagaaccct      1020
caggaaggcc tgtacaatga actgcagaaa gataagatgg cggaggccta cagtgagatt    1080
gggatgaaag gcgagcgccg gaggggcaag gggcacgatg gcctttacca gggtctcagt    1140
acagccacca ggacaccta cgacgccctt cacatgcagg ccctgcctcc tcgctaa        1197
```

<210> SEQ ID NO 87
<211> LENGTH: 1902
<212> TYPE: DNA
<213> ORGANISM: Artificial Sequence
<220> FEATURE:
<223> OTHER INFORMATION: Nucleic acid sequence encoding APRIL-CAR dAPRIL-HCH2CH3pvaa-CD28OXZ

<400> SEQUENCE: 87

```
atgggcacct ccctgctgtg ctggatggcc ctgtgcctgc tgggagccga ccacgccgac     60
ggcaagccca ttcccaaccc cctgctgggc ctggactcca cctctggcgg aggcggcagc    120
gtgctgcacc tggtgcccat caacgccacc agcaaggacg actctgatgt gaccgaggtg    180
```

| | |
|---|---|
| atgtggcagc cagccctgag acggggcaga ggcctgcagg cccagggcta cggcgtgaga | 240 |
| atccaggacg ctggcgtgta cctgctgtac tcccaggtgc tgttccagga cgtgaccttc | 300 |
| acaatgggcc aggtggtgag ccgggagggc cagggcagac aggagaccct gttccggtgc | 360 |
| atccggagca tgcccagcca ccccgacaga gcctacaaca gctgctacag cgctggcgtg | 420 |
| tttcacctgc accagggcga catcctgagc gtgatcatcc cagagccag agccaagctg | 480 |
| aacctgtccc ccacggcac ctttctgggc ttcgtgaagc tgtctggagg cggctcggat | 540 |
| cccgccgagc ccaaatctcc tgacaaaact cacacatgcc caccgtgccc agcacctccc | 600 |
| gtggccggcc cgtcagtctt cctcttcccc ccaaaaccca aggacaccct catgatcgcc | 660 |
| cggacccctg aggtcacatg cgtggtggtg gacgtgagcc acgaagaccc tgaggtcaag | 720 |
| ttcaactggt acgtggacgg cgtggaggtg cataatgcca agacaaagcc gcgggaggag | 780 |
| cagtacaaca gcacgtaccg tgtggtcagc gtcctcaccg tcctgcacca ggactggctg | 840 |
| aatggcaagg agtacaagtg caaggtctcc aacaaagccc tcccagcccc catcgagaaa | 900 |
| accatctcca agccaaagg gcagcccga gaaccacagg tgtacaccct gcccccatcc | 960 |
| cgggatgagc tgaccaagaa ccaggtcagc ctgacctgcc tggtcaaagg cttctatccc | 1020 |
| agcgacatcg ccgtggagtg ggagagcaat gggcaaccgg agaacaacta caagaccacg | 1080 |
| cctcccgtgc tggactccga cggctccttc ttcctctaca gcaagctcac cgtggacaag | 1140 |
| agcaggtggc agcaggggaa cgtcttctca tgctccgtga tgcatgaggc tctgcacaac | 1200 |
| cactacacgc agaagagcct ctccctgtct ccgggtaaaa agatcccaa attttgggtg | 1260 |
| ctggtggtgg ttggtggagt cctggcttgc tatagcttgc tagtaacagt ggcctttatt | 1320 |
| attttctggg tgaggagtaa gaggagcagg ctcctgcaca gtgactacat gaacatgact | 1380 |
| ccccgccgcc ccgggcccac ccgcaagcat taccagccct atgccccacc acgcgacttc | 1440 |
| gcagcctatc gctccaggga ccagaggctg ccccccgatg cccacaagcc cctggggga | 1500 |
| ggcagttttcc ggaccccat ccaagaggag caggccgacg cccactccac cctggccaag | 1560 |
| atcagagtga agttcagcag gagcgcagac gcccccgcgt accagcaggg ccagaaccag | 1620 |
| ctctataacg agctcaatct aggacgaaga gaggagtacg atgttttgga caagagacgt | 1680 |
| ggccgggacc ctgagatggg gggaaagccg agaaggaaga cccctcagga aggcctgtac | 1740 |
| aatgaactgc agaaagataa gatggcggag gcctacagtg agattgggat gaaaggcgag | 1800 |
| cgccggaggg gcaaggggca cgatggcctt taccagggtc tcagtacagc caccaaggac | 1860 |
| acctacgacg cccttcacat gcaggccctg cctcctcgct aa | 1902 |

<210> SEQ ID NO 88
<211> LENGTH: 1332
<212> TYPE: DNA
<213> ORGANISM: Artificial Sequence
<220> FEATURE:
<223> OTHER INFORMATION: Nucleic acid sequence encoding APRIL-CAR
    dAPRIL-CD8STK-CD28OXZ

<400> SEQUENCE: 88

| | |
|---|---|
| atgggcacct ccctgctgtg ctggatggcc ctgtgcctgc tgggagccga ccacgccgac | 60 |
| ggcaagccca ttcccaaccc cctgctgggc ctggactcca cctctggcgg aggcggcagc | 120 |
| gtgctgcacc tggtgcccat caacgccacc agcaaggacg actctgatgt gaccgaggtg | 180 |
| atgtggcagc cagccctgag acggggcaga ggcctgcagg cccagggcta cggcgtgaga | 240 |
| atccaggacg ctggcgtgta cctgctgtac tcccaggtgc tgttccagga cgtgaccttc | 300 |

| | |
|---|---|
| acaatgggcc aggtggtgag ccgggagggc cagggcagac aggagaccct gttccggtgc | 360 |
| atccggagca tgcccagcca ccccgacaga gcctacaaca gctgctacag cgctggcgtg | 420 |
| tttcacctgc accagggcga catcctgagc gtgatcatcc cagagccag agccaagctg | 480 |
| aacctgtccc cccacggcac ctttctgggc ttcgtgaagc tgtctggagg cggctcggat | 540 |
| cccaccacga cgccagcgcc gcgaccacca acaccggcgc ccaccatcgc gtcgcagccc | 600 |
| ctgtccctgc gcccagaggc gtgccggcca cggcgggggg gcgcagtgca cacgaggggg | 660 |
| ctggacttcg cctgtgatat cttttgggtg ctggtggtgg ttggtggagt cctggcttgc | 720 |
| tatagcttgc tagtaacagt ggcctttatt attttctggg tgaggagtaa gaggagcagg | 780 |
| ctcctgcaca gtgactacat gaacatgact ccccgccgcc ccgggcccac ccgcaagcat | 840 |
| taccagccct atgccccacc acgcgacttc gcagcctatc gctccaggga ccagaggctg | 900 |
| cccccgatg cccacaagcc ccctggggga ggcagtttcc ggaccccat ccaagaggag | 960 |
| caggccgacg cccactccac cctggccaag atcagagtga agttcagcag gagcgcagac | 1020 |
| gcccccgcgt accagcaggg ccagaaccag ctctataacg agctcaatct aggacgaaga | 1080 |
| gaggagtacg atgttttgga caagagacgt ggccgggacc ctgagatggg gggaaagccg | 1140 |
| agaaggaaga accctcagga aggcctgtac aatgaactgc agaaagataa gatggcggag | 1200 |
| gcctacagtg agattgggat gaaaggcgag cgccggaggg gcaaggggca cgatggcctt | 1260 |
| taccagggtc tcagtacagc caccaaggac acctacgacg cccttcacat gcaggccctg | 1320 |
| cctcctcgct aa | 1332 |

<210> SEQ ID NO 89
<211> LENGTH: 1254
<212> TYPE: DNA
<213> ORGANISM: Artificial Sequence
<220> FEATURE:
<223> OTHER INFORMATION: Nucleic acid sequence encoding APRIL-CAR dAPRIL-HNG-CD28OXZ

<400> SEQUENCE: 89

| | |
|---|---|
| atgggcacct ccctgctgtg ctggatggcc ctgtgcctgc tgggagccga ccacgccgac | 60 |
| ggcaagccca ttcccaaccc cctgctgggc ctggactcca cctctggcgg aggcggcagc | 120 |
| gtgctgcacc tggtgcccat caacgccacc agcaaggacg actctgatgt gaccgaggtg | 180 |
| atgtggcagc cagccctgag acggggcaga ggcctgcagg cccagggcta cggcgtgaga | 240 |
| atccaggacg ctggcgtgta cctgctgtac tcccaggtgc tgttccagga cgtgaccttc | 300 |
| acaatgggcc aggtggtgag ccgggagggc cagggcagac aggagaccct gttccggtgc | 360 |
| atccggagca tgcccagcca ccccgacaga gcctacaaca gctgctacag cgctggcgtg | 420 |
| tttcacctgc accagggcga catcctgagc gtgatcatcc cagagccag agccaagctg | 480 |
| aacctgtccc cccacggcac ctttctgggc ttcgtgaagc tgtctggagg cggctcggat | 540 |
| cccgccagc ccaaatctcc tgacaaaact cacacatgcc caccgtgccc aaaagatccc | 600 |
| aaattttggg tgctggtggt ggttggtgga gtcctggctt gctatagctt gctagtaaca | 660 |
| gtggccttta ttattttctg ggtgaggagt aagaggagca ggctcctgca cagtgactac | 720 |
| atgaacatga ctccccgccg ccccgggccc accgcaagc attaccagcc ctatgcccca | 780 |
| ccacgcgact tcgcagccta tcgctccagg accagaggc tgcccccga tgcccacaag | 840 |
| cccccctgggg gaggcagttt ccggaccccc atccaagagg agcaggccga cgcccactcc | 900 |
| accctggcca agatcagagt gaagttcagc aggagcgcag acgcccccgc gtaccagcag | 960 |

```
ggccagaacc agctctataa cgagctcaat ctaggacgaa gagaggagta cgatgttttg    1020
gacaagagac gtggccggga ccctgagatg gggggaaagc cgagaaggaa gaaccctcag    1080
gaaggcctgt acaatgaact gcagaaagat aagatggcgg aggcctacag tgagattggg    1140
atgaaaggcg agcgccggag gggcaagggg cacgatggcc tttaccaggg tctcagtaca    1200
gccaccaagg acacctacga cgcccttcac atgcaggccc tgcctcctcg ctaa          1254
```

<210> SEQ ID NO 90
<211> LENGTH: 424
<212> TYPE: PRT
<213> ORGANISM: Artificial Sequence
<220> FEATURE:
<223> OTHER INFORMATION: CD8 stalk APRIL CAR

<400> SEQUENCE: 90

```
Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Thr Pro Ala Pro Thr
                165                 170                 175

Ile Ala Ser Gln Pro Leu Ser Leu Arg Pro Glu Ala Cys Arg Pro Ala
            180                 185                 190

Ala Gly Gly Ala Val His Thr Arg Gly Leu Asp Phe Ala Cys Asp Ile
        195                 200                 205

Phe Trp Val Leu Val Val Val Gly Gly Val Leu Ala Cys Tyr Ser Leu
    210                 215                 220

Leu Val Thr Val Ala Phe Ile Ile Phe Trp Val Arg Ser Lys Arg Ser
225                 230                 235                 240

Arg Leu Leu His Ser Asp Tyr Met Asn Met Thr Pro Arg Arg Pro Gly
                245                 250                 255

Pro Thr Arg Lys His Tyr Gln Pro Tyr Ala Pro Pro Arg Asp Phe Ala
            260                 265                 270

Ala Tyr Arg Ser Arg Asp Gln Arg Leu Pro Pro Asp Ala His Lys Pro
        275                 280                 285

Pro Gly Gly Gly Ser Phe Arg Thr Pro Ile Gln Glu Glu Gln Ala Asp
    290                 295                 300

Ala His Ser Thr Leu Ala Lys Ile Arg Val Lys Phe Ser Arg Ser Ala
305                 310                 315                 320
```

```
Asp Ala Pro Ala Tyr Gln Gly Gln Asn Gln Leu Tyr Asn Glu Leu
            325                 330                 335

Asn Leu Gly Arg Arg Glu Tyr Asp Val Leu Asp Lys Arg Arg Gly
            340                 345                 350

Arg Asp Pro Glu Met Gly Gly Lys Pro Arg Arg Lys Asn Pro Gln Glu
            355                 360                 365

Gly Leu Tyr Asn Glu Leu Gln Lys Asp Lys Met Ala Glu Ala Tyr Ser
370                 375                 380

Glu Ile Gly Met Lys Gly Glu Arg Arg Arg Gly Lys Gly His Asp Gly
385                 390                 395                 400

Leu Tyr Gln Gly Leu Ser Thr Ala Thr Lys Asp Thr Tyr Asp Ala Leu
            405                 410                 415

His Met Gln Ala Leu Pro Pro Arg
            420

<210> SEQ ID NO 91
<211> LENGTH: 398
<212> TYPE: PRT
<213> ORGANISM: Artificial Sequence
<220> FEATURE:
<223> OTHER INFORMATION: APRIL IgG1 hinge based CAR

<400> SEQUENCE: 91

Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Lys Asp Pro Lys Phe Trp Val Leu Val Val Val Gly Gly Val
            180                 185                 190

Leu Ala Cys Tyr Ser Leu Leu Val Thr Val Ala Phe Ile Ile Phe Trp
        195                 200                 205

Val Arg Ser Lys Arg Ser Arg Leu Leu His Ser Asp Tyr Met Asn Met
    210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser Arg Asp Gln Arg Leu Pro
                245                 250                 255
```

```
Pro Asp Ala His Lys Pro Pro Gly Gly Gly Ser Phe Arg Thr Pro Ile
            260                 265                 270

Gln Glu Glu Gln Ala Asp Ala His Ser Thr Leu Ala Lys Ile Arg Val
        275                 280                 285

Lys Phe Ser Arg Ser Ala Asp Ala Pro Ala Tyr Gln Gln Gly Gln Asn
    290                 295                 300

Gln Leu Tyr Asn Glu Leu Asn Leu Gly Arg Arg Glu Glu Tyr Asp Val
305                 310                 315                 320

Leu Asp Lys Arg Arg Gly Arg Asp Pro Glu Met Gly Gly Lys Pro Arg
                325                 330                 335

Arg Lys Asn Pro Gln Glu Gly Leu Tyr Asn Glu Leu Gln Lys Asp Lys
            340                 345                 350

Met Ala Glu Ala Tyr Ser Glu Ile Gly Met Lys Gly Glu Arg Arg Arg
        355                 360                 365

Gly Lys Gly His Asp Gly Leu Tyr Gln Gly Leu Ser Thr Ala Thr Lys
    370                 375                 380

Asp Thr Tyr Asp Ala Leu His Met Gln Ala Leu Pro Pro Arg
385                 390                 395

<210> SEQ ID NO 92
<211> LENGTH: 614
<212> TYPE: PRT
<213> ORGANISM: Artificial Sequence
<220> FEATURE:
<223> OTHER INFORMATION: APRIL Fc-pvaa based CAR

<400> SEQUENCE: 92

Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Ala Pro Pro Val Ala Gly Pro Ser Val Phe Leu Phe Pro Pro
            180                 185                 190

Lys Pro Lys Asp Thr Leu Met Ile Ala Arg Thr Pro Glu Val Thr Cys
        195                 200                 205

Val Val Val Asp Val Ser His Glu Asp Pro Glu Val Lys Phe Asn Trp
    210                 215                 220
```

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
            245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
            275                 280                 285

Gln Pro Arg Glu Pro Gln Val Tyr Thr Leu Pro Pro Ser Arg Asp Glu
290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
            325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
            355                 360                 365

Val Phe Ser Cys Ser Val Met His Glu Ala Leu His Asn His Tyr Thr
370                 375                 380

Gln Lys Ser Leu Ser Leu Ser Pro Gly Lys Lys Asp Pro Lys Phe Trp
385                 390                 395                 400

Val Leu Val Val Val Gly Gly Val Leu Ala Cys Tyr Ser Leu Leu Val
            405                 410                 415

Thr Val Ala Phe Ile Ile Phe Trp Val Arg Ser Lys Arg Ser Arg Leu
            420                 425                 430

Leu His Ser Asp Tyr Met Asn Met Thr Pro Arg Arg Pro Gly Pro Thr
            435                 440                 445

Arg Lys His Tyr Gln Pro Tyr Ala Pro Pro Arg Asp Phe Ala Ala Tyr
450                 455                 460

Arg Ser Arg Asp Gln Arg Leu Pro Pro Asp Ala His Lys Pro Pro Gly
465                 470                 475                 480

Gly Gly Ser Phe Arg Thr Pro Ile Gln Glu Glu Gln Ala Asp Ala His
            485                 490                 495

Ser Thr Leu Ala Lys Ile Arg Val Lys Phe Ser Arg Ser Ala Asp Ala
            500                 505                 510

Pro Ala Tyr Gln Gln Gly Gln Asn Gln Leu Tyr Asn Glu Leu Asn Leu
            515                 520                 525

Gly Arg Arg Glu Glu Tyr Asp Val Leu Asp Lys Arg Arg Gly Arg Asp
530                 535                 540

Pro Glu Met Gly Gly Lys Pro Arg Arg Lys Asn Pro Gln Glu Gly Leu
545                 550                 555                 560

Tyr Asn Glu Leu Gln Lys Asp Lys Met Ala Glu Ala Tyr Ser Glu Ile
            565                 570                 575

Gly Met Lys Gly Glu Arg Arg Gly Lys Gly His Asp Gly Leu Tyr
            580                 585                 590

Gln Gly Leu Ser Thr Ala Thr Lys Asp Thr Tyr Asp Ala Leu His Met
            595                 600                 605

Gln Ala Leu Pro Pro Arg
            610

<210> SEQ ID NO 93
<211> LENGTH: 633

<212> TYPE: PRT
<213> ORGANISM: Artificial Sequence
<220> FEATURE:
<223> OTHER INFORMATION: APRIL CAR with a V5 epitope tag
    dAPRIL-HCH2CH3pvaa-CD28OXZ

<400> SEQUENCE: 93

```
Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
            20                  25                  30

Ser Thr Ser Gly Gly Gly Gly Ser Val Leu His Leu Val Pro Ile Asn
        35                  40                  45

Ala Thr Ser Lys Asp Asp Ser Asp Val Thr Glu Val Met Trp Gln Pro
    50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
            100                 105                 110

Arg Gln Glu Thr Leu Phe Arg Cys Ile Arg Ser Met Pro Ser His Pro
        115                 120                 125

Asp Arg Ala Tyr Asn Ser Cys Tyr Ser Ala Gly Val Phe His Leu His
    130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Ala Glu Pro Lys Ser Pro Asp Lys Thr His Thr
            180                 185                 190

Cys Pro Pro Cys Pro Ala Pro Val Ala Gly Pro Ser Val Phe Leu
        195                 200                 205

Phe Pro Pro Lys Pro Lys Asp Thr Leu Met Ile Ala Arg Thr Pro Glu
    210                 215                 220

Val Thr Cys Val Val Val Asp Val Ser His Glu Asp Pro Glu Val Lys
225                 230                 235                 240

Phe Asn Trp Tyr Val Asp Gly Val Glu Val His Asn Ala Lys Thr Lys
                245                 250                 255

Pro Arg Glu Glu Gln Tyr Asn Ser Thr Tyr Arg Val Val Ser Val Leu
            260                 265                 270

Thr Val Leu His Gln Asp Trp Leu Asn Gly Lys Glu Tyr Lys Cys Lys
        275                 280                 285

Val Ser Asn Lys Ala Leu Pro Ala Pro Ile Glu Lys Thr Ile Ser Lys
    290                 295                 300

Ala Lys Gly Gln Pro Arg Glu Pro Gln Val Tyr Thr Leu Pro Pro Ser
305                 310                 315                 320

Arg Asp Glu Leu Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Val Leu Asp Ser Asp Gly
        355                 360                 365

Ser Phe Phe Leu Tyr Ser Lys Leu Thr Val Asp Lys Ser Arg Trp Gln
    370                 375                 380
```

Gln Gly Asn Val Phe Ser Cys Ser Val Met His Glu Ala Leu His Asn
385                 390                 395                 400

His Tyr Thr Gln Lys Ser Leu Ser Leu Ser Pro Gly Lys Lys Asp Pro
            405                 410                 415

Lys Phe Trp Val Leu Val Val Val Gly Gly Val Leu Ala Cys Tyr Ser
            420                 425                 430

Leu Leu Val Thr Val Ala Phe Ile Ile Phe Trp Val Arg Ser Lys Arg
            435                 440                 445

Ser Arg Leu Leu His Ser Asp Tyr Met Asn Met Thr Pro Arg Arg Pro
        450                 455                 460

Gly Pro Thr Arg Lys His Tyr Gln Pro Tyr Ala Pro Pro Arg Asp Phe
465                 470                 475                 480

Ala Ala Tyr Arg Ser Arg Asp Gln Arg Leu Pro Pro Asp Ala His Lys
            485                 490                 495

Pro Pro Gly Gly Gly Ser Phe Arg Thr Pro Ile Gln Glu Glu Gln Ala
            500                 505                 510

Asp Ala His Ser Thr Leu Ala Lys Ile Arg Val Lys Phe Ser Arg Ser
        515                 520                 525

Ala Asp Ala Pro Ala Tyr Gln Gln Gly Gln Asn Gln Leu Tyr Asn Glu
        530                 535                 540

Leu Asn Leu Gly Arg Arg Glu Glu Tyr Asp Val Leu Asp Lys Arg Arg
545                 550                 555                 560

Gly Arg Asp Pro Glu Met Gly Gly Lys Pro Arg Arg Lys Asn Pro Gln
            565                 570                 575

Glu Gly Leu Tyr Asn Glu Leu Gln Lys Asp Lys Met Ala Glu Ala Tyr
            580                 585                 590

Ser Glu Ile Gly Met Lys Gly Glu Arg Arg Arg Gly Lys Gly His Asp
        595                 600                 605

Gly Leu Tyr Gln Gly Leu Ser Thr Ala Thr Lys Asp Thr Tyr Asp Ala
    610                 615                 620

Leu His Met Gln Ala Leu Pro Pro Arg
625                 630

<210> SEQ ID NO 94
<211> LENGTH: 443
<212> TYPE: PRT
<213> ORGANISM: Artificial Sequence
<220> FEATURE:
<223> OTHER INFORMATION: APRIL CAR with a V5 epitope tag
      dAPRIL-CD8STK-CD28OXZ

<400> SEQUENCE: 94

Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
            20                  25                  30

Ser Thr Ser Gly Gly Gly Gly Ser Val Leu His Leu Val Pro Ile Asn
        35                  40                  45

Ala Thr Ser Lys Asp Asp Ser Asp Val Thr Glu Val Met Trp Gln Pro
    50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly

```
            100                 105                 110
Arg Gln Glu Thr Leu Phe Arg Cys Ile Arg Ser Met Pro Ser His Pro
            115                 120                 125

Asp Arg Ala Tyr Asn Ser Cys Tyr Ser Ala Gly Val Phe His Leu His
        130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Thr Thr Thr Pro Ala Pro Arg Pro Pro Thr Pro
            180                 185                 190

Ala Pro Thr Ile Ala Ser Gln Pro Leu Ser Leu Arg Pro Glu Ala Cys
        195                 200                 205

Arg Pro Ala Ala Gly Gly Ala Val His Thr Arg Gly Leu Asp Phe Ala
    210                 215                 220

Cys Asp Ile Phe Trp Val Leu Val Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Asp Gln Arg Leu Pro Pro Asp Ala
    290                 295                 300

His Lys Pro Pro Gly Gly Gly Ser Phe Arg Thr Pro Ile Gln Glu Glu
305                 310                 315                 320

Gln Ala Asp Ala His Ser Thr Leu Ala Lys Ile Arg Val Lys Phe Ser
                325                 330                 335

Arg Ser Ala Asp Ala Pro Ala Tyr Gln Gln Gly Gln Asn Gln Leu Tyr
            340                 345                 350

Asn Glu Leu Asn Leu Gly Arg Arg Glu Glu Tyr Asp Val Leu Asp Lys
        355                 360                 365

Arg Arg Gly Arg Asp Pro Glu Met Gly Gly Lys Pro Arg Arg Lys Asn
    370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415

His Asp Gly Leu Tyr Gln Gly Leu Ser Thr Ala Thr Lys Asp Thr Tyr
            420                 425                 430

Asp Ala Leu His Met Gln Ala Leu Pro Pro Arg
        435                 440

<210> SEQ ID NO 95
<211> LENGTH: 417
<212> TYPE: PRT
<213> ORGANISM: Artificial Sequence
<220> FEATURE:
<223> OTHER INFORMATION: APRIL CAR with a V5 epitope tag
      dAPRIL-HNG-CD28OXZ

<400> SEQUENCE: 95

Met Gly Thr Ser Leu Leu Cys Trp Met Ala Leu Cys Leu Leu Gly Ala
1               5                   10                  15
```

```
Asp His Ala Asp Gly Lys Pro Ile Pro Asn Pro Leu Leu Gly Leu Asp
             20                  25                  30

Ser Thr Ser Gly Gly Gly Ser Val Leu His Leu Val Pro Ile Asn
         35                  40                  45

Ala Thr Ser Lys Asp Asp Ser Asp Val Thr Glu Val Met Trp Gln Pro
 50                  55                  60

Ala Leu Arg Arg Gly Arg Gly Leu Gln Ala Gln Gly Tyr Gly Val Arg
 65                  70                  75                  80

Ile Gln Asp Ala Gly Val Tyr Leu Leu Tyr Ser Gln Val Leu Phe Gln
                 85                  90                  95

Asp Val Thr Phe Thr Met Gly Gln Val Val Ser Arg Glu Gly Gln Gly
            100                 105                 110

Arg Gln Glu Thr Leu Phe Arg Cys Ile Arg Ser Met Pro Ser His Pro
        115                 120                 125

Asp Arg Ala Tyr Asn Ser Cys Tyr Ser Ala Gly Val Phe His Leu His
    130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Ala Glu Pro Lys Ser Pro Asp Lys Thr His Thr
            180                 185                 190

Cys Pro Pro Cys Pro Lys Asp Pro Lys Phe Trp Val Leu Val Val Val
        195                 200                 205

Gly Gly Val Leu Ala Cys Tyr Ser Leu Leu Val Thr Val Ala Phe Ile
    210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
                245                 250                 255

Pro Tyr Ala Pro Pro Arg Asp Phe Ala Ala Tyr Arg Ser Arg Asp Gln
            260                 265                 270

Arg Leu Pro Pro Asp Ala His Lys Pro Pro Gly Gly Gly Ser Phe Arg
        275                 280                 285

Thr Pro Ile Gln Glu Glu Gln Ala Asp Ala His Ser Thr Leu Ala Lys
    290                 295                 300

Ile Arg Val Lys Phe Ser Arg Ser Ala Asp Ala Pro Ala Tyr Gln Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
    370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 96
```

<211> LENGTH: 425
<212> TYPE: PRT
<213> ORGANISM: Artificial Sequence
<220> FEATURE:
<223> OTHER INFORMATION: Sequence of APRILiTE#01

<400> SEQUENCE: 96

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Arg Tyr Thr Met His Trp Val Lys Gln Arg Pro Gly Gln Gly
    50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Thr Leu Thr Val Ser Ser Gly Gly Gly Gly
    130                 135                 140

Ser Gly Gly Gly Gly Ser Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Val Ser Tyr Met Asn Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Ala His Phe Arg Gly Ser Gly Ser Gly Thr Ser
210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ser Asp Pro Ala Glu Pro Lys Ser Pro Asp
            260                 265                 270

Lys Thr His Thr Cys Pro Pro Cys Pro Lys Asp Pro Lys Ser Gly Gly
        275                 280                 285

Gly Gly Ser Val Leu His Leu Val Pro Ile Asn Ala Thr Ser Lys Asp
    290                 295                 300

Asp Ser Asp Val Thr Glu Val Met Trp Gln Pro Ala Leu Arg Arg Gly
305                 310                 315                 320

Arg Gly Leu Gln Ala Gln Gly Tyr Gly Val Arg Ile Gln Asp Ala Gly
                325                 330                 335

Val Tyr Leu Leu Tyr Ser Gln Val Leu Phe Gln Asp Val Thr Phe Thr
            340                 345                 350

Met Gly Gln Val Val Ser Arg Glu Gly Gln Gly Arg Gln Glu Thr Leu
        355                 360                 365

Phe Arg Cys Ile Arg Ser Met Pro Ser His Pro Asp Arg Ala Tyr Asn
    370                 375                 380

Ser Cys Tyr Ser Ala Gly Val Phe His Leu His Gln Gly Asp Ile Leu
385                 390                 395                 400

Ser Val Ile Ile Pro Arg Ala Arg Ala Lys Leu Asn Leu Ser Pro His
                405                 410                 415

Gly Thr Phe Leu Gly Phe Val Lys Leu
            420                 425

<210> SEQ ID NO 97
<211> LENGTH: 450
<212> TYPE: PRT
<213> ORGANISM: Artificial Sequence
<220> FEATURE:
<223> OTHER INFORMATION: Sequence of APRILiTE#03

<400> SEQUENCE: 97

Met Glu Thr Asp Thr Leu Leu Leu Trp Val Leu Leu Trp Val Pro
1               5                   10                  15

Gly Ser Thr Gly Gln Val Gln Leu Gln Gln Ser Gly Ala Glu Leu Ala
                20                  25                  30

Arg Pro Gly Ala Ser Val Lys Met Ser Cys Lys Ala Ser Gly Tyr Thr
                35                  40                  45

Phe Thr Arg Tyr Thr Met His Trp Val Lys Gln Arg Pro Gly Gln Gly
            50                  55                  60

Leu Glu Trp Ile Gly Tyr Ile Asn Pro Ser Arg Gly Tyr Thr Asn Tyr
65              70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
                100                 105                 110

Val Tyr Tyr Cys Ala Arg Tyr Tyr Asp Asp His Tyr Cys Leu Asp Tyr
                115                 120                 125

Trp Gly Gln Gly Thr Thr Leu Thr Val Ser Ser Gly Gly Gly Gly
            130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met Asn Trp Tyr Gln Gln
                180                 185                 190

Lys Ser Gly Thr Ser Pro Lys Arg Trp Ile Tyr Asp Thr Ser Lys Leu
            195                 200                 205

Ala Ser Gly Val Pro Ala His Phe Arg Gly Ser Gly Ser Gly Thr Ser
            210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ser Asp Pro Thr Thr Thr Pro Ala Pro Arg
                260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ser Gly Gly Gly Gly Ser Val Leu His Leu
305                 310                 315                 320

```
Val Pro Ile Asn Ala Thr Ser Lys Asp Asp Ser Asp Val Thr Glu Val
                325                 330                 335

Met Trp Gln Pro Ala Leu Arg Arg Gly Arg Gly Leu Gln Ala Gln Gly
                340                 345                 350

Tyr Gly Val Arg Ile Gln Asp Ala Gly Val Tyr Leu Leu Tyr Ser Gln
                355                 360                 365

Val Leu Phe Gln Asp Val Thr Phe Thr Met Gly Gln Val Val Ser Arg
                370                 375                 380

Glu Gly Gln Gly Arg Gln Glu Thr Leu Phe Arg Cys Ile Arg Ser Met
385                 390                 395                 400

Pro Ser His Pro Asp Arg Ala Tyr Asn Ser Cys Tyr Ser Ala Gly Val
                405                 410                 415

Phe His Leu His Gln Gly Asp Ile Leu Ser Val Ile Ile Pro Arg Ala
                420                 425                 430

Arg Ala Lys Leu Asn Leu Ser Pro His Gly Thr Phe Leu Gly Phe Val
                435                 440                 445

Lys Leu
    450

<210> SEQ ID NO 98
<211> LENGTH: 456
<212> TYPE: PRT
<213> ORGANISM: Artificial Sequence
<220> FEATURE:
<223> OTHER INFORMATION: Sequence of APRILiTE#06

<400> SEQUENCE: 98

Met Gly Thr Ser Leu Leu Cys Trp Met Ala Leu Cys Leu Leu Gly Ala
1               5                   10                  15

Asp His Ala Asp Gly Val Leu His Leu Val Pro Ile Asn Ala Thr Ser
                20                  25                  30

Lys Asp Asp Ser Asp Val Thr Glu Val Met Trp Gln Pro Ala Leu Arg
                35                  40                  45

Arg Gly Arg Gly Leu Gln Ala Gln Gly Tyr Gly Val Arg Ile Gln Asp
            50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
                100                 105                 110

Tyr Asn Ser Cys Tyr Ser Ala Gly Val Phe His Leu His Gln Gly Asp
                115                 120                 125

Ile Leu Ser Val Ile Ile Pro Arg Ala Arg Ala Lys Leu Asn Leu Ser
            130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Pro Thr Pro Ala Pro Thr
                165                 170                 175

Ile Ala Ser Gln Pro Leu Ser Leu Arg Pro Glu Ala Cys Arg Pro Ala
                180                 185                 190

Ala Gly Gly Ala Val His Thr Arg Gly Leu Asp Phe Ala Cys Asp Ser
            195                 200                 205

Gly Gly Gly Gly Ser Gln Val Gln Leu Gln Gln Ser Gly Ala Glu Leu
210                 215                 220
```

Ala Arg Pro Gly Ala Ser Val Lys Met Ser Cys Lys Ala Ser Gly Tyr
225                 230                 235                 240

Thr Phe Thr Arg Tyr Thr Met His Trp Val Lys Gln Arg Pro Gly Gln
            245                 250                 255

Gly Leu Glu Trp Ile Gly Tyr Ile Asn Pro Ser Arg Gly Tyr Thr Asn
        260                 265                 270

Tyr Asn Gln Lys Phe Lys Asp Lys Ala Thr Leu Thr Thr Asp Lys Ser
    275                 280                 285

Ser Ser Thr Ala Tyr Met Gln Leu Ser Ser Leu Thr Ser Glu Asp Ser
290                 295                 300

Ala Val Tyr Tyr Cys Ala Arg Tyr Tyr Asp Asp His Tyr Cys Leu Asp
305                 310                 315                 320

Tyr Trp Gly Gln Gly Thr Thr Leu Thr Val Ser Ser Gly Gly Gly
            325                 330                 335

Gly Ser Gly Gly Gly Gly Ser Gly Gly Gly Gly Ser Gln Ile Val Leu
            340                 345                 350

Thr Gln Ser Pro Ala Ile Met Ser Ala Ser Pro Gly Glu Lys Val Thr
        355                 360                 365

Met Thr Cys Ser Ala Ser Ser Val Ser Tyr Met Asn Trp Tyr Gln
370                 375                 380

Gln Lys Ser Gly Thr Ser Pro Lys Arg Trp Ile Tyr Asp Thr Ser Lys
385                 390                 395                 400

Leu Ala Ser Gly Val Pro Ala His Phe Arg Gly Ser Gly Ser Gly Thr
            405                 410                 415

Ser Tyr Ser Leu Thr Ile Ser Gly Met Glu Ala Glu Asp Ala Ala Thr
        420                 425                 430

Tyr Tyr Cys Gln Gln Trp Ser Ser Asn Pro Phe Thr Phe Gly Ser Gly
    435                 440                 445

Thr Lys Leu Glu Ile Asn Arg Ser
    450                 455

<210> SEQ ID NO 99
<211> LENGTH: 18
<212> TYPE: PRT
<213> ORGANISM: Artificial Sequence
<220> FEATURE:
<223> OTHER INFORMATION: Linker

<400> SEQUENCE: 99

Ser Gly Gly Gly Gly Ser Ser Gly Gly Gly Gly Ser Ser Gly Gly Gly
1               5                   10                  15

Gly Ser

<210> SEQ ID NO 100
<211> LENGTH: 6
<212> TYPE: PRT
<213> ORGANISM: Artificial Sequence
<220> FEATURE:
<223> OTHER INFORMATION: Furin cleavage site

<400> SEQUENCE: 100

Lys Gln Lys Lys Gln Lys
1               5

<210> SEQ ID NO 101
<211> LENGTH: 5
<212> TYPE: PRT
<213> ORGANISM: Artificial Sequence

```
<220> FEATURE:
<223> OTHER INFORMATION: Linker

<400> SEQUENCE: 101

Gly Gly Gly Gly Ser
1               5

<210> SEQ ID NO 102
<211> LENGTH: 70
<212> TYPE: DNA
<213> ORGANISM: Artificial Sequence
<220> FEATURE:
<223> OTHER INFORMATION: Synthetic polypeptide (M200X)
<220> FEATURE:
<221> NAME/KEY: misc_feature
<222> LOCATION: (51)..(53)
<223> OTHER INFORMATION: n is a, c, g, or t

<400> SEQUENCE: 102
gccgggaggg ccagggcaga caggagaccc tgttccggtg catccggagc nnnccagcc      60 accccgacag                                                            70

<210> SEQ ID NO 103
<211> LENGTH: 70
<212> TYPE: DNA
<213> ORGANISM: Artificial Sequence
<220> FEATURE:
<223> OTHER INFORMATION: Synthetic polynucleotide (M200C)

<400> SEQUENCE: 103
gccgggaggg ccagggcaga caggagaccc tgttccggtg catccggagc tgtcccagcc     60
accccgacag                                                            70

<210> SEQ ID NO 104
<211> LENGTH: 70
<212> TYPE: DNA
<213> ORGANISM: Artificial Sequence
<220> FEATURE:
<223> OTHER INFORMATION: Synthetic polynucleotide (M200L)

<400> SEQUENCE: 104
gccgggaggg ccagggcaga caggagaccc tgttccggtg catccggagc ttgcccagcc     60
accccgacag                                                            70

<210> SEQ ID NO 105
<211> LENGTH: 70
<212> TYPE: DNA
<213> ORGANISM: Artificial Sequence
<220> FEATURE:
<223> OTHER INFORMATION: Synthetic polynucleotide (M200S)

<400> SEQUENCE: 105
gccgggaggg ccagggcaga caggagaccc tgttccggtg catccggagc agacccagcc     60
accccgacag                                                            70

<210> SEQ ID NO 106
<211> LENGTH: 70
<212> TYPE: DNA
<213> ORGANISM: Artificial Sequence
<220> FEATURE:
<223> OTHER INFORMATION: Synthetic polynucleotide (M200*)

<400> SEQUENCE: 106
gccgggaggg ccagggcaga caggagaccc tgttccggtg catccggagc tgacccagcc     60
```
accccgacag                                                            70

<210> SEQ ID NO 107
<211> LENGTH: 70
<212> TYPE: DNA
<213> ORGANISM: Artificial Sequence
<220> FEATURE:
<223> OTHER INFORMATION: Synthetic polynucleotide (M200A)

<400> SEQUENCE: 107
gccgggaggg ccagggcaga caggagaccc tgttccggtg catccggagc gcgcccagcc    60
accccgacag                                                            70

<210> SEQ ID NO 108
<211> LENGTH: 70
<212> TYPE: DNA
<213> ORGANISM: Artificial Sequence
<220> FEATURE:
<223> OTHER INFORMATION: Synthetic polynucleotide (M200G)

<400> SEQUENCE: 108
gccgggaggg ccagggcaga caggagaccc tgttccggtg catccggagc ggtcccagcc    60
accccgacag                                                            70

<210> SEQ ID NO 109
<211> LENGTH: 70
<212> TYPE: DNA
<213> ORGANISM: Artificial Sequence
<220> FEATURE:
<223> OTHER INFORMATION: Synthetic polynucleotide (M200N)

<400> SEQUENCE: 109
gccgggaggg ccagggcaga caggagaccc tgttccggtg catccggagc aatcccagcc    60
accccgacag                                                            70

<210> SEQ ID NO 110
<211> LENGTH: 70
<212> TYPE: DNA
<213> ORGANISM: Artificial Sequence
<220> FEATURE:
<223> OTHER INFORMATION: Synthetic polynucleotide (P201X)
<220> FEATURE:
<221> NAME/KEY: misc_feature
<222> LOCATION: (54)..(56)
<223> OTHER INFORMATION: n is a, c, g, or t

<400> SEQUENCE: 110
gccgggaggg ccagggcaga caggagaccc tgttccggtg catccggagc atgnnnagcc    60
accccgacag                                                            70

<210> SEQ ID NO 111
<211> LENGTH: 70
<212> TYPE: DNA
<213> ORGANISM: Artificial Sequence
<220> FEATURE:
<223> OTHER INFORMATION: Synthetic polynucleotide (P201G-4_406.seq)

<400> SEQUENCE: 111
gccgggaggg ccagggcaga caggagaccc tgttccggtg catccggagc atgggcagcc    60
accccgacag                                                            70

<210> SEQ ID NO 112

```
<211> LENGTH: 70
<212> TYPE: DNA
<213> ORGANISM: Artificial Sequence
<220> FEATURE:
<223> OTHER INFORMATION: Synthetic polynucleotide (P201A-18_406.seq)

<400> SEQUENCE: 112
gccgggaggg ccagggcaga caggagaccc tgttccggtg catccggagc atggctagcc    60
accccgacag                                                          70

<210> SEQ ID NO 113
<211> LENGTH: 70
<212> TYPE: DNA
<213> ORGANISM: Artificial Sequence
<220> FEATURE:
<223> OTHER INFORMATION: Synthetic polynucleotide (P201V-38_406.seq)

<400> SEQUENCE: 113
gccgggaggg ccagggcaga caggagaccc tgttccggtg catccggagc atggttagcc    60
accccgacag                                                          70

<210> SEQ ID NO 114
<211> LENGTH: 70
<212> TYPE: DNA
<213> ORGANISM: Artificial Sequence
<220> FEATURE:
<223> OTHER INFORMATION: Synthetic polynucleotide (P201W-46_406.seq)

<400> SEQUENCE: 114
gccgggaggg ccagggcaga caggagaccc tgttccggtg catccggagc atgtggagcc    60
accccgacag                                                          70

<210> SEQ ID NO 115
<211> LENGTH: 70
<212> TYPE: DNA
<213> ORGANISM: Artificial Sequence
<220> FEATURE:
<223> OTHER INFORMATION: Synthetic polynucleotide (P201R-28_406.seq)

<400> SEQUENCE: 115
gccgggaggg ccagggcaga caggagaccc tgttccggtg catccggagc atgcgaagcc    60
accccgacag                                                          70

<210> SEQ ID NO 116
<211> LENGTH: 70
<212> TYPE: DNA
<213> ORGANISM: Artificial Sequence
<220> FEATURE:
<223> OTHER INFORMATION: Synthetic polynucleotide (P201Y-44_406.seq)

<400> SEQUENCE: 116
gccgggaggg ccagggcaga caggagaccc tgttccggtg catccggagc atgtatagcc    60
accccgacag                                                          70

<210> SEQ ID NO 117
<211> LENGTH: 70
<212> TYPE: DNA
<213> ORGANISM: Artificial Sequence
<220> FEATURE:
<223> OTHER INFORMATION: Synthetic polynucleotide (S202X)
<220> FEATURE:
<221> NAME/KEY: misc_feature
<222> LOCATION: (57)..(59)
<223> OTHER INFORMATION: n is a, c, g, or t
```

```
<400> SEQUENCE: 117
gccgggaggg ccagggcaga caggagaccc tgttccggtg catccggagc atgcccnnnc    60
accccgacag                                                          70

<210> SEQ ID NO 118
<211> LENGTH: 70
<212> TYPE: DNA
<213> ORGANISM: Artificial Sequence
<220> FEATURE:
<223> OTHER INFORMATION: Synthetic polynucleotide (S202G-5_406)

<400> SEQUENCE: 118
gccgggaggg ccagggcaga caggagaccc tgttccggtg catccggagc atgcccggtc    60
accccgacag                                                          70

<210> SEQ ID NO 119
<211> LENGTH: 70
<212> TYPE: DNA
<213> ORGANISM: Artificial Sequence
<220> FEATURE:
<223> OTHER INFORMATION: Synthetic polynucleotide (S202P-20_406)

<400> SEQUENCE: 119
gccgggaggg ccagggcaga caggagaccc tgttccggtg catccggagc atgccccccc    60
accccgacag                                                          70

<210> SEQ ID NO 120
<211> LENGTH: 70
<212> TYPE: DNA
<213> ORGANISM: Artificial Sequence
<220> FEATURE:
<223> OTHER INFORMATION: Synthetic polynucleotide (S202F-22_406.seq)

<400> SEQUENCE: 120
gccgggaggg ccagggcaga caggagaccc tgttccggtg catccggagc atgcccttcc    60
accccgacag                                                          70

<210> SEQ ID NO 121
<211> LENGTH: 70
<212> TYPE: DNA
<213> ORGANISM: Artificial Sequence
<220> FEATURE:
<223> OTHER INFORMATION: Synthetic polynucleotide (S202V-H203N-26_4)

<400> SEQUENCE: 121
gccgggaggg ccagggcaga caggagaccc tgttccggtg catccggagc atgcccgtga    60
accccgacag                                                          70

<210> SEQ ID NO 122
<211> LENGTH: 70
<212> TYPE: DNA
<213> ORGANISM: Artificial Sequence
<220> FEATURE:
<223> OTHER INFORMATION: Synthetic polynucleotide (S202D-40_406.seq)

<400> SEQUENCE: 122
gccgggaggg ccagggcaga caggagaccc tgttccggtg catccggagc atgcccgatc    60
accccgacag                                                          70

<210> SEQ ID NO 123
```

```
<211> LENGTH: 140
<212> TYPE: DNA
<213> ORGANISM: Artificial Sequence
<220> FEATURE:
<223> OTHER INFORMATION: Synthetic polynucleotide (T175X)
<220> FEATURE:
<221> NAME/KEY: misc_feature
<222> LOCATION: (46)..(48)
<223> OTHER INFORMATION: n is a, c, g, or t

<400> SEQUENCE: 123
gctggcgtgt acctgctgta ctcccaggtg ctgttccagg acgtgnnntt cacaatgggc      60
caggtggtga gccgggaggg ccagggcaga caggagaccc tgttccggtg catccggagc     120
atgcccagcc accccgacag                                                 140

<210> SEQ ID NO 124
<211> LENGTH: 140
<212> TYPE: DNA
<213> ORGANISM: Artificial Sequence
<220> FEATURE:
<223> OTHER INFORMATION: Synthetic polynucleotide (T175G-S202G-4_40)
<220> FEATURE:
<221> NAME/KEY: misc_feature
<222> LOCATION: (46)..(48)
<223> OTHER INFORMATION: n is a, c, g, or t

<400> SEQUENCE: 124
gctggcgtgt acctgctgta ctcccaggtg ctgttccagg acgtgnnntt cacaatgggc      60
caggtggtga gccgggaggg ccagggcaga caggagaccc tgttccggtg catccggagc     120
atgcccggcc accccgacag                                                 140

<210> SEQ ID NO 125
<211> LENGTH: 140
<212> TYPE: DNA
<213> ORGANISM: Artificial Sequence
<220> FEATURE:
<223> OTHER INFORMATION: Synthetic polynucleotide (T175G_S202V-6_40)
<220> FEATURE:
<221> NAME/KEY: misc_feature
<222> LOCATION: (46)..(48)
<223> OTHER INFORMATION: n is a, c, g, or t

<400> SEQUENCE: 125
gctggcgtgt acctgctgta ctcccaggtg ctgttccagg acgtgnnntt cacaatgggc      60
caggtggtga gccgggaggg ccagggcaga caggagaccc tgttccggtg catccggagc     120
atgcccgtgc accccgacag                                                 140

<210> SEQ ID NO 126
<211> LENGTH: 140
<212> TYPE: DNA
<213> ORGANISM: Artificial Sequence
<220> FEATURE:
<223> OTHER INFORMATION: Synthetic polynucleotide (T175H-11_406.seq)
<220> FEATURE:
<221> NAME/KEY: misc_feature
<222> LOCATION: (46)..(48)
<223> OTHER INFORMATION: n is a, c, g, or t

<400> SEQUENCE: 126
gctggcgtgt acctgctgta ctcccaggtg ctgttccagg acgtgnnntt cacaatgggc      60
caggtggtga gccgggaggg ccagggcaga caggagaccc tgttccggtg catccggagc     120
atgcccagcc accccgacag                                                 140
```

```
<210> SEQ ID NO 127
<211> LENGTH: 140
<212> TYPE: DNA
<213> ORGANISM: Artificial Sequence
<220> FEATURE:
<223> OTHER INFORMATION: Synthetic polynucleotide (T175P-15_406.seq)
<220> FEATURE:
<221> NAME/KEY: misc_feature
<222> LOCATION: (46)..(48)
<223> OTHER INFORMATION: n is a, c, g, or t

<400> SEQUENCE: 127
gctggcgtgt acctgctgta ctcccaggtg ctgttccagg acgtgnnntt cacaatgggc    60
caggtggtga gccgggaggg ccagggcaga caggagaccc tgttccggtg catccggagc   120
atgcccagcc accccgacag                                               140

<210> SEQ ID NO 128
<211> LENGTH: 140
<212> TYPE: DNA
<213> ORGANISM: Artificial Sequence
<220> FEATURE:
<223> OTHER INFORMATION: Synthetic polynucleotide (T175S-16_406.seq)
<220> FEATURE:
<221> NAME/KEY: misc_feature
<222> LOCATION: (46)..(48)
<223> OTHER INFORMATION: n is a, c, g, or t

<400> SEQUENCE: 128
gctggcgtgt acctgctgta ctcccaggtg ctgttccagg acgtgnnntt cacaatgggc    60
caggtggtga gccgggaggg ccagggcaga caggagaccc tgttccggtg catccggagc   120
atgcccagtc accccgacag                                               140

<210> SEQ ID NO 129
<211> LENGTH: 140
<212> TYPE: DNA
<213> ORGANISM: Artificial Sequence
<220> FEATURE:
<223> OTHER INFORMATION: Synthetic polynucleotide (T175G-19_406.seq)
<220> FEATURE:
<221> NAME/KEY: misc_feature
<222> LOCATION: (46)..(48)
<223> OTHER INFORMATION: n is a, c, g, or t

<400> SEQUENCE: 129
gctggcgtgt acctgctgta ctcccaggtg ctgttccagg acgtgnnntt cacaatgggc    60
caggtggtga gccgggaggg ccagggcaga caggagaccc tgttccggtg catccggagc   120
atgcccagcc accccgacag                                               140

<210> SEQ ID NO 130
<211> LENGTH: 140
<212> TYPE: DNA
<213> ORGANISM: Artificial Sequence
<220> FEATURE:
<223> OTHER INFORMATION: Synthetic polynucleotide (T175A_S202E-24_4)
<220> FEATURE:
<221> NAME/KEY: misc_feature
<222> LOCATION: (46)..(48)
<223> OTHER INFORMATION: n is a, c, g, or t

<400> SEQUENCE: 130
gctggcgtgt acctgctgta ctcccaggtg ctgttccagg acgtgnnntt cacaatgggc    60
caggtggtga gccgggaggg ccagggcaga caggagaccc tgttccggtg catccggagc   120
atgcccgagc accccgacag                                               140
```

<210> SEQ ID NO 131
<211> LENGTH: 140
<212> TYPE: DNA
<213> ORGANISM: Artificial Sequence
<220> FEATURE:
<223> OTHER INFORMATION: Synthetic polynucleotide (T175S_S202G-25_4)
<220> FEATURE:
<221> NAME/KEY: misc_feature
<222> LOCATION: (46)..(48)
<223> OTHER INFORMATION: n is a, c, g, or t

<400> SEQUENCE: 131
gctggcgtgt acctgctgta ctcccaggtg ctgttccagg acgtgnnntt cacaatgggc    60
caggtggtga gccgggaggg ccagggcaga caggagaccc tgttccggtg catccggagc   120
atgcccggtc accccgacag                                                140

<210> SEQ ID NO 132
<211> LENGTH: 140
<212> TYPE: DNA
<213> ORGANISM: Artificial Sequence
<220> FEATURE:
<223> OTHER INFORMATION: Synthetic polynucleotide (V174X)
<220> FEATURE:
<221> NAME/KEY: misc_feature
<222> LOCATION: (43)..(45)
<223> OTHER INFORMATION: n is a, c, g, or t

<400> SEQUENCE: 132
gctggcgtgt acctgctgta ctcccaggtg ctgttccagg acnnnacctt cacaatgggc    60
caggtggtga gccgggaggg ccagggcaga caggagaccc tgttccggtg catccggagc   120
atgcccagcc accccgacag                                                140

<210> SEQ ID NO 133
<211> LENGTH: 140
<212> TYPE: DNA
<213> ORGANISM: Artificial Sequence
<220> FEATURE:
<223> OTHER INFORMATION: Synthetic polynucleotide (V174T_S202V-1_40)

<400> SEQUENCE: 133
gctggcgtgt acctgctgta ctcccaggtg ctgttccagg acacaacctt cacaatgggc    60
caggtggtga gccgggaggg ccagggcaga caggagaccc tgttccggtg catccggagc   120
atgcccgtcc accccgacag                                                140

<210> SEQ ID NO 134
<211> LENGTH: 140
<212> TYPE: DNA
<213> ORGANISM: Artificial Sequence
<220> FEATURE:
<223> OTHER INFORMATION: Synthetic polynucleotide (V174G-4_406.seq)

<400> SEQUENCE: 134
gctggcgtgt acctgctgta ctcccaggtg ctgttccagg acgggacctt cacaatgggc    60
caggtggtga gccgggaggg ccagggcaga caggagaccc tgttccggtg catccggagc   120
atgcccagcc accccgacag                                                140

<210> SEQ ID NO 135
<211> LENGTH: 140
<212> TYPE: DNA
<213> ORGANISM: Artificial Sequence
<220> FEATURE:
<223> OTHER INFORMATION: Synthetic polynucleotide (V174G_S202E-7_40)

-continued

<400> SEQUENCE: 135

```
gctggcgtgt acctgctgta ctcccaggtg ctgttccagg acgggacctt cacaatgggc    60
caggtggtga gccgggaggg ccagggcaga caggagaccc tgttccggtg catccggagc   120
atgcccgagc accccgacag                                                140
```

<210> SEQ ID NO 136
<211> LENGTH: 140
<212> TYPE: DNA
<213> ORGANISM: Artificial Sequence
<220> FEATURE:
<223> OTHER INFORMATION: Synthetic polynucleotide (V174G_S202A-10_4)

<400> SEQUENCE: 136

```
gctggcgtgt acctgctgta ctcccaggtg ctgttccagg acgggacctt cacaatgggc    60
caggtggtga gccgggaggg ccagggcaga caggagaccc tgttccggtg catccggagc   120
atgcccgcgc accccgacag                                                140
```

<210> SEQ ID NO 137
<211> LENGTH: 140
<212> TYPE: DNA
<213> ORGANISM: Artificial Sequence
<220> FEATURE:
<223> OTHER INFORMATION: Synthetic polynucleotide (V174G_S202G-15_4)

<400> SEQUENCE: 137

```
gctggcgtgt acctgctgta ctcccaggtg ctgttccagg acgggacctt cacaatgggc    60
caggtggtga gccgggaggg ccagggcaga caggagaccc tgttccggtg catccggagc   120
atgcccggtc accccgacag                                                140
```

<210> SEQ ID NO 138
<211> LENGTH: 140
<212> TYPE: DNA
<213> ORGANISM: Artificial Sequence
<220> FEATURE:
<223> OTHER INFORMATION: Synthetic polynucleotide (V174H_S202G-31_4)

<400> SEQUENCE: 138

```
gctggcgtgt acctgctgta ctcccaggtg ctgttccagg accacacctt cacaatgggc    60
caggtggtga gccgggaggg ccagggcaga caggagaccc tgttccggtg catccggagc   120
atgcccggtc accccgacag                                                140
```

<210> SEQ ID NO 139
<211> LENGTH: 140
<212> TYPE: DNA
<213> ORGANISM: Artificial Sequence
<220> FEATURE:
<223> OTHER INFORMATION: Synthetic polynucleotide (V174E_S202Y-41_4)

<400> SEQUENCE: 139

```
gctggcgtgt acctgctgta ctcccaggtg ctgttccagg acgagacctt cacaatgggc    60
caggtggtga gccgggaggg ccagggcaga caggagaccc tgttccggtg catccggagc   120
atgcccggac accccgacag                                                140
```

<210> SEQ ID NO 140
<211> LENGTH: 59
<212> TYPE: DNA
<213> ORGANISM: Artificial Sequence
<220> FEATURE:

```
<223> OTHER INFORMATION: Synthetic polynucleotide (D205X R206X)
<220> FEATURE:
<221> NAME/KEY: misc_feature
<222> LOCATION: (16)..(21)
<223> OTHER INFORMATION: n is a, c, g, or t

<400> SEQUENCE: 140
atgcccagcc accccnnnnn ngcctacaac agctgctaca gcgctggcgt gtttcacct        59

<210> SEQ ID NO 141
<211> LENGTH: 59
<212> TYPE: DNA
<213> ORGANISM: Artificial Sequence
<220> FEATURE:
<223> OTHER INFORMATION: Synthetic polynucleotide (D205P-1_406.seq)

<400> SEQUENCE: 141
atgcccagcc acccccccag agcctacaac agctgctaca gcgctggcgt gtttcacct        59

<210> SEQ ID NO 142
<211> LENGTH: 59
<212> TYPE: DNA
<213> ORGANISM: Artificial Sequence
<220> FEATURE:
<223> OTHER INFORMATION: Synthetic polynucleotide (D205R_R206G-27_4)

<400> SEQUENCE: 142
atgcccagcc accccgcgg agcctacaac agctgctaca gcgctggcgt gtttcacct         59

<210> SEQ ID NO 143
<211> LENGTH: 59
<212> TYPE: DNA
<213> ORGANISM: Artificial Sequence
<220> FEATURE:
<223> OTHER INFORMATION: Synthetic polynucleotide (D205P_R206K-33_4)

<400> SEQUENCE: 143
atgcccagcc acccccaaa agcctacaac agctgctaca gcgctggcgt gtttcacct         59

<210> SEQ ID NO 144
<211> LENGTH: 59
<212> TYPE: DNA
<213> ORGANISM: Artificial Sequence
<220> FEATURE:
<223> OTHER INFORMATION: Synthetic polynucleotide (D205P_R206N-35_4)

<400> SEQUENCE: 144
atgcccagcc acccccccaa cgcctacaac agctgctaca gcgctggcgt gtttcacct        59

<210> SEQ ID NO 145
<211> LENGTH: 59
<212> TYPE: DNA
<213> ORGANISM: Artificial Sequence
<220> FEATURE:
<223> OTHER INFORMATION: Synthetic polynucleotide (D205P_R206I-44_4)

<400> SEQUENCE: 145
atgcccagcc accccctat agcctacaac agctgctaca gcgctggcgt gtttcacct         59

<210> SEQ ID NO 146
<211> LENGTH: 59
<212> TYPE: DNA
<213> ORGANISM: Artificial Sequence
<220> FEATURE:
<223> OTHER INFORMATION: Synthetic polynucleotide (D205S_R206H-4_40)

<400> SEQUENCE: 146
```

```
atgcccagcc acccctccca cgcctacaac agctgctaca gcgctggcgt gtttcacct    59
```

<210> SEQ ID NO 147
<211> LENGTH: 59
<212> TYPE: DNA
<213> ORGANISM: Artificial Sequence
<220> FEATURE:
<223> OTHER INFORMATION: Synthetic polynucleotide (D205Y_R206stop-1)

<400> SEQUENCE: 147

```
atgcccagcc acccctactg agcctacaac agctgctaca gcgctggcgt gtttcacct    59
```

<210> SEQ ID NO 148
<211> LENGTH: 60
<212> TYPE: DNA
<213> ORGANISM: Artificial Sequence
<220> FEATURE:
<223> OTHER INFORMATION: Synthetic polynucleotide (D20512_406)

<400> SEQUENCE: 148

```
atgcccagcc acccccgaca gagcctacaa cagctgctac agcgctggcg tgtttcacct   60
```

<210> SEQ ID NO 149
<211> LENGTH: 59
<212> TYPE: DNA
<213> ORGANISM: Artificial Sequence
<220> FEATURE:
<223> OTHER INFORMATION: Synthetic polynucleotide (D205H_R206L-16_4)

<400> SEQUENCE: 149

```
atgcccagcc accccatct cgcctacaac agctgctaca gcgctggcgt gtttcacct     59
```

<210> SEQ ID NO 150
<211> LENGTH: 59
<212> TYPE: DNA
<213> ORGANISM: Artificial Sequence
<220> FEATURE:
<223> OTHER INFORMATION: Synthetic polynucleotide (D205S_R206P-22_4)

<400> SEQUENCE: 150

```
atgcccagcc acccctcccc agcctacaac agctgctaca gcgctggcgt gtttcacct    59
```

<210> SEQ ID NO 151
<211> LENGTH: 70
<212> TYPE: DNA
<213> ORGANISM: Artificial Sequence
<220> FEATURE:
<223> OTHER INFORMATION: Synthetic polynucleotide (A125X)
<220> FEATURE:
<221> NAME/KEY: misc_feature
<222> LOCATION: (36)..(38)
<223> OTHER INFORMATION: n is a, c, g, or t

<400> SEQUENCE: 151

```
gaggcggcag cgtgctgcac ctggtgccca tcaacnnnac cagcaaggac gactctgatg   60
tgaccgaggt                                                          70
```

<210> SEQ ID NO 152
<211> LENGTH: 70
<212> TYPE: DNA
<213> ORGANISM: Artificial Sequence
<220> FEATURE:
<223> OTHER INFORMATION: Synthetic polynucleotide (A125T-5_406)

<400> SEQUENCE: 152

```
gaggcggcag cgtgctgcac ctggtgccca tcaacacgac cagcaaggac gactctgatg    60
tgaccgaggt                                                           70
```

＃ LIGAND

INCORPORATION BY REFERENCE OF MATERIALS SUBMITTED ELECTRONICALLY

This application contains, as a separate part of the disclosure, a Sequence Listing in computer readable form (Filename: 51001A_SubSeqListing.txt; Size: 192,512 bytes; Created: Aug. 11, 2017), which is incorporated by reference in its entirety.

FIELD OF THE INVENTION

The present invention relates to a variant proliferation-inducing ligand (APRIL) which binds the B cell maturation antigen (BCMA). Therapeutic agents comprising such a variant APRIL are useful in the treatment of plasma cell diseases such as multiple myeloma.

BACKGROUND TO THE INVENTION

Multiple Myeloma

Multiple Myeloma (myeloma) is a bone-marrow malignancy of plasma cells. Collections of abnormal plasma cells accumulate in the bone marrow, where they interfere with the production of normal blood cells. Myeloma is the second most common hematological malignancy in the U.S. (after non-Hodgkin lymphoma), and constitutes 13% of haematologic malignancies and 1% of all cancers. The disease is burdensome in terms of suffering as well as medical expenditure since it causes pathological fractures, susceptibility to infection, renal and then bone-marrow failure before death.

Unlike many lymphomas, myeloma is currently incurable. Standard chemotherapy agents used in lymphoma are largely ineffective for myeloma. In addition, since CD20 expression is lost in plasma cells, Rituximab cannot be used against this disease. New agents such as Bortezamib and Lenolidomide are partially effective, but fail to lead to long-lasting remissions.

There is thus a need for alternative agents for the treatment of myeloma which have increased efficacy and improved long-term effects.

BCMA

BCMA, also known as TNFRSF17, is a plasma cell specific surface antigen which is expressed exclusively on B-lineage haemopoietic cells or dendritic cells. It is a member of the TNF receptor family. BCMA is not expressed on naïve B cells but is up-regulated during B-cell differentiation into plasmablasts, and is brightly expressed on memory B cells, plasmablasts and bone marrow plasma cells. BCMA is also expressed on the majority of primary myeloma cells. Apart from low levels of mRNA detected on dendritic cells, BCMA expression appears to be absent on other tissues, indicating the potential as a target for novel therapeutics for multiple myeloma.

BCMA functions within a network of interconnected ligands and receptors which is shown schematically in FIG. 1. Two other TNF receptors share the ligands APRIL and BAFF with BCMA—transmembrane activator and calcium modulator and cyclophilin ligand interactor (TACI, also known as TNFRSF13B), which is found on activated T-cells and all B-cells; and BAFF-R (TNFRSF13C) which is predominantly expressed on B-lymphocytes. Multiple myeloma cells express TACI in some cases and BCMA in most cases, but never BAFF-R.

The natural ligand APRIL is potentially useful as or as part of a BCMA-targeting therapeutic. However, cross-reaction with TACI is potentially a problem, because TACI is found on activated T-cells and all B-cells, so treatment with an agent directed to BCMA on myeloma cells may also cause a pathological depletion of non-cancerous B and T cell subsets.

APRIL is also potentially useful in diagnostic applications to identify plasma cells, in particular the presence of malignant plasma cells in conditions such as multiple myeloma. However, again, the capacity of APRIL to also bind TACI means that APRII-based diagnostics will also identify generally activated T-cells and all B-cells, meaning that the results are ambiguous.

There is thus a need to develop anti-BCMA therapeutics and diagnostics which are not associated with these disadvantages.

B-cell-activating factor (BAFF, TNFSF13B) interacts with BAFF-Receptor (BAFF-R, TNFRSF13C), B-cell membrane antigen (BCMA, TNFRSF17) and transmembrane activator and calcium modulator and cyclophilin ligand interactor (TACI, TNFRSF13B) while A proliferation-inducing ligand (APRIL, TNFSF13) interacts with BCMA, TACI and proteoglycans. BAFF-R activation affects peripheral B-cell survival, while BCMA may affect plasma cell survival. APRIL interaction with proteoglycans involves acidic sulphated glycol-saminoglycan side-chain containing amino-terminus of APRIL.

Figure 1:
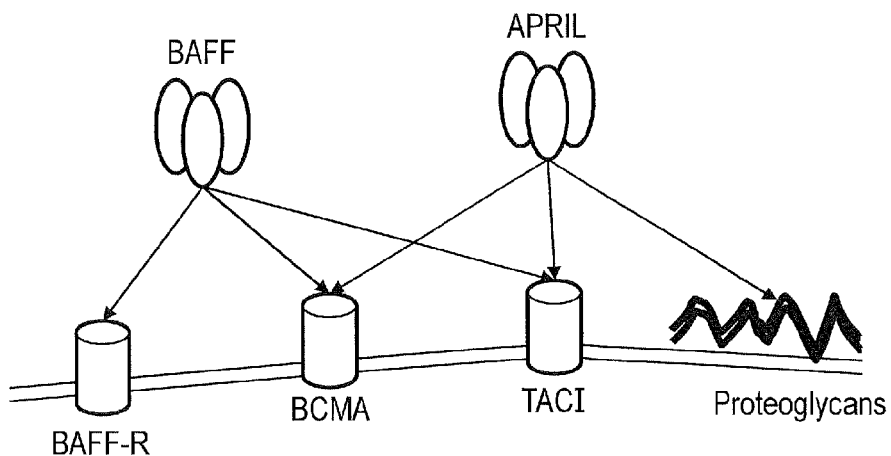
FIG. 1—Ligand Specificity and Function Assignment of APRIL and BAFF
Figure 2:
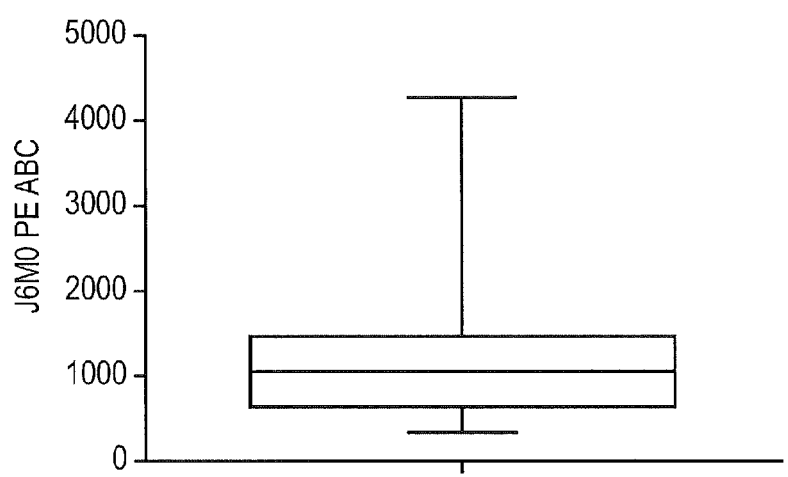

FIG. 2—Expression data of BCMA on Myeloma

Myeloma cells from bone marrow samples from 39 multiple myeloma patients were isolated by a CD138+ magnetic bead selection. These cells were stained with the anti-BCMA monoclonal antibody J6MO conjugated with PE (GSK). Antigen copy number was quantified using PE Quantibrite beads (Becton Dickenson) as per the manufacturer's instructions. A box and whiskers plot of antigen copy number is presented along with the range, interquartile and median values plotted. We found the range is 348.7-4268.4 BCMA copies per cell with a mean of 1181 and a median of 1084.9.

Figure 3:
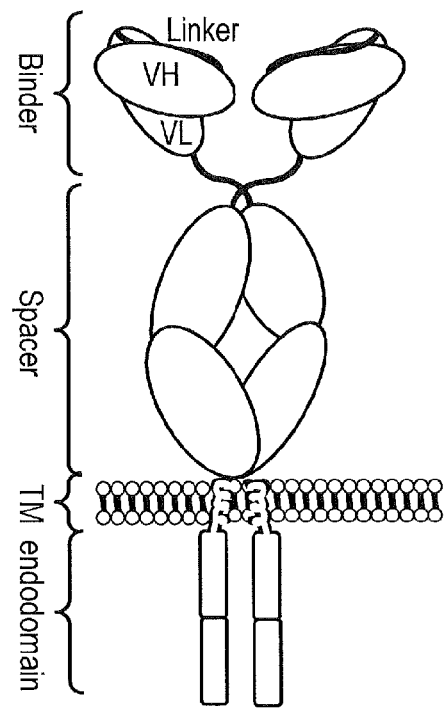

FIG. 3—Standard design of a Chimeric Antigen Receptor

The typical format of a chimeric antigen receptor is shown. These are type I transmembrane proteins. An ectodomain recognizes antigen. This is composed of an antibody derived single-chain variable fragment (scFv) which is attached to a spacer domain. This in turn is connected to a transmembrane domain which acts to anchor the molecule in the membrane. Finally, this is connected to an endodomain which acts to transmits intracellular signals to the cell. This is composed of one or more signalling domains.

Figure 4:
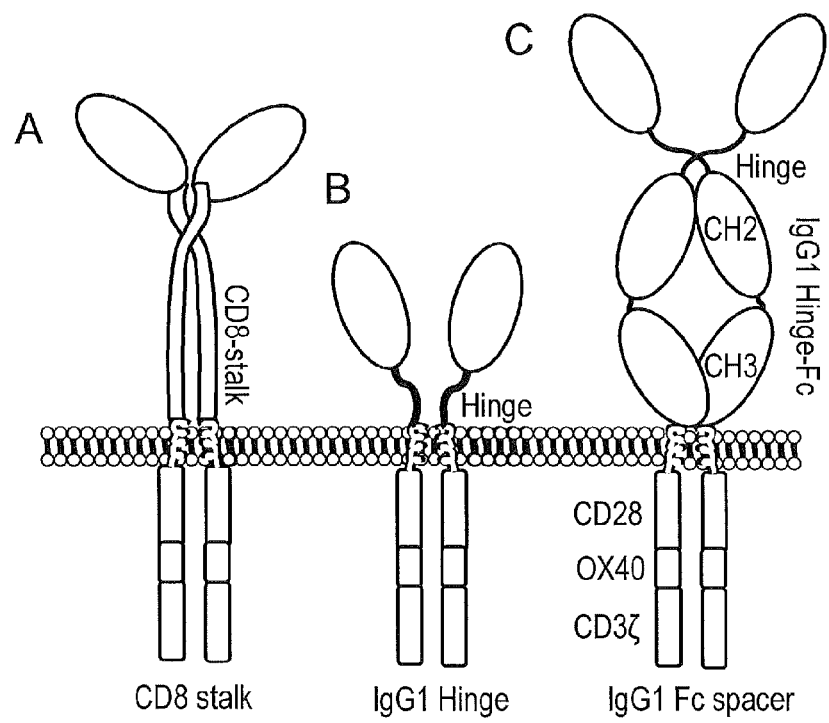

FIG. 4—Design of the different APRIL-based CARs generated.

The CAR design as shown in FIG. 3 was modified so that the scFv was replaced with a modified form of APRIL to act as an antigen binding domain: APRIL was truncated so that the proteoglycan binding amino-terminus is absent. A signal peptide was then attached to truncated APRIL amino-terminus to direct the protein to the cell surface. Three CARs were generated with this APRIL based binding domain: A. In the first CAR, the human CD8 stalk domain was used as a spacer domain. B. In the second CAR, the hinge from IgG1 was used as a spacer domain. C. In the third CAR, the hinge, CH2 and CH3 domains of human IgG1 modified with the pva/a mutations described by Hombach et al (2010 Gene Ther. 17:1206-1213) to reduce Fc Receptor binding was used as a spacer (henceforth referred as Fc-pvaa). In all CARs, these spacers were connected to the CD28 transmembrane domain and then to a tripartite endodomain containing a fusion of the CD28, OX40 and the CD3-Zeta endodomain (Pule et al, Molecular therapy, 2005: Volume 12; Issue 5; Pages 933-41).

FIGS. 5A-5C—Annotated Amino acid sequence of the above three APRIL-CARS

FIG. 5A: Shows the annotated amino acid sequence of the CD8 stalk APRIL CAR (SEQ ID NO: 76); FIG. 5B: Shows the annotated amino acid sequence of the APRIL IgG1 hinge based CAR (SEQ ID NO: 77); FIG. 5C: Shows the annotated amino acid sequence of the APRIL Fc-pvaa based CAR (SEQ ID NO: 75).

Figure 6A:
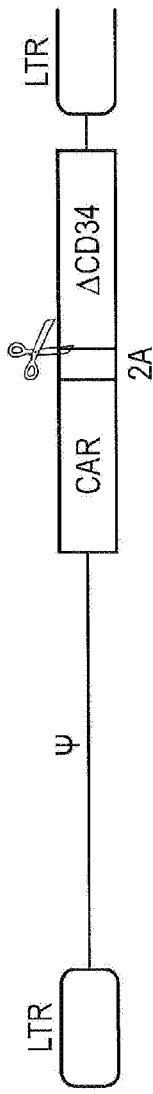
Figure 6B:
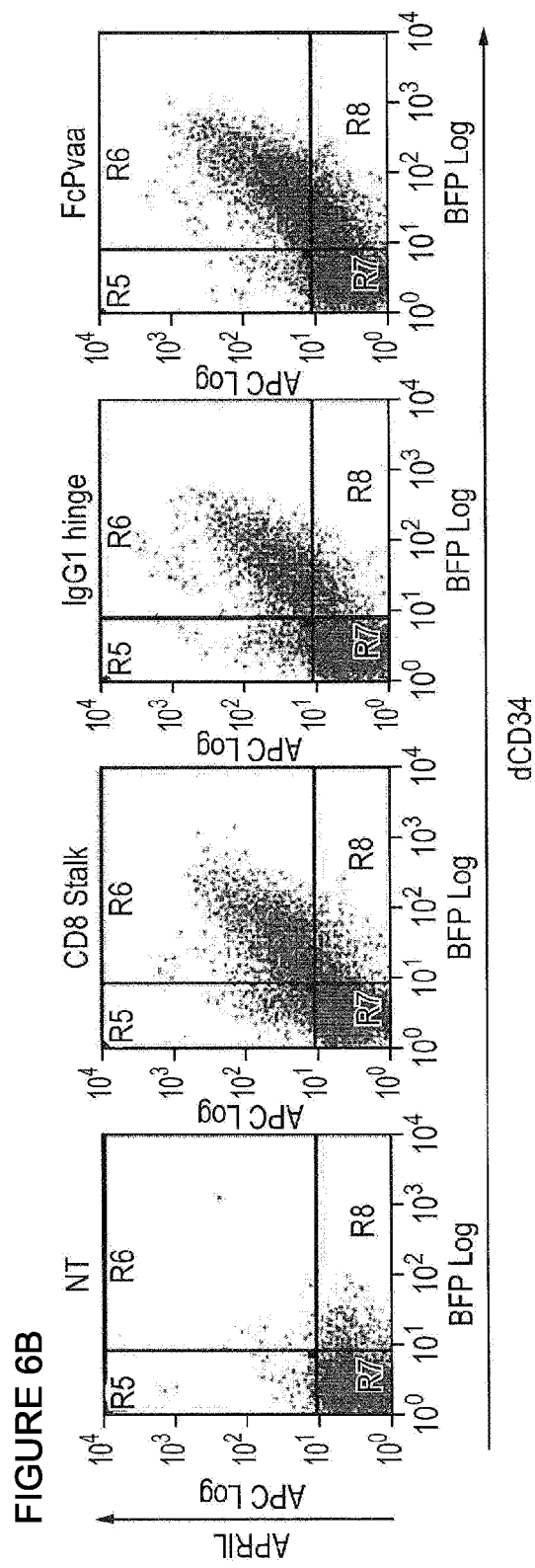
Figure 6C:
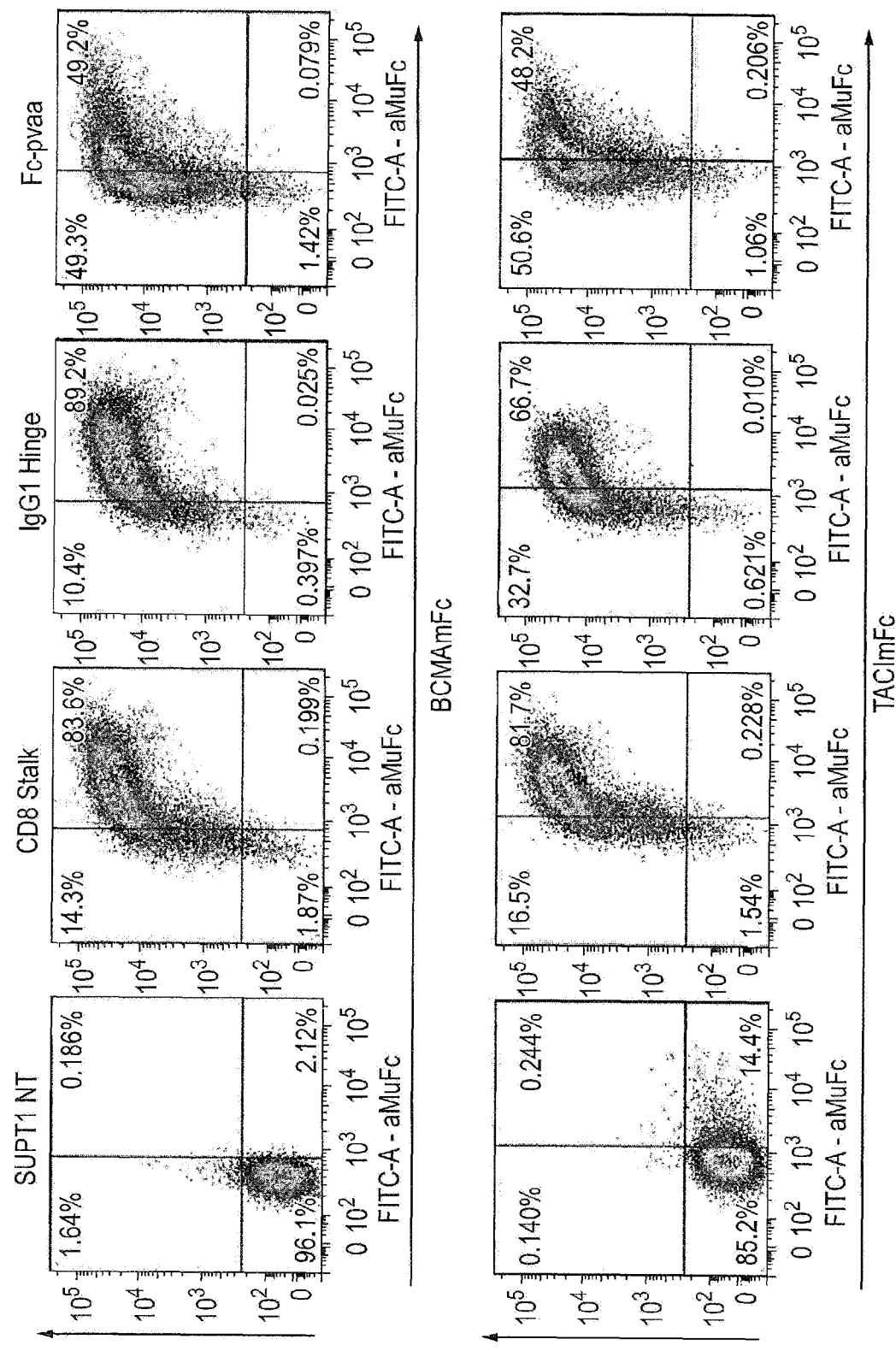

FIGS. 6A-6C—Expression and ligand binding of different APRIL based CARs FIG. 6A. The receptors were co-expressed with a marker gene truncated CD34 in a retroviral gene vector. Expression of the marker gene on transduced cells allows confirmation of transduction. FIG. 6B. T-cells were transduced with APRIL based CARs with either the CD8 stalk spacer, IgG1 hinge or Fc spacer. To test whether these receptors could be stably expressed on the cell surface, T-cells were then stained with anti-APRIL-biotin/Streptavidin APC and anti-CD34. Flow-cytometric analysis was performed. APRIL was equally detected on the cell surface in the three CARs suggesting they are equally stably expressed. FIG. 6C. Next, the capacity of the CARs to recognize TACI and BCMA was determined. The transduced T-cells were stained with either recombinant BCMA or TACI fused to mouse IgG2a Fc fusion along with an anti-mouse secondary and anti-CD34. All three receptor formats showed binding to both BCMA and TACI. A surprising finding was that binding to BCMA seemed greater than to TACI. A further surprising finding was that although all three CARs were equally expressed, the CD8 stalk and IgG1 hinge CARs appeared better at recognizing BCMA and TACI than that with the Fc spacer.

Figure 7A:
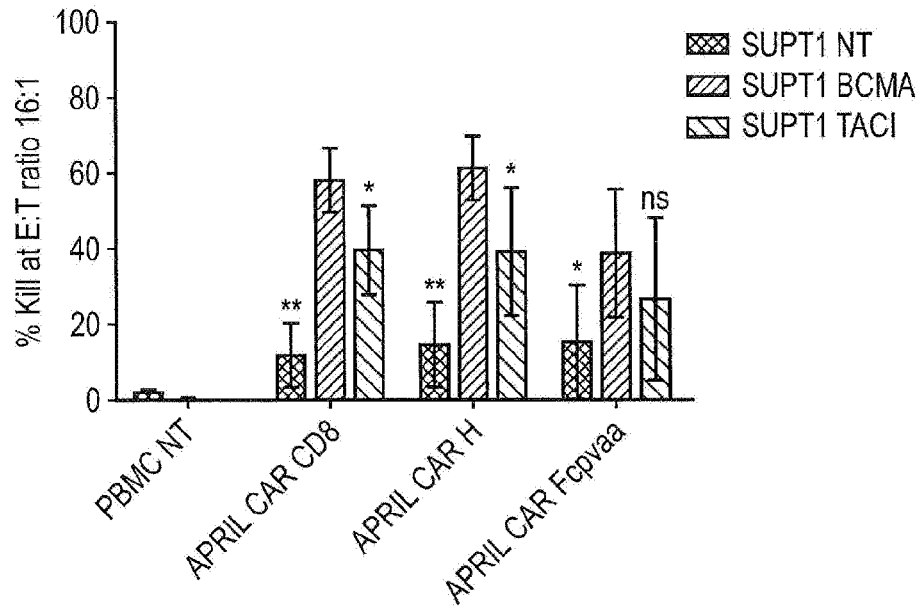
Figure 7B:
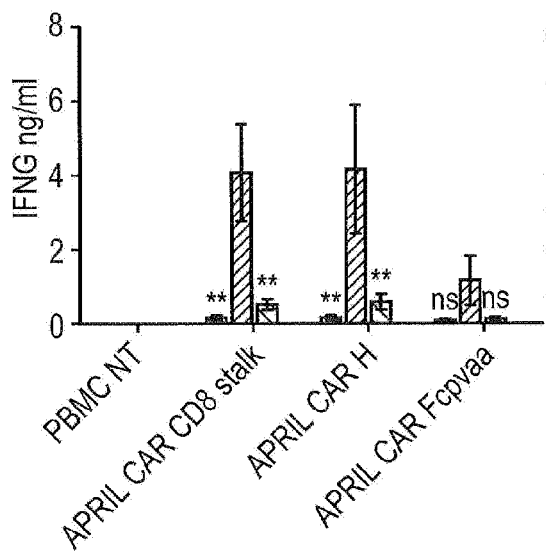
Figure 7C:
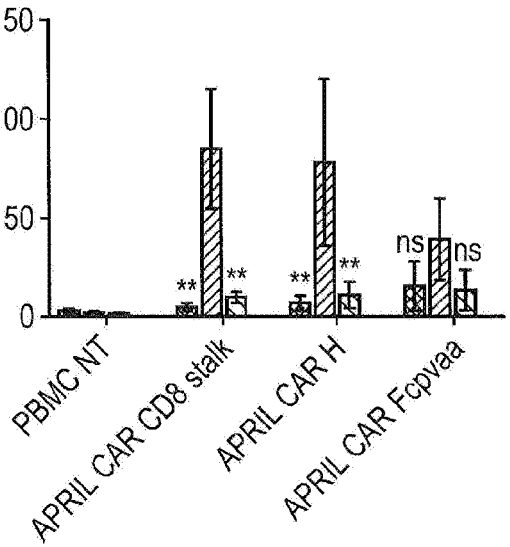

FIGS. 7A-7C—Function of the different CAR constructs.

Functional assays were performed of the three different APRIL based CARs. Normal donor peripheral blood T-cells either non-transduced (NT), or transduced to express the different CARs. Transduction was performed using equal titer supernatant. These T-cells were then CD56 depleted to remove non-specific NK activity and used as effectors. SupT1 cells either non-transduced (NT), or transduced to express BCMA or TACI were used as targets. Data shown is mean and standard deviation from 5 independent experiments. FIG. 7A. Specific killing of BCMA and TACI expressing T-cells was determined using Chromium release. FIG. 7B. Interferon-γ release was also determined. Targets and effectors were co-cultured at a ratio of 1:1. After 24 hours, Interferon-γ in the supernatant was assayed by ELISA. FIG. 7C. Proliferation/survival of CAR T-cells were also determined by counting number of CAR T-cells in the same co-culture incubated for a further 6 days. All 3 CARs direct responses against BCMA and TACI expressing targets. The responses to BCMA were greater than for TACI.

Figure 8:
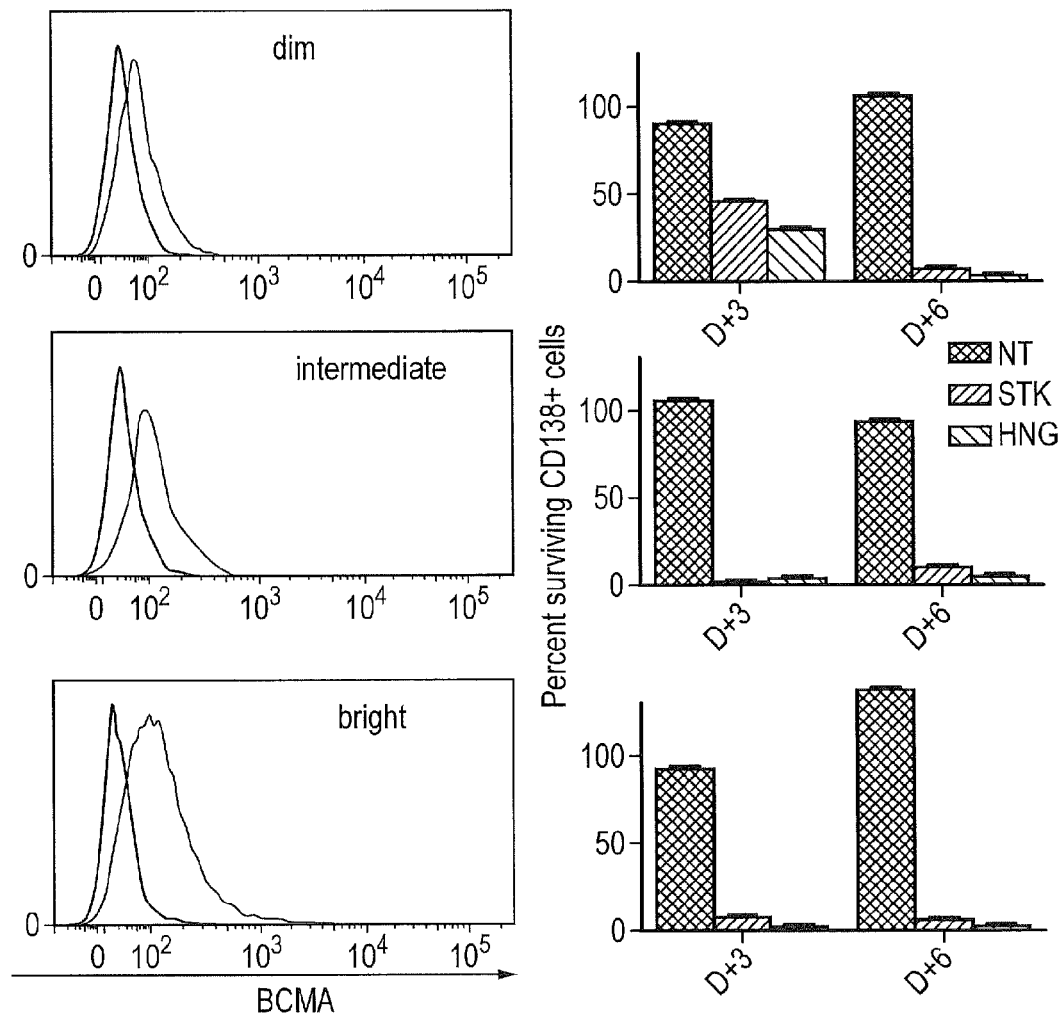

FIG. 8—Killing of primary Myeloma cells by APRIL CAR T-cells

Since most primary myeloma cells express a low number of BCMA molecules on their surface, it was investigated whether killing of primary myeloma cells occurs despite low-density expression. Three cases were selected which represented the range of BCMA expression described in FIG. 2: the first had dim expression (lower than mean); the second case had intermediate expression (approximately mean expression) and the third had bright (above mean expression). A histogram of BCMA staining against isotype control for all three cases is shown on the left. In this assay, only the CD8 stalk and hinge APRIL CARs were tested. On the left, survival of myeloma cells compared with starting numbers is shown at day 3 and day 6 after a 1:1 co-culture of myeloma cells and CAR T-cells. By day 6, >95% of the myeloma cells were eliminated, including those with dim BCMA expression.

Figure 9A:
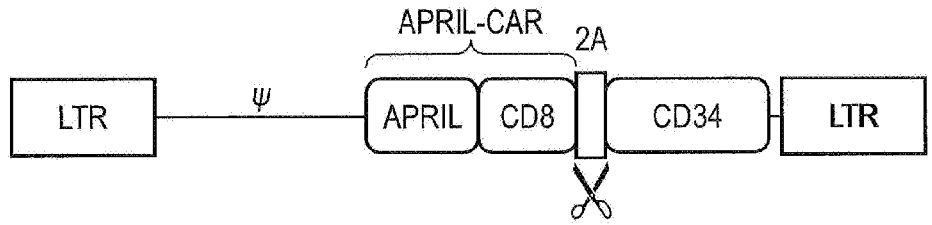
Figure 9B:
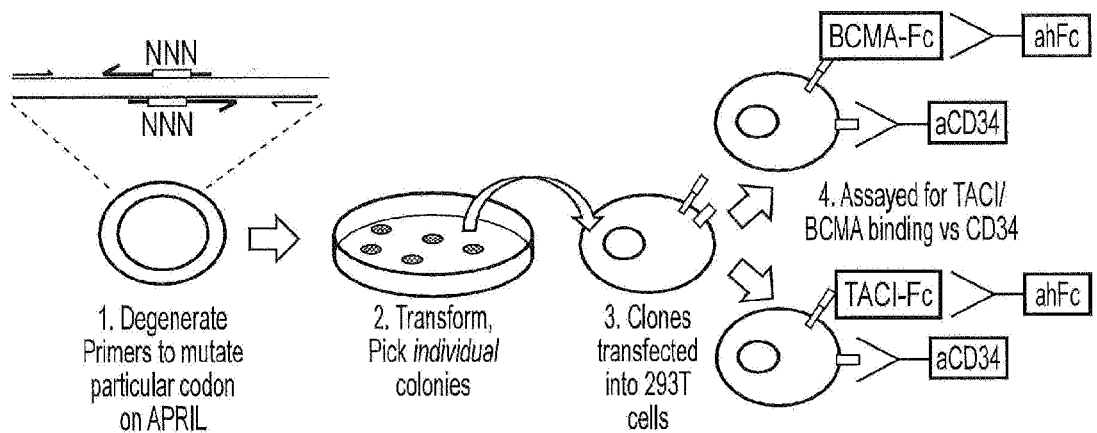
Figure 9C:
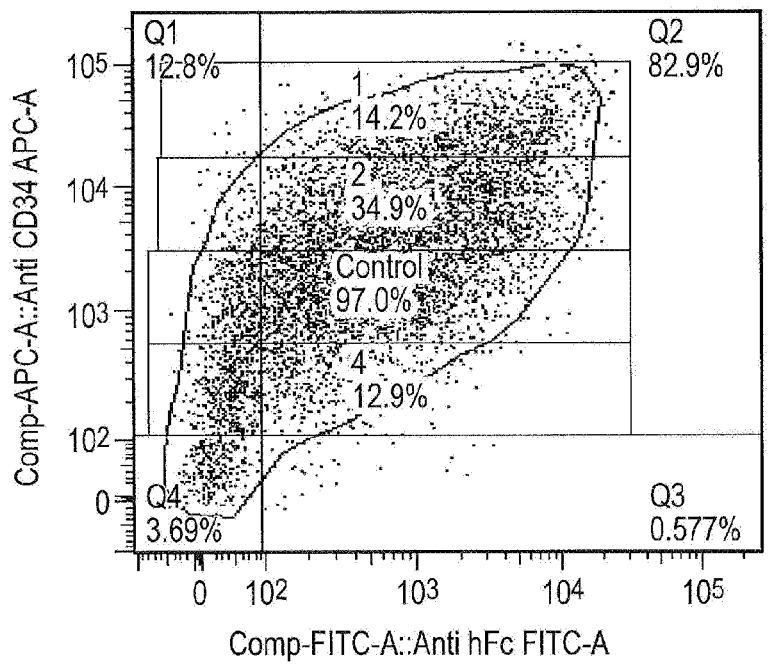

FIGS. 9A-9C—Methods used to develop novel APRIL mutants useful for BCMA targeting.

FIG. 9A. Candidate APRIL molecules were displayed in the CD8 stalk CAR format (but without a signalling endodomain) and were co-expressed with CD34 using a foot-and-mouth disease 2A sequence. FIG. 9B. Residues which appeared important for BCMA specificity or affinity from crystallographic data were randomized by splicing-by-overlap PCR using oligonucleotides which were degenerate over the coding codon as primers. These PCR products were ligated into the CD8 stalk CAR format and used to transform bacteria. Individual bacterial colonies (each containing a single mutant) were cultured. Plasmid DNA was isolated from these cultures and used to transfect 293T cells. After transfection, 293T cells were stained with either BCMA-Fc fusion or TACI-Fc fusion separately, along with the marker gene. FIG. 9C. How relative binding to BCMA and TACI was estimated during screening: the slope of fluorescent intensity of CD34 staining versus either BCMA or TACI was calculated. Next, the ratio of this slope to that of wild-type APRIL was calculated. This value was used as the read-out.

Figure 10:
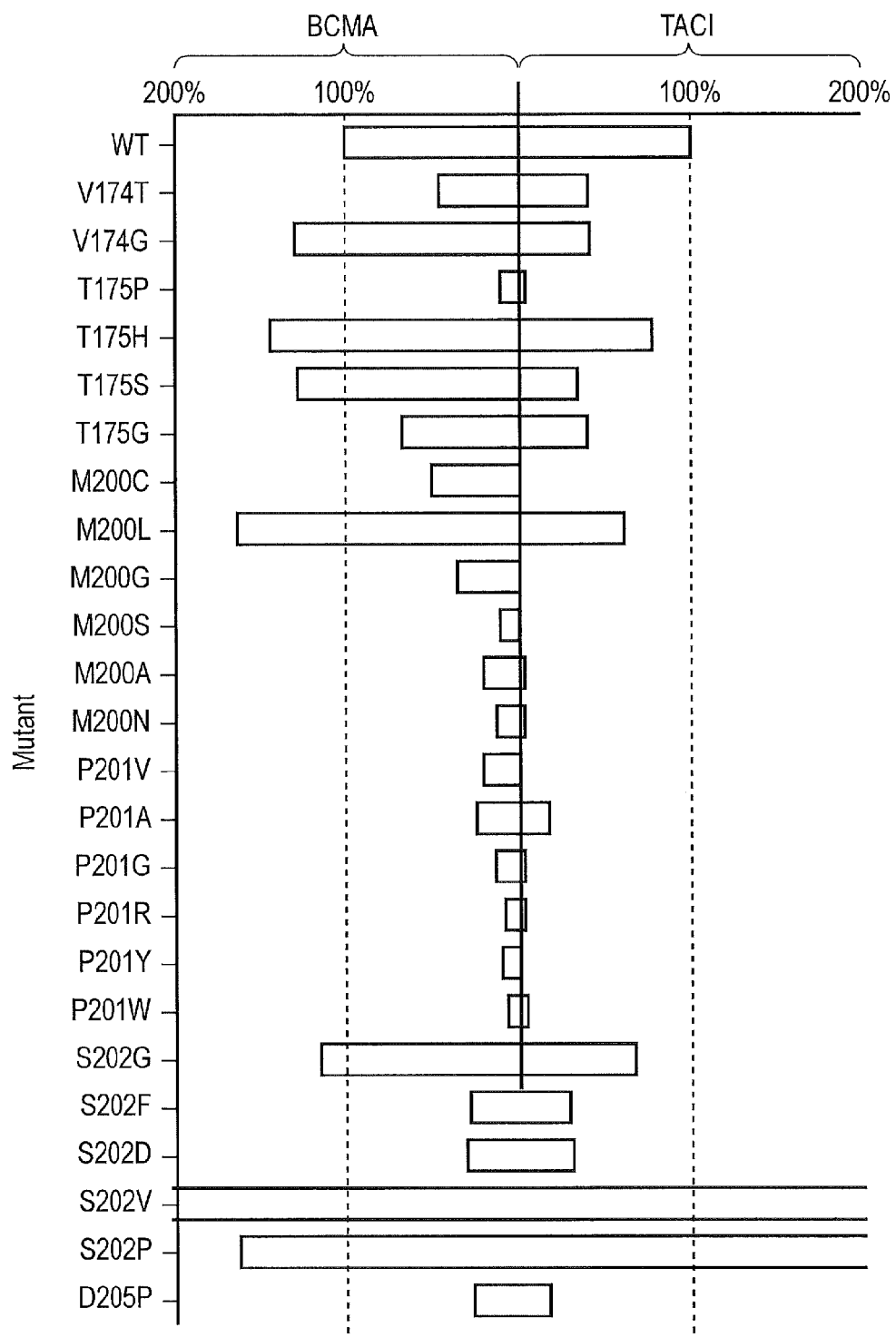

FIG. 10—Summary of APRIL mutants—single residue mutations.

Mutations which show altered binding to BCMA-Fc and TACI-Fc are summarized in comparison with that of wild type APRIL.

Figure 11:
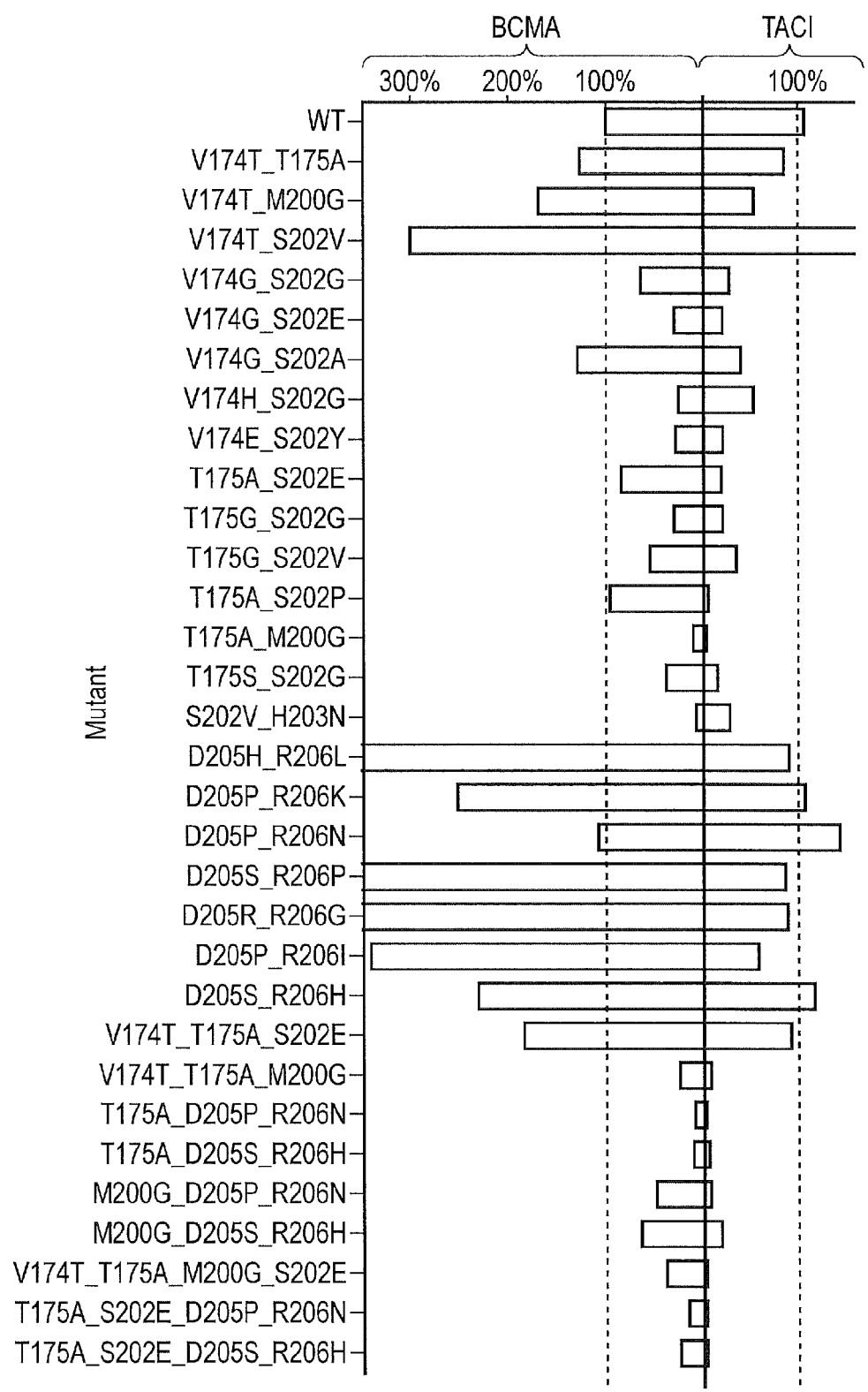
Figure 12A:
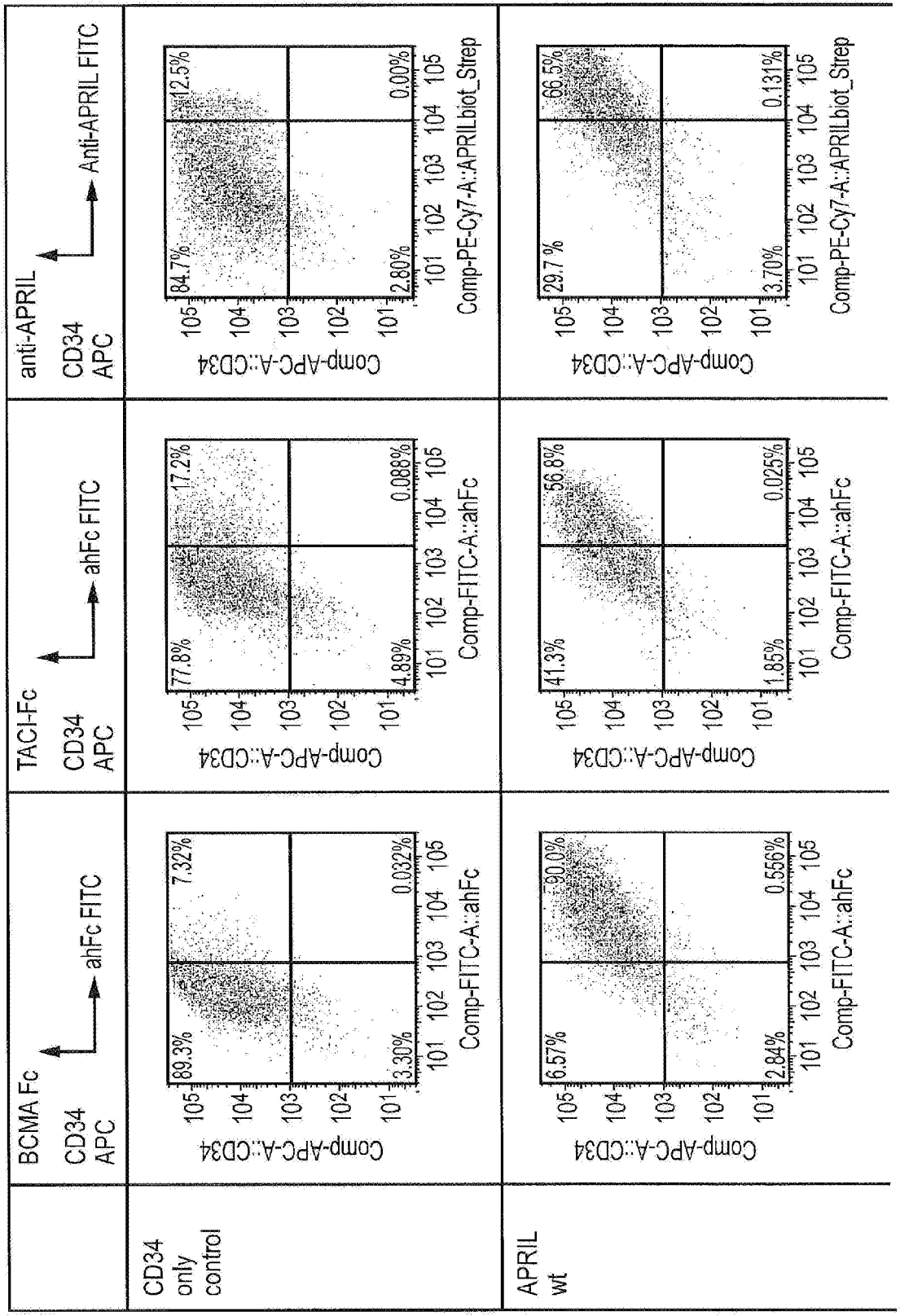
Figure 12B:
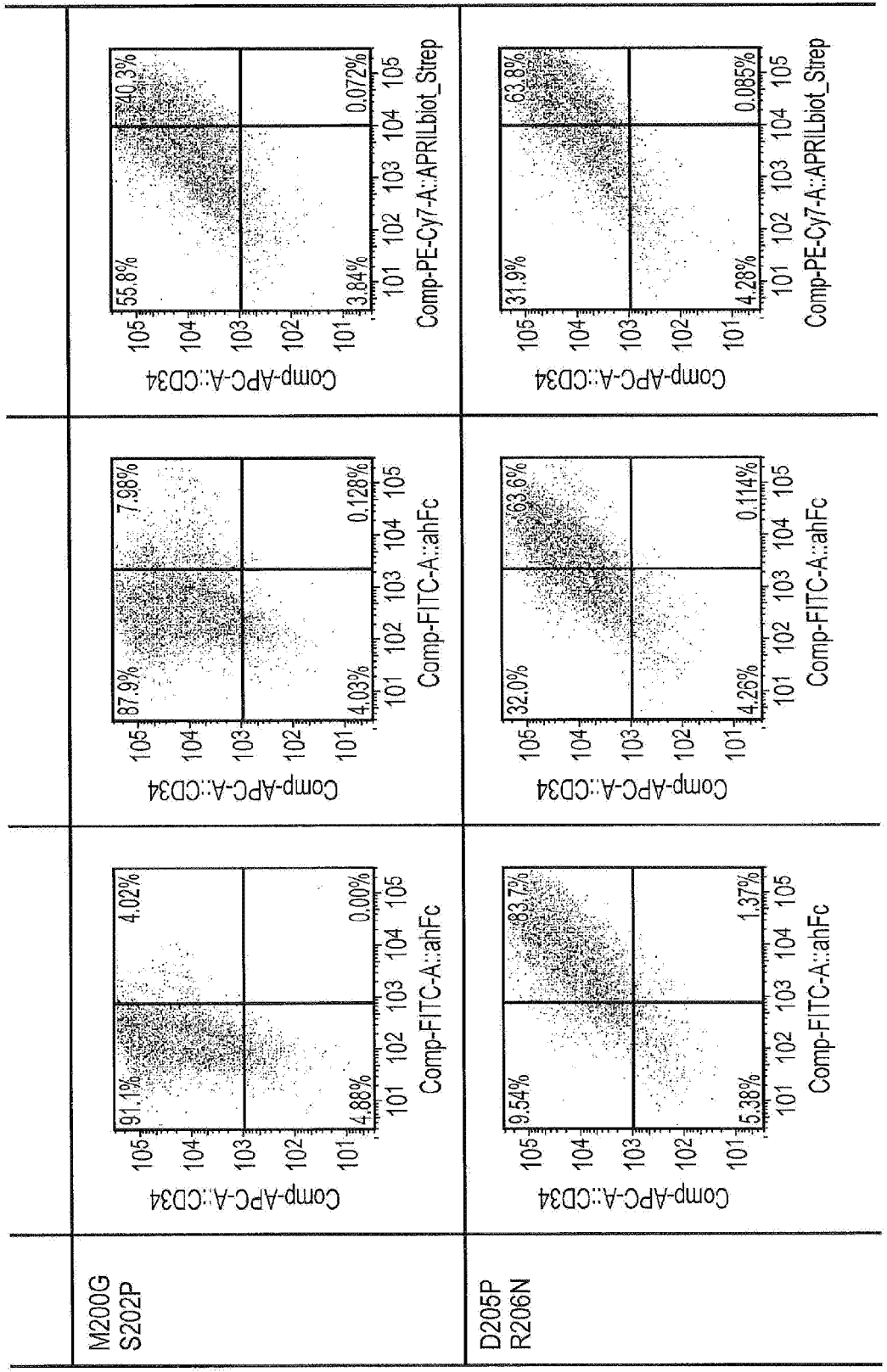
Figure 12C:
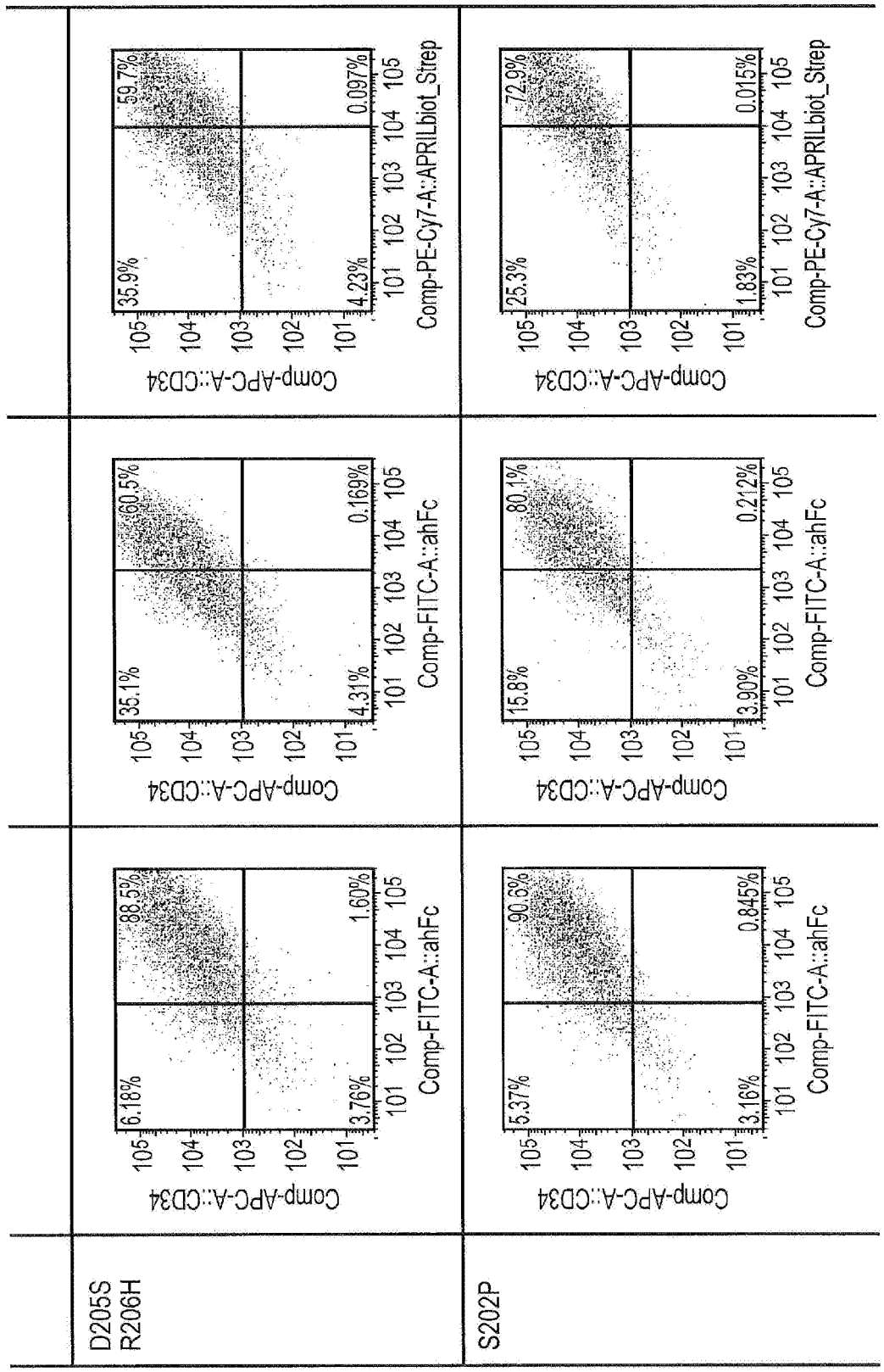
Figure 12D:
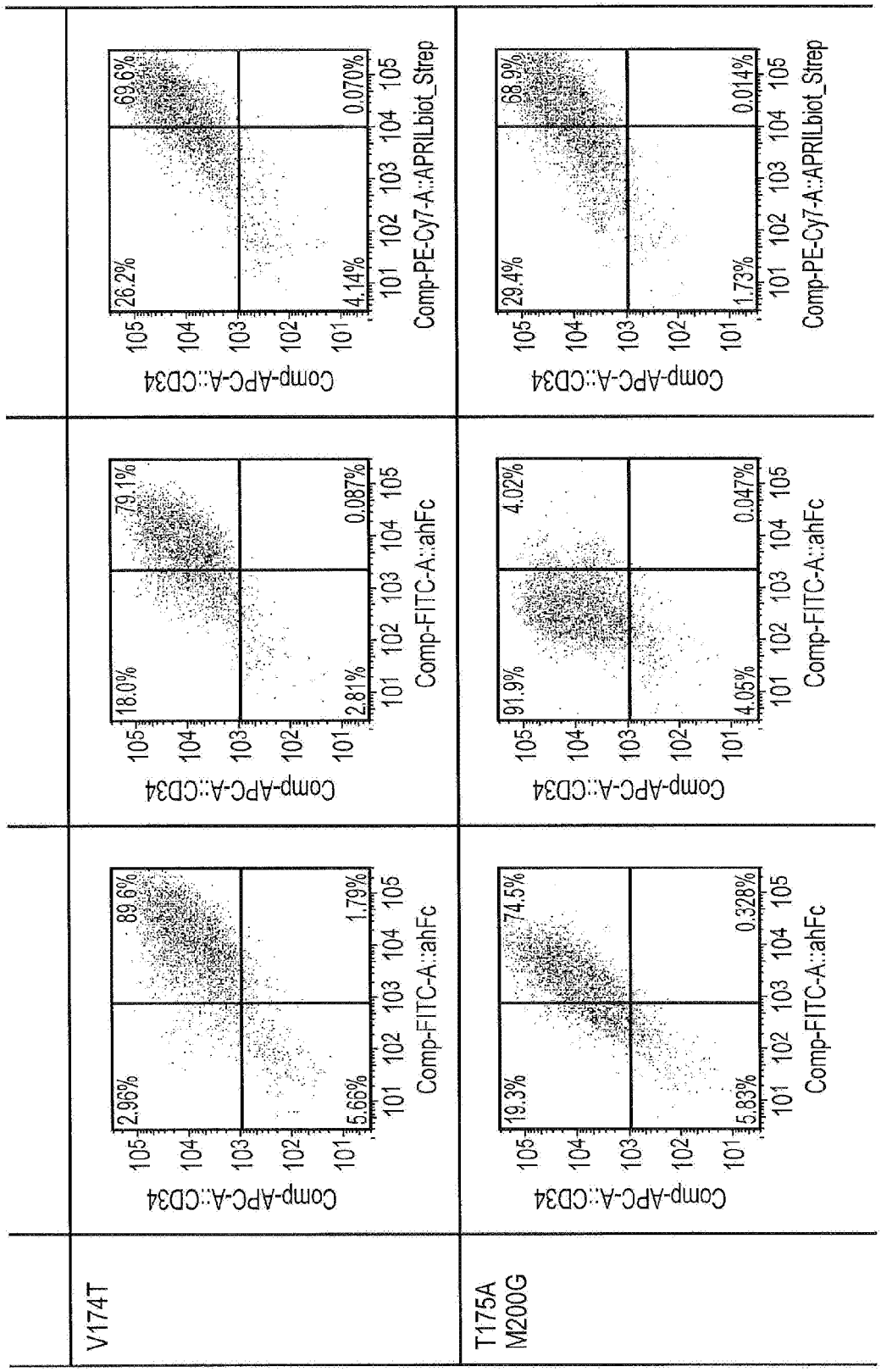
Figure 12E:
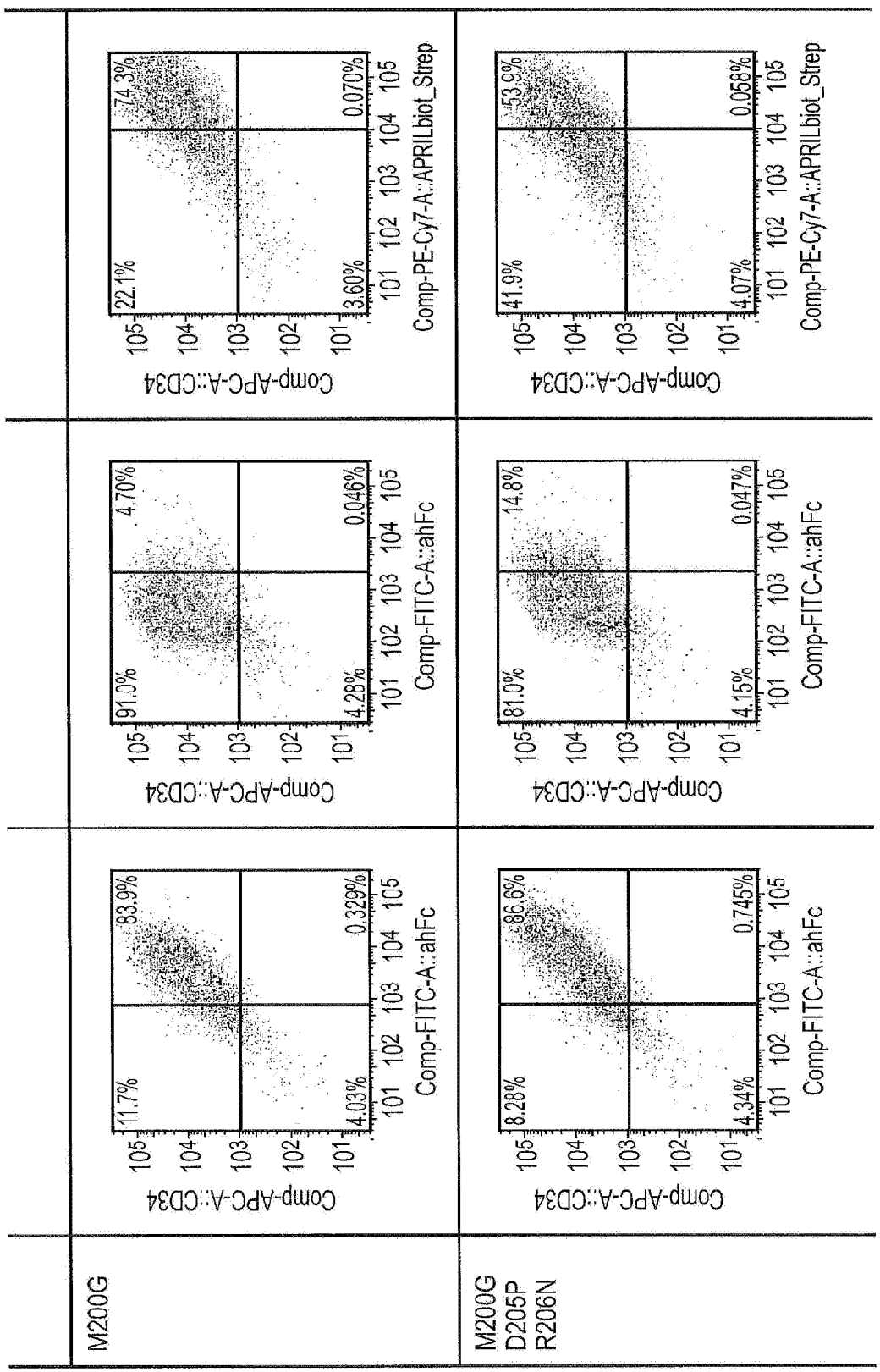
Figure 12F:
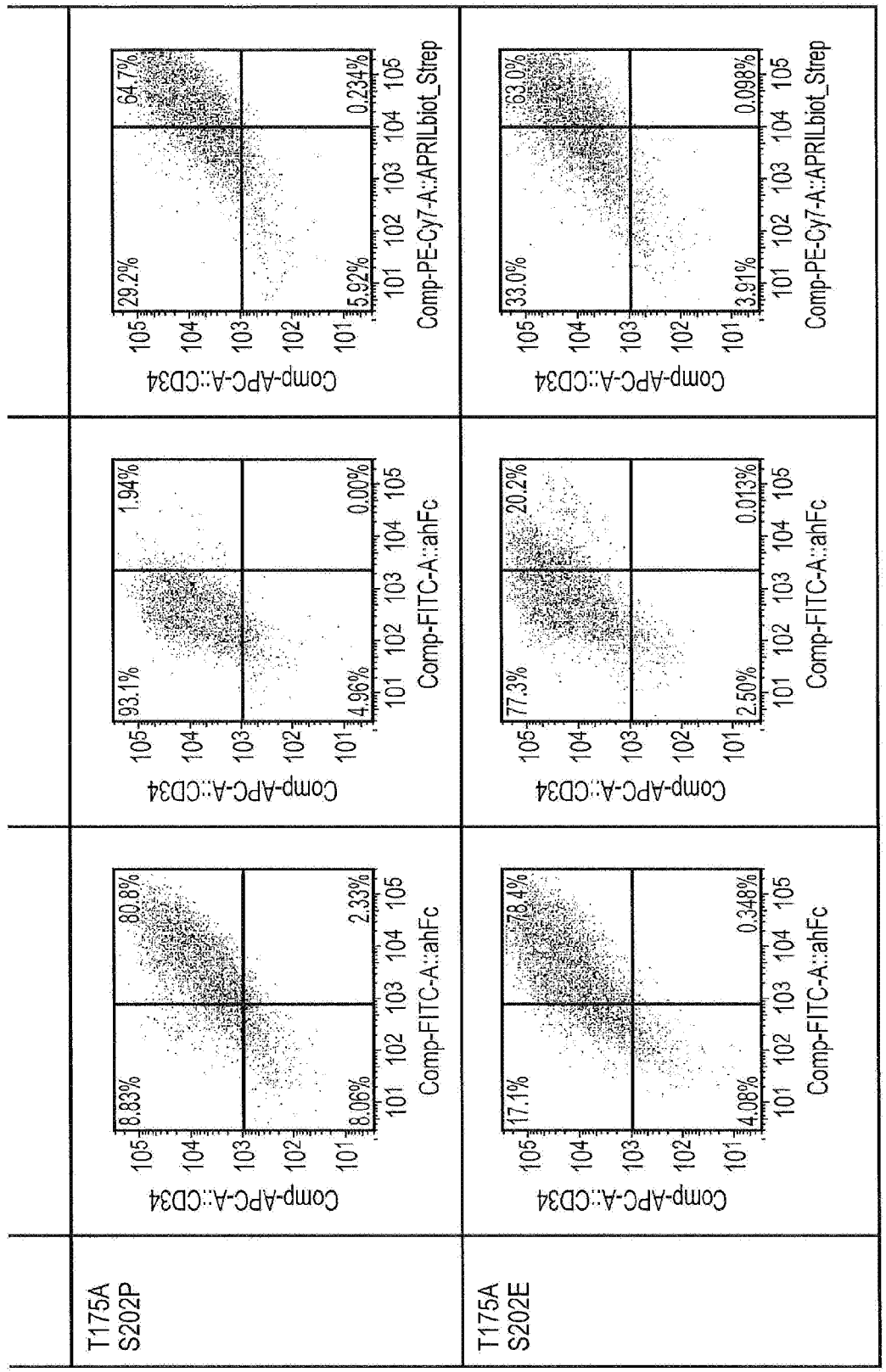

FIG. 11—Summary of APRIL mutants—multiple residue mutations.

Promising mutants were crossed either once or multiply with other mutants and characterized. Altered binding to BCMA-Fc and TACI-Fc is shown here again compared to wild-type APRIL.

FIGS. 12A-12F—BCMA-FC, TACI-FC and APRIL binding of some selected mutants

Flow cytometry plots of selected mutants are shown in a table. The first column shows BCMA-Fc staining vs that of CD34. The second column shows TACI-Fc staining vs that of CD34. The third column shows APRIL staining vs that of CD34. The first row shows wild-type APRIL staining as a control. The second row shows CD34 alone control.

Figure 13:
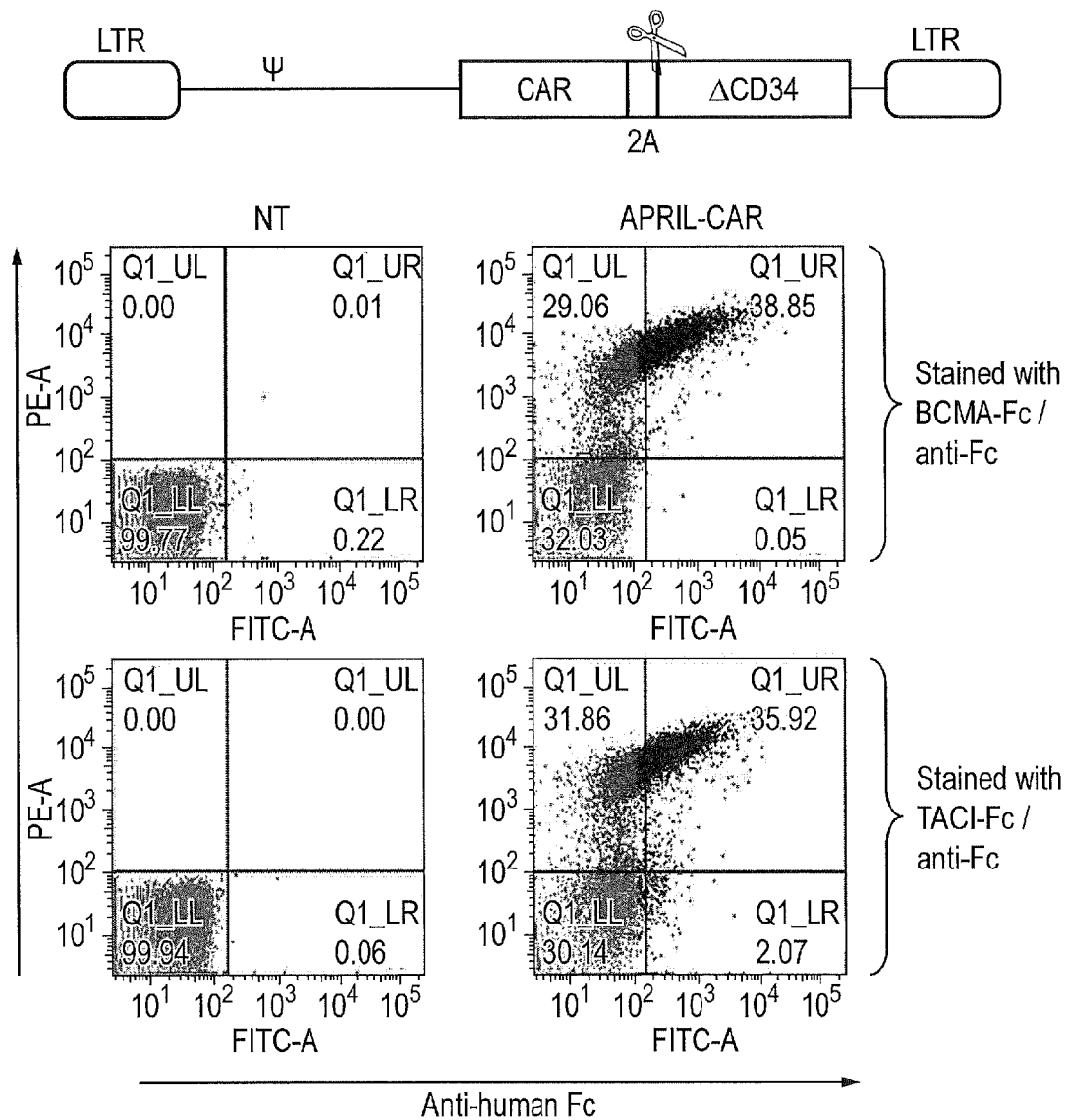

FIG. 13—Vector co-expressing APRIL based CAR with truncated CD34

A cell line expressing the vector used for screening was incubated with either BCMA-Fc or TACI-Fc and stained with both anti-CD34 and anti-human-Fc PE and FITC conjugated mAbs. The cells were then studied by flow-cytometry. This shows a typical pattern of binding of BCMA and TACI relative to the marker gene CD34.

Figure 14A:
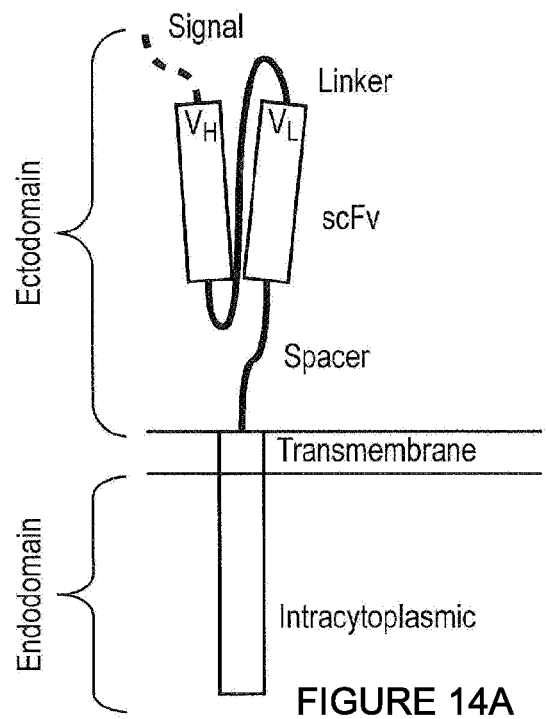

FIG. 14A—Schematic diagram illustrating a classical CAR

Figure 14B:
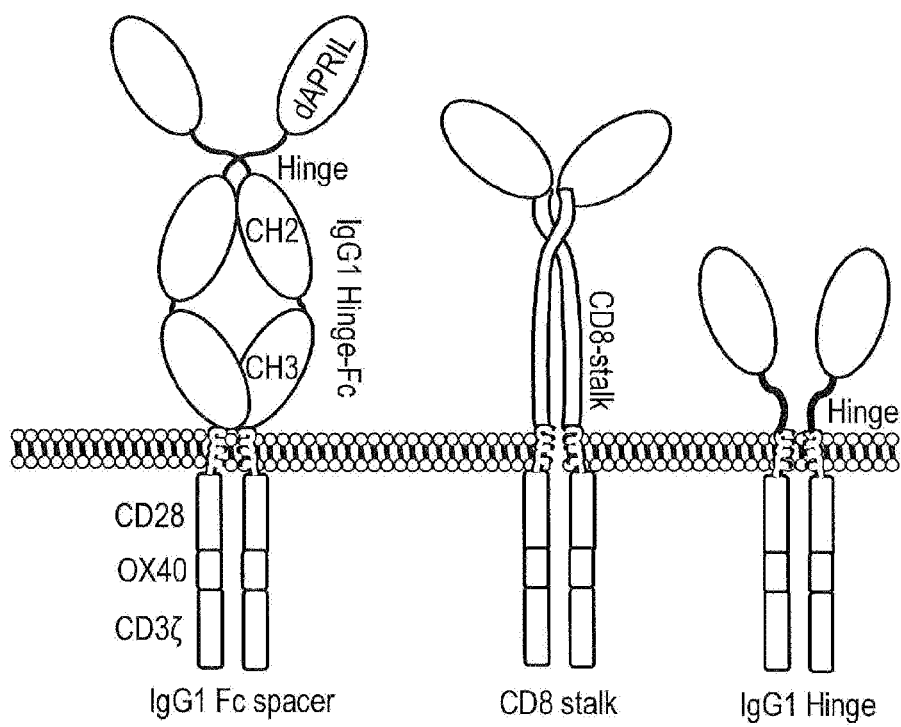

FIG. 14B: Design of the different APRIL-based CARs generated.

A signal peptide ias attached to truncated APRIL amino-terminus. This was fused to different spacers: either the hinge, CH2 and CH3 domains of human IgG1 modified with the pvaa mutation described by Hombach et al (2010 Gene Ther. 17:1206-1213) to reduce Fc Receptor binding; the stalk of human CD8α; and the hinge of IgG1. These spacers were connected to a tripartite endodomain containing CD28 transmembrane domain, the OX40 endodomain and the CD3-Zeta endodomain.

Figure 15:
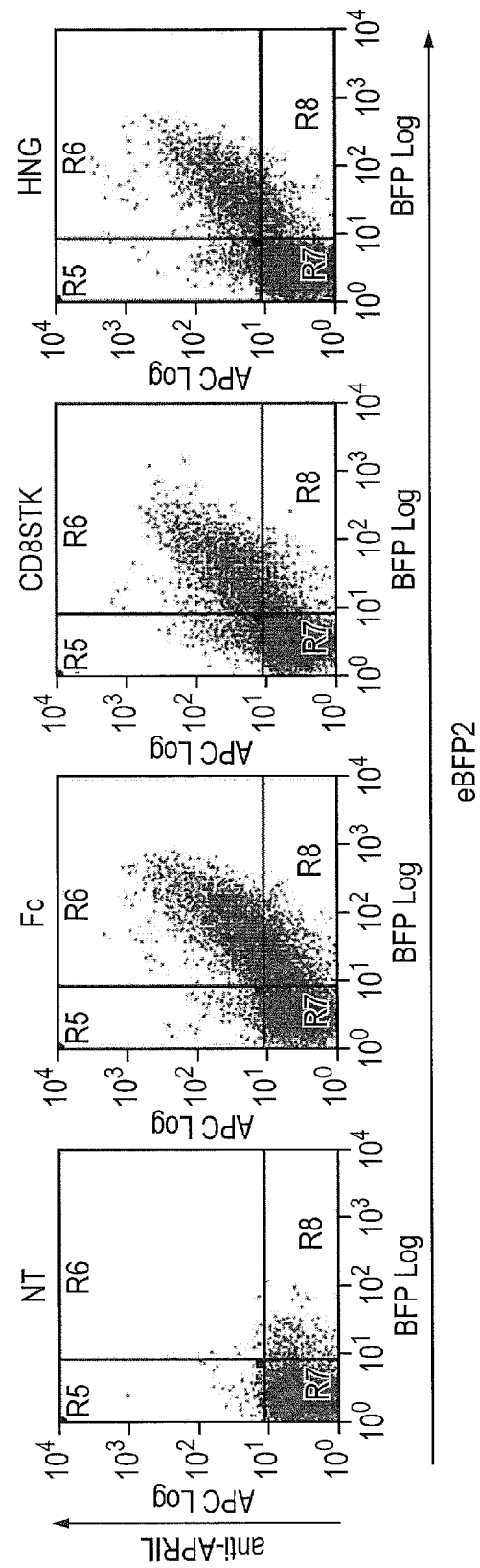

FIG. 15—Expression of different CARs

The receptors were co-expressed with enhanced blue fluorescence protein 2 (eBFP2) using an IRES sequence. Primary human T-cells were transduced and stained with anti-APRIL-biotin/Streptavidin APC. Flow-cytometric analysis was performed. eBFP2 signal is shown against APRIL detection. All three CARs are stably expressed (representative experiment of 3 independent experiments performed using 3 different normal donor T-cells).

Figure 16:
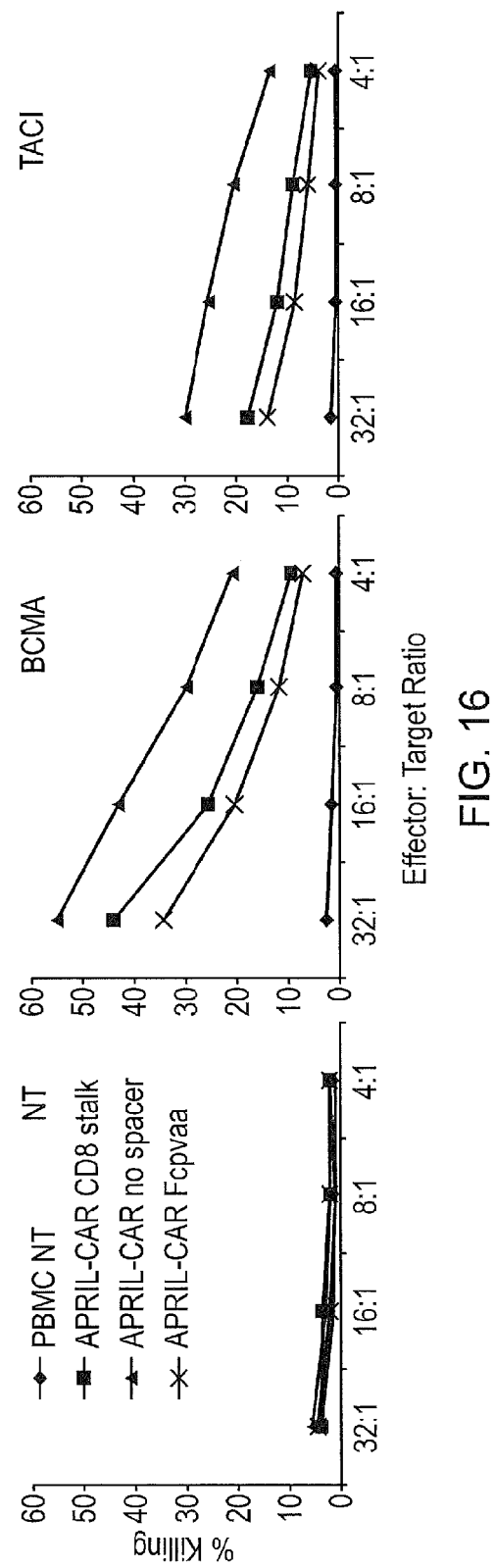

FIG. 16—Chromium release assay

Using normal donor peripheral blood T-cells either non-transduced (NT), or transduced to express different spacer CARs as effectors, and SupT1 cells either non-transduced (NT), or transduced to express BCMA or TACI as targets. The T-cells were CD56 depleted to reduce NK activity. This is a representative of three independent experiments and is shown as an example. Cumulative killing data is shown in FIG. 7A. Specific killing of BCMA and TACI expressing T-cells is seen with no activity against negative target cells.

Figure 17:
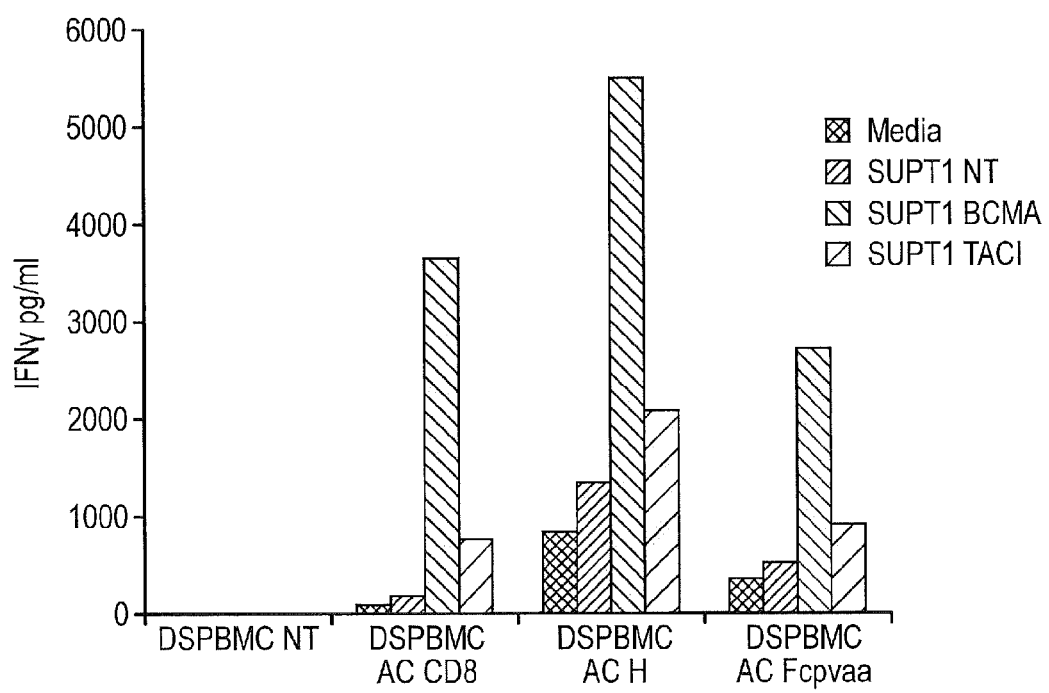

FIG. 17—Interferon-gamma release

From a 1:1 co-culture of effectors and targets is measured by ELISA. The CD8 stalk construct appears to have the best specificity while the hinge construct results in the most Interferon release demonstrates some non-specific activity. This is representative of 3 independent experiments and is shown as an example. Cumulative interferon-gamma release data is shown in FIG. 7B.

Figure 18:
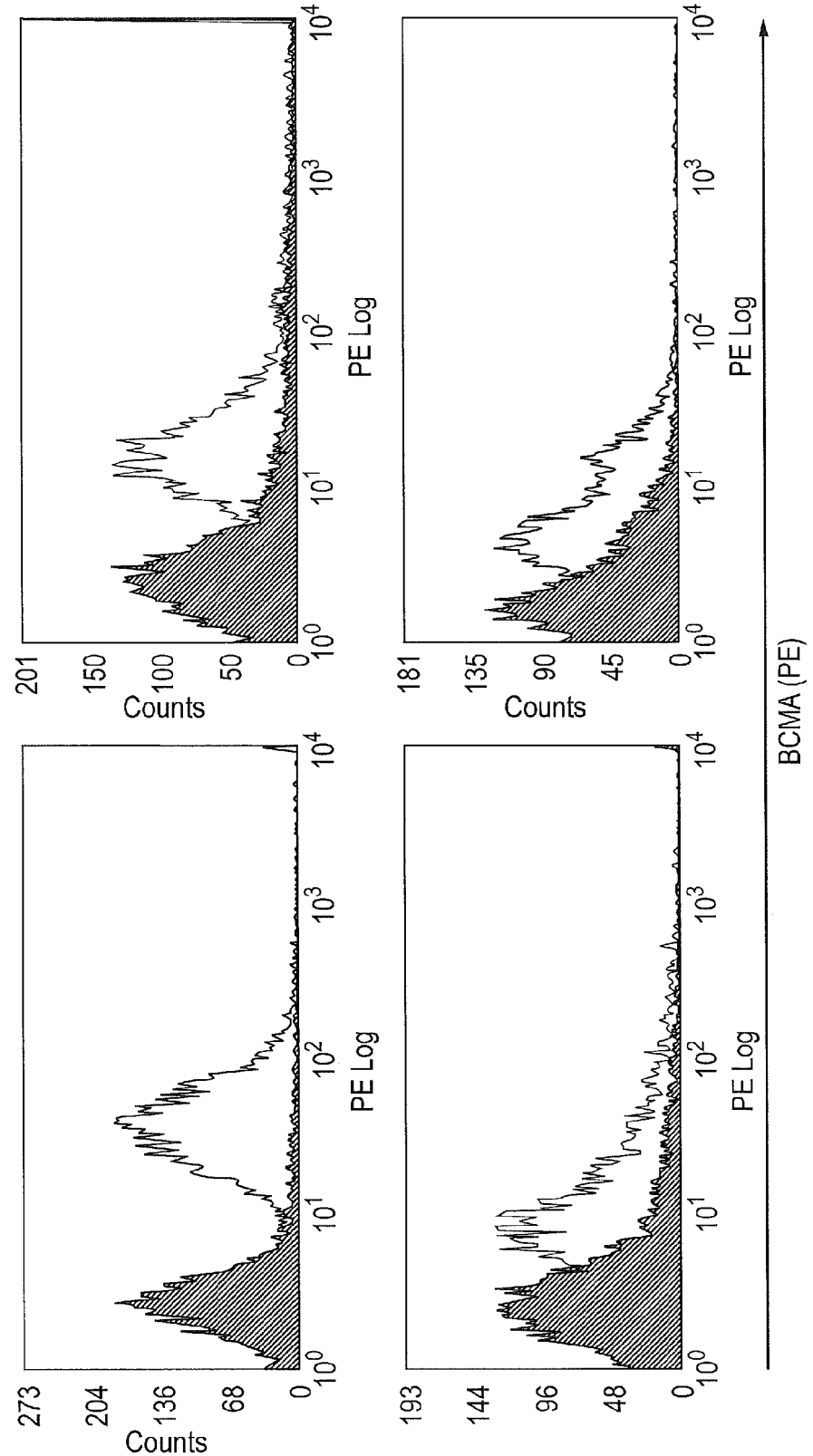

FIG. 18—Examples of BCMA expression on primary myelomas

Four examples of myeloma samples stained with the rat anti-human BCMA mAb Vicky1 is shown. The first panel shows bright BCMA staining in a patient with a plasma cell leukemia (an unusual, advanced and aggressive form of myeloma). The other three cases are clinically and morphologically typical myelomas. They show the intermediate or dim staining typically seen. Staining with isotype control (grey) is superimposed. These are examples of cumulative BCMA expression data shown in FIG. 2.

FIGS. 19A-19C—Amino acid sequence of APRIL-CARS with a V5 epitope tag.

FIG. 19A: dAPRIL-HCH2CH3pvaa-CD28OXZ (SEQ ID NO: 78)

FIG. 19B: dAPRIL-CD8STK-CD28OXZ (SEQ ID NO: 79)

FIG. 19C: dAPRIL-HNG-CD28OXZ (SEQ ID NO: 80)

Sequences in this figure differ from those in FIG. 5 have a different signal peptide and no V5 tag.

Figure 20A:
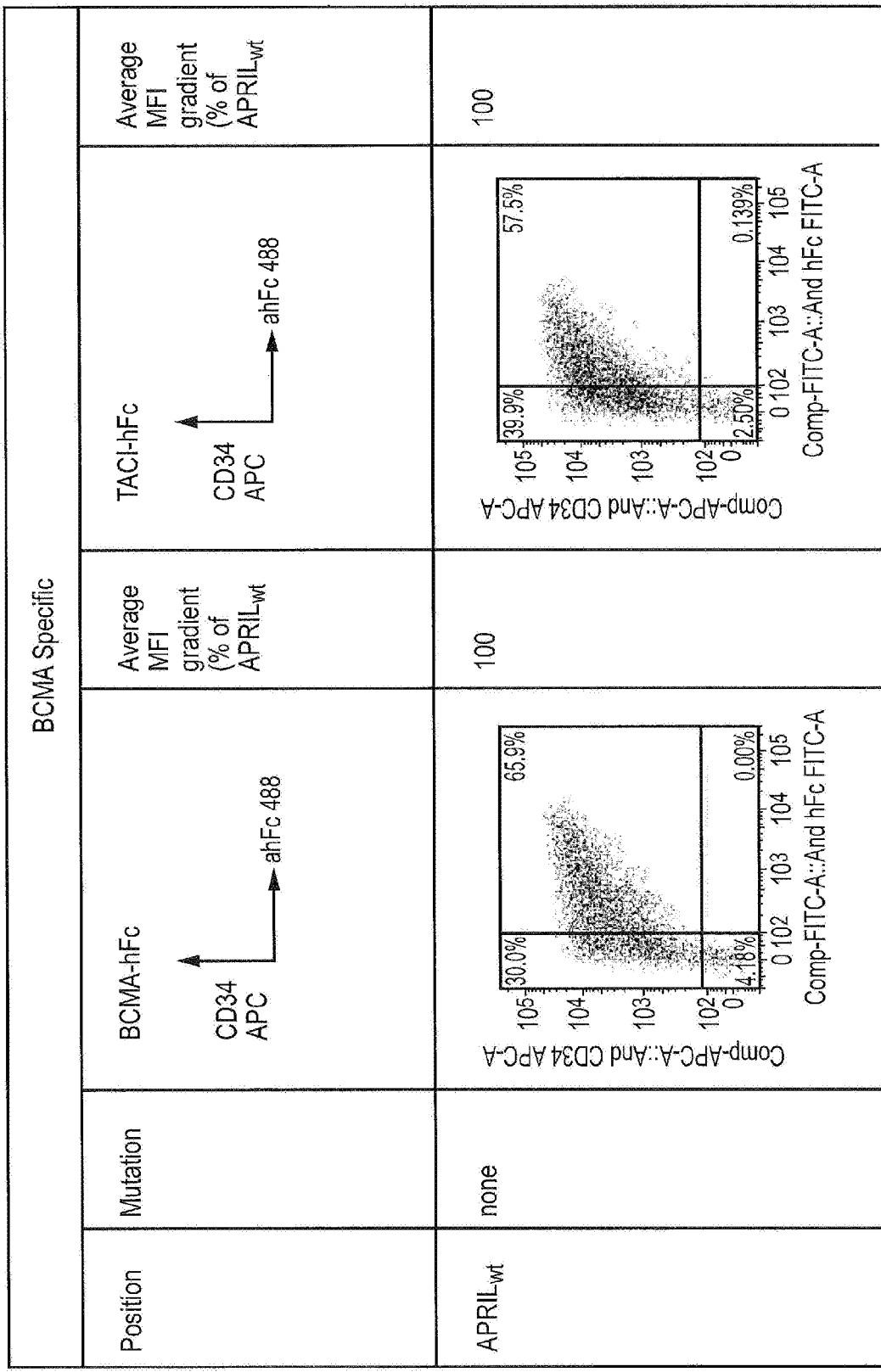
Figure 20B:
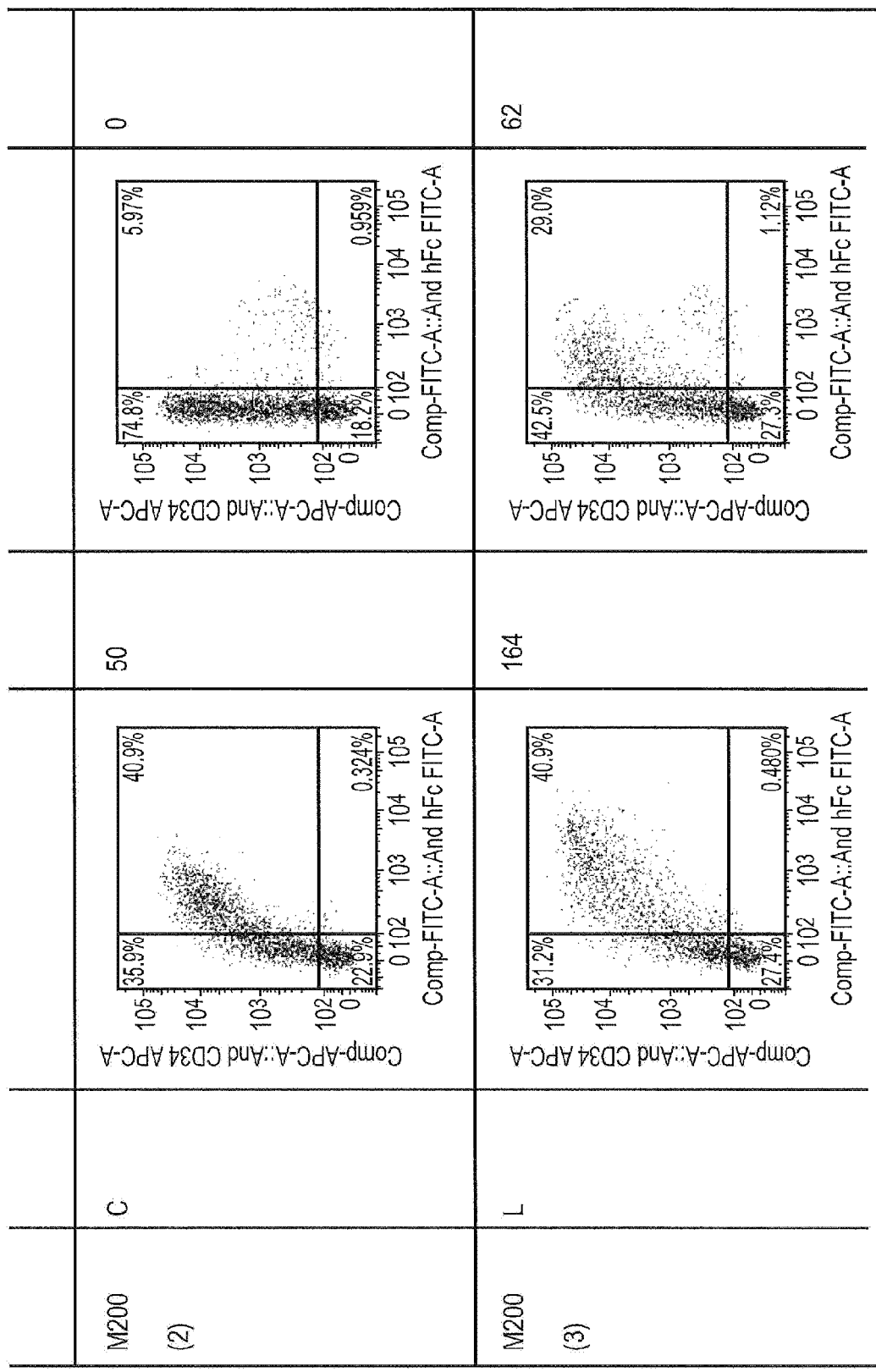
Figure 20C:
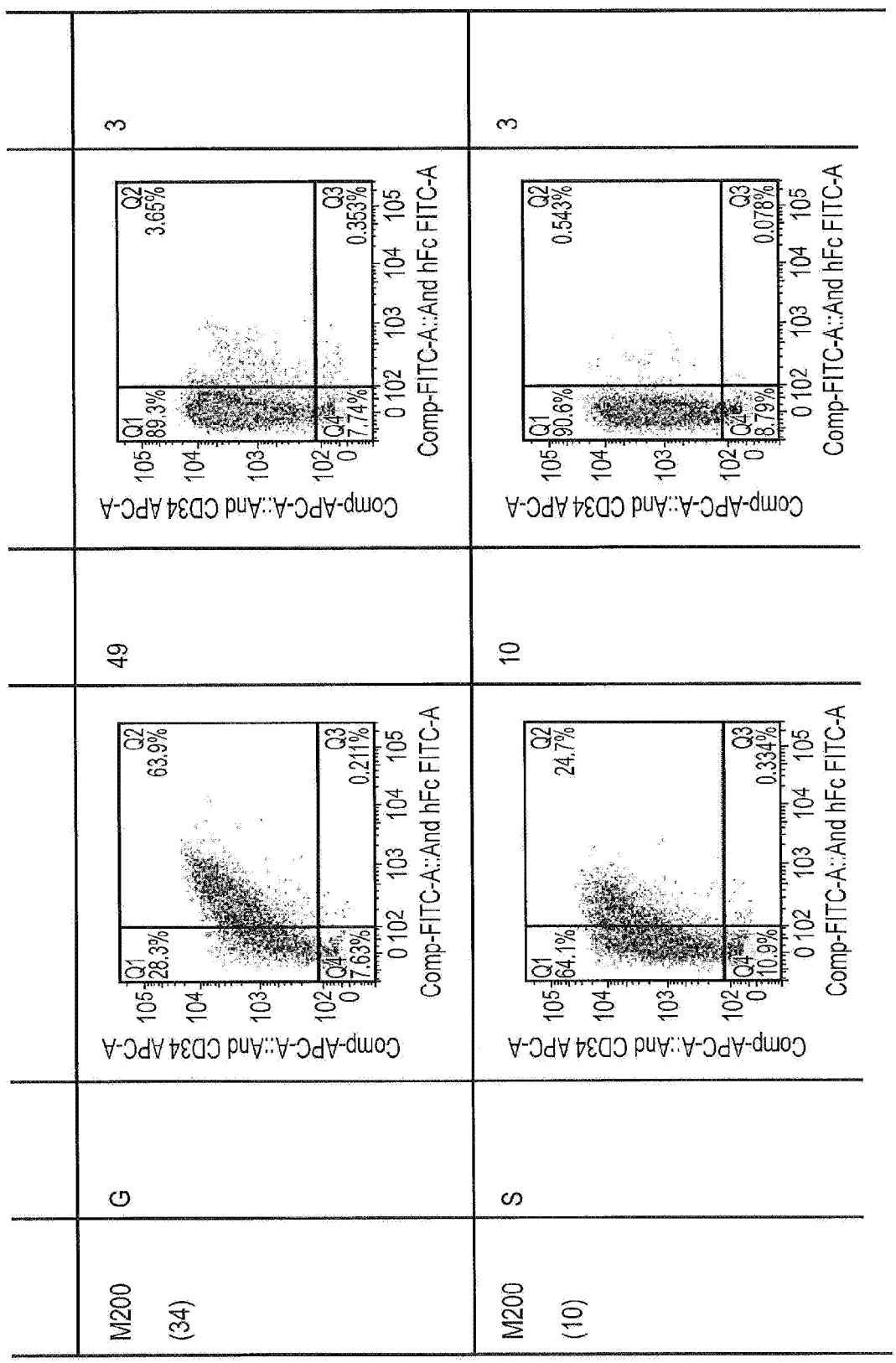
Figure 20D:
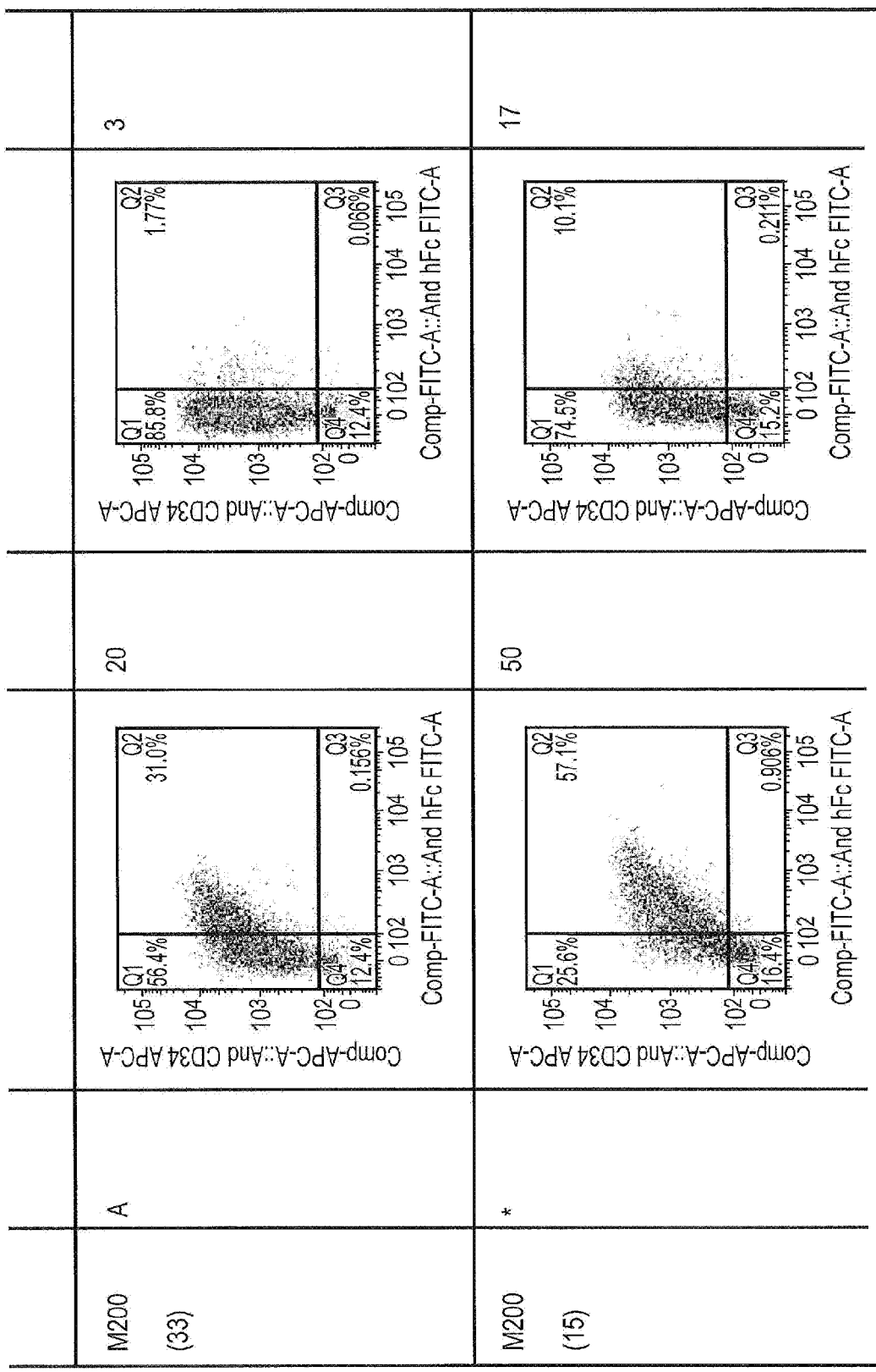
Figure 20E:
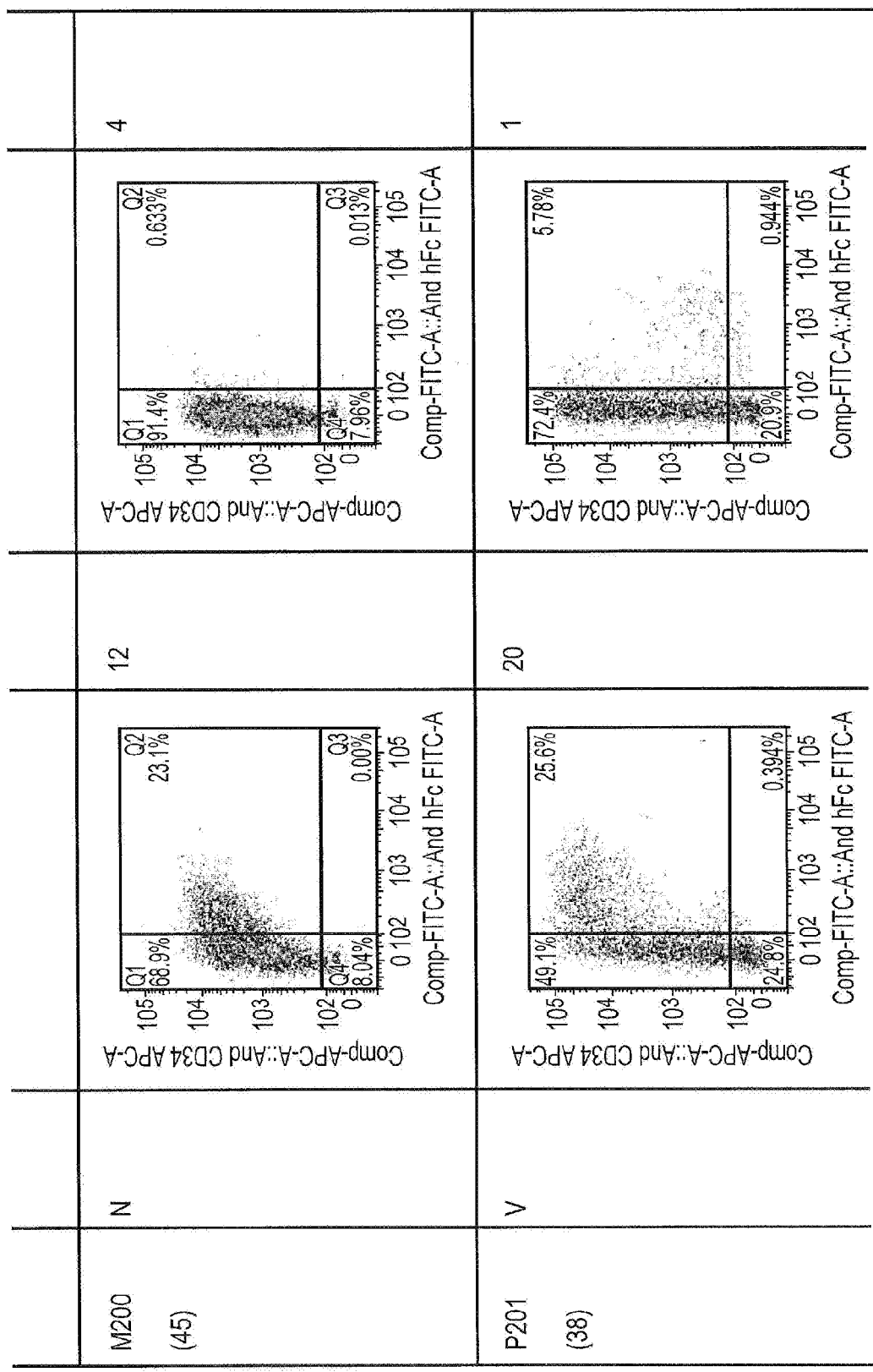
Figure 20F:
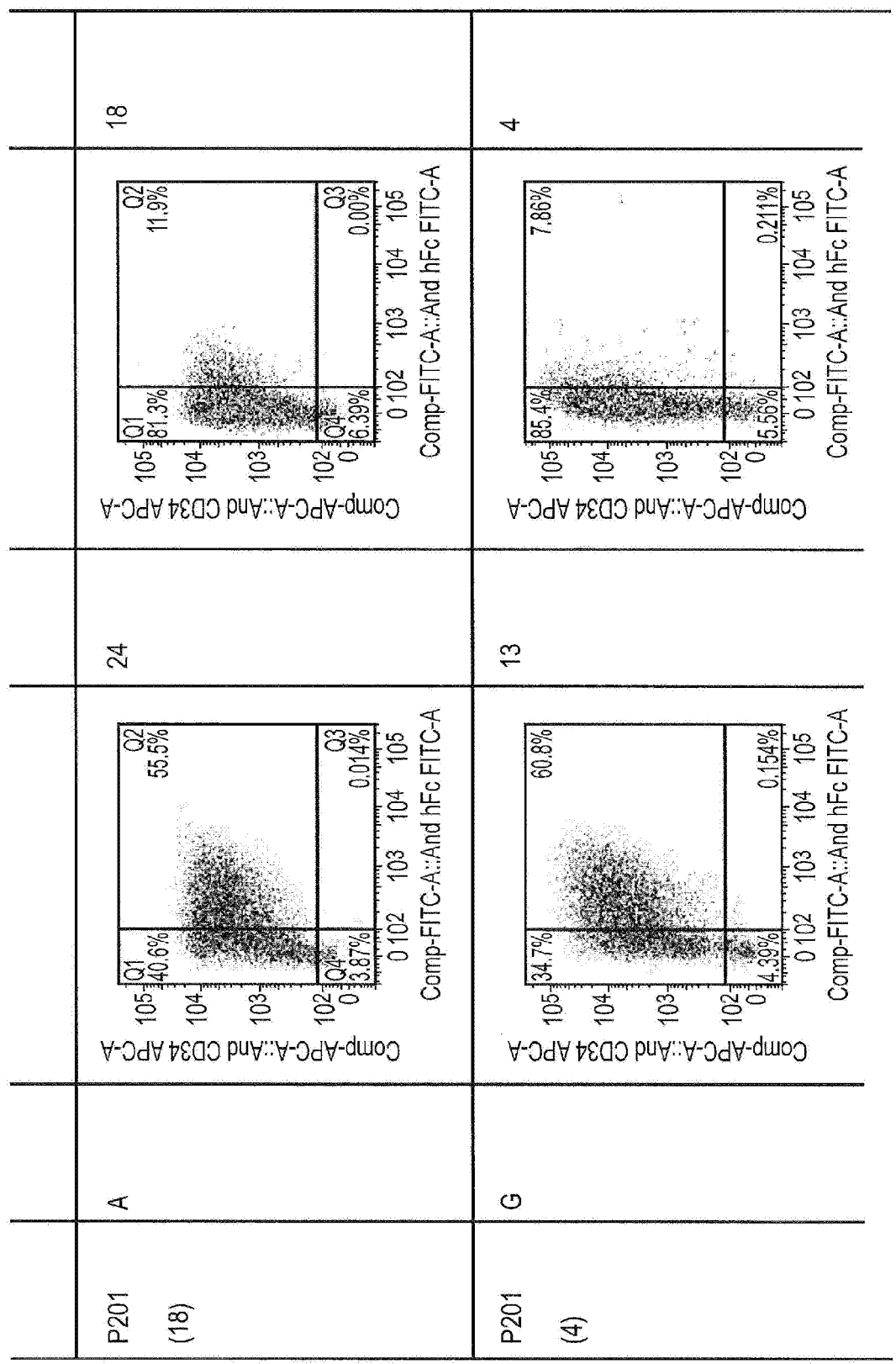
Figure 20G:
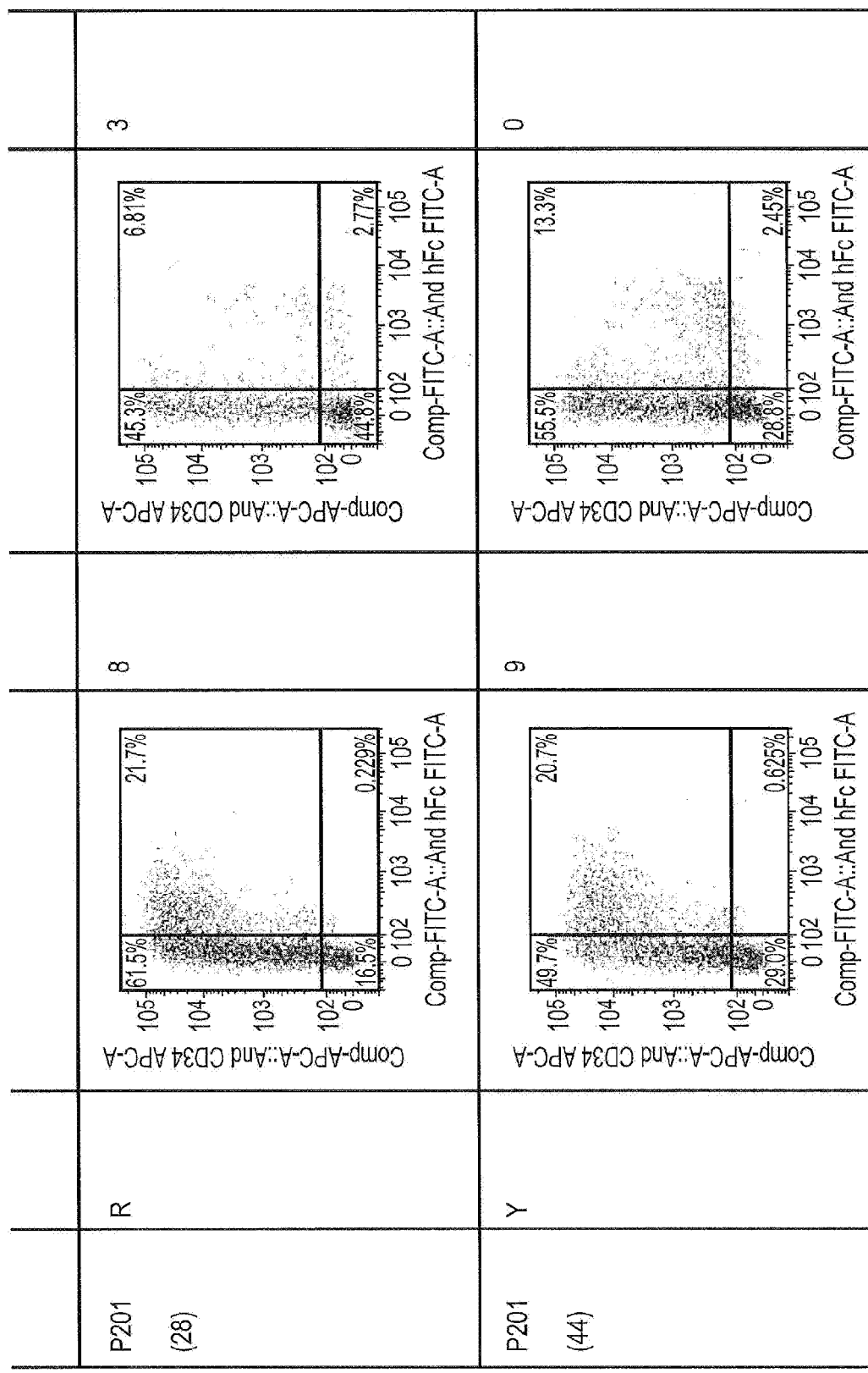
Figure 20H:
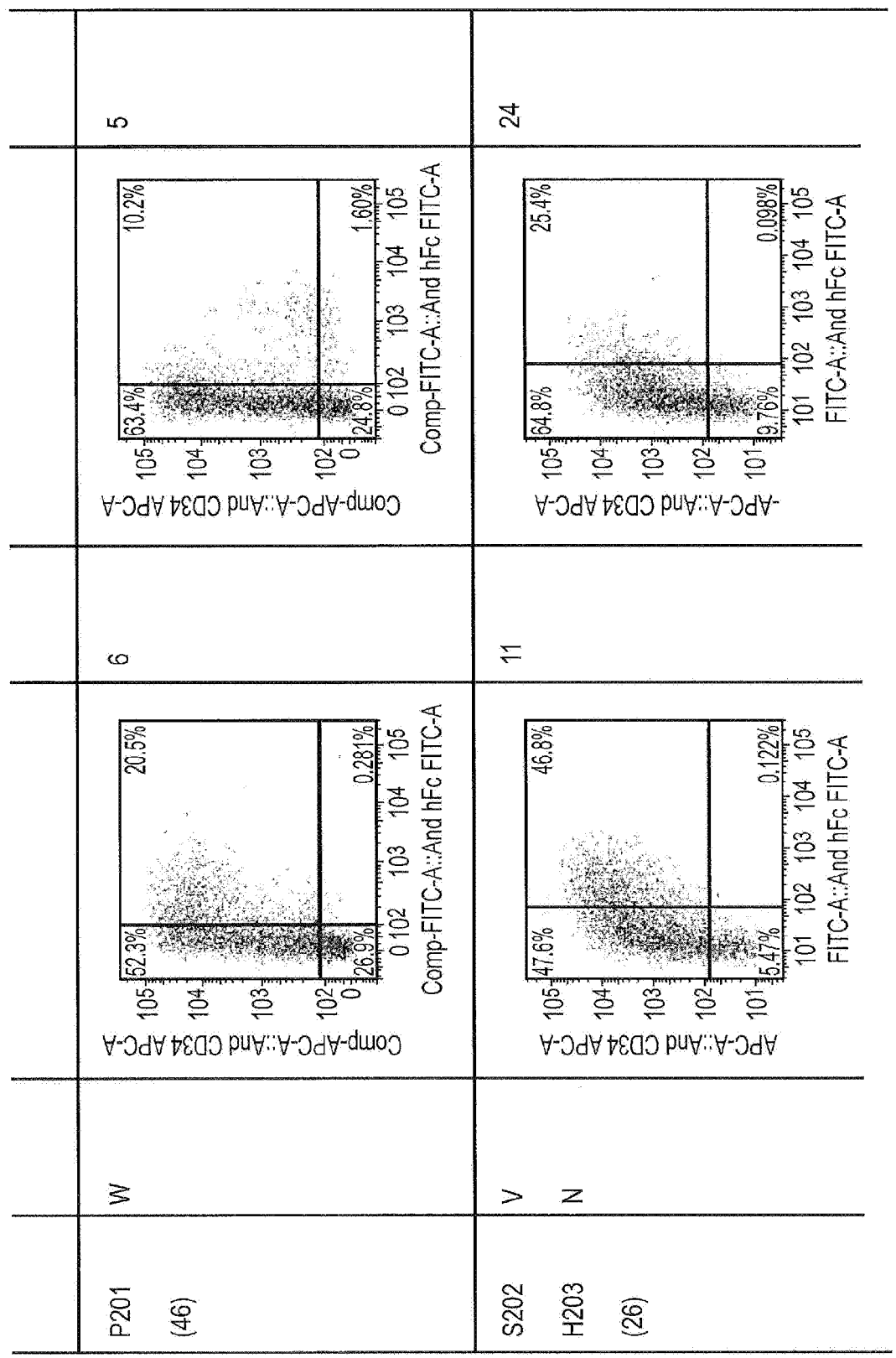
Figure 20I:
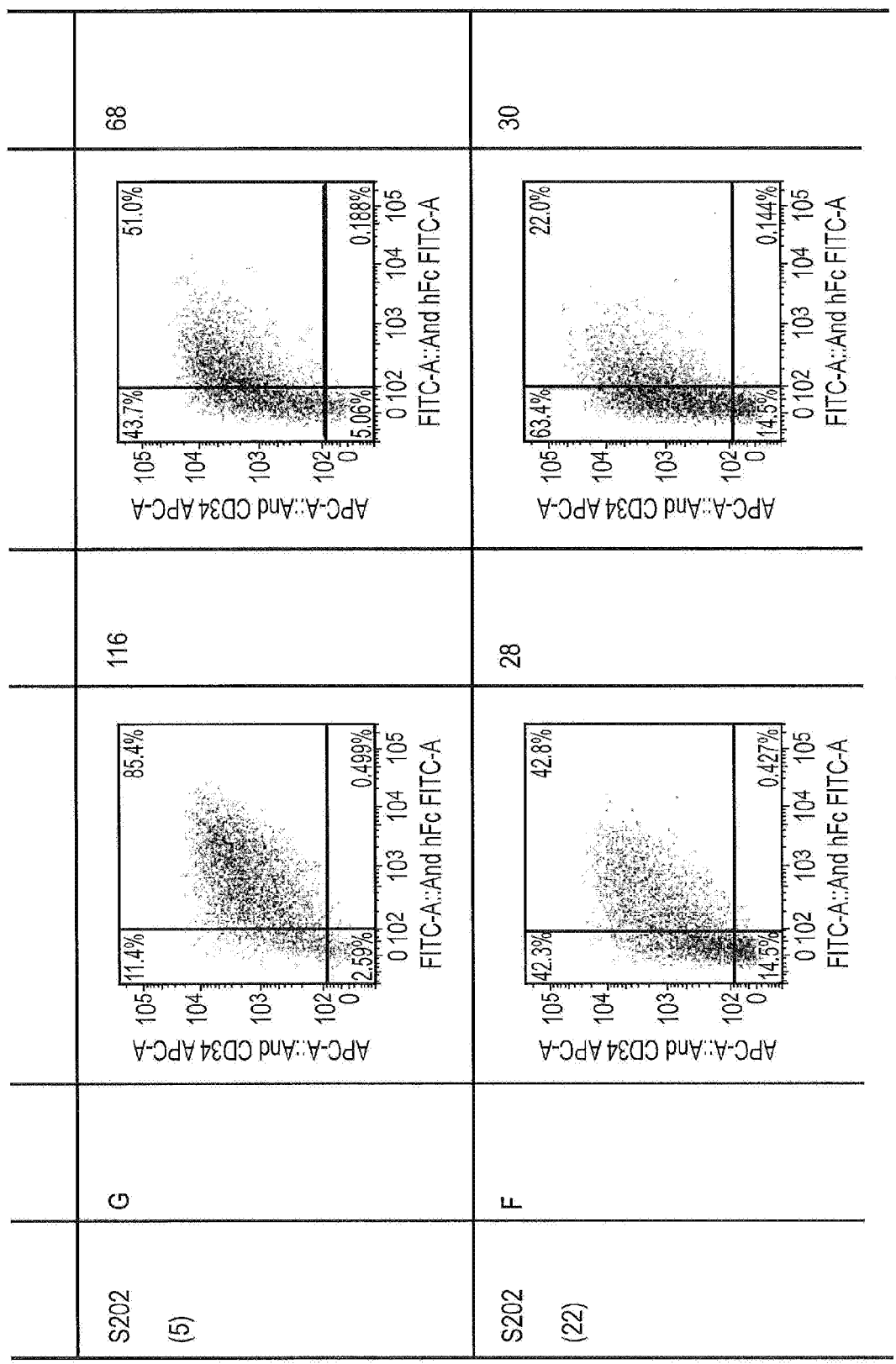
Figure 20J:
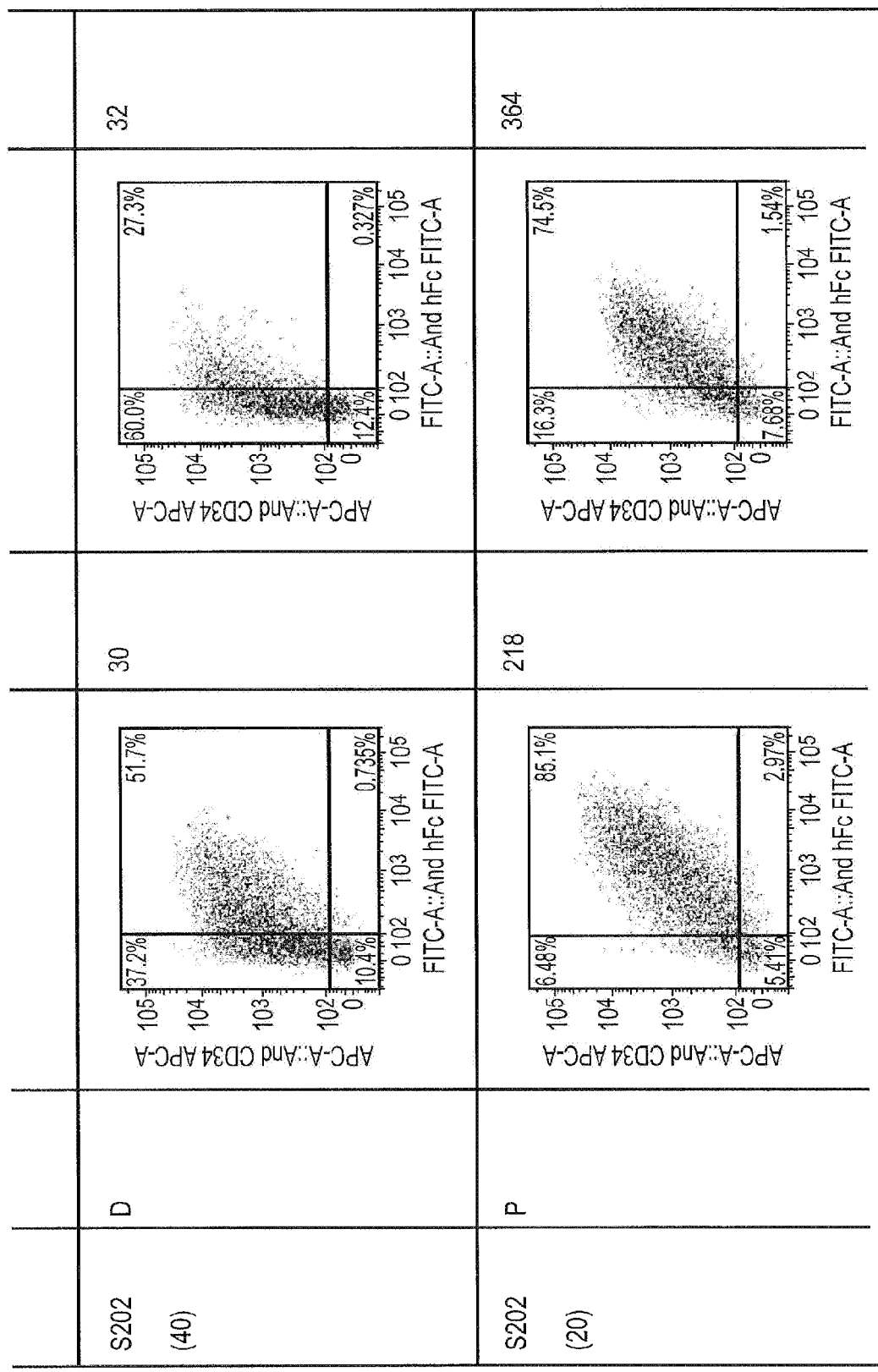
Figure 20K:
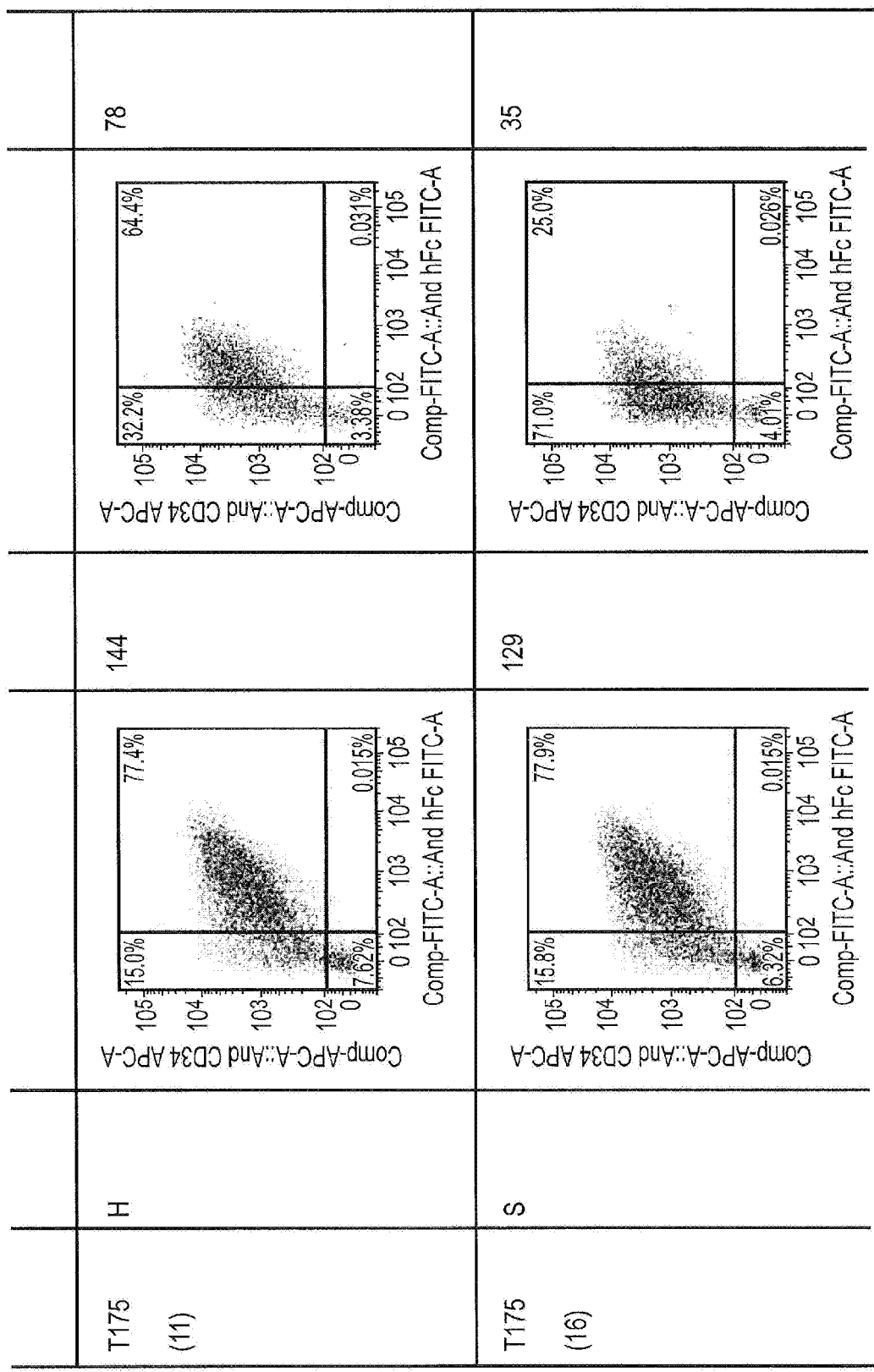
Figure 20L:
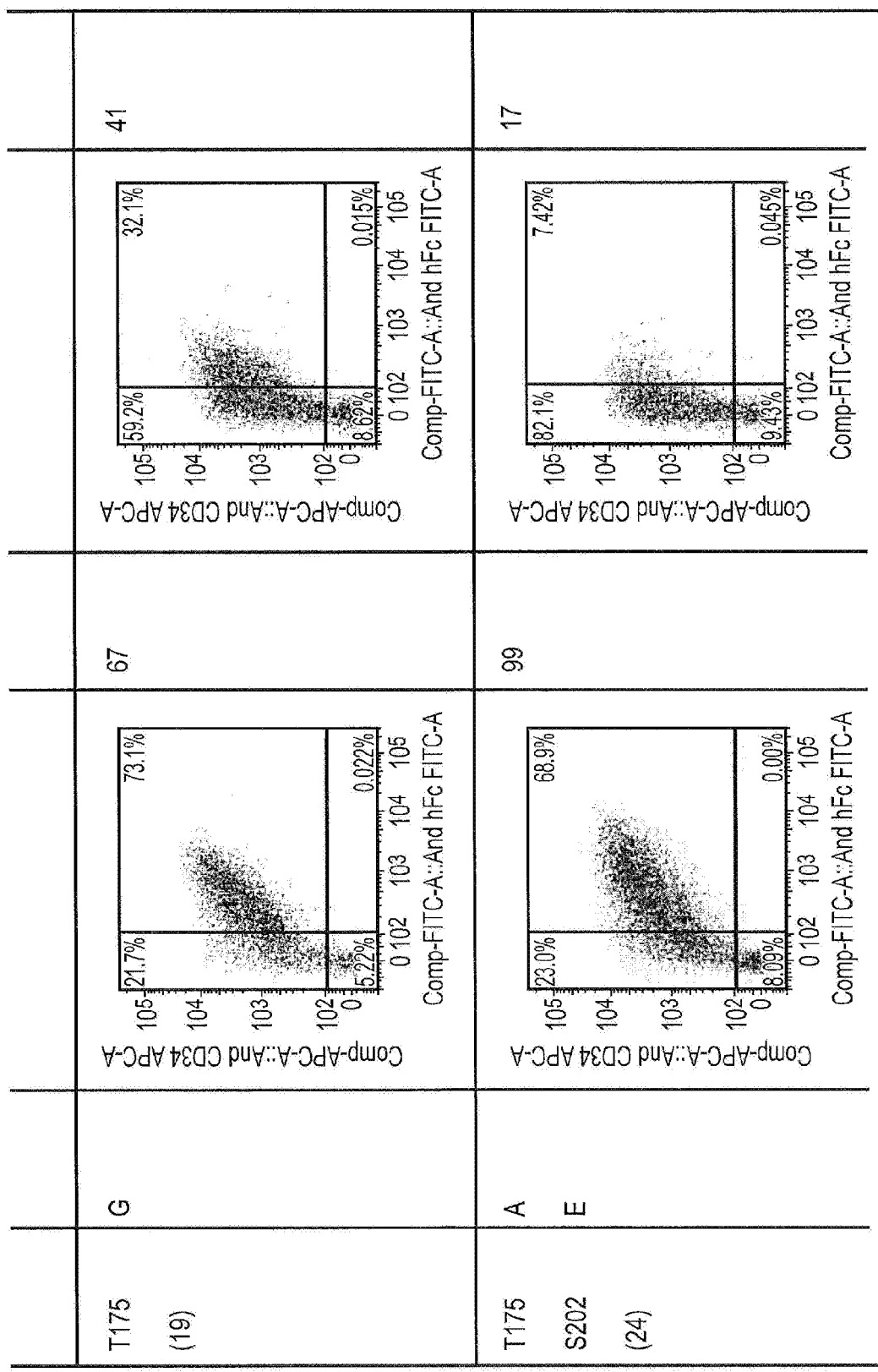
Figure 20M:
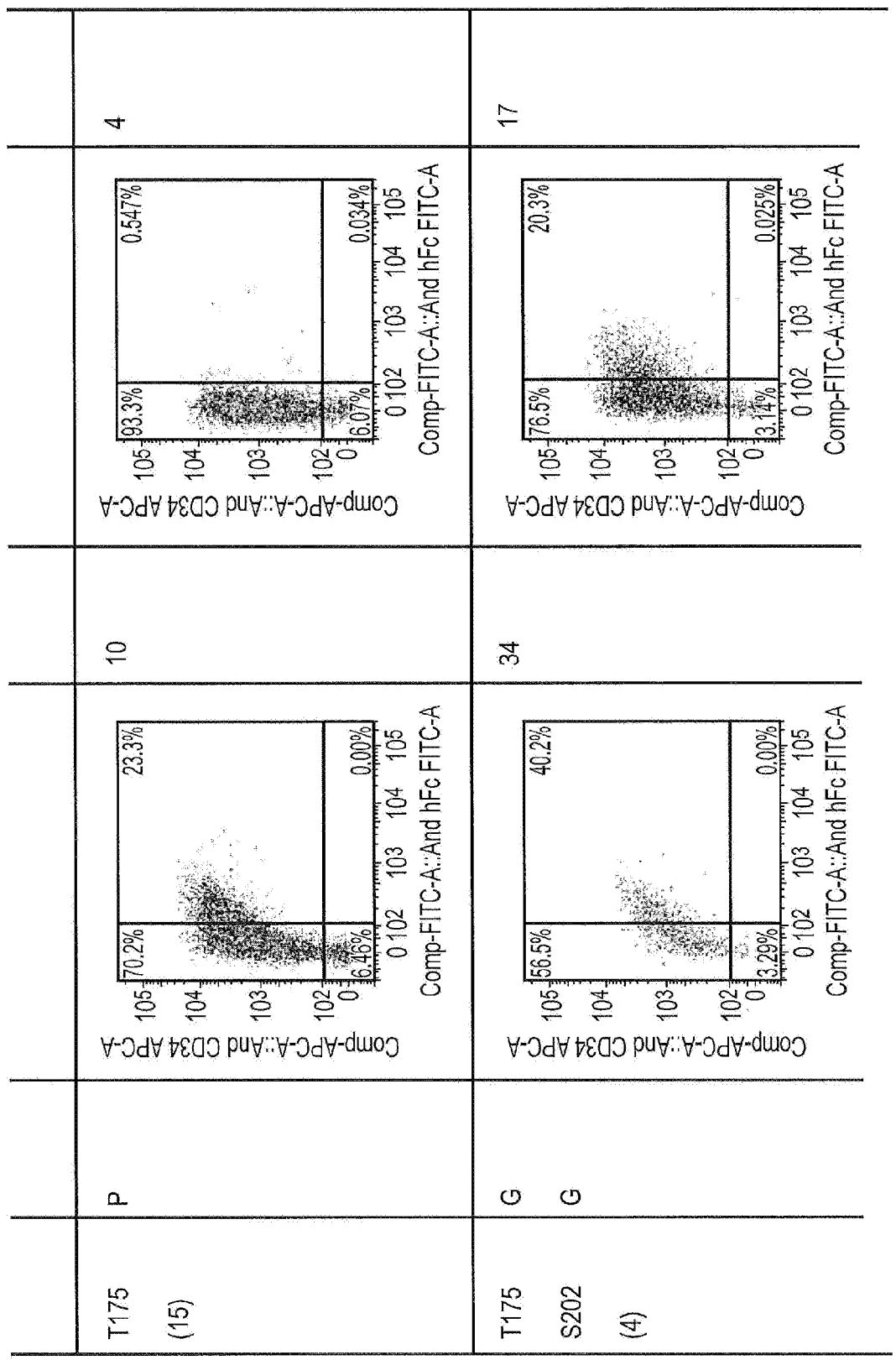
Figure 20N:
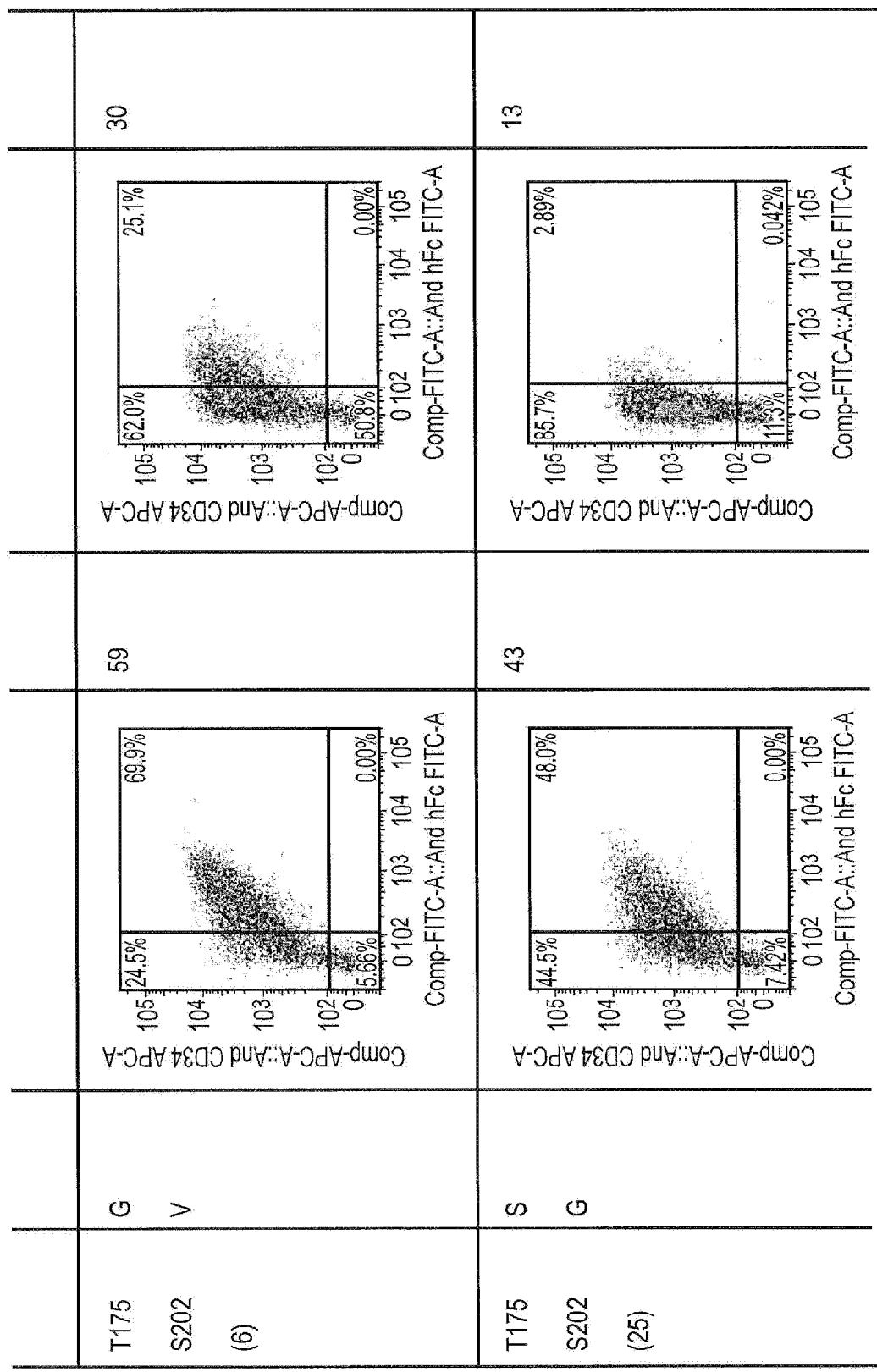
Figure 20O:
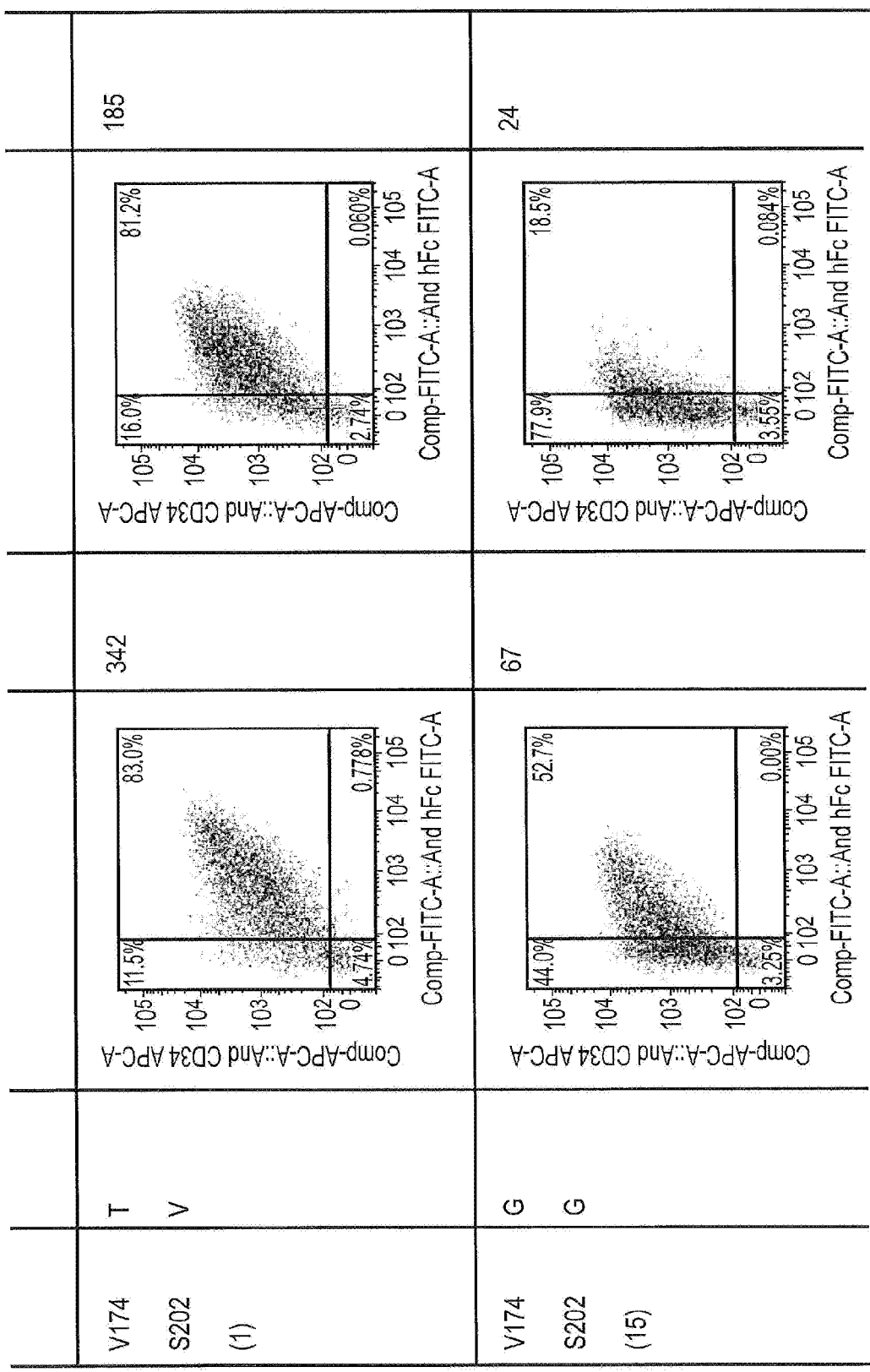
Figure 20P:
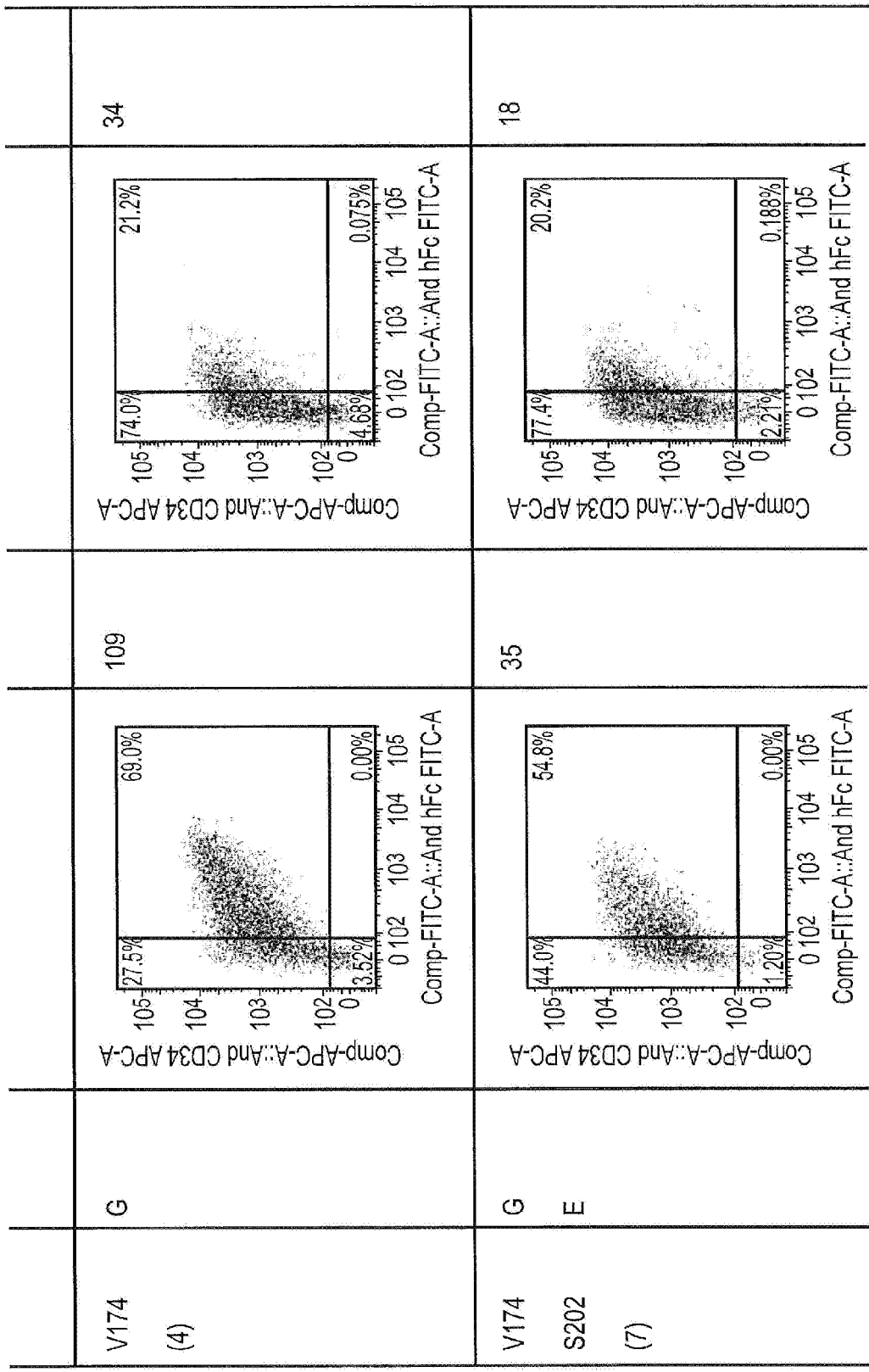
Figure 20Q:
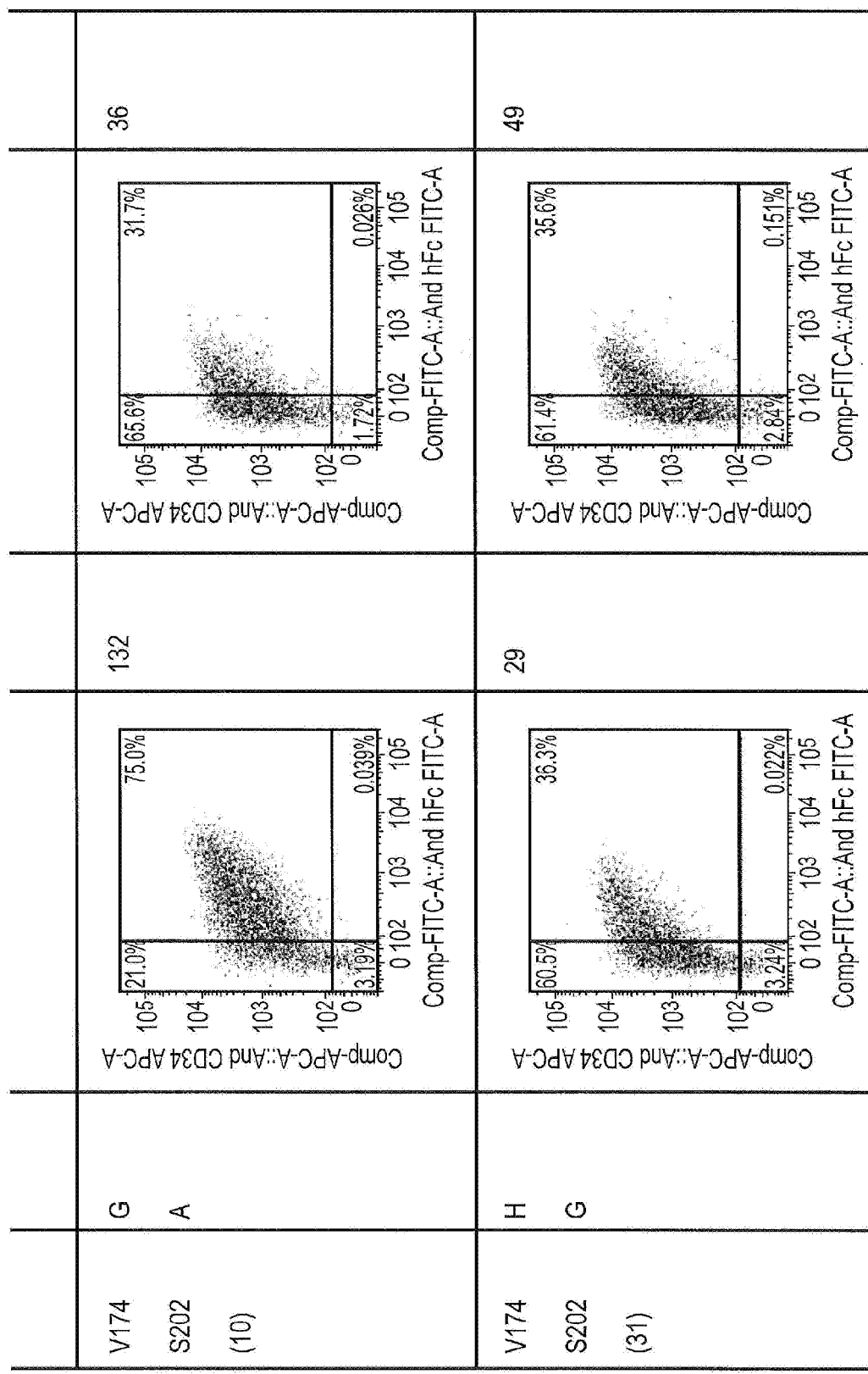
Figure 20R:
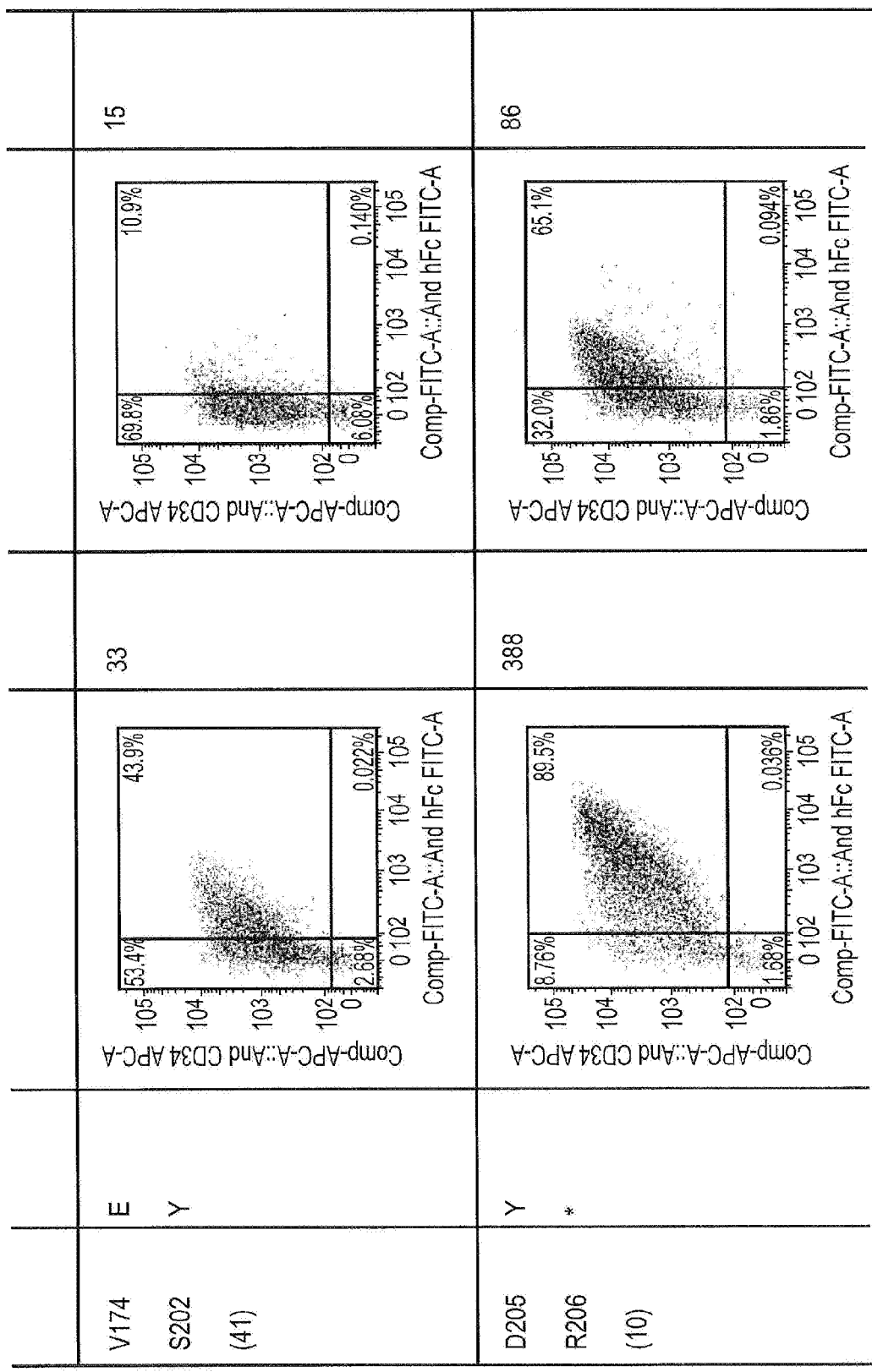
Figure 20S:
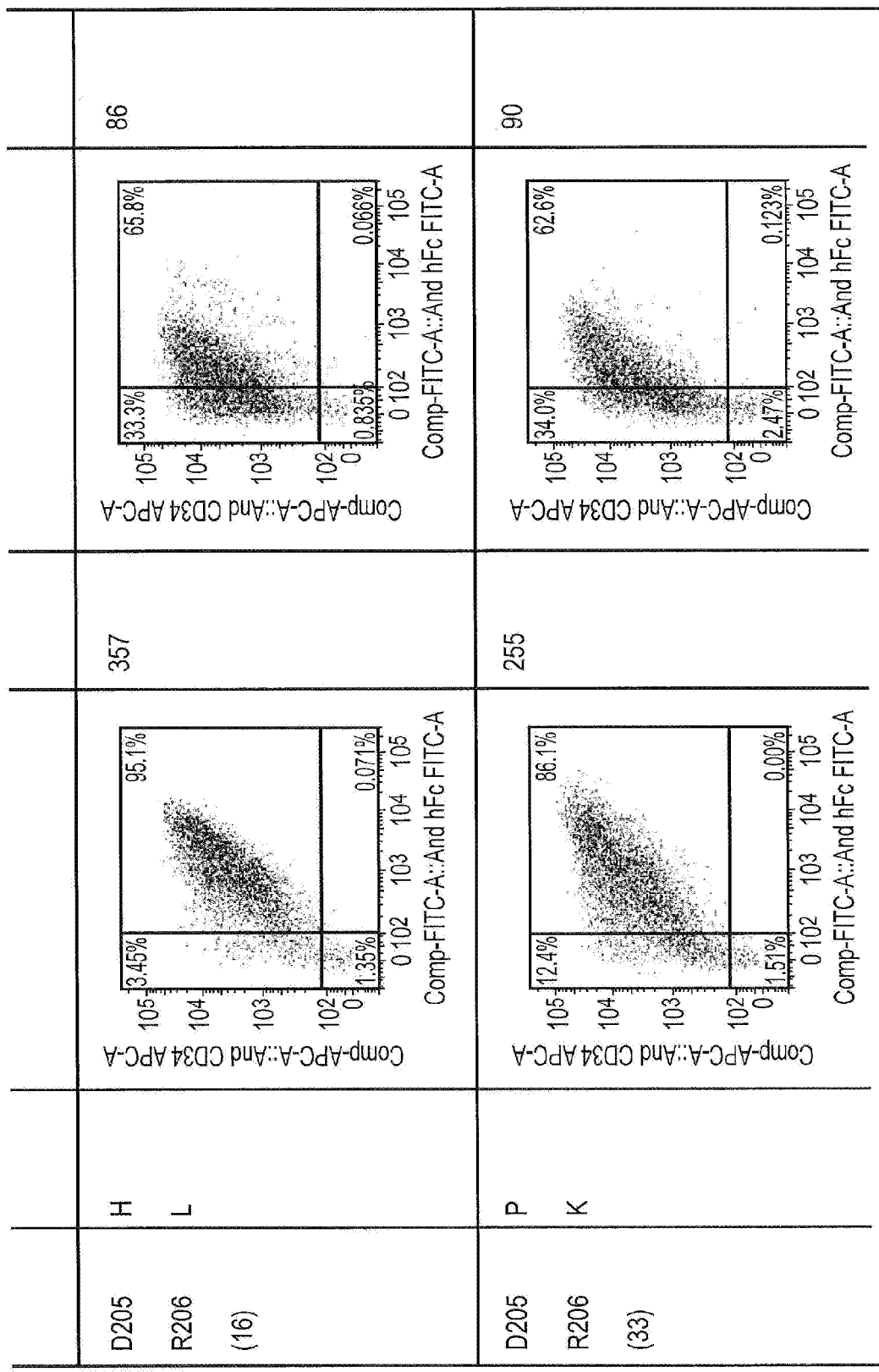
Figure 20T:
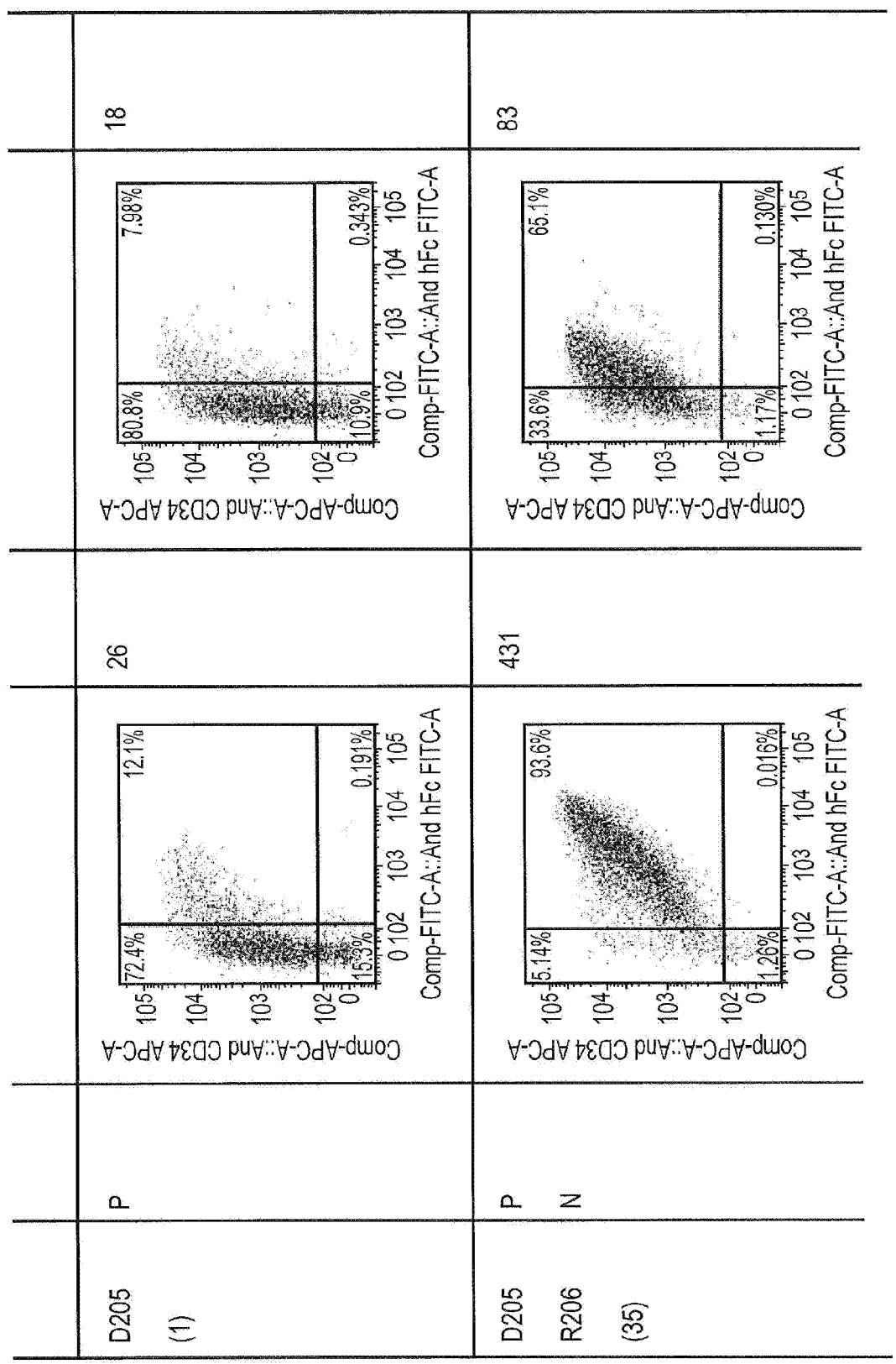
Figure 20U:
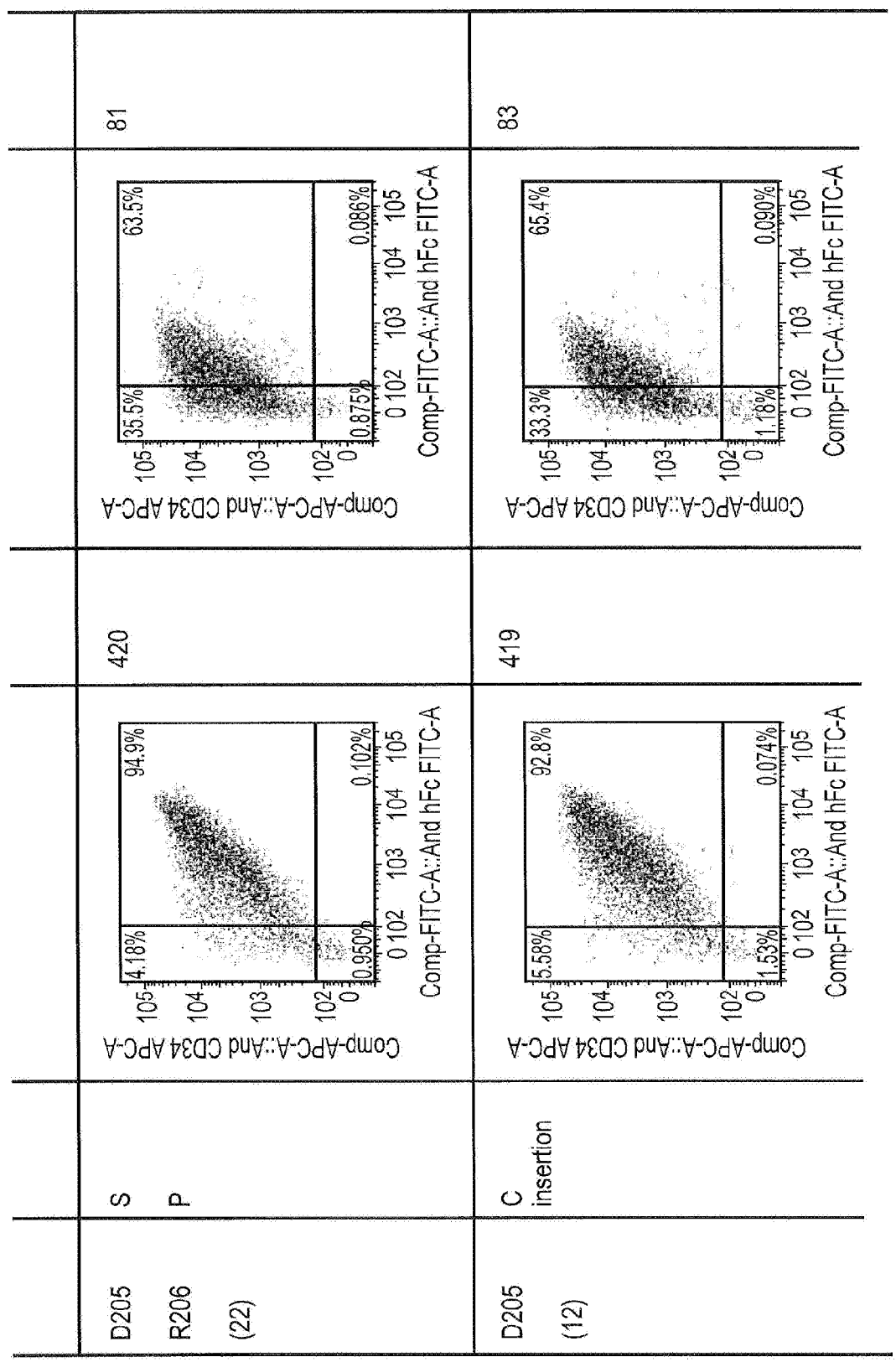
Figure 20V:
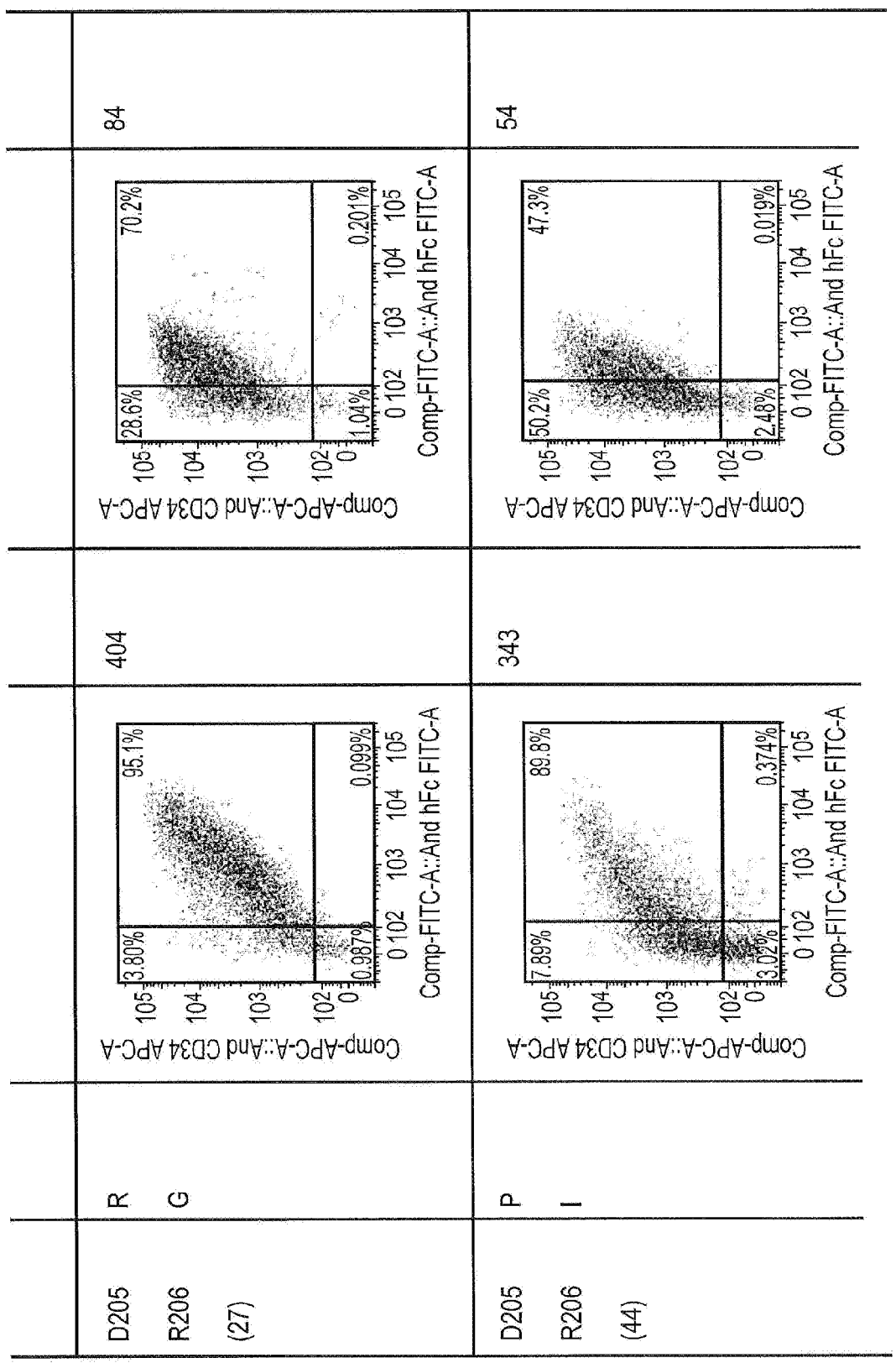
Figure 20W:
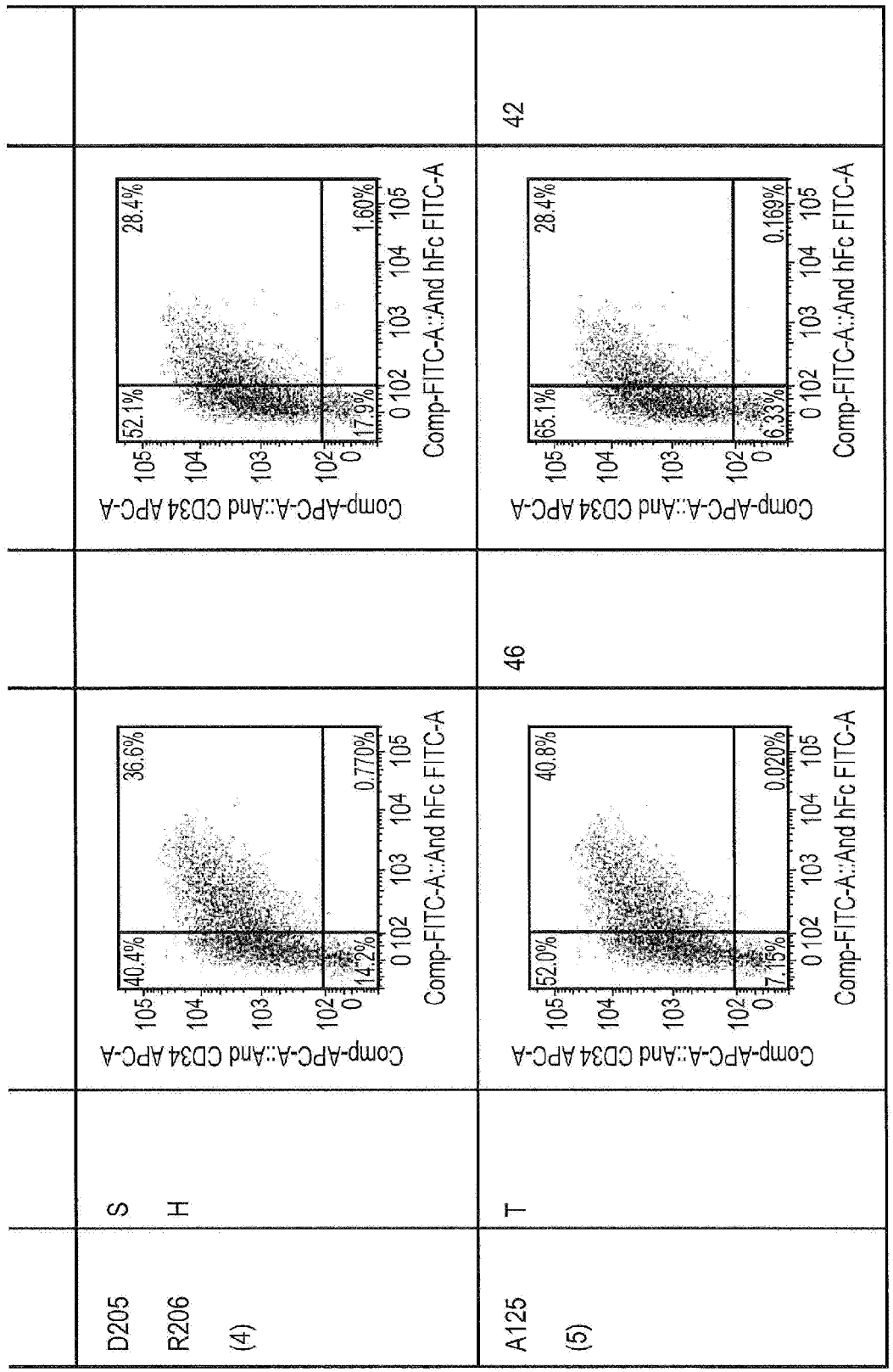

FIGS. 20A-20W—Summary of screening BCMA specific APRIL mutants

Altered binding to BCMA-Fc and TACI-Fc. This is an example of initial screening data miniprep DNA. Mutants were screened in batches with inter-experimental variation corrected for by expressed the average MFI gradient of APRIL mutant compared to wild type APRIL checked with each batch.

FIGS. 21A-21B—Sequence alignment of BCMA specific APRIL mutants

Minipreps selected during the random mutagenesis process were screened for expression by staining with BCMA-Fc and TACI-Fc. Mutants with potentially useful or informative phenotypes were sequenced by capillary sequences and aligned with the original APRIL sequence they were derived from. Shown in this figure are alignments of example mutants identified during such a screening process.

M200X—SEQ ID NO: 102; M200C—SEQ ID NO: 103; M200L—SEQ ID NO: 104; M200S—SEQ ID NO: 105; M200*—SEQ ID NO: 106; M200A—SEQ ID NO: 107; M200G—SEQ ID NO: 108; M200N—SEQ ID NO: 109; P201X—SEQ ID NO: 110; P201G-4_406.seq—SEQ ID NO: 111; P201A-18_406.seq—SEQ ID NO: 112; P201V-38_406.seq—SEQ ID NO: 113; P201A-46_406.seq—SEQ ID NO: 114; P201A-28_406.seq—SEQ ID NO: 115; P201A-44_406.seq—SEQ ID NO: 116; S202X—SEQ ID NO: 117; S202G-5_406—SEQ ID NO: 118; S202P-20_406—SEQ ID NO: 119; S202F-22_406.seq—SEQ ID NO: 120; S202V_H203N-26_4—SEQ ID NO: 121; S202D-40_406.seq—SEQ ID NO: 122; T175X—SEQ ID NO: 123; T175G_S202G-4_40—SEQ ID NO: 124; T175G_S202V-6_40—SEQ ID NO: 125; T175H-11_406.seq—SEQ ID NO: 126; T175P-15_406.seq—SEQ ID NO: 127; T175H-16_406.seq—SEQ ID NO: 128; T175G-19_406.seq—SEQ ID NO: 129; T175A_S202E-24_4—SEQ ID NO: 130; T175S_S202G-25_4—SEQ ID NO: 131; V174X—SEQ ID NO: 132; V174T_S202V-1_40—SEQ ID NO: 133; V174G-4_406.seq—SEQ ID NO: 134; V174G_S202E-7_40—SEQ ID NO: 135; V174G_S202A-10_4—SEQ ID NO: 136; V174G_S202G-15_4—SEQ ID NO: 137; V174H_S202G-31_4—SEQ ID NO: 138; V174E_S202Y-41_4—SEQ ID NO: 139; D205X R206X—SEQ ID NO: 140; D205P-1_406.seq—SEQ ID NO: 141; D205P-R206G-27_4—SEQ ID NO: 142; D205P-R206K-33_4—SEQ ID NO: 143; D205P-R206N-35_4—SEQ ID NO: 144; D205P-R206I-44_4—SEQ ID NO: 145; D205S-R206H-4_40—SEQ ID NO: 146; D205Y-R206stop-1—SEQ ID NO: 147; D205+C-12_406—SEQ ID NO: 148; D205H-R206L-16_4—SEQ ID NO: 149; D205S-R206P-22_4—SEQ ID NO: 150; A125X—SEQ ID NO: 151; A125I-5_406—SEQ ID NO: 152.

Figure 22:
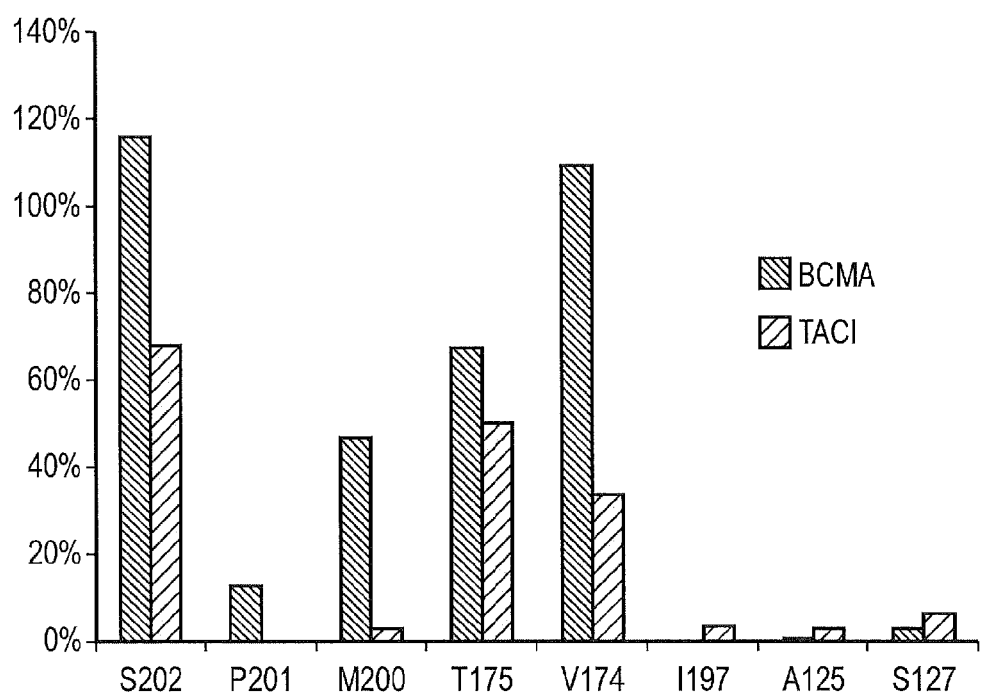
Figure 23A:
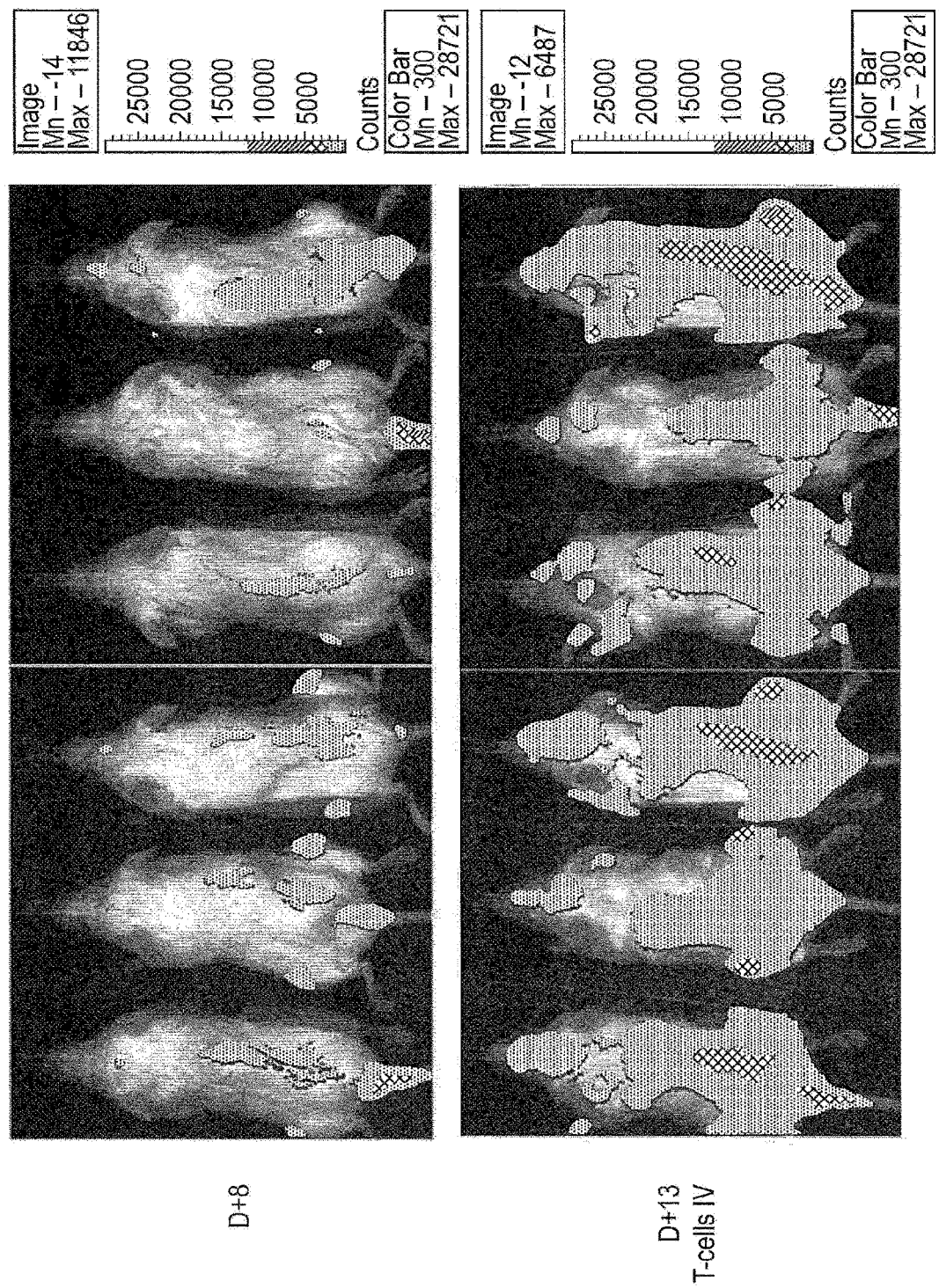
Figure 23B:
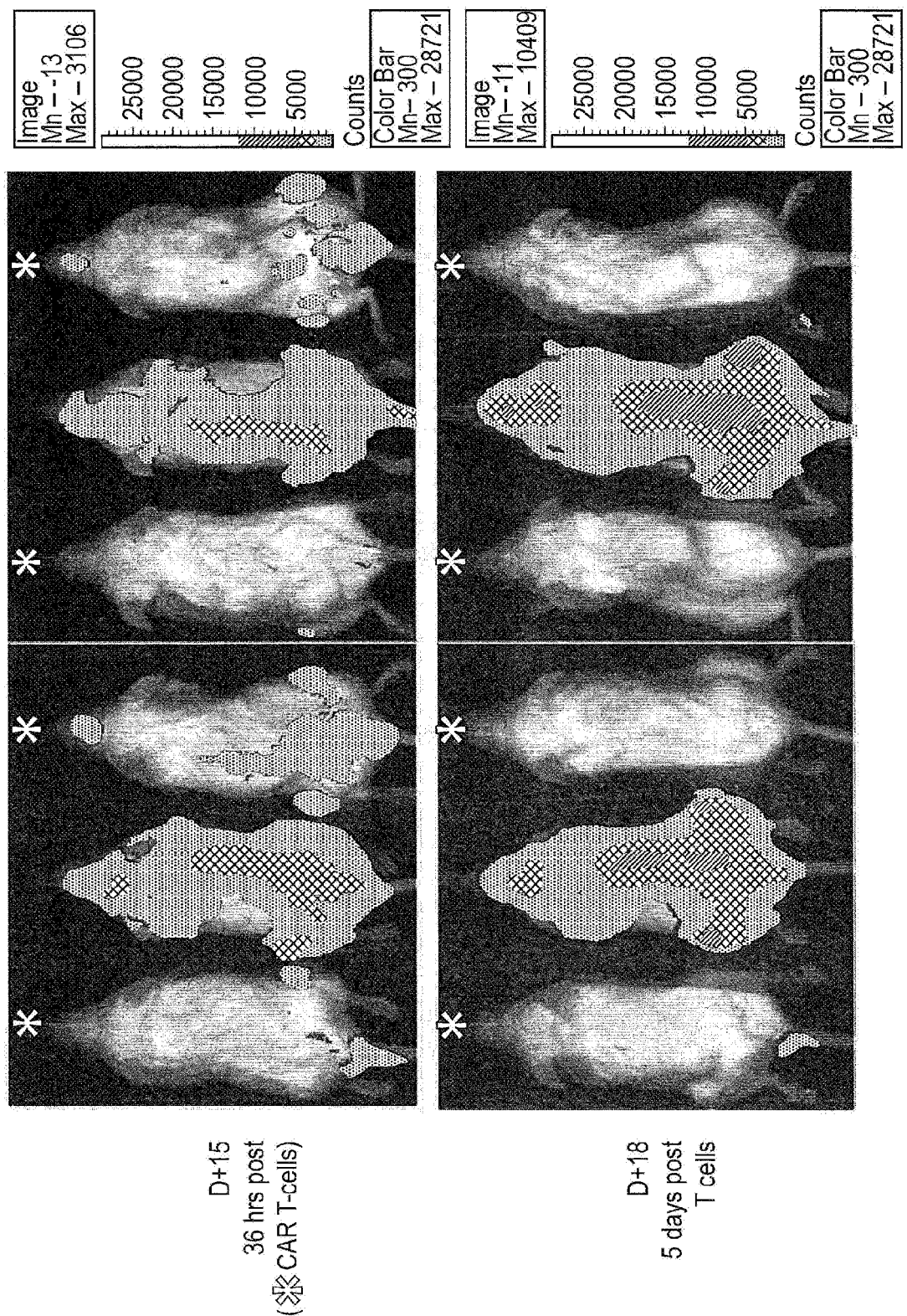

FIG. 22—Graph of altered BCMA and TACI binding with glycine substitutions at targeted residues FIGS. 23A-23B—Demonstration of in vivo function of APRIL CAR T-cells Six 3 month old female NSG mice received $1\times10^7$ MM1.s.FLuc cells vial tail-vein injection. Mice were imaged with bioluminescence at day 8 and day 13. After imaging on day 13, four mice received $5\times10^6$ APRIL CAR T-cells via tail vein injection. Mice were imaged on day 13 and day 18. Mice which received CAR T-cells are indicated with (*). Remission of Myeloma could be observed by Day 18 in all treated mice, while disease in untreated mice progressed.

FIGS. 24A-24G: Different APRIL-BiTE formats designed and constructed

FIG. 24A: OKT3 scFv connected to truncated APRIL by the IgG1 hinge; FIG. 24B: OKT3 scFv connected to truncated APRIL via a (SGGGGS)3 linker; FIG. 24C: OKT3 scFv connected to truncated APRIL via the CD8 stalk; FIG. 24D: truncated APRIL connected to OKT3 scFv via an IgG1 hinge; FIG. 24E: truncated APRIL connected to the OKT3 scFv via a (SGGGGS)3 linker; FIG. 24F truncated APRIL connected to the OKT3 scFv via a CD8 spacer. Constructs in FIG. 24C and FIG. 24F should form homodimers through disulphide bonds in the CD8 spacer.

Figure 24G:
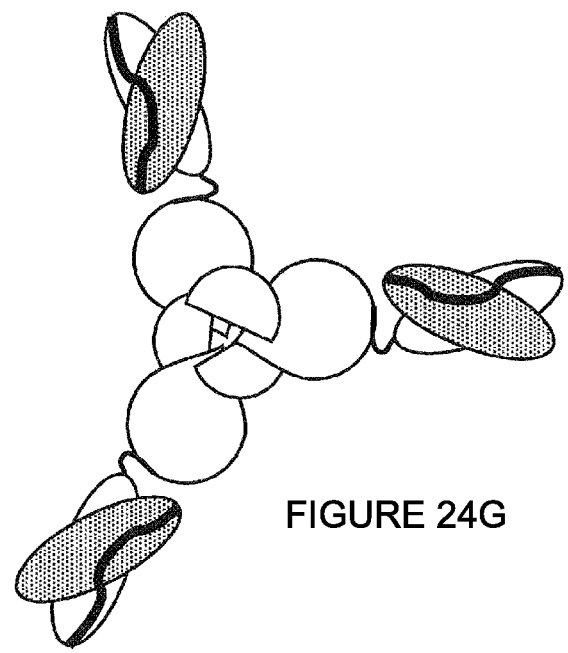

FIG. 24G: schematic diagram of molecular clustering on the cell-to-cell interface upon binding of the APRILiTE.

Figure 25:
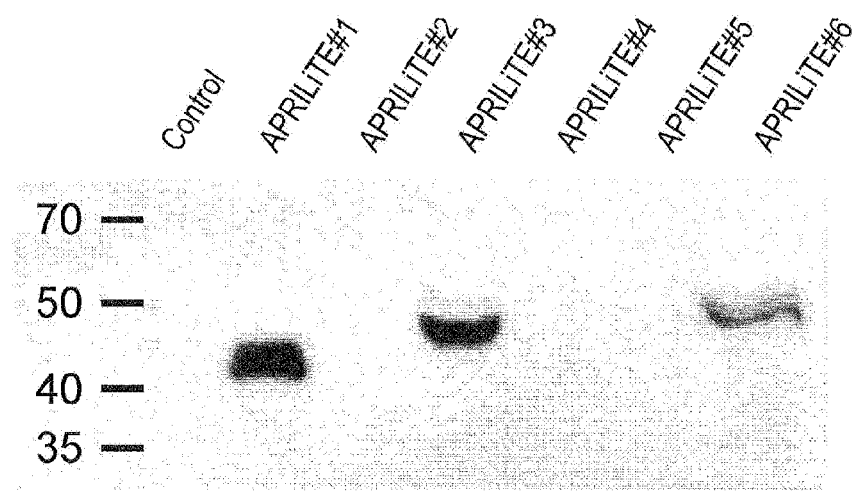

FIG. 25—Western blot of supernatant from 293T cells transfected with the different APRILiTE constructs. Blotting was done with anti-APRIL.

Figure 26A:
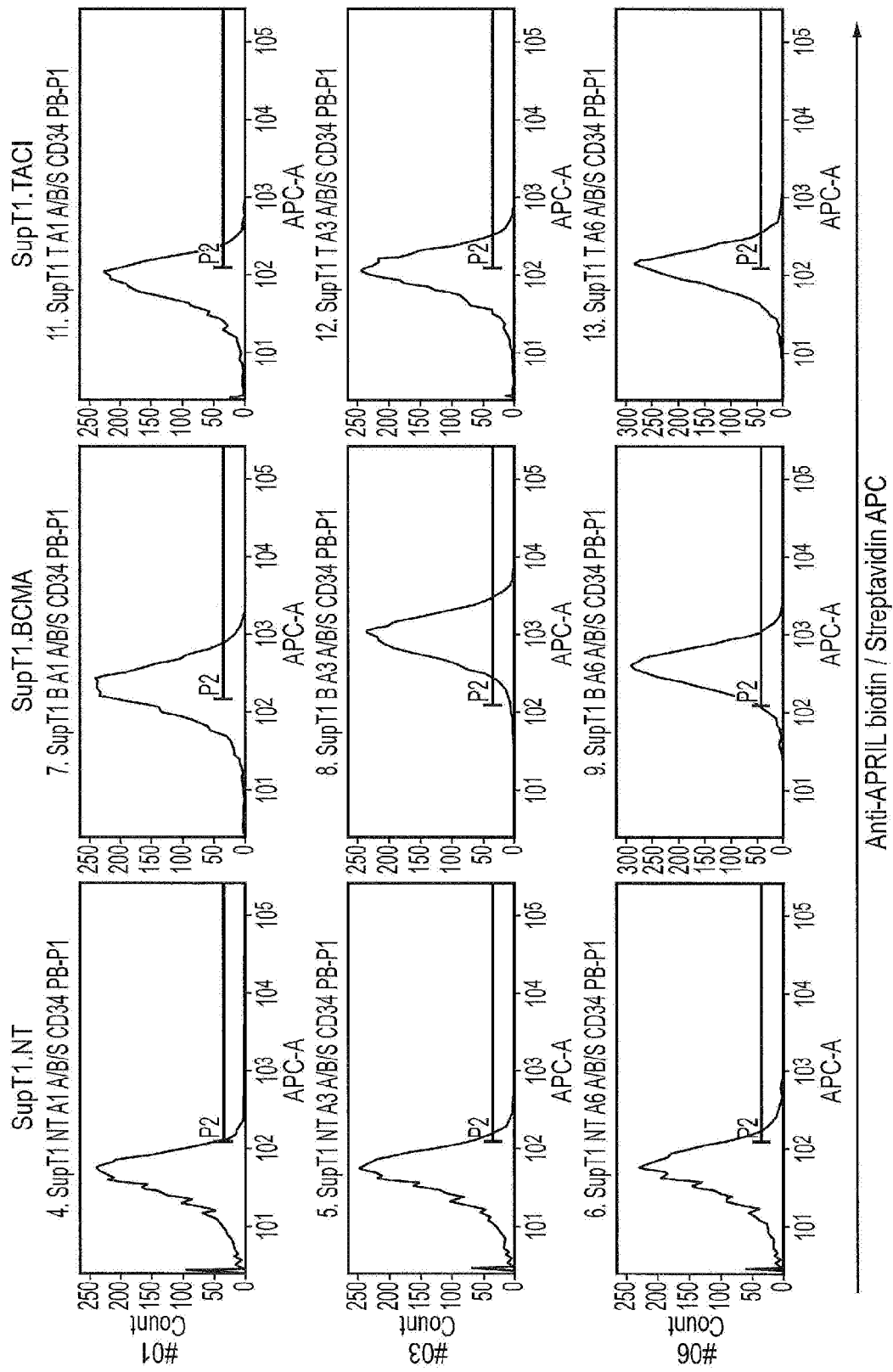

FIG. 26A—Binding of APRILiTES 1, 3 and 6 to wild-type SupT1 cells and SupT1 cells engineered to express BCMA and TACI. Staining is with anti-APRIL biotin/

Streptavidin APC. Aprilites show no binding to WT SupT1 cells but bind to BCMA expressing cells, and to a lesser extent to TACI expressing cells.

Figure 26B:
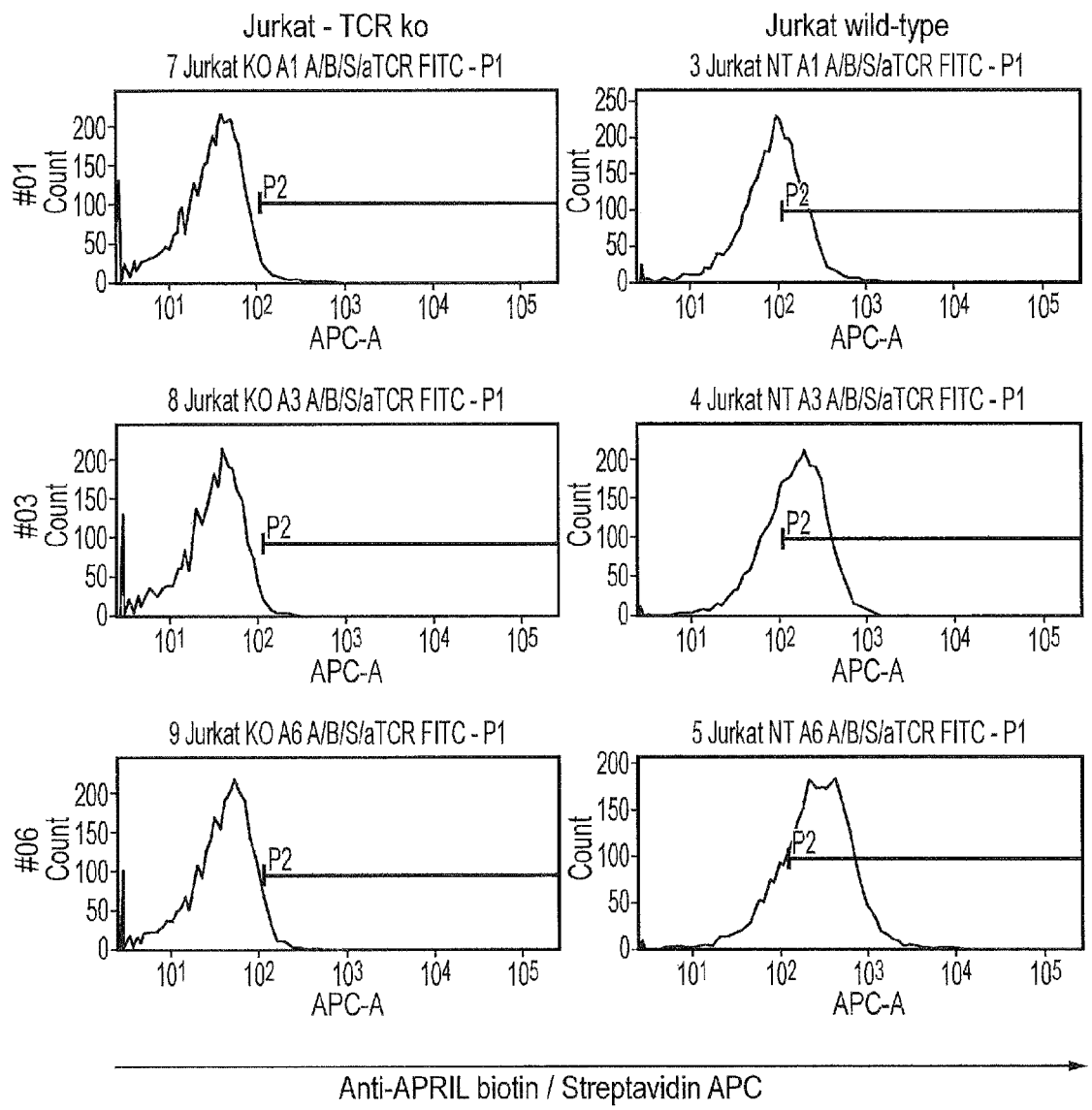

FIG. 26B—Binding of APRILiTEs to wild-type Jurkats, but not to Jurkats with no T-cell receptor. This demonstrates that the APRILiTES bind the T-cell receptor.

Figure 27:
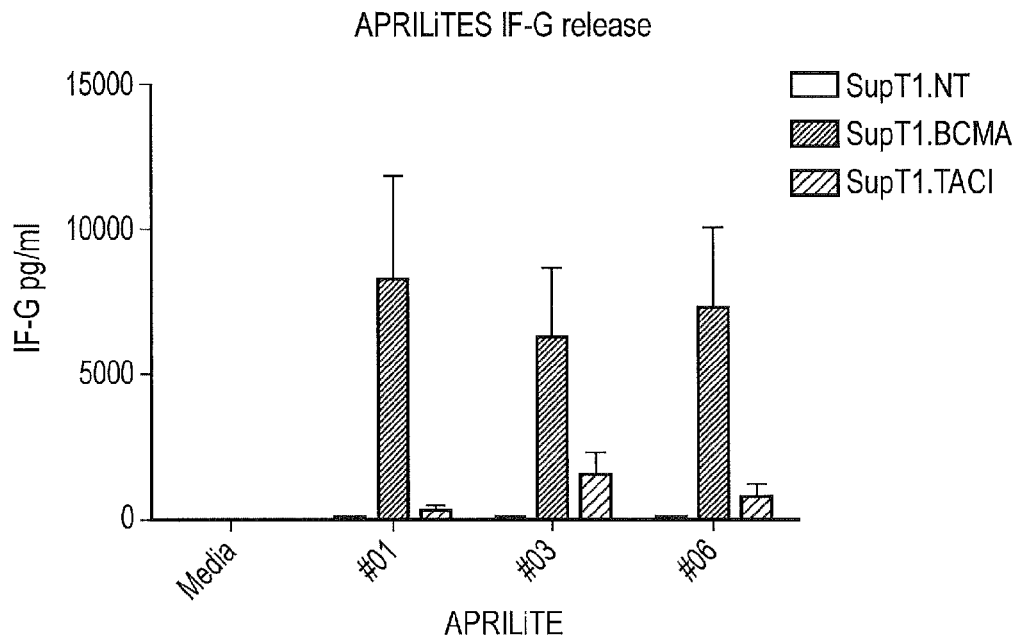

FIG. 27—Co-culture of T-cells 1:1 non-transduced or engineered SupT1 cells in the presence of blank media or the 3 APRILiTES.

Figure 28:
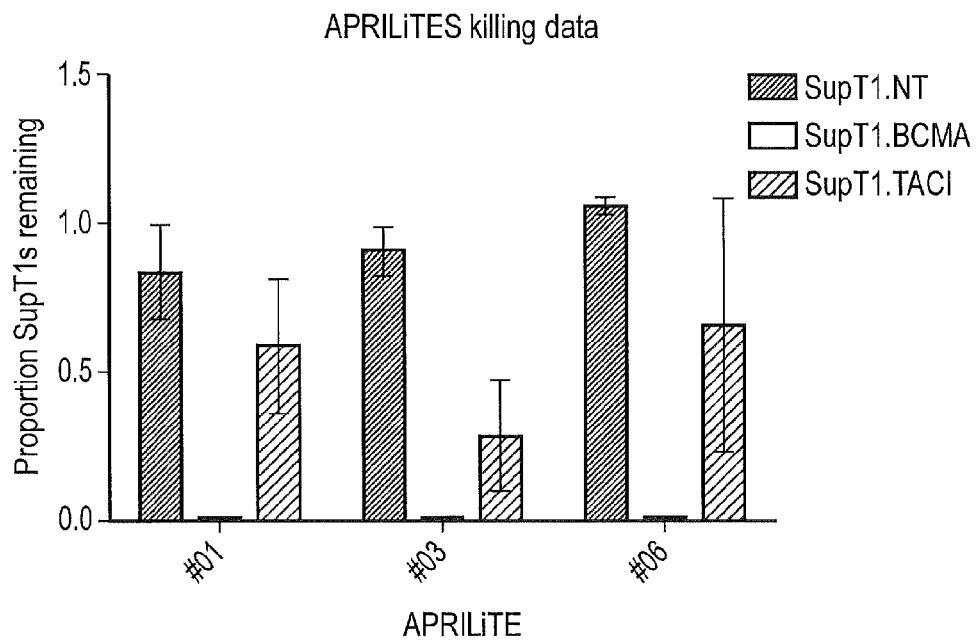

FIG. 28—Complete deletion of BCMA expressing SupT1 cells was observed after 3 day co-culture in the presence of APRILiTE 1, 3 and 6.

Figure 29:
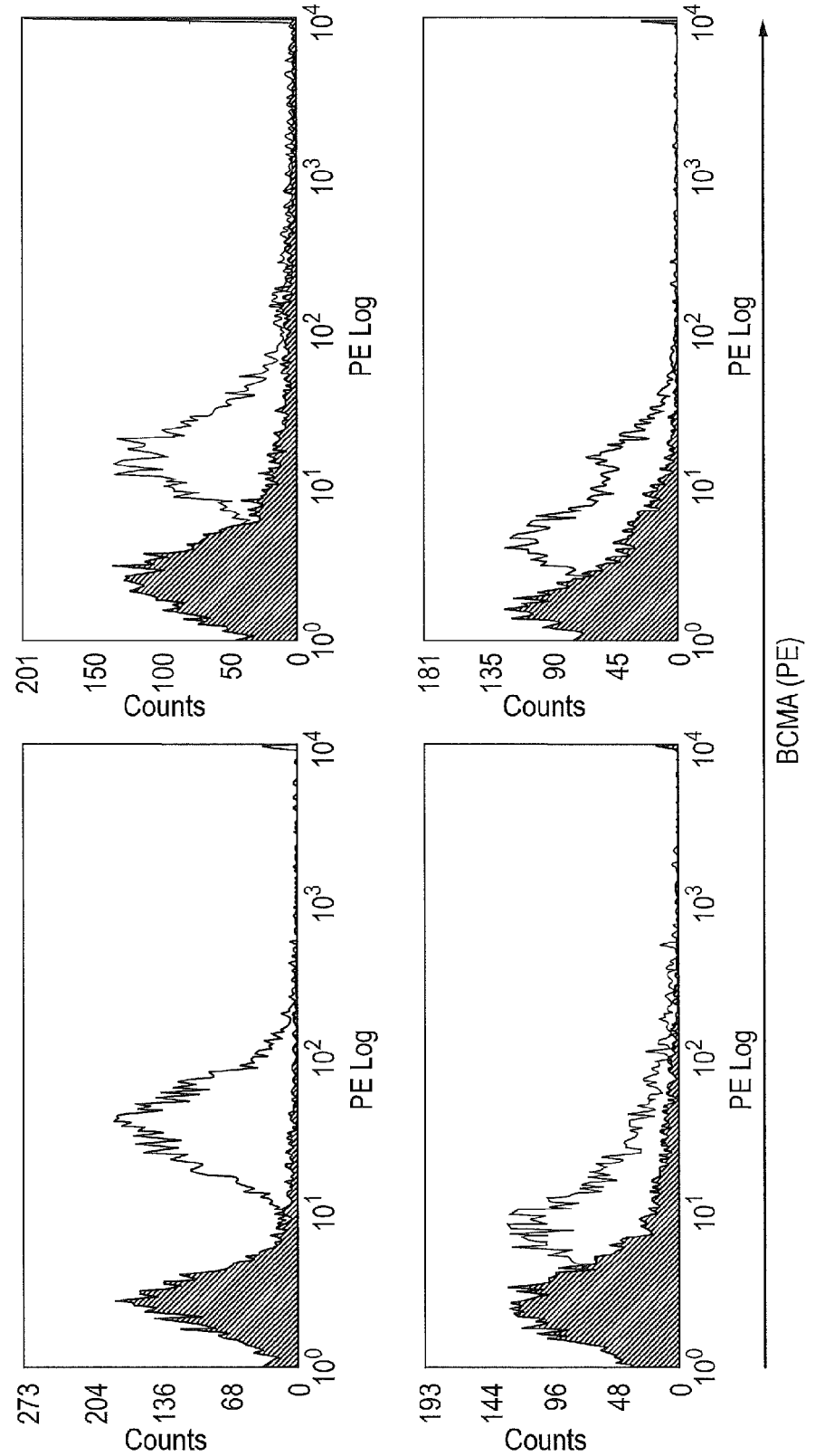

FIG. 29—Examples of BCMA expression on primary myelomas. Four examples of myeloma samples stained with the rat anti-human BCMA mAb Vicky1 is shown. The first panel shows bright BCMA staining in a patient with a plasma cell leukemia (an unusual, advanced and aggressive form of myeloma). The other three cases are clinically and morphologically typical myelomas. They show the intermediate or dim staining typically seen. Staining with isotype control (grey) is superimposed.

FIGS. 30A-30C—Amino acid sequence of APRILiTEs

FIG. 30A: APRILiTE #01 (SEQ ID NO: 96); FIG. 30B: APRILiTE #03 (SEQ ID NO: 97); FIG. 30C: APRILiTE #06 (SEQ ID NO: 98)

Figure 31:
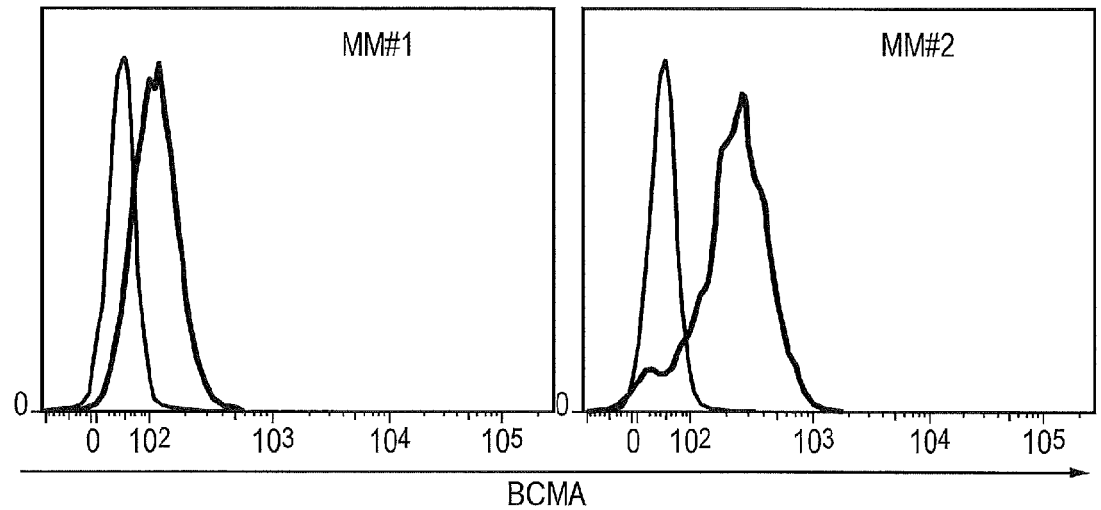

FIG. 31—Staining of myeloma samples for BCMA overlaid on isotype control. These myeloma cells express BCMA but at low levels FIG. 32—Low-power microscopy of co-cultures and controls at day 1. Clear clumping/activation of T-cells can be seen when cultured with myeloma cells in the presence of an APRILiTE.

Figure 33:
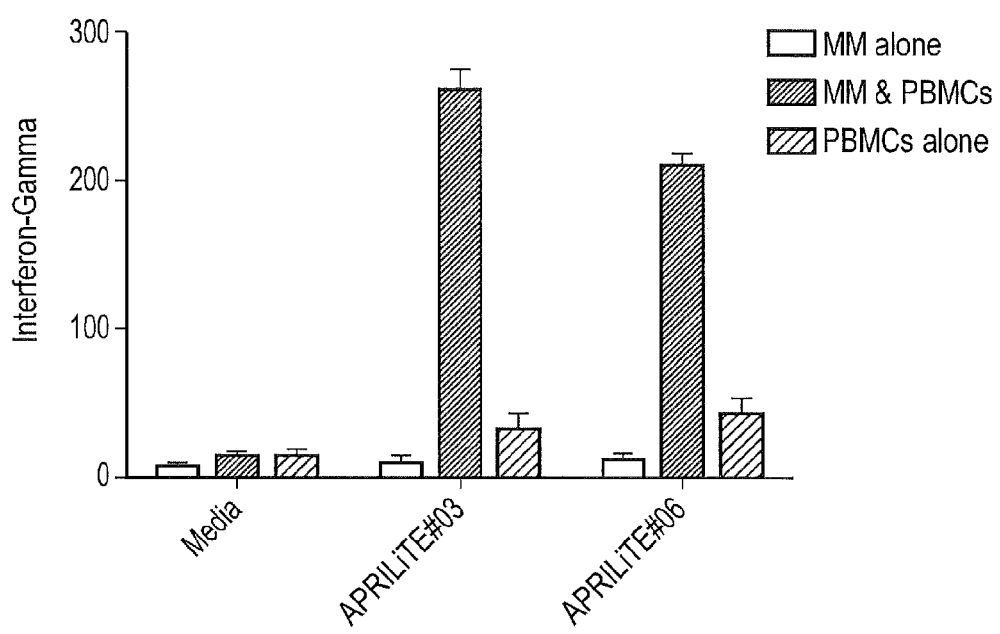

FIG. 33—Inteferon-gamma release with myeloma cells alone, co-cultured with peripheral blood T-cells, both together in the absence of and presence of APRILiTES #3 and #6

Figure 34:
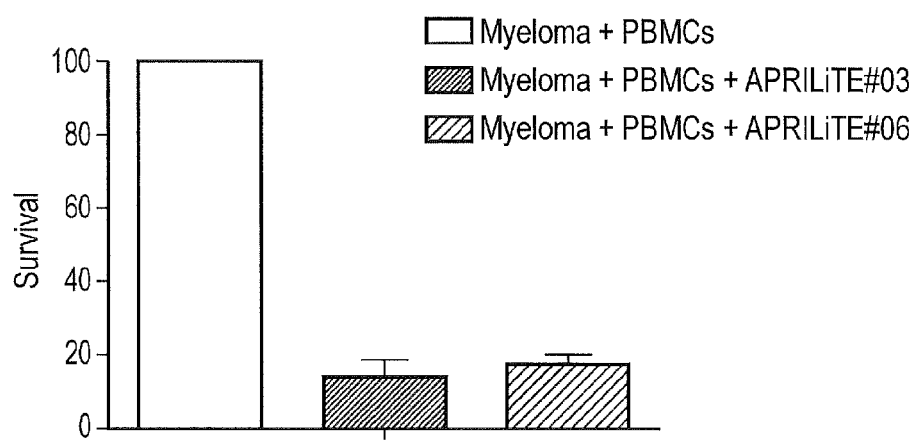

FIG. 34—Survival at day 6 of co-culture of myeloma cells in culture. Both APRILiTES tested result in efficient killing of primary myeloma cells in the presence of PBMCs.

Figure 35:
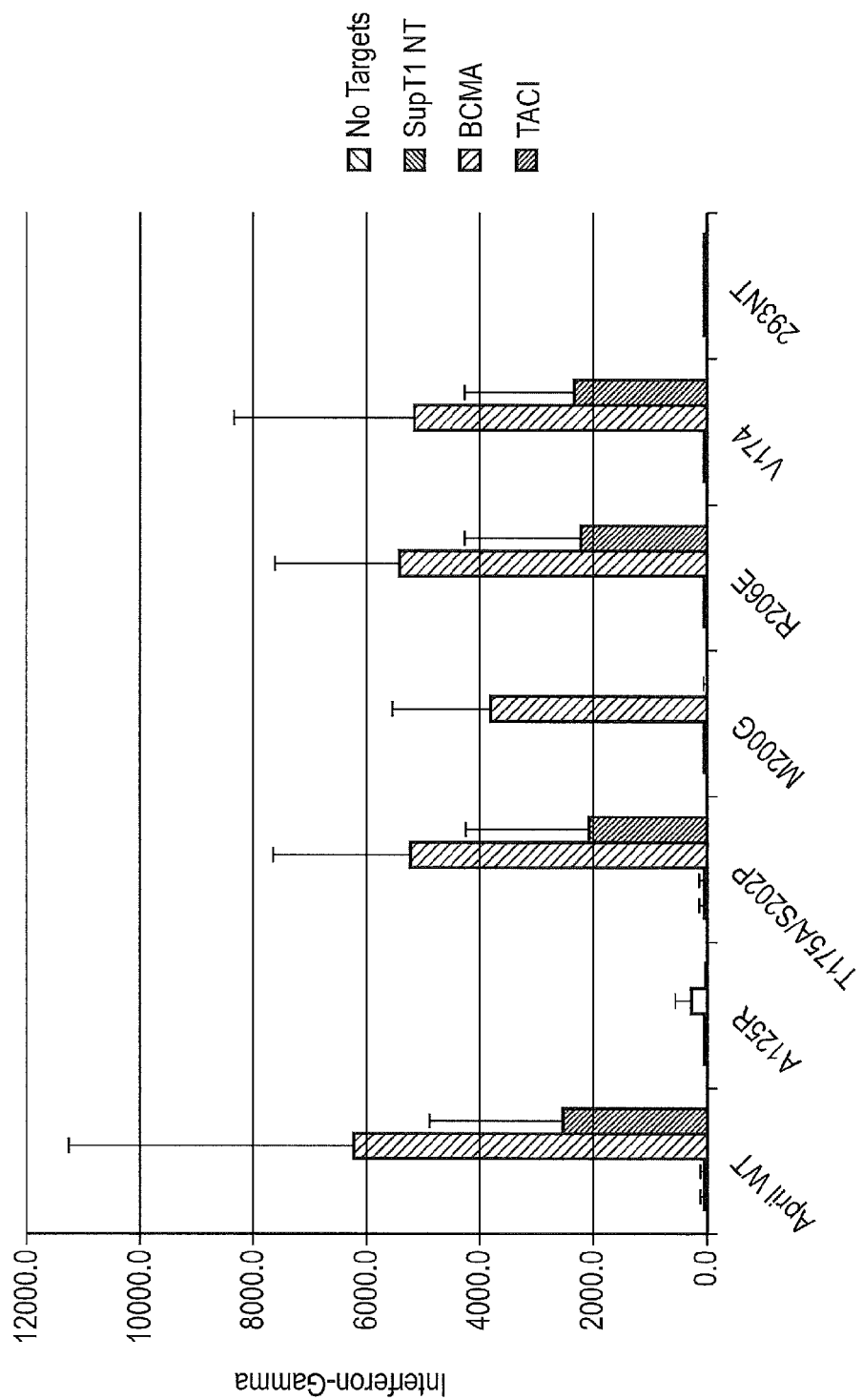

FIG. 35—Testing function of various APRIL mutants in a BITE format

Four normal donor PBMCs were incubated with SupT1 cells, SupT1 cells engineered to express BCMA, SupT1 cells engineered to express TACI or alone in the presence of different BiTES based on either WT APRIL or various mutants. Interferon-gamma levels were measured 24 hours later.

SUMMARY OF ASPECTS OF THE INVENTION

The present inventors have activated developed mutants of the BCMA-binding ligand APRIL, which have a higher BCMA:TACI binding ratio that wild-type APRIL. These mutants exhibit a greater degree of specificity for BCMA so provide more focussed targeting of BCMA-expressing cells for therapeutic and diagnostic applications.

Thus, in a first aspect the present invention provides a variant proliferation-inducing ligand (APRIL), which has a higher binding affinity to BCMA than wild-type APRIL; and/or altered binding kinetics compared with wild-type APRIL, and/or a higher BCMA:TACI (transmembrane activator and calcium modulator and cyclophilin ligand interactor) binding ratio than wild-type APRIL and which comprises mutations at one or more of the following positions: A125, V174, T175, M200, P201, S202, H203, D205 and R206.

The variant APRIL may comprise one of following the single mutations:
A125T,
V174T, V174G,
T175H, T175S, T175G,
M200C, M200L, M200G, M200S, M200A, M200N,
P201V, P201A, P201G, P201R, P201Y, P201W,
S202G, S202F, S202D, S202V, S202P, D205P.

The variant APRIL may comprise a combination of mutations at the following positions: V174 and T175; or V174 and M200; or V174 and S202; or T175 and M200, or T175 and S202; or D205 and R206; or V174, T175 and M200; or V174, T175 and S202; or T175, D205 and R206; or M200, D205 and R206; or V174, T175, M200 and S202; or T175, S202, D205 and R206.

The variant APRIL may comprise one of the following mutation combinations:
V174T and T175A; or V174T and M200G; or V174S and S202G; or
V174T and S202V; or V174G and S202G, or V174G and S202E; or
V174G and S202A; or V174G and S202G; or V174E and S202Y; or
T175A and S202E; or T175G and S202G; or T175G and S202V; or
T175A and S202P; or T175A and M200G; or T175S and S202G; or
S202V and H203N; or D205H and R206L; or D205P and R206K; or
D205P and R206N; or D205S and R206P; or D205R and R206G; or
D205P and R206I; or D205S and R206H; or
V174T, T175A and S202E; or V174T, T175A and M200G; or
T175A, D205P and R206N; or T175A, D205S and R206H; or
M200G, D205P and R206N; or M200G, D205S and R206H; or
V174T, T175A, M200G and S202E; or
T175A, S202E, D205P and R206N; or
T175A, S202E, D205S and R206H.

The present invention also provides a variant proliferation-inducing ligand (APRIL) which comprises the mutation M200G.

The present invention also provides a chimeric antigen receptor (CAR) which comprises an antigen-binding domain, a transmembrane domain and an endodomain, wherein the antigen-binding domain comprises a variant APRIL according to any the first aspect of the invention.

The present invention also provides a bispecific T-cell engager (BiTE) which comprises and antigen-binding domain and a T-cell activation domain, wherein the antigen-binding domain comprises a variant APRIL according to the first aspect of the invention.

In a second aspect, the present invention provides a nucleic acid sequence encoding a variant APRIL according to the first aspect of the invention, or a CAR or BiTE comprising such a variant APRIL.

In a third aspect the present invention provides a vector comprising a nucleic acid sequence according to the second aspect of the invention.

The present invention also provides a cell which comprises a chimeric antigen receptor comprising a variant APRIL according to the first aspect of the invention.

The present invention also provides a method for making such a cell which comprises the step of transducing or transfecting a cell with a vector according to the third aspect of the invention which comprises a nucleic acid sequence encoding a chimeric antigen receptor.

In a fourth aspect, the present invention provides a therapeutic agent which comprises a variant APRIL according to the first aspect of the invention, a CAR or BiTE comprising such a variant APRIL, a cell comprising such a CAR, a nucleic acid according to the second aspect of the invention or a vector according to the third aspect of the invention.

There is also provided a method for treating a plasma cell disorder which comprises the step of administering a therapeutic agent according to the fourth aspect of the invention to a subject.

There is also provided a therapeutic agent according to the fourth aspect of the invention for use in treating a plasma cell disorder.

There is also provided the use of a therapeutic agent according to the fourth aspect of the invention in the manufacture of a medicament for treating a plasma cell disorder.

In a fifth aspect, the present invention provides a diagnostic agent for detecting plasma cells which comprises a variant APRIL according to the first aspect of the invention.

There is also provided the diagnostic agent according to the fifth aspect of the invention for diagnosing a plasma cell disorder.

There is also provided a method for diagnosing a plasma cell disorder in a subject in vivo which comprises the step of administering a diagnostic agent according to the fifth aspect of the invention to the subject.

The is also provided a method for diagnosing a plasma cell disorder in a subject which comprises the step of adding a diagnostic agent according to the fifth aspect of the invention to a sample from the subject in vitro.

The sample may be, or be derived from, a blood sample.

The plasma cell disorder may be selected from: plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance and smoldering multiple myeloma.

The plasma cell disorder may be multiple myeloma.

DETAILED DESCRIPTION

APRIL

The present invention relates to a variant proliferation-inducing ligand (APRIL), which has a higher binding affinity to BCMA than wild-type APRIL; and/or altered binding kinetics compared with wild-type APRIL, and/or a higher BCMA:TACI (transmembrane activator and calcium modulator and cyclophilin ligand interactor) binding ratio than wild-type APRIL. APRIL is also known as TNFSF13.

The term "variant" is synonymous with "mutant" or "engineered" and means APRIL comprising one or more mutations, such as substitution(s), addition(s) or deletions(s). Typically the mutation is a substitution.

The wild-type sequence of APRIL is available at UNIPROT/O75888 and is shown below (SEQ ID No. 1). It is not a classical secreted protein in that it has no signal peptide. It has a furin cleavage site "KQKKQK" (underlined in SEQ ID No. 1). The amino terminus is involved in proteoglycan binding.

Kimberley et al (2009, FASEB J 23:1584-1595) is a study investigating the role of heparin sulphate proteoglycan (HSPG) interaction in APRIL signalling. Point mutations were generated as follows:

1) APRIL-triple (designated WT-triple), containing 3 point mutations: R146S, R189S, H220E;
2) APRIL-HSPG (designated HSPG), containing three point mutations in the hydrophobic motif (QKQKK$^{113}$Q);
3) APRIL-HSPG-triple (designated HSPG-triple), in which all 6 amino acids were mutated at both these sites.
4) APRIL-R231A, a form of APRIL capable of binding HSPGs but lacking the ability to bind either TACI or BCMA (FIG. 2) which comprises a key arginine to alanine mutation within the receptor binding region.

All mutants except APRIL-R231A retained the ability to bind both BCMA and TACI. The R23IA mutant showed complete loss of binding to both receptors but retained its ability to bind HSPGs.

The variant APRIL of the present invention may comprise the BCMA-binding site of APRIL. The variant APRIL may comprise a fragment of APRIL which comprises the BCMA-binding site.

The variant APRIL may comprise a truncated APRIL, which lacks the amino terminal end of the molecule. The truncated APRIL may retain BCMA and TACI binding but lose proteoglycan binding. Truncated APRIL can be cleaved at or immediately after the furin cleavage site. Truncated APRIL may lack the amino terminal 116 amino acids from the wild-type APRIL molecule shown as SEQ ID No. 1. Truncated APRIL may comprise the sequence shown as SEQ ID No. 2 (which corresponds to the portion of SEQ ID No. 1 shown in bold) or a variant thereof. This corresponds to the portion of the molecule which is needed for BCMA and TACI binding.

```
                                                            SEQ ID No. 1
         10         20         30         40         50         60
MPASSPFLLA PKGPPGNMGG PVREPALSVA LWLSWGAALG AVACAMALLT QQTELQSLRR 70         80         90        100        110        120
EVSRLQGTGG PSQNGEGYPW QSLPEQSSDA LEAWENGERS RKRRAVLTQK QKKQHSVLHL 130        140        150        160        170        180
VPINATSKDD SDVTEVMWQP ALRRGRGLQA QGYGVRIQDA GVYLLYSQVL FQDVTFTMGQ 190        200        210        220        230        240
VVSREGQGRQ ETLFRCIRSM PSHPDRAYNS CYSAGVFHLH QGDILSVIIP RARAKLNLSP

250
HGTFLGFVKL
                                                            SEQ ID No. 2
VLHLVPINATSKDDSDVTEVMWQPALRRGRGLQAQGYGVRIQDAGVYLLYSQVLFQDVTFTMG
QVVSREGQGRQETLFRCIRSMPSHPDRAYNSCYSAGVFHLHQGDILSVIIPRARAKLNLSPHG
TFLGFVKL
```

The variant APRIL or variant truncated APRIL has binding characteristics which make it more specific that wild-type APRIL. For instance, in some embodiments or applications, the variant APRIL has higher affinity to BCMA than wild-type APRIL. In some embodiments or applications, the variant APRIL has different binding kinetics to BCMA than wild-type APRIL. In some applications, the variant APRIL has a BCMA:TACI binding ratio is higher than wild-type APRIL or a combination thereof. The mutant APRIL comprises mutations at one or more of the following positions: A125, V174, T175, M200, P201, S202, H203, D205 and R206 (shown in grey in SEQ ID No. 1).

In particular, the variant APRIL may comprise one of following the single mutations: (SEQ IDs 3 to 26):

A125T,
V174T, V174G,
T175H, T175S, T175G,
M200C, M200L, M200G, M200S, M200A, M200N,
P201V, P201A, P201G, P201R, P201Y, P201W,
S202G, S202F, S202D, S202V, S202P, D205P.

These mutations have been determined to alter binding to BCMA and TACI in a manner which may be useful to BCMA targeting. The relative binding to BCMA and TACI is shown in Table 1, illustrated in FIG. 10 with some examples shown in FIG. 12A-12F.

TABLE 1

| Mutation | % BCMA WT | % TACI WT | Sequence |
|---|---|---|---|
| A125T | 46 | 42 | SEQ ID NO: 3 |
| V174T | 379 | 500 | SEQ ID NO: 4 |
| V174G | 109 | 34 | SEQ ID NO: 5 |
| T175H | 144 | 78 | SEQ ID NO: 6 |
| T175S | 129 | 35 | SEQ ID NO: 7 |
| T175G | 67 | 41 | SEQ ID NO: 8 |
| M200C | 50 | 0 | SEQ ID NO: 9 |
| M200L | 164 | 62 | SEQ ID NO: 10 |
| M200G | 35 | 0 | SEQ ID NO: 11 |
| M200S | 10 | 0 | SEQ ID NO: 12 |
| M200A | 20 | 3 | SEQ ID NO: 13 |
| M200N | 12 | 4 | SEQ ID NO: 14 |
| P201V | 20 | 1 | SEQ ID NO: 15 |
| P201A | 24 | 18 | SEQ ID NO: 16 |
| P201G | 13 | 4 | SEQ ID NO: 17 |
| P201R | 8 | 3 | SEQ ID NO: 18 |
| P201Y | 9 | 0 | SEQ ID NO: 19 |
| P201W | 6 | 5 | SEQ ID NO: 20 |
| S202G | 116 | 68 | SEQ ID NO: 21 |
| S202F | 28 | 30 | SEQ ID NO: 22 |
| S202D | 30 | 32 | SEQ ID NO: 23 |
| S202V | 204 | 232 | SEQ ID NO: 24 |
| S202P | 163 | 218 | SEQ ID NO: 25 |
| D205P | 26 | 18 | SEQ ID NO: 26 |

SEQ ID 3 (A125T)
VLHLVPINTTSKDDSDVTEVMWQPALRRGRGLQAQGYGVRIQDAGVYLLYSQVLFQDVTFTMG
QVVSREGQGRQETLFRCIRSMPSHPDRAYNSCYSAGVFHLHQGDILSVIIPRARAKLNLSPHG
TFLGFVKL

SEQ ID 4 (V174T)
VLHLVPINATSKDDSDVTEVMWQPALRRGRGLQAQGYGVRIQDAGVYLLYSQVLFQDTTFTMG
QVVSREGQGRQETLFRCIRSMPSHPDRAYNSCYSAGVFHLHQGDILSVIIPRARAKLNLSPHG
TFLGFVKL

TABLE 1-continued

| Mutation | % BCMA WT | % TACI WT | Sequence |
|---|---|---|---|

SEQ ID 5 (V174G)
VLHLVPINATSKDDSDVTEVMWQPALRRGRGLQAQGYGVRIQDAGVYLLYSQVLFQDGTFTMG
QVVSREGQGRQETLFRCIRSMPSHPDRAYNSCYSAGVFHLHQGDILSVIIPRARAKLNLSPHG
TFLGFVKL

SEQ ID 6 (T175H)
VLHLVPINATSKDDSDVTEVMWQPALRRGRGLQAQGYGVRIQDAGVYLLYSQVLFQDVHFTMG
QVVSREGQGRQETLFRCIRSMPSHPDRAYNSCYSAGVFHLHQGDILSVIIPRARAKLNLSPHG
TFLGFVKL

SEQ ID 7 (T175S)
VLHLVPINATSKDDSDVTEVMWQPALRRGRGLQAQGYGVRIQDAGVYLLYSQVLFQDVSFTMG
QVVSREGQGRQETLFRCIRSMPSHPDRAYNSCYSAGVFHLHQGDILSVIIPRARAKLNLSPHG
TFLGFVKL

SEQ ID 8 (T175G)
VLHLVPINATSKDDSDVTEVMWQPALRRGRGLQAQGYGVRIQDAGVYLLYSQVLFQDVGFTMG
QVVSREGQGRQETLFRCIRSMPSHPDRAYNSCYSAGVFHLHQGDILSVIIPRARAKLNLSPHG
TFLGFVKL

SEQ ID 9 (M200C)
VLHLVPINATSKDDSDVTEVMWQPALRRGRGLQAQGYGVRIQDAGVYLLYSQVLFQDVTFTMG
QVVSREGQGRQETLFRCIRSCPSHPDRAYNSCYSAGVFHLHQGDILSVIIPRARAKLNLSPHG
TFLGFVKL

SEQ ID 10 (M200L)
VLHLVPINATSKDDSDVTEVMWQPALRRGRGLQAQGYGVRIQDAGVYLLYSQVLFQDVTFTMG
QVVSREGQGRQETLFRCIRSLPSHPDRAYNSCYSAGVFHLHQGDILSVIIPRARAKLNLSPHG
TFLGFVKL

SEQ ID 11 (M200G)
VLHLVPINATSKDDSDVTEVMWQPALRRGRGLQAQGYGVRIQDAGVYLLYSQVLFQDVTFTMG
QVVSREGQGRQETLFRCIRSGPSHPDRAYNSCYSAGVFHLHQGDILSVIIPRARAKLNLSPHG
TFLGFVKL

SEQ ID 12 (M200S)
VLHLVPINATSKDDSDVTEVMWQPALRRGRGLQAQGYGVRIQDAGVYLLYSQVLFQDVTFTMG
QVVSREGQGRQETLFRCIRSSPSHPDRAYNSCYSAGVFHLHQGDILSVIIPRARAKLNLSPHG
TFLGFVKL

SEQ ID 13 (M200A)
VLHLVPINATSKDDSDVTEVMWQPALRRGRGLQAQGYGVRIQDAGVYLLYSQVLFQDVTFTMG
QVVSREGQGRQETLFRCIRSAPSHPDRAYNSCYSAGVFHLHQGDILSVIIPRARAKLNLSPHG
TFLGFVKL

SEQ ID 14 (M200N)
VLHLVPINATSKDDSDVTEVMWQPALRRGRGLQAQGYGVRIQDAGVYLLYSQVLFQDVTFTMG
QVVSREGQGRQETLFRCIRSNPSHPDRAYNSCYSAGVFHLHQGDILSVIIPRARAKLNLSPHG
TFLGFVKL

SEQ ID 15 (P201V)
VLHLVPINATSKDDSDVTEVMWQPALRRGRGLQAQGYGVRIQDAGVYLLYSQVLFQDVTFTMG
QVVSREGQGRQETLFRCIRSMVSHPDRAYNSCYSAGVFHLHQGDILSVIIPRARAKLNLSPHG
TFLGFVKL

SEQ ID 16 (P201A)
VLHLVPINATSKDDSDVTEVMWQPALRRGRGLQAQGYGVRIQDAGVYLLYSQVLFQDVTFTMG
QVVSREGQGRQETLFRCIRSMASHPDRAYNSCYSAGVFHLHQGDILSVIIPRARAKLNLSPHG
TFLGFVKL

SEQ ID 17 (P201G)
VLHLVPINATSKDDSDVTEVMWQPALRRGRGLQAQGYGVRIQDAGVYLLYSQVLFQDVTFTMG
QVVSREGQGRQETLFRCIRSMGSHPDRAYNSCYSAGVFHLHQGDILSVIIPRARAKLNLSPHG
TFLGFVKL

SEQ ID 18 (P201Y)
VLHLVPINATSKDDSDVTEVMWQPALRRGRGLQAQGYGVRIQDAGVYLLYSQVLFQDVTFTMG
QVVSREGQGRQETLFRCIRSMYSHPDRAYNSCYSAGVFHLHQGDILSVIIPRARAKLNLSPHG
TFLGFVKL

SEQ ID 19 (P201R)
VLHLVPINATSKDDSDVTEVMWQPALRRGRGLQAQGYGVRIQDAGVYLLYSQVLFQDVTFTMG
QVVSREGQGRQETLFRCIRSMRSHPDRAYNSCYSAGVFHLHQGDILSVIIPRARAKLNLSPHG
TFLGFVKL

TABLE 1-continued

| Mutation | % BCMA WT | % TACI WT | Sequence |
|---|---|---|---|

SEQ ID 20 (P201W)
VLHLVPINATSKDDSDVTEVMWQPALRRGRGLQAQGYGVRIQDAGVYLLYSQVLFQDVTFTMG
QVVSREGQGRQETLFRCIRSMWSHPDRAYNSCYSAGVFHLHQGDILSVIIPRARAKLNLSPHG
TFLGFVKL

SEQ ID 21 (S202G)
VLHLVPINATSKDDSDVTEVMWQPALRRGRGLQAQGYGVRIQDAGVYLLYSQVLFQDVTFTMG
QVVSREGQGRQETLFRCIRSMPGHPDRAYNSCYSAGVFHLHQGDILSVIIPRARAKLNLSPHG
TFLGFVKL

SEQ ID 22 (S202F)
VLHLVPINATSKDDSDVTEVMWQPALRRGRGLQAQGYGVRIQDAGVYLLYSQVLFQDVTFTMG
QVVSREGQGRQETLFRCIRSMPFHPDRAYNSCYSAGVFHLHQGDILSVIIPRARAKLNLSPHG
TFLGFVKL

SEQ ID 23 (S202D)
VLHLVPINATSKDDSDVTEVMWQPALRRGRGLQAQGYGVRIQDAGVYLLYSQVLFQDVTFTMG
QVVSREGQGRQETLFRCIRSMPDHPDRAYNSCYSAGVFHLHQGDILSVIIPRARAKLNLSPHG
TFLGFVKL

SEQ ID 24 (S202V)
VLHLVPINATSKDDSDVTEVMWQPALRRGRGLQAQGYGVRIQDAGVYLLYSQVLFQDVTFTMG
QVVSREGQGRQETLFRCIRSMPVHPDRAYNSCYSAGVFHLHQGDILSVIIPRARAKLNLSPHG
TFLGFVKL

SEQ ID 25 (S202P)
VLHLVPINATSKDDSDVTEVMWQPALRRGRGLQAQGYGVRIQDAGVYLLYSQVLFQDVTFTMG
QVVSREGQGRQETLFRCIRSMPPHPDRAYNSCYSAGVFHLHQGDILSVIIPRARAKLNLSPHG
TFLGFVKL

SEQ ID 26 (D205P)
VLHLVPINATSKDDSDVTEVMWQPALRRGRGLQAQGYGVRIQDAGVYLLYSQVLFQDVTFTMG
QVVSREGQGRQETLFRCIRSMPSHPPRAYNSCYSAGVFHLHQGDILSVIIPRARAKLNLSPHG
TFLGFVKL

The variant APRIL may comprise a combination of mutations at the following positions: V174 and T175; or V174 and M200; or V174 and S202; or T175 and M200, or T175 and S202; or S202 and H203; or D205 and R206; or V174, T175 and M200; or V174, T175 and S202; or T175, D205 and R206; or M200, D205 and R206; or V174, T175, M200 and S202; or T175, S202, D205 and R206;

In particular, the variant APRIL may comprise one of the following specific combined mutations:
- V174T and T175A; or V174T and M200G; or V174S and S202G; or
- V174T and S202V; or V174G and S202G, or V174G and S202E; or
- V174G and S202A; or V174G and S202G; or V174E and S202Y; or
- T175A and S202E; or T175G and S202G; or T175G and S202V; or
- T175A and S202P; or T175A and M200G; or T175S and S202G; or
- S202V and H203N; or D205H and R206L; or D205P and R206K; or
- D205P and R206N; or D205S and R206P; or D205R and R206G; or
- D205P and R206I; or D205S and R206H; or
- V174T, T175A and S202E; or V174T, T175A and M200G; or
- T175A, D205P and R206N; or T175A, D205S and R206H; or
- M200G, D205P and R206N; or M200G, D205S and R206H; or
- V174T, T175A, M200G and S202E; or
- T175A, S202E, D205P and R206N; or
- T175A, S202E, D205S and R206H.

These specific combined mutations have been shown to alter binding to BCMA and TACI in a manner which is useful to BCMA targeting (see Table 2 and FIG. 11).

TABLE 2

| Mutation | % BCMA WT | % TACI WT | Sequence |
|---|---|---|---|
| V174T, T175A | 131 | 80 | SEQ ID 27 |
| V174T, M200G | 172 | 49 | SEQ ID 28 |
| V174S, S202G | 43 | 13 | SEQ ID 29 |
| V174T, S202V | 303 | 613 | SEQ ID 30 |
| V174G, S202G | 67 | 24 | SEQ ID 31 |
| V174G, S202E | 35 | 18 | SEQ ID 32 |
| V174G, S202A | 132 | 36 | SEQ ID 33 |

TABLE 2-continued

| Mutation | % BCMA WT | % TACI WT | Sequence |
|---|---|---|---|
| V174G, S202G | 29 | 49 | SEQ ID 34 |
| V174E, S202Y | 33 | 15 | SEQ ID 35 |
| T175A, S202E | 87 | 15 | SEQ ID 36 |
| T175G, S202G | 34 | 17 | SEQ ID 37 |
| T175G, S202V | 59 | 30 | SEQ ID 38 |
| T175A, S202P | 100 | 0 | SEQ ID 39 |
| T175A, M200G | 14 | 1 | SEQ ID 40 |
| T175s, s202G | 43 | 13 | SEQ ID 41 |
| S202V, H203N | 11 | 24 | SEQ ID 42 |
| D205H, R206L | 357 | 86 | SEQ ID 43 |
| D205P, R206K | 255 | 90 | SEQ ID 44 |
| D205P, R206N | 111 | 138 | SEQ ID 45 |
| D205S, R206P | 420 | 81 | SEQ ID 46 |
| D205R, R206G | 404 | 84 | SEQ ID 47 |
| D205P, R206I | 343 | 54 | SEQ ID 48 |
| D205S, R206H | 234 | 112 | SEQ ID 49 |
| V174T, T175A, S202E | 186 | 87 | SEQ ID 50 |
| V174T, T175A, M200G | 28 | 4 | SEQ ID 51 |
| T175A, D205P, R206N | 13 | 1 | SEQ ID 52 |
| T175A, D205S, R206H | 15 | 2 | SEQ ID 53 |
| M200G, D205P, R206N | 53 | 4 | SEQ ID 54 |
| M200G, D205S, T206H | 68 | 15 | SEQ ID 55 |
| V174T, T175A, M200G, S202E | 43 | 0 | SEQ ID 56 |
| T175A, S202E, D205P, T206N | 19 | 0 | SEQ ID 57 |
| T175A, S202E, D205S, T206H | 28 | 0 | SEQ ID 58 |

SEQ ID 27 (V174T, T175A)
VLHLVPINATSKDDSDVTEVMWQPALRRGRGLQAQGYGVRIQDAGVYLLYSQVLFQDTAFTMG
QVVSREGQGRQETLFRCIRSMPSHPDRAYNSCYSAGVFHLHQGDILSVIIPRARAKLNLSPHG
TFLGFVKL

SEQ ID 28 (V174T, M200G)
VLHLVPINATSKDDSDVTEVMWQPALRRGRGLQAQGYGVRIQDAGVYLLYSQVLFQDTTFTMG
QVVSREGQGRQETLFRCIRSGPSHPDRAYNSCYSAGVFHLHQGDILSVIIPRARAKLNLSPHG
TFLGFVKL

SEQ ID 29 (V174S, S202G)
VLHLVPINATSKDDSDVTEVMWQPALRRGRGLQAQGYGVRIQDAGVYLLYSQVLFQDSTFTMG
QVVSREGQGRQETLFRCIRSMPGHPDRAYNSCYSAGVFHLHQGDILSVIIPRARAKLNLSPHG
TFLGFVKL

SEQ ID 30 (V174T, S202V)
VLHLVPINATSKDDSDVTEVMWQPALRRGRGLQAQGYGVRIQDAGVYLLYSQVLFQDTTFTMG
QVVSREGQGRQETLFRCIRSMPVHPDRAYNSCYSAGVFHLHQGDILSVIIPRARAKLNLSPHG
TFLGFVKL

SEQ ID 31 (V174G, S202G)
VLHLVPINATSKDDSDVTEVMWQPALRRGRGLQAQGYGVRIQDAGVYLLYSQVLFQDGTFTMG
QVVSREGQGRQETLFRCIRSMPGHPDRAYNSCYSAGVFHLHQGDILSVIIPRARAKLNLSPHG
TFLGFVKL

TABLE 2-continued

| Mutation | % BCMA WT | % TACI WT | Sequence |
| --- | --- | --- | --- |

SEQ ID 32 (V174G, S202E)
VLHLVPINATSKDDSDVTEVMWQPALRRGRGLQAQGYGVRIQDAGVYLLYSQVLFQDGTFTMG
QVVSREGQGRQETLFRCIRSMPEHPDRAYNSCYSAGVFHLHQGDILSVIIPRARAKLNLSPHG
TFLGFVKL

SEQ ID 33 (V174G, S202A)
VLHLVPINATSKDDSDVTEVMWQPALRRGRGLQAQGYGVRIQDAGVYLLYSQVLFQDGTFTMG
QVVSREGQGRQETLFRCIRSMPAHPDRAYNSCYSAGVFHLHQGDILSVIIPRARAKLNLSPHG
TFLGFVKL

SEQ ID 34 (V174G, S202G)
VLHLVPINATSKDDSDVTEVMWQPALRRGRGLQAQGYGVRIQDAGVYLLYSQVLFQDGTFTMG
QVVSREGQGRQETLFRCIRSMPGHPDRAYNSCYSAGVFHLHQGDILSVIIPRARAKLNLSPHG
TFLGFVKL

SEQ ID 35 (V174E, S202Y)
VLHLVPINATSKDDSDVTEVMWQPALRRGRGLQAQGYGVRIQDAGVYLLYSQVLFQDETFTMG
QVVSREGQGRQETLFRCIRSMPYHPDRAYNSCYSAGVFHLHQGDILSVIIPRARAKLNLSPHG
TFLGFVKL

SEQ ID 36 (T175A, S202E)
VLHLVPINATSKDDSDVTEVMWQPALRRGRGLQAQGYGVRIQDAGVYLLYSQVLFQDVAFTMG
QVVSREGQGRQETLFRCIRSMPEHPDRAYNSCYSAGVFHLHQGDILSVIIPRARAKLNLSPHG
TFLGFVKL

SEQ ID 37 (T175G, S202G)
VLHLVPINATSKDDSDVTEVMWQPALRRGRGLQAQGYGVRIQDAGVYLLYSQVLFQDVGFTMG
QVVSREGQGRQETLFRCIRSMPGHPDRAYNSCYSAGVFHLHQGDILSVIIPRARAKLNLSPHG
TFLGFVKL

SEQ ID 38 (T175G, S202V)
VLHLVPINATSKDDSDVTEVMWQPALRRGRGLQAQGYGVRIQDAGVYLLYSQVLFQDVGFTMG
QVVSREGQGRQETLFRCIRSMPVHPDRAYNSCYSAGVFHLHQGDILSVIIPRARAKLNLSPHG
TFLGFVKL

SEQ ID 39 (T175A, S202P)
VLHLVPINATSKDDSDVTEVMWQPALRRGRGLQAQGYGVRIQDAGVYLLYSQVLFQDVAFTMG
QVVSREGQGRQETLFRCIRSMPPHPDRAYNSCYSAGVFHLHQGDILSVIIPRARAKLNLSPHG
TFLGFVKL

SEQ ID 40 (T175A, M200G)
VLHLVPINATSKDDSDVTEVMWQPALRRGRGLQAQGYGVRIQDAGVYLLYSQVLFQDVAFTMG
QVVSREGQGRQETLFRCIRSGPSHPDRAYNSCYSAGVFHLHQGDILSVIIPRARAKLNLSPHG
TFLGFVKL

SEQ ID 41 T175S, S202G
VLHLVPINATSKDDSDVTEVMWQPALRRGRGLQAQGYGVRIQDAGVYLLYSQVLFQDVSFTMG
QVVSREGQGRQETLFRCIRSMPGHPDRAYNSCYSAGVFHLHQGDILSVIIPRARAKLNLSPHG
TFLGFVKL

SEQ ID 42 (S202V, H203N)
VLHLVPINATSKDDSDVTEVMWQPALRRGRGLQAQGYGVRIQDAGVYLLYSQVLFQDVTFTMG
QVVSREGQGRQETLFRCIRSMPVNPDRAYNSCYSAGVFHLHQGDILSVIIPRARAKLNLSPHG
TFLGFVKL

SEQ ID 43 (D205H, R206L)
VLHLVPINATSKDDSDVTEVMWQPALRRGRGLQAQGYGVRIQDAGVYLLYSQVLFQDVTFTMG
QVVSREGQGRQETLFRCIRSMPSHPHLAYNSCYSAGVFHLHQGDILSVIIPRARAKLNLSPHG
TFLGFVKL

SEQ ID 44 (D205P, R206K)
VLHLVPINATSKDDSDVTEVMWQPALRRGRGLQAQGYGVRIQDAGVYLLYSQVLFQDVTFTMG
QVVSREGQGRQETLFRCIRSMPSHPPKAYNSCYSAGVFHLHQGDILSVIIPRARAKLNLSPHG
TFLGFVKL

SEQ ID 45 (D205P, R206N)
VLHLVPINATSKDDSDVTEVMWQPALRRGRGLQAQGYGVRIQDAGVYLLYSQVLFQDVTFTMG
QVVSREGQGRQETLFRCIRSMPSHPPNAYNSCYSAGVFHLHQGDILSVIIPRARAKLNLSPHG
TFLGFVKL

SEQ ID 46 (D205S, R206P)
VLHLVPINATSKDDSDVTEVMWQPALRRGRGLQAQGYGVRIQDAGVYLLYSQVLFQDVTFTMG
QVVSREGQGRQETLFRCIRSMPSHPSPAYNSCYSAGVFHLHQGDILSVIIPRARAKLNLSPHG
TFLGFVKL

TABLE 2-continued

| Mutation | % BCMA WT | % TACI WT | Sequence |
|---|---|---|---|

SEQ ID 47 (D205R, R206G)
VLHLVPINATSKDDSDVTEVMWQPALRRGRGLQAQGYGVRIQDAGVYLLYSQVLFQDVTFTMG
QVVSREGQGRQETLFRCIRSMPSHPRGAYNSCYSAGVFHLHQGDILSVIIPRARAKLNLSPHG
TFLGFVKL

SEQ ID 48 (D205P, R206I)
VLHLVPINATSKDDSDVTEVMWQPALRRGRGLQAQGYGVRIQDAGVYLLYSQVLFQDVTFTMG
QVVSREGQGRQETLFRCIRSMPSHPPIAYNSCYSAGVFHLHQGDILSVIIPRARAKLNLSPHG
TFLGFVKL

SEQ ID 49 (D205S, R206H)
VLHLVPINATSKDDSDVTEVMWQPALRRGRGLQAQGYGVRIQDAGVYLLYSQVLFQDVTFTMG
QVVSREGQGRQETLFRCIRSMPSHPSHAYNSCYSAGVFHLHQGDILSVIIPRARAKLNLSPHG
TFLGFVKL

SEQ ID 50 (V174T, T175A, S202E)
VLHLVPINATSKDDSDVTEVMWQPALRRGRGLQAQGYGVRIQDAGVYLLYSQVLFQDTAFTMG
QVVSREGQGRQETLFRCIRSMPEHPDRAYNSCYSAGVFHLHQGDILSVIIPRARAKLNLSPHG
TFLGFVKL

SEQ ID 51 (V174T, T175A, M200G)
VLHLVPINATSKDDSDVTEVMWQPALRRGRGLQAQGYGVRIQDAGVYLLYSQVLFQDTAFTMG
QVVSREGQGRQETLFRCIRSGPSHPDRAYNSCYSAGVFHLHQGDILSVIIPRARAKLNLSPHG
TFLGFVKL

SEQ ID 52 (T175A, D205P, R206N)
VLHLVPINATSKDDSDVTEVMWQPALRRGRGLQAQGYGVRIQDAGVYLLYSQVLFQDVAFTMG
QVVSREGQGRQETLFRCIRSMPSHPPNAYNSCYSAGVFHLHQGDILSVIIPRARAKLNLSPHG
TFLGFVKL

SEQ ID 53 (T175A, D205S, R206H)
VLHLVPINATSKDDSDVTEVMWQPALRRGRGLQAQGYGVRIQDAGVYLLYSQVLFQDVAFTMG
QVVSREGQGRQETLFRCIRSMPSHPSHAYNSCYSAGVFHLHQGDILSVIIPRARAKLNLSPHG
TFLGFVKL

SEQ ID 54 (M200G, D205P, R206N)
VLHLVPINATSKDDSDVTEVMWQPALRRGRGLQAQGYGVRIQDAGVYLLYSQVLFQDVTFTMG
QVVSREGQGRQETLFRCIRSGPSHPPNAYNSCYSAGVFHLHQGDILSVIIPRARAKLNLSPHG
TFLGFVKL

SEQ ID 55 (M200G, D205S, R206H)
VLHLVPINATSKDDSDVTEVMWQPALRRGRGLQAQGYGVRIQDAGVYLLYSQVLFQDVTFTMG
QVVSREGQGRQETLFRCIRSGPSHPSHAYNSCYSAGVFHLHQGDILSVIIPRARAKLNLSPHG
TFLGFVKL

SEQ ID 56 (V174T, T175A, M200G, S202E)
VLHLVPINATSKDDSDVTEVMWQPALRRGRGLQAQGYGVRIQDAGVYLLYSQVLFQDTAFTMG
QVVSREGQGRQETLFRCIRSGPEHPDRAYNSCYSAGVFHLHQGDILSVIIPRARAKLNLSPHG
TFLGFVKL

SEQ ID 57 (T175A, S202E, D205P, R206N)
VLHLVPINATSKDDSDVTEVMWQPALRRGRGLQAQGYGVRIQDAGVYLLYSQVLFQDVAFTMG
QVVSREGQGRQETLFRCIRSMPEHPPNAYNSCYSAGVFHLHQGDILSVIIPRARAKLNLSPHG
TFLGFVKL

SEQ ID 58 (T175A, S202E, D205S, R206H)
VLHLVPINATSKDDSDVTEVMWQPALRRGRGLQAQGYGVRIQDAGVYLLYSQVLFQDVAFTMG
QVVSREGQGRQETLFRCIRSMPEHPDHAYNSCYSAGVFHLHQGDILSVIIPRARAKLNLSPHG
TFLGFVKL

T Cell Activation

The present invention also provides a bi-specific molecule which comprises
  (i) a first domain which binds B cell maturation antigen (BCMA) and comprises a mutant APRIL according to the first aspect of the invention; and
  (ii) a second domain capable of activating a T-cell.

The second domain of the molecule of the present invention is capable of activating T cells. T cells have a T cell-receptor (TCR) at the cell surface which recognises antigenic peptides when presented by an MHC molecule on the surface of an antigen presenting cell. Such antigen recognition results in the phosphorylation of immunoreceptor tyrosine-based activation motifs (ITAMs) by Src family kinases, triggering recruitment of further kinases which results in T cell activation including $Ca^{2+}$ release.

The second domain may cause T cell activation by triggering the same pathway triggered by antigen-specific recognition by the TCR.

Cluster of Differentiation 3 (CD3)

The second domain of the bi-specific molecule of the invention may bind CD3.

CD3 is a protein complex composed of four distinct chains: a CD3γ chain, a CD3δ chain, and two CD3ε chains. CD3 associates with the T-cell receptor (TCR) and the ζ-chain on the surface of a T cell to generate an activation signal. The TCR, ζ-chain, and CD3 molecule together comprise the TCR complex.

Clustering of CD3 on T cells, e.g. by immobilized anti-CD3-antibodies, leads to T cell activation similar to the engagement of the T cell receptor, but independent from its clone typical specificity.

Due to its central role in modulating T cell activity, there have been attempts to develop molecules that are capable of binding TCR/CD3. Much of this work has focused on the generation of antibodies that are specific for the human CD3 antigen.

The second domain may comprise an antibody or part thereof which specifically binds CD3, such as OKT3, WT32, anti-leu-4, UCHT-1, SPV-3TA, TR66, SPV-T3B or affinity tuned variants thereof.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'$_2$, Fv, single chain Fv (ScFv) fragment, Nanobody or single chain variable domain (which may be a VH or VL chain, having 3 CDRs). The antibody may be a bifunctional antibody. The antibody may be non-human, chimeric, humanised or fully human.

Alternatively the second domain may comprise a CD3-binding molecule which is not derived from or based on an immunoglobulin. A number of "antibody mimetic" designed repeat proteins (DRPs) have been developed to exploit the binding abilities of non-antibody polypeptides. Such molecules include ankyrin or leucine-rich repeat proteins e.g. DARPins (Designed Ankyrin Repeat Proteins), Anticalins, Avimers and Versabodies.

The second domain of the bi-specific molecule of the invention may comprise all or part of the monoclonal antibody OKT3, which was the first monoclonal antibody approved by the FDA. OKT3 is available from ATCC CRL 8001. The antibody sequences are published in U.S. Pat. No. 7,381,803.

The second domain may comprise one or more CDRs from OKT3. The second binding domain may comprise CDR3 from the heavy-chain of OKT3 and/or CDR3 from the light chain of OKT3. The second binding domain may comprise all 6 CDRs from OKT3, as shown below.

```
Heavy Chain
CDR1:
                                        (SEQ ID No. 59)
KASGYTFTRYTMH CDR2:
                                        (SEQ ID No. 60)
INPSRGYTNYNQKFKD CDR3:
                                        (SEQ ID No. 61)
YYDDHYCLDY Light Chain
CDR1:
                                        (SEQ ID No. 62)
SASSSVSYMN
```

```
-continued
CDR2:
                                        (SEQ ID No. 63)
RWIYDTSKLAS CDR3:
                                        (SEQ ID No. 64)
QQWSSNPFT
```

The second binding domain may comprise a scFv which comprises the CDR sequences from OKT3. The second binding domain may comprise the scFv sequence shown below as SEQ IN No. 65 or a variant thereof having at least 80% sequence identity, which retains the capacity to bind CD3.

```
                                        SEQ ID No. 65
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSSSGGGGSGGGGSGGGGSQIVLTQSPAIMS

ASPGEKVTMTCSASSSVSYMNWYQQKSGTSPKRWIYDTSKLASGVPAHF

RGSGSGTSYSLTISGMEAEDAATYYCQQWSSNPFTFGSGTKLEINR
```

A variant sequence from SEQ ID No. 65 may have at least 80, 85, 90, 95, 98 or 99% sequence identity and have equivalent or improved CD3 binding and/or TCR activation capabilities as the sequence shown as SEQ ID No. 65.

Bi-Specific T-Cell Engagers (Bites)

BiTES are a new class of therapeutics which approximate a target antigen with the T-cell receptor (TCR). The original design was of two scFvs connected together by a linker with one scFv targeting antigen and the other activating a T-cell.

BiTEs are commonly made by fusing an anti-CD3 scFv to an anti-target antigen scFv via a short five residue peptide linker (GGGGS). In 1995, a tandem scFv targeting EpCAM (epithelial 17-1A antigen) and human CD3 in CHO cells was produced. This new kind of bi-specific antibody format proved to be highly cytotoxic at nanomolar concentrations against various cell lines, using unstimulated human PBMCs in the absence of co-signaling. Later, a fusion between a murine anti-CD19 scFv and a murine anti-CD3 scFv was created. This molecule demonstrated outstanding in vitro properties, including efficient cytotoxicity, without the need of co-signaling (e.g., through CD28).

Blinatumomab, a murine anti-human CD3× anti-human CD19 was the first BiTE developed and is the most advanced BiTE in clinical trials. The candidate is being studied as a treatment of lymphoma and leukemia.

MT110, an anti-human EpCAM× anti-human CD3 TaFv, was the second BiTE tested in clinical trial and the first directed to a wide spectrum of solid tumors. In vitro characterizations of MT110 have recapitulated the results obtained with MT103 on tumor cell lines, thereby demonstrating the generality of the BiTE format. MT110 is currently in clinical trial for lung, colorectal and gastrointestinal cancer patients.

The bi-specific molecule of the present invention is based on a BiTE-like format, but instead of having a scFv or other antibody-based binding domain binding the target antigen, it has a binding domain based on the ligand for BCMA, namely APRIL.

This "APRILiTE" format is favourable compared with a classical scFv-scFv format for various reasons: (a) a single domain—scFv fusion is likely more stable and easier to make than other formats; (b) the assembly of BCMA and APRIL on the cell surface require trimerization of each binding partner. This induces clustering of T-cell activating domain at a protein level making the protein highly specific and highly potent.

The molecule of the present invention may comprise one of the following amino acid sequences, but with a mutation at one of the following positions in the portion of the sequence corresponding to APRIL (with reference to the position numbering shown in SEQ ID No. 1): S202, P201, M200, T175, V174, A125, H203, D205 and R206:

SEQ ID No. 66
METDILLLWVLLLWVPGSTGQVQLQQSGAELARPGASVKMSCKASGYTFTR
YTMHWVKQRPGQGLEWIGYINPSRGYTNYNQKFKDKATLTTDKSSSTAYMQ
LSSLTSEDSAVYYCARYYDDHYCLDYWGQGTTLTVSSSGGGGSGGGGSGGG
GSQIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFGSG
TKLEINRSDPAEPKSPDKTHTCPPCPKDPKSGGGGSVLHLVPINATSKDDS
DVTEVMWQPALRRGRGLQAQGYGVRIQDAGVYLLYSQVLFQDVTFTMGQVV
SREGQGRQETLFRCIRSMPSHPDRAYNSCYSAGVFHLHQGDILSVIIPRAR
AKLNLSPHGTFLGFVKL

SEQ ID No. 67
METDTLLLWVLLLWVPGSTGQVQLQQSGAELARPGASVKMSCKASGYTFTR
YTMHWVKQRPGQGLEWIGYINPSRGYTNYNQKFKDKATLTTDKSSSTAYMQ
LSSLTSEDSAVYYCARYYDDHYCLDYWGQGTTLTVSSSGGGGSGGGGSGGG
GSQIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFGSG
TKLEINRSDPTTTPAPRPPTPAPTIASQPLSLRPEACRPAAGGAVHTRGLD
FACDSGGGGSVLHLVPINATSKDDSDVTEVMWQPALRRGRGLQAQGYGVRI
QDAGVYLLYSQVLFQDVTFTMGQVVSREGQGRQETLFRCIRSMPSHPDRAY
NSCYSAGVFHLHQGDILSVIIPRARAKLNLSPHGTFLGFVKL

SEQ ID No. 68
MGTSLLCWMALCLLGADHADGVLHLVPINATSKDDSDVTEVMWQPALRRGR
GLQAQGYGVRIQDAGVYLLYSQVLFQDVTFTMGQVVSREGQGRQETLFRCI
RSMPSHPDRAYNSCYSAGVFHLHQGDILSVIIPRARAKLNLSPHGTFLGFV
KLSGGGSDPTTTPAPRPPTPAPTIASQPLSLRPEACRPAAGGAVHTRGLDF
ACDSGGGGSQVQLQQSGAELARPGASVKMSCKASGYTFTRYTMHWVKQRPG
QGLEWIGYINPSRGYTNYNQKFKDKATLTTDKSSSTAYMQLSSLTSEDSAV
YYCARYYDDHYCLDYWGQGTTLTVSSSGGGGSGGGGSGGGGSQIVLTQSPA
IMSASPGEKVTMTCSASSSVSYMNWYQQKSGTSPKRWIYDTSKLASGVPAH
FRGSGSGTSYSLTISGMEAEDAATYYCQQWSSNPFTFGSGTKLEINRS

The molecule of the invention may comprise a variant of the sequence shown as SEQ ID No. 66, 67 or 68 having at least 80, 85, 90, 95, 98 or 99% sequence identity, provided that the variant sequence is a molecule as defined in the first aspect of the invention, i.e. a bi-specific molecule which comprises:
(i) a first domain which binds B cell maturation antigen (BCMA) and comprises at least part of a proliferation-inducing ligand (APRIL); and
(ii) a second domain capable of activating a T cell.

Signal Peptide

The bi-specific molecule of the invention may comprise a signal peptide to aid in its production. The signal peptide may cause the bi-specific molecule to be secreted by a host cell, such that the bi-specific molecule can be harvested from the host cell supernatant.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The bi-specific molecule may have the general formula:

Signal peptide-first domain-second domain.

The signal peptide may comprise the SEQ ID No. 69 or 70 or a variant thereof having 5, 4, 3, 2 or 1 amino acid mutations (insertions, substitutions or additions) provided that the signal peptide still functions to cause secretion of the bi-specific molecule.

SEQ ID No. 69:
METDTLLLWVLLLWVPGSTG

SEQ ID No. 70:
MGTSLLCWMALCLLGADHADG

The signal peptides of SEQ ID No. 69 and 70 are compact and highly efficient. They are predicted to give about 95% cleavage after the terminal glycine, giving efficient removal by signal peptidase.

Spacer

The molecule of the present invention may comprise a spacer sequence to connect the first domain with the second domain and spatially separate the two domains.

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

The spacer may be a short spacer, for example a spacer which comprises less than 100, less than 80, less than 60 or less than 45 amino acids. The spacer may be or comprise an IgG1 hinge or a CD8 stalk or a modified version thereof.

Examples of amino acid sequences for these linkers are given below:

SEQ ID No. 71 (IgG1 hinge):
AEPKSPDKTHTCPPCPKDPKSGGGGS

SEQ ID No. 72 (CD8 stalk):
TTTPAPRPPTPAPTIASQPLSLRPEACRPAAGGAVHTRGLDFACD

The CD8 stalk has a sequence such that it may induce the formation of homodimers (see FIG. 2). If this is not desired, one or more cysteine residues may be substituted or removed from the CD8 stalk sequence. The bispecific molecule of the invention may include a spacer which comprises or consists of the sequence shown as SEQ ID No. 72 or a variant thereof having at least 80, 85, 90, 95, 98 or 99% sequence identity, provided that the variant sequence is a molecule which causes approximately equivalent spacing of the first and second domains and/or that the variant sequence causes homodimerisation of the bi-specific molecule.

The molecule of the invention may have the general formula:

Signal peptide–first domain–spacer–second domain.

The spacer may also comprise one or more linker motifs to introduce a chain-break. A chain break separate two distinct domains but allows orientation in different angles. Such sequences include the sequence SDP, and the sequence SGGGSDP (SEQ ID No. 73).

The linker may comprise a serine-glycine linker, such as SGGGGS (SEQ ID No. 74).

Chimeric Antigen Receptors (CARs)

Chimeric antigen receptors (CARs), also known as chimeric T cell receptors, artificial T cell receptors and chimeric immunoreceptors, are engineered receptors, which graft an arbitrary specificity onto an immune effector cell. In a classical CAR (FIG. 3), the specificity of a monoclonal antibody is grafted on to a T cell or NK cell. CAR-encoding nucleic acids may be introduced into T cells or NK cells using, for example, retroviral vectors. In this way, a large number of cancer-specific T cells or NK cells can be generated for adoptive cell transfer. Early clinical studies of this approach have shown efficacy in some cancers, primarily when targeting the pan-B-cell antigen CD19 to treat B-cell malignancies.

The target-antigen binding domain of a CAR is commonly fused via a spacer and transmembrane domain to a signaling endodomain. When the CAR binds the target-antigen, this results in the transmission of an activating signal to the T-cell it is expressed on.

The CAR may comprise:
(i) a variant APRIL, acting as the B cell maturation antigen (BCMA)-binding domain;
(ii) a optional spacer
(iii) a transmembrane domain; and
(iv) an endodomain.

The endodomain may comprise or associate with an intracellular T-cell signalling domain.

The CAR of the present invention may comprise one of the following amino acid sequences, but with a mutation at one of the following positions in the portion of the sequence corresponding to APRIL (with reference to the position numbering shown in SEQ ID No. 1): S202, P201, M200, T175, V174, A125, H203, D205 and R206:

SEQ ID No. 75 (dAPRIL-HCH2CH3pvaa-CD28OXZ)
METDTLLLWVLLLWVPGSTGSVLHLVPINATSKDDSDVTEVMWQPALRRG

RGLQAQGYGVRIQDAGVYLLYSQVLFQDVTFTMGQVVSREGQGRQETLFR

CIRSMPSHPDRAYNSCYSAGVFHLHQGDILSVIIPRARAKLNLSPHGTFL

GFVKLSGGGSDPAEPKSPDKTHTCPPCPAPPVAGPSVFLFPPKPKDTLMI

ARTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKDPKFW

VLVVVGGVLACYSLLVTVAFIIFWVRSKRSRLLHSDYMNMTPRRPGPTRK

HYQPYAPPRDFAAYRSRDQRLPPDAHKPPGGGSFRTPIQEEQADAHSTLA

-continued
KIRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATK

DTYDALHMQALPPR

SEQ ID No. 76 (dAPRIL-CD8STK-CD28OXZ)
METDTLLLWVLLLWVPGSTGSVLHLVPINATSKDDSDVTEVMWQPALRRG

RGLQAQGYGVRIQDAGVYLLYSQVLFQDVTFTMGQVVSREGQGRQETLFR

CIRSMPSHPDRAYNSCYSAGVFHLHQGDILSVIIPRARAKLNLSPHGTFL

GFVKLSGGGSDPTTTPAPRPPTPAPTIASQPLSLRPEACIRPAAGGAVHT

RGLDFACDIFWVLVVVGGVLACYSLLVTVAFIIFWVRSKRSRLLHSDYMN

MTPRRPGPTRKHYQPYAPPRDFAAYRSRDQRLPPDAHKPPGGGSFRTPIQ

EEQADAHSTLAKIRVKFSRSADAPAYQQGQNQLYNELNLGRREEYDVLDK

RRGRDPEMGGKPRRKNPQEGLYNELQKDKMAEAYSEIGMKGERRRGKGHD

GLYQGLSTATKDTYDALHMQALPPR

SEQ ID No. 77 (dAPRIL-HNG-CD28OXZ)
METDTLLLWVLLLWVPGSTGSVLHLVPINATSKDDSDVTEVMWQPALRRG

RGLQAQGYGVRIQAGVYLLYSQVLFQDVTFTMGQVVSREGQGRQETLFRC

IRSMPSHPDRAYNSCYSAGVFHLHQGDILSVIIPRARAKLNLSPHGTFLG

FVKLSGGGSDPAEPKSPDKTHTCPPCPKDPKFWVLVVVGGVLACYSLLVT

VAFIIFWVRSKRSRLLHSDYMNMTPRRPGPTRKHYQPYAPPRDFAAYRSR

DIQRLPPDAHKPPGGGSFRTPIQEEQADAHSTLAKIRVKFSRSADAPAYQ

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR

SEQ ID No. 78 (dAPRIL-HCH2CH3pvaa-CD28OXZ)
MGTSLLCWMALCLLGADHADGKPIPNPLLGLDSTSGGGGSVLHLVPINAT

SKDDSDVTEVMWQPALRRGRGLQAQGYGVRIQDAGVYLLYSQVLFQDVTF

TMGQVVSREGQGRQETLFRCIRSMPSHPDRAYNSCYSAGVFHLHQGDILS

VIIPRARAKLNLSPHGTFLGFVKLSGGGSDPAEPKSPDKTHTCPPCPAPP

VAGPSVFLFPPKPKDTLMIARTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYITLPPSRDELTKNQVSLTCLVKGFYPSDIAVEWES

NGQPENNYKTTPPVLDSDGSFFLYSKLTVDKSRWQQGNVFSCSVMHEALH

NHYTQKSLSLSPGKKDPKFWVLVVVGGVLACYSLLVTVAFIIFWVRSKRS

RLLHSDYMNMTPRRPGPTRKHYQPYAPPRDFAAYRSRDQRLPPDAHKPPG

GGSFRTPIQEEQADAHSTLAKIRVKFSRSADAPAYQQGQNQLYNELNLGR

REEYDVLDKRRGRDPEMGGKPRRKNPQEGLYNELQKDKMAEAYSEIGMKG

ERRRGKGHDGLYQGLSTATKDTYDALHMQALPPR

SEQ ID No. 79 (dAPRIL-CD8STK-CD28OXZ)
MGTSLLCWMALCLLGADHADGKPIPNPLLGLDSTSGGGGSVLHLVPINAT

SKDDSDVTEVMWQPALRRGRGLQAQGYGVRIQDAGVYLLYSQVLFQDVTF

TMGQVVSREGQGRQETLFRCIRSMPSHPDRAYNSCYSAGVFHLHQGDILS

VIIPRARAKLNLSPHGTFLGFVKLSGGGSDPTTTPAPRPPTPAPTIASQP

LSLRPEACRPAAGGAVHTRGLDFACDIFWVLVVVGGVLACYSLLVTVAFI

IFWVRSKRSRLLHSDYMNMTPRRPGPTRKHYQPYAPPRDFAAYRSRDQRL

-continued
PPDAHKPPGGGSFRTPIQEEQADAHSTLAKIRVKFSRSADAPAYQQGQNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR

SEQ ID No. 80 (dAPRIL-HNG-CD280XZ)
MGTSLLCWMALCLLGADHADGKPIPNPLLGLDSTSGGGGSVLHLVPINAT

SKDDSDVTEVMWQPALRRGRGLQAQGYGVRIQDAGVYLLYSQVLFQDVTF

TMGQVVSREGQGRQETLFRCIRSMPSHPDRAYNSCYSAGVFHLHQGDILS

VIIPRARAKLNLSPHGTFLGFVKLSGGGSDPAEPKSPDKTHTCPPCPKDP

KFWVLVVVGGVLACYSLLVTVAFIIFWVRSKRSRLLHSDYMNMTPRRPGP

TRKHYQPYAPPRDFAAYRSRDQRLPPDAHKPPGGGSFRTPIQEEQADAHS

TLAKIRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR

The molecule of the invention may comprise a variant of the sequence shown as SEQ ID No. 75, 76, 77, 78, 79 or 80 having at least 80, 85, 90, 95, 98 or 99% sequence identity, provided that the variant sequence is a molecule as defined in the first aspect of the invention, i.e. a CAR which comprises:
(i) a BCMA-binding domain;
(ii) a optional spacer domain
(iii) a transmembrane domain; and
(iv) an endodomain;
and comprises a mutation at one of the following positions in the portion of the sequence corresponding to APRIL (with reference to the position numbering shown in SEQ ID No. 1): S202, P201, M200, T175, V174, A125, H203, D205 and R206.

The percentage identity between two polypeptide sequences may be readily determined by programs such as BLAST which is freely available at http://blast.ncbi.nlm.nih.gov.

Nucleic Acid Sequence

The present invention also provides a nucleic acid sequence encoding a variant APRIL, a CAR comprising a variant APRIL or a BiTE comprising a variant APRIL as defined above.

The nucleic acid sequence may be RNA or DNA, it may be double or single-stranded.

Nucleic acid sequences encoding APRIL-BiTEs are shown as SEQ ID No. 81-83. The nucleic acid sequence of the present invention may encode the amino acid sequence as encoded by SEQ ID No. 81, 82 or 83, but with a mutation at one of the following positions in the portion of the sequence corresponding to APRIL (with reference to the position numbering shown in SEQ ID No. 1): S202, P201, M200, T175, V174, A125, H203, D205 and R206.

SEQ ID No. 81 (APRILiTE#01)
ATGGAGACCGACACCCTGCTGCTGTGGGTGCTGCTGCTGTGGGTGCCAGG

CAGCACCGGCCAGGTGCAGCTGCAGCAGAGCGGAGCCGAGCTGGCCAGAC

CAGGCGCCAGCGTGAAGATGAGCTGCAAGGCCAGCGGCTACACCTTCACC

CGGTACACCATGCACTGGGTGAAGCAGCGGCCAGGCCAGGGCCTGGAGTG

GATCGGCTACATCAACCCCAGCAGAGGCTACACCAACTACAACCAGAAGT

TCAAGGACAAGGCCACCCTGACCACCGACAAGAGCAGCAGCACCGCCTAC

ATGCAGCTGAGCAGCCTGACCAGCGAGGACAGCGCCGTGTACTACTGCGC

CAGATACTACGACGACCACTACTGCCTGGACTACTGGGGCCAGGGCACCA

CCCTGACCGTGAGCAGCTCTGGCGGAGGCGGCTCTGGCGGAGGCGGCTCT

GGCGGAGGCGGCAGCCAGATCGTGCTGACCCAGAGCCCAGCCATCATGAG

CGCCAGCCCAGGCGAGAAGGTGACCATGACCTGCAGCGCCAGCAGCAGCG

TGAGCTACATGAACTGGTACCAGCAGAAGAGCGGCACCAGCCCCAAGCGG

TGGATCTACGACACCAGCAAGCTGGCCAGCGGCGTGCCAGCCCACTTCAG

AGGCAGCGGCAGCGGCACCAGCTACAGCCTGACCATCAGCGGCATGGAGG

CCGAGGATGCCGCCACCTACTACTGCCAGCAGTGGAGCAGCAACCCCTTC

ACCTTCGGCAGCGGCACCAAGCTGGAGATCAACCGGTCGGATCCCGCCGA

GCCCAAATCTCCTGACAAAACTCACACATGCCCACCGTGCCCAAAAGATC

CCAAATCTGGCGGAGGCGGCAGCGTGCTGCACCTGGTGCCCATCAACGCC

ACCAGCAAGGACGACTCTGATGTGACCGAGGTGATGTGGCAGCCAGCCCT

GAGACGGGGCAGAGGCCTGCAGGCCCAGGGCTACGGCGTGAGAATCCAGG

ACGCTGGCGTGTACCTGCTGTACTCCCAGGTGCTGTTCCAGGACGTGACC

TTCACAATGGGCCAGGTGGTGAGCCGGGAGGGCCAGGGCAGACAGGAGAC

CCTGTTCCGGTGCATCCGGAGCATGCCCAGCCACCCCGACAGAGCCTACA

ACAGCTGCTACAGCGCTGGCGTGTTTCACCTGCACCAGGGCGACATCCTG

AGCGTGATCATCCCCAGAGCCAGAGCCAAGCTGAACCTGTCCCCCCACGG

CACCTTTCTGGGCTTCGTGAAGCTGTGA

SEQ ID No. 82 (APRILiTE#03)
ATGGAGACCGACACCCTGCTGCTGTGGGTGCTGCTGCTGTGGGTGCCAGG

CAGCACCGGCCAGGTGCAGCTGCAGCAGAGCGGAGCCGAGCTGGCCAGAC

CAGGCGCCAGCGTGAAGATGAGCTGCAAGGCCAGCGGCTACACCTTCACC

CGGTACACCATGCACTGGGTGAAGCAGCGGCCAGGCCAGGGCCTGGAGTG

GATCGGCTACATCAACCCCAGCAGAGGCTACACCAACTACAACCAGAAGT

TCAAGGACAAGGCCACCCTGACCACCGACAAGAGCAGCAGCACCGCCTAC

ATGCAGCTGAGCAGCCTGACCAGCGAGGACAGCGCCGTGTACTACTGCGC

CAGATACTACGACGACCACTACTGCCTGGACTACTGGGGCCAGGGCACCA

CCCTGACCGTGAGCAGCTCTGGCGGAGGCGGCTCTGGCGGAGGCGGCTCT

GGCGGAGGCGGCAGCCAGATCGTGCTGACCCAGAGCCCAGCCATCATGAG

CGCCAGCCCAGGCGAGAAGGTGACCATGACCTGCAGCGCCAGCAGCAGCG

TGAGCTACATGAACTGGTACCAGCAGAAGAGCGGCACCAGCCCCAAGCGG

TGGATCTACGACACCAGCAAGCTGGCCAGCGGCGTGCCAGCCCACTTCAG

AGGCAGCGGCAGCGGCACCAGCTACAGCCTGACCATCAGCGGCATGGAGG

CCGAGGATGCCGCCACCTACTACTGCCAGCAGTGGAGCAGCAACCCCTTC

ACCTTCGGCAGCGGCACCAAGCTGGAGATCAACCGGTCGGATCCCACCAC

GACGCCAGCGCCGCGACCACCAACACCGGCGCCCACCATCGCGTCGCAGC

CCCTGTCCCTGCGCCCAGAGGCGTGCCGGCCAGCGGCGGGGGCGCAGTG

CACACGAGGGGGCTGGACTTCGCCTGTGATTCTGGCGGAGGCGGCAGCGT

-continued
GCTGCACCTGGTGCCCATCAACGCCACCAGCAAGGACGACTCTGATGTGA

CCGAGGTGATGTGGCAGCCAGCCCTGAGACGGGGCAGAGGCCTGCAGGCC

CAGGGCTACGGCGTGAGAATCCAGGACGCTGGCGTGTACCTGCTGTACTC

CCAGGTGCTGTTCCAGGACGTGACCTTCACAATGGGCCAGGTGGTGAGCC

GGGAGGGCCAGGGCAGACAGGAGACCCTGTTCCGGTGCATCCGGAGCATG

CCCAGCCACCCCGACAGAGCCTACAACAGCTGCTACAGCGCTGGCGTGTT

TCACCTGCACCAGGGCGACATCCTGAGCGTGATCATCCCCAGAGCCAGAG

CCAAGCTGAACCTGTCCCCCCACGGCACCTTTCTGGGCTTCGTGAAGCTG

TGA

SEQ ID No. 83 (APRILiTE#06)
ATGGGCACCTCCCTGCTGTGCTGGATGGCCCTGTGCCTGCTGGGAGCCGA

CCACGCCGACGGCGTGCTGCACCTGGTGCCCATCAACGCCACCAGCAAGG

ACGACTCTGATGTGACCGAGGTGATGTGGCAGCCAGCCCTGAGACGGGGC

AGAGGCCTGCAGGCCCAGGGCTACGGCGTGAGAATCCAGGACGCTGGCGT

GTACCTGCTGTACTCCCAGGTGCTGTTCCAGGACGTGACCTTCACAATGG

GCCAGGTGGTGAGCCGGGAGGGCCAGGGCAGACAGGAGACCCTGTTCCGG

TGCATCCGGAGCATGCCCAGCCACCCCGACAGAGCCTACAACAGCTGCTA

CAGCGCTGGCGTGTTTCACCTGCACCAGGGCGACATCCTGAGCGTGATCA

TCCCCAGAGCCAGAGCCAAGCTGAACCTGTCCCCCCACGGCACCTTTCTG

GGCTTCGTGAAGCTGTCTGGAGGCGGCTCGGATCCCACCACGACGCCAGC

GCCGCGACCACCAACACCGGCGCCCACCATCGCGTCGCAGCCCCTGTCCC

TGCGCCCAGAGGCGTGCCGGCCAGCGGCGGGGGCGCAGTGCACACGAGG

GGGCTGGACTTCGCCTGTGATAGCGGTGGCGGTGGCAGCCAGGTGCAGCT

GCAGCAGAGCGGAGCCGAGCTGGCCAGACCAGGCGCCAGCGTGAAGATGA

GCTGCAAGGCCAGCGGCTACACCTTCACCCGGTACACCATGCACTGGGTG

AAGCAGCGGCCAGGCCAGGGCCTGGAGTGGATCGGCTACATCAACCCCAG

CAGAGGCTACACCAACTACAACCAGAAGTTCAAGGACAAGGCCACCCTGA

CCACCGACAAGAGCAGCAGCACCGCCTACATGCAGCTGAGCAGCCTGACC

AGCGAGGACAGCGCCGTGTACTACTGCGCCAGATACTACGACGACCACTA

CTGCCTGGACTACTGGGGCCAGGGCACCACCCTGACCGTGAGCAGCTCTG

GCGGAGGCGGCTCTGGCGGAGGCGGCTCTGGCGGAGGCGGCAGCCAGATC

GTGCTGACCCAGAGCCCAGCCATCATGAGCGCCAGCCCAGGCGAGAAGGT

GACCATGACCTGCAGCGCCAGCAGCAGCGTGAGCTACATGAACTGGTACC

AGCAGAAGAGCGGCACCAGCCCCAAGCGGTGGATCTACGACACCAGCAAG

CTGGCCAGCGGCGTGCCAGCCCACTTCAGAGGCAGCGGCAGCGGCACCAG

CTACAGCCTGACCATCAGCGGCATGGAGGCCGAGGATGCCGCCACCTACT

ACTGCCAGCAGTGGAGCAGCAACCCCTTCACCTTCGGCAGCGGCACCAAG

CTGGAGATCAACCGGTCGTGA

Nucleic acid sequences encoding APRIL-CARs are shown as SEQ ID No. 84-89. The nucleic acid sequence of the present invention may encode the amino acid sequence as encoded by SEQ ID No. 84, 85, 86, 87, 88 or 89, but with a mutation at one of the following positions in the portion of the sequence corresponding to APRIL (with reference to the position numbering shown in SEQ ID No. 1): S202, P201, M200, T175, V174, A125, H203, D205 and R206.

SEQ ID No. 84 (dAPRIL-HCH2CH3pvaa-CD28OXZ)
ATGGAGACCGACACCCTGCTGCTGTGGGTGCTGCTGCTGTGGGTGCCAGG

CAGCACCGGCAGCGTGCTCCACCTGGTGCCCATCAACGCCACCAGCAAGG

ACGACTCTGATGTGACCGAGGTGATGTGGCAGCCAGCCCTGAGACGGGGC

AGAGGCCTGCAGGCCCAGGGCTACGGCGTGAGAATCCAGGACGCTGGCGT

GTACCTGCTGTACTCCCAGGTGCTGTTCCAGGACGTGACCTTCACAATGG

GCCAGGTGGTGAGCCGGGAGGGCCAGGGCAGACAGGAGACCCTGTTCCGG

TGCATCCGGAGCATGCCCAGCCACCCCGACAGAGCCTACAACAGCTGCTA

CAGCGCTGGCGTGTTTCACCTGCACCAGGGCGACATCCTGAGCGTGATCA

TCCCCAGAGCCAGAGCCAAGCTGAACCTGTCCCCCCACGGCACCTTTCTG

GGCTTCGTGAAGCTGTCTGGAGGCGGCTCGGATCCCGCCGAGCCCAAATC

TCCTGACAAAACTCACACATGCCCACCGTGCCCAGCACCTCCCGTGGCCG

GCCCGTCAGTCTTCCTCTTCCCCCCAAAACCCAAGGACACCCTCATGATC

GCCCGGACCCCTGAGGTCACATGCGTGGTGGTGGACGTGAGCCACGAAGA

CCCTGAGGTCAAGTTCAACTGGTACGTGGACGGCGTGGAGGTGCATAATG

CCAAGACAAAGCCGCGGGAGGAGCAGTACAACAGCACGTACCGTGTGGTC

AGCGTCCTCACCGTCCTGCACCAGGACTGGCTGAATGGCAAGGAGTACAA

GTGCAAGGTCTCCAACAAAGCCCTCCCAGCCCCCATCGAGAAAACCATCT

CCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAA

AGGCTTCTATCCCAGCGACATCGCCGTGGAGTGGGAGAGCAATGGGCAAC

CGGAGAACAACTACAAGACCACGCCTCCCGTGCTGGACTCCGACGGCTCC

TTCTTCCTCTACAGCAAGCTCACCGTGGACAAGAGCAGGTGGCAGCAGGG

GAACGTCTTCTCATGCTCCGTGATGCATGAGGCTCTGCACAACCACTACA

CGCAGAAGAGCCTCTCCCTGTCTCCGGGTAAAAAAGATCCCAAATTTTGG

GTGCTGGTGGTGGTTGGTGGAGTCCTGGCTTGCTATAGCTTGCTAGTAAC

AGTGGCCTTTATTATTTTCTGGGTGAGGAGTAAGAGGAGCAGGCTCCTGC

ACAGTGACTACATGAACATGACTCCCCGCCGCCCCGGGCCCACCCGCAAG

CATTACCAGCCCTATGCCCCACCACGCGACTTCGCAGCCTATCGCTCCAG

GGACCAGAGGCTGCCCCCCGATGCCCACAAGCCCCTGGGGGAGGCAGTT

TCCGGACCCCCATCCAAGAGGAGCAGGCCGACGCCCACTCCACCCTGGCC

AAGATCAGAGTGAAGTTCAGCAGGAGCGCAGACGCCCCCGCGTACCAGCA

GGGCCAGAACCAGCTCTATAACGAGCTCAATCTAGGACGAAGAGAGGAGT

ACGATGTTTTGGACAAGAGACGTGGCCGGGACCCTGAGATGGGGGGAAAG

CCGAGAAGGAAGAACCCTCAGGAAGGCCTGTACAATGAACTGCAGAAAGA

TAAGATGGCGGAGGCCTACAGTGAGATTGGGATGAAAGGCGAGCGCCGGA

GGGGCAAGGGGCACGATGGCCTTTACCAGGGTCTCAGTACAGCCACCAAG

GACACCTACGACGCCCTTCACATGCAGGCCCTGCCTCCTCGCTAA

SEQ ID No. 85 (dAPRIL-CD8STK-CD280XZ)
ATGGAGACCGACACCCTGCTGCTGTGGGTGCTGCTGCTGTGGGTGCCAGG

CAGCACCGGCAGCGTGCTCCACCTGGTGCCCATCAACGCCACCAGCAAGG

ACGACTCTGATGTGACCGAGGTGATGTGGCAGCCAGCCCTGAGACGGGGC

AGAGGCCTGCAGGCCCAGGGCTACGGCGTGAGAATCCAGGACGCTGGCGT

GTACCTGCTGTACTCCCAGGTGCTGTTCCAGGACGTGACCTTCACAATGG

CCAGGTGGTGAGCGGGAGGGCCAGGGCAGACAGGAGACCCTGTTCCGG

TGCATCCGGAGCATGCCCAGCCACCCCGACAGAGCCTACAACAGCTGCTA

CAGCGCTGGCGTGTTTCACCTGCACCAGGGCGACATCCTGAGCGTGATCA

TCCCCAGAGCCAGAGCCAAGCTGAACCTGTCCCCCCACGGCACCTTTCTG

GGCTTCGTGAAGCTGTCTGGAGGCGGCTCGGATCCCACCACGACGCCAGC

GCCGCGACCACCAACACCGGCGCCCACCATCGCGTCGCAGCCCCTGTCCC

TGCGCCCAGAGGCGTGCCGGCCAGCGGCGGGGGGCGCAGTGCACACGAGG

GGGCTGGACTTCGCCTGTGATATCTTTTGGGTGCTGGTGGTGGTTGGTGG

AGTCCTGGCTTGCTATAGCTTGCTAGTAACAGTGGCCTTTATTATTTTCT

GGGTGAGGAGTAAGAGGAGCAGGCTCCTGCACAGTGACTACATGAACATG

ACTCCCCGCCGCCCGGGCCCACCCGCAAGCATTACCAGCCCTATGCCCC

ACCACGCGACTTCGCAGCCTATCGCTCCAGGGACCAGAGGCTGCCCCCCG

ATGCCCACAAGCCCCTGGGGGAGGCAGTTTCCGGACCCCCATCCAAGAG

GAGCAGGCCGACGCCCACTCCACCCTGGCCAAGATCAGAGTGAAGTTCAG

CAGGAGCGCAGACGCCCCCGCGTACCAGCAGGGCCAGAACCAGCTCTATA

ACGAGCTCAATCTAGGACGAAGAGAGGAGTACGATGTTTTGGACAAGAGA

CGTGGCCGGGACCCTGAGATGGGGGGAAAGCCGAGAAGGAAGAACCCTCA

GGAAGGCCTGTACAATGAACTGCAGAAAGATAAGATGGCGGAGGCCTACA

GTGAGATTGGGATGAAAGGCGAGCGCCGGAGGGGCAAGGGGCACGATGGC

CTTTACCAGGGTCTCAGTACAGCCACCAAGGACACCTACGACGCCCTTCA

CATGCAGGCCCTGCCTCCTCGCTAA

SEQ ID No. 86 (dAPRIL-HNG-CD280XZ)
ATGGAGACCGACACCCTGCTGCTGTGGGTGCTGCTGCTGTGGGTGCCAGG

CAGCACCGGCAGCGTGCTCCACCTGGTGCCCATCAACGCCACCAGCAAGG

ACGACTCTGATGTGACCGAGGTGATGTGGCAGCCAGCCCTGAGACGGGGC

AGAGGCCTGCAGGCCCAGGGCTACGGCGTGAGAATCCAGGACGCTGGCGT

GTACCTGCTGTACTCCCAGGTGCTGTTCCAGGACGTGACCTTCACAATGG

CCAGGTGGTGAGCGGGAGGGCCAGGGCAGACAGGAGACCCTGTTCCGG

TGCATCCGGAGCATGCCCAGCCACCCCGACAGAGCCTACAACAGCTGCTA

CAGCGCTGGCGTGTTTCACCTGCACCAGGGCGACATCCTGAGCGTGATCA

TCCCCAGAGCCAGAGCCAAGCTGAACCTGTCCCCCCACGGCACCTTTCTG

GGCTTCGTGAAGCTGTCTGGAGGCGGCTCGGATCCCGCCGAGCCCAAATC

TCCTGACAAAACTCACACATGCCCACCGTGCCCAAAAGATCCCAAATTTT

GGGTGCTGGTGGTGGTTGGTGGAGTCCTGGCTTGCTATAGCTTGCTAGTA

ACAGTGGCCTTTATTATTTTCTGGGTGAGGAGTAAGAGGAGCAGGCTCCT

GCACAGTGACTACATGAACATGACTCCCCGCCGCCCCGGGCCCACCCGCA

AGCATTACCAGCCCTATGCCCCACCACGCGACTTCGCAGCCTATCGCTCC

AGGGACCAGAGGCTGCCCCCCGATGCCCACAAGCCCCTGGGGGAGGCAG

TTTCCGGACCCCCATCCAAGAGGAGCAGGCCGACGCCCACTCCACCCTGG

CCAAGATCAGAGTGAAGTTCAGCAGGAGCGCAGACGCCCCCGCGTACCAG

CAGGGCCAGAACCAGCTCTATAACGAGCTCAATCTAGGACGAAGAGAGGA

GTACGATGTTTTGGACAAGAGACGTGGCCGGGACCCTGAGATGGGGGGAA

AGCCGAGAAGGAAGAACCCTCAGGAAGGCCTGTACAATGAACTGCAGAAA

GATAAGATGGCGGAGGCCTACAGTGAGATTGGGATGAAAGGCGAGCGCCG

GAGGGGCAAGGGGCACGATGGCCTTTACCAGGGTCTCAGTACAGCCACCA

AGGACACCTACGACGCCCTTCACATGCAGGCCCTGCCTCCTCGCTAA

SEQ ID No. 87 (dAPRIL-HCH2CH3pvaa-CD280XZ)
ATGGGCACCTCCCTGCTGTGCTGGATGGCCCTGTGCCTGCTGGGAGCCGA

CCACGCCGACGGCAAGCCCATTCCCAACCCCCTGCTGGGCCTGGACTCCA

CCTCTGGCGGAGGCGGCAGCGTGCTGCACCTGGTGCCCATCAACGCCACC

AGCAAGGACGACTCTGATGTGACCGAGGTGATGTGGCAGCCAGCCCTGAG

ACGGGGCAGAGGCCTGCAGGCCCAGGGCTACGGCGTGAGAATCCAGGACG

CTGGCGTGTACCTGCTGTACTCCCAGGTGCTGTTCCAGGACGTGACCTTC

ACAATGGCCAGGTGGTGAGCGGGAGGGCCAGGGCAGACAGGAGACCCT

GTTCCGGTGCATCCGGAGCATGCCCAGCCACCCCGACAGAGCCTACAACA

GCTGCTACAGCGCTGGCGTGTTTCACCTGCACCAGGGCGACATCCTGAGC

GTGATCATCCCCAGAGCCAGAGCCAAGCTGAACCTGTCCCCCCACGGCAC

CTTTCTGGGCTTCGTGAAGCTGTCTGGAGGCGGCTCGGATCCCGCCGAGC

CCAAATCTCCTGACAAAACTCACACATGCCCACCGTGCCCAGCACCTCCC

GTGGCCGGCCCGTCAGTCTTCCTCTTCCCCCCAAAACCCAAGGACACCCT

CATGATCGCCCGGACCCCTGAGGTCACATGCGTGGTGGTGGACGTGAGCC

ACGAAGACCCTGAGGTCAAGTTCAACTGGTACGTGGACGGCGTGGAGGTG

CATAATGCCAAGACAAAGCCGCGGGAGGAGCAGTACAACAGCACGTACCG

TGTGGTCAGCGTCCTCACCGTCCTGCACCAGGACTGGCTGAATGGCAAGG

AGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCT

GCCCCCATCCCGGGATGAGCTGACCAAGAACCAGGTCAGCCTGACCTGCC

TGGTCAAAGGCTTCTATCCCAGCGACATCGCCGTGGAGTGGGAGAGCAAT

GGGCAACCGGAGAACAACTACAAGACCACGCCTCCCGTGCTGGACTCCGA

CGGCTCCTTCTTCCTCTACAGCAAGCTCACCGTGGACAAGAGCAGGTGGC

AGCAGGGGAACGTCTTCTCATGCTCCGTGATGCATGAGGCTCTGCACAAC

CACTACACGCAGAAGAGCCTCTCCCTGTCTCCGGGTAAAAAAGATCCCAA

ATTTTGGGTGCTGGTGGTGGTTGGTGGAGTCCTGGCTTGCTATAGCTTGC

TAGTAACAGTGGCCTTTATTATTTTCTGGGTGAGGAGTAAGAGGAGCAGG

CTCCTGCACAGTGACTACATGAACATGACTCCCCGCCGCCCCGGGCCCAC

CCGCAAGCATTACCAGCCCTATGCCCCACCACGCGACTTCGCAGCCTATC

GCTCCAGGGACCAGAGGCTGCCCCCCGATGCCCACAAGCCCCTGGGGGA

```
-continued
GGCAGTTTCCGGACCCCCATCCAAGAGGAGCAGGCCGACGCCCACTCCAC

CCTGGCCAAGATCAGAGTGAAGTTCAGCAGGAGCGCAGACGCCCCCGCGT

ACCAGCAGGGCCAGAACCAGCTCTATAACGAGCTCAATCTAGGACGAAGA

GAGGAGTACGATGTTTTGGACAAGAGACGTGGCCGGGACCCTGAGATGGG

GGGAAAGCCGAGAAGGAAGAACCCTCAGGAAGGCCTGTACAATGAACTGC

AGAAAGATAAGATGGCGGAGGCCTACAGTGAGATTGGGATGAAAGGCGAG

CGCCGGAGGGGCAAGGGGCACGATGGCCTTTACCAGGGTCTCAGTACAGC

CACCAAGGACACCTACGACGCCCTTCACATGCAGGCCCTGCCTCCTCGCT

AA

SEQ ID No. 88 (dAPRIL-CD8STK-CD28OXZ)
ATGGGCACCTCCCTGCTGTGCTGGATGGCCCTGTGCCTGCTGGGAGCCGA

CCACGCCGACGGCAAGCCCATTCCCAACCCCCTGCTGGGCCTGGACTCCA

CCTCTGGCGGAGGCGGCAGCGTGCTGCACCTGGTGCCCATCAACGCCACC

AGCAAGGACGACTCTGATGTGACCGAGGTGATGTGGCAGCCAGCCCTGAG

ACGGGGCAGAGGCCTGCAGGCCCAGGGCTACGGCGTGAGAATCCAGGACG

CTGGCGTGTACCTGCTGTACTCCCAGGTGCTGTTCCAGGACGTGACCTTC

ACAATGGGCCAGGTGGTGAGCCGGGAGGGCCAGGGCAGACAGGAGACCCT

GTTCCGGTGCATCCGGAGCATGCCCAGCCACCCCGACAGAGCCTACAACA

GCTGCTACAGCGCTGGCGTGTTTCACCTGCACCAGGGCGACATCCTGAGC

GTGATCATCCCCAGAGCCAGAGCCAAGCTGAACCTGTCCCCCCACGGCAC

CTTTCTGGGCTTCGTGAAGCTGTCTGGAGGCGGCTCGGATCCCACCACGA

CGCCAGCGCCGCGACCACCAACACCGGCGCCCACCATCGCGTCGCAGCCC

CTGTCCCTGCGCCCAGAGGCGTGCCGGCCAGCGGCGGGGGCGCAGTGCA

CACGAGGGGGCTGGACTTCGCCTGTGATATCTTTTGGGTGCTGGTGGTGG

TTGGTGGAGTCCTGGCTTGCTATAGCTTGCTAGTAACAGTGGCCTTTATT

ATTTTCTGGGTGAGGAGTAAGAGGAGCAGGCTCCTGCACAGTGACTACAT

GAACATGACTCCCCGCCGCCCCGGGCCCACCCGCAAGCATTACCAGCCCT

ATGCCCCACCACGCGACTTCGCAGCCTATCGCTCCAGGGACCAGAGGCTG

CCCCCCGATGCCCACAAGCCCCTGGGGGAGGCAGTTTCCGGACCCCCAT

CCAAGAGGAGCAGGCCGACGCCCACTCCACCCTGGCCAAGATCAGAGTGA

AGTTCAGCAGGAGCGCAGACGCCCCCGCGTACCAGCAGGGCCAGAACCAG

CTCTATAACGAGCTCAATCTAGGACGAAGAGAGGAGTACGATGTTTTGGA

CAAGAGACGTGGCCGGGACCCTGAGATGGGGGGAAAGCCGAGAAGGAAGA

ACCCTCAGGAAGGCCTGTACAATGAACTGCAGAAAGATAAGATGGCGGAG

GCCTACAGTGAGATTGGGATGAAAGGCGAGCGCCGGAGGGGCAAGGGGCA

CGATGGCCTTTACCAGGGTCTCAGTACAGCCACCAAGGACACCTACGACG

CCCTTCACATGCAGGCCCTGCCTCCTCGCTAA

SEQ ID No. 89 (dAPRIL-HNG-CD28OXZ)
ATGGGCACCTCCCTGCTGTGCTGGATGGCCCTGTGCCTGCTGGGAGCCGA

CCACGCCGACGGCAAGCCCATTCCCAACCCCCTGCTGGGCCTGGACTCCA

CCTCTGGCGGAGGCGGCAGCGTGCTGCACCTGGTGCCCATCAACGCCACC

AGCAAGGACGACTCTGATGTGACCGAGGTGATGTGGCAGCCAGCCCTGAG
```

```
-continued
ACGGGGCAGAGGCCTGCAGGCCCAGGGCTACGGCGTGAGAATCCAGGACG

CTGGCGTGTACCTGCTGTACTCCCAGGTGCTGTTCCAGGACGTGACCTTC

ACAATGGGCCAGGTGGTGAGCCGGGAGGGCCAGGGCAGACAGGAGACCCT

GTTCCGGTGCATCCGGAGCATGCCCAGCCACCCCGACAGAGCCTACAACA

GCTGCTACAGCGCTGGCGTGTTTCACCTGCACCAGGGCGACATCCTGAGC

GTGATCATCCCCAGAGCCAGAGCCAAGCTGAACCTGTCCCCCCACGGCAC

CTTTCTGGGCTTCGTGAAGCTGTCTGGAGGCGGCTCGGATCCCGCCGAGC

CCAAATCTCCTGACAAAACTCACACATGCCCACCGTGCCCAAAAGATCCC

AAATTTTGGGTGCTGGTGGTGGTTGGTGGAGTCCTGGCTTGCTATAGCTT

GCTAGTAACAGTGGCCTTTATTATTTTCTGGGTGAGGAGTAAGAGGAGCA

GGCTCCTGCACAGTGACTACATGAACATGACTCCCCGCCGCCCCGGGCCC

ACCCGCAAGCATTACCAGCCCTATGCCCCACCACGCGACTTCGCAGCCTA

TCGCTCCAGGGACCAGAGGCTGCCCCCCGATGCCCACAAGCCCCTGGGG

GAGGCAGTTTCCGGACCCCCATCCAAGAGGAGCAGGCCGACGCCCACTCC

ACCCTGGCCAAGATCAGAGTGAAGTTCAGCAGGAGCGCAGACGCCCCCGC

GTACCAGCAGGGCCAGAACCAGCTCTATAACGAGCTCAATCTAGGACGAA

GAGAGGAGTACGATGTTTTGGACAAGAGACGTGGCCGGGACCCTGAGATG

GGGGGAAAGCCGAGAAGGAAGAACCCTCAGGAAGGCCTGTACAATGAACT

GCAGAAAGATAAGATGGCGGAGGCCTACAGTGAGATTGGGATGAAAGGCG

AGCGCCGGAGGGGCAAGGGGCACGATGGCCTTTACCAGGGTCTCAGTACA

GCCACCAAGGACACCTACGACGCCCTTCACATGCAGGCCCTGCCTCCTCG

CTAA
```

The nucleic acid sequence may encode the same amino acid sequence as that encoded by SEQ ID No. 81, 82, 83, 84, 85, 86, 87, 88 or 89 comprising the variation mentioned above, but may have a different nucleic acid sequence, due to the degeneracy of the genetic code. The nucleic acid sequence may have at least 80, 85, 90, 95, 98 or 99% identity to the sequence shown as SEQ ID No. 81 to 89, provided that it encodes a molecule as defined in the first aspect of the invention.

The nucleic acid sequence may encode the amino acid sequence as encoded by SEQ ID No. 81 to 89, but with one of following the single mutations (SEQ IDs 22 to 45):
A125T,
V174T, V174G,
T175H, T175S, T175G,
M200C, M200L, M200G, M200S, M200A, M200N,
P201V, P201A, P201G, P201R, P201Y, P201W,
S202G, S202F, S202D, S202V, S202P, D205P.

The nucleic acid sequence may encode the amino acid sequence as encoded by SEQ ID No. 81 to 89, but with a combination of mutations at the following positions: V174 and T175; or V174 and M200; or V174 and S202; or T175 and M200, or T175 and S202; or D205 and R206; or V174, T175 and M200; or V174, T175 and S202; or T175, D205 and R206; or M200, D205 and R206; or V174, T175, M200 and S202; or T175, S202, D205 and R206;

The nucleic acid sequence may encode the amino acid sequence as encoded by SEQ ID No. 81 to 89, but with one of the following specific mutation combinations:
V174T and T175A; or V174T and M200G; or V174S and S202G; or V174T and S202V; or V174G and S202G, or V174G and S202E; or V174G and S202A; or V174G and S202G; or V174E and S202Y; or T175A and S202E; or T175G and S202G; or T175G and S202V; or T175A and S202P; or T175A and M200G; or T175S and S202G; or S202V and H203N; or D205H and R206L; or D205P and R206K; or D205P and R206N; or D205S and R206P; or D205R and R206G; or D205P and R206I; or D205S and R206H; or V174T, T175A and S202E; or V174T, T175A and M200G; or T175A, D205P and R206N; or T175A, D205S and R206H; or M200G, D205P and R206N; or M200G, D205S and R206H; or V174T, T175A, M200G and S202E; or T175A, S202E, D205P and R206N; or T175A, S202E, D205S and R206H.

Vector

The present invention also provides a vector which comprises a nucleic acid sequence according to the present invention. Such a vector may be used to introduce the nucleic acid sequence into a host cell so that it expresses and produces a variant APRIL according to the first aspect of the invention.

The vector may, for example, be a plasmid or synthetic mRNA or a viral vector, such as a retroviral vector or a lentiviral vector.

The vector may be capable of transfecting or transducing an effector cell.

Cell

The invention also provides a host cell which comprises a nucleic acid according to the invention.

The invention also provides a cell which comprises a CAR according to the invention.

The cell may be an immune cell such as a T-cell or natural killer (NK) cell. It may be a primary cell or a cell from a cell line.

The invention also provides a cell composition comprising a plurality of CAR-expressing cells of the invention.

The invention also provides a method for making a cell according to the present invention which comprises the step of transducing or transfecting a cell with a vector of the invention which comprises a nucleic acid sequence encoding a chimeric antigen receptor.

The cell may be transfected or transduced ex vivo and then reimplanted into the same or a different subject.

Therapeutic Agent

The present invention provides a therapeutic agent which comprises a variant APRIL, a nucleic acid, a vector a CAR-expressing cell or a BiTE as defined above.

The therapeutic agent may comprise a variant APRIL as the targeting portion, to target the agent to BCMA-expressing cells, such as plasma cells. The therapeutic agent may also comprise a functional domain which exerts a therapeutic affect, for example by acting directly on the plasma cell or recruiting other cells of the immune system to act on the plasma cell.

The variant APRIL may be conjugated to a drug, such as a cytotoxic drug.

The Variant APRIL may be part of a chimeric antigen receptor, or Bispecific T-cell engager (BiTE)

Pharmaceutical Composition

The present invention also relates to a pharmaceutical composition containing a therapeutic agent of the invention together with a pharmaceutically acceptable carrier, diluent or excipient, and optionally one or more further pharmaceutically active polypeptides and/or compounds. Such a formulation may, for example, be in a form suitable for intravenous infusion).

Method of Treatment

The therapeutic agent and pharmaceutical composition of the present invention may be used for the treatment of a cancerous disease, in particular a plasma cell disorder or a B cell disorder which correlates with enhanced BCMA expression.

Plasma cell disorders include plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma (POEMS Syndrome) and heavy chain diseases as well as the clinically unclear monoclonal gammopathy of undetermined significance/smoldering multiple myeloma.

The disease may be multiple myeloma.

Examples for B cell disorders which correlate with elevated BCMA expression levels are CLL (chronic lymphocytic leukemia) and non-Hodgkins lymphoma (NHL). The bispecific binding agents of the invention may also be used in the therapy of autoimmune diseases like Systemic Lupus Erythematosus (SLE), multiple sclerosis (MS) and rheumatoid arthritis (RA).

The method of the present invention may be for treating a cancerous disease, in particular a plasma cell disorder or a B cell disorder which correlates with enhanced BCMA expression.

A method for the treatment of disease relates to the therapeutic use of an agent or composition of the invention. In this respect, the agent or composition may be administered to a subject having an existing disease or condition in order to lessen, reduce or improve at least one symptom associated with the disease and/or to slow down, reduce or block the progression of the disease. The method of the invention may cause or promote T-cell mediated killing of BCMA-expressing cells, such as plasma cells.

Diagnosis

The present invention also provides a diagnostic agent for detecting plasma cells which comprises a variant APRIL of the invention.

The diagnostic agent may also comprise a detectable label, such as a radioactive or fluorescent label or a dye.

The diagnostic agent may be for diagnosing a plasma cell disorder.

The diagnostic method may be carried out in vivo or in vitro. In the in vivo method, the diagnostic agent is administered to the subject.

In the in vitro method, the variant APRIL is added to a sample from the subject in vitro. The sample may comprise plasma cells. The sample may be or be derived from a blood sample, such as a PBMC sample.

The invention will now be further described by way of Examples, which are meant to serve to assist one of ordinary skill in the art in carrying out the invention and are not intended in any way to limit the scope of the invention.

EXAMPLES

Example 1—Characterisation of BCMA as a Target for Myeloma

Primary myeloma cells were isolated by performing a CD138 immunomagnetic selection on fresh bone marrow samples from Multiple myeloma patients that were known to have frank disease. These cells were stained with the BCMA specific J6MO mAb (GSK) which was conjugated to PE. At the same time, a standard of beads with known numbers of binding sites was generated using the PE Quantibrite bead kit (Becton Dickenson) as per the manufacturer's instructions. The BCMA copy number on myeloma cells could be derived by correlating the mean-fluorescent intensity from the myeloma cells with the standard curve derived from the beads. It was found that the range of BCMA copy number on a myeloma cell surface is low: at 348.7-4268.4 BCMA copies per cell with a mean of 1181 and a median of 1084.9 (FIG. 2). This is considerably lower than e.g. CD19 and GD2, classic targets for CARs. Presence of BCMA expression on primary myeloma cells was also confirmed with the Vicky-1 antibody (Abcam Ab17323), examples of which are shown in FIG. 18.

Example 2—Design and Construction of APRIL Based CARs

APRIL in its natural form is a secreted type II protein. The use of APRIL as a BCMA binding domain for a CAR requires conversion of this type II secreted protein to a type I membrane bound protein and for this protein to be stable and to retain binding to BCMA in this form. To generate candidate molecules, the extreme amino-terminus of APRIL was deleted to remove binding to proteoglycans. Next, a signal peptide was added to direct the nascent protein to the endoplasmic reticulum and hence the cell surface. Also, because the nature of spacer used can alter the function of a CAR, three different spacer domains were tested: an APRIL based CAR was generated comprising (i) a human IgG1 spacer altered to remove Fc binding motifs; (ii) a CD8 stalk; and (iii) the IgG1 hinge alone (cartoon in FIG. 4 and amino acid sequences in FIGS. 5A-5C, and also amino acid sequences in FIGS. 19A-19C which differ from the sequences in FIG. 5 by having a different signal peptide and the V5 epitope tag). These CARs were expressed in a bicistronic retroviral vector (FIG. 6A) so that a marker protein—truncated CD34 could be co-expressed as a convenient marker gene.

Example 3—Expression and Function of APRIL Based CARs

The aim of this study was to test whether the APRIL based CARs which had been constructed were expressed on the cell surface and whether APRIL had folded to form the native protein. T-cells were transduced with these different CAR constructs and stained using a commercially available anti-APRIL mAb, along with staining for the marker gene and analysed by flow-cytometry. The results of this experiment are shown in FIG. 6B where APRIL binding is plotting against marker gene fluorescence. These data show that in this format, the APRIL based CARs are expressed on the cell surface and APRIL folds sufficiently to be recognized by an anti-APRIL mAb.

Next, it was determined whether APRIL in this format could recognize BCMA and TACI. Recombinant BCMA and TACI were generated as fusions with mouse IgG2a-Fc. These recombinant proteins were incubated with the transduced T-cells. After this, the cells were washed and stained with an anti-mouse fluorophore conjugated antibody and an antibody to detect the marker gene conjugated to a different fluorophore. The cells were analysed by flow cytometry and the results are presented in FIG. 6C. The different CARs were able to bind both BCMA and TACI. Surprisingly, the CARs were better able to bind BCMA than TACI. Also, surprisingly CARs with a CD8 stalk or IgG1 hinge spacer were better able to bind BCMA and TACI than CAR with an Fc spacer.

Example 4—APRIL Based Chimeric Antigen Receptors are Active Against BCMA Expressing Cells T-cells from normal donors were transduced with the different APRIL CARs and tested against SupT1 cells either wild-type, or engineered to express BCMA and TACI. Several different assays were used to determine function. A classical chromium release assay was performed. Here, the target cells (the SupT1 cells) were labelled with $^{51}$Cr and mixed with effectors (the transduced T-cells) at different ratio. Lysis of target cells was determined by counting $^{51}$Cr in the co-culture supernatant (FIG. 6A shows the cumulative data, example data from a single assay with different effector:target ratios is shown in FIG. 16).

In addition, supernatant from T-cells cultured 1:1 with SupT1 cells was assayed by ELISA for Interferon-gamma (FIG. 6B shows cumulative data, example data from a single assay is shown in FIG. 17). Measurement of T-cell expansion after one week of co-culture with SupT1 cells was also performed (FIG. 6C). T-cells were counted by flow-cytometry calibrated with counting beads. These experimental data show that APRIL based CARs can kill BCMA expressing targets. Further, these data show that CARs based on the CD8 stalk or IgG1 hinge performed better than the Fc-pvaa based CAR.

Example 5—APRIL Based CARs are Able to Kill Primary Myeloma Cells

The above data are encouraging since they demonstrate that it in principle, it is possible to make an APRIL based CAR. However, since most primary myeloma cells express a low number of BCMA molecules on their surface, it was investiagated whether such an APRIL based CAR would cause killing of primary myeloma cells, particularly in cases with low-density expression. Three cases were selected which represented the range of BCMA expression described in FIG. 2: the first had dim expression (lower than mean); the second case had intermediate expression (approximately mean expression) and the third had bright (above mean expression). FIG. 8 shows a histogram of BCMA staining against isotype control for all three cases on the left to illustrate BCMA expression. Since when comparing APRIL based CARs with different spacers it had been determined that CARs with CD8 stalk spacer and IgG1 hinge spacer performed better than the Fc-pvaa spacered CAR, in this assay, only the CD8 stalk and hinge APRIL CARs were tested. On the left, survival of myeloma cells compared with starting numbers is shown at day 3 and day 6 after a 1:1 co-culture of myeloma cells and CAR T-cells. By day 6, >95% of the myeloma cells were eliminated, including those with dim BCMA expression. Dim BCMA expressing myeloma cells can be targeted by the APRIL CARs albeit with a slower tempo of killing than higher expressers.

Example 6—Construction of a Series of "APRILITES"

The present inventors have constructed a series of bi-specific engagers which connect a scFv from OKT3 to the extracellular domain of APRIL, as shown in FIG. 24A. Several design considerations were made during the construction of these molecules: (a) the proteoglycan binding amino terminus of APRIL was truncated to prevent non-specific binding; (b) in constructs 4, 5 and 6, a signal peptide was attached to the mature ectodomain of APRIL; (c) the OKT3 was re-formatted as a scFv with a linker connecting the heavy and light chain variable regions; (d) various different spacers were tried between the scFv and APRIL.

The various different formats were as follows:
(1) OKT3 scFv connected to truncated APRIL by the IgG1 hinge;
(2) OKT3 scFv connected to truncated APRIL via a (SGGGGS)3 linker;
(3) OKT3 scFv connected to truncated APRIL via the CD8 stalk;
(4) truncated APRIL connected to OKT3 scFv via an IgG1 hinge;
(5) truncated APRIL connected to the OKT3 scFv via a (SGGGGS)3 linker; and
(6) truncated APRIL connected to the OKT3 scFv via a CD8 spacer.

Constructs (3) and (6) form homodimers through disulphide bonds in the CD8 spacer. The amino acid sequences for constructs (1), (3) and (6) are shown in FIGS. 30A-30C.

Example 7—Expression of APRILiTEs in 293T Cells

293 T cells were transfected with expression plasmids coding for the APRILiTE constructs listed above. Supernatant from the 293T cells was run on an acrylamide gel and proteins transferred to a membrane. The membrane was then stained with an antibody which recognized APRIL. The results are shown in FIG. 25. Proteins 1, 3 and 6 were detected at the expected molecular weight. Proteins 2, 4 and 5 were not detected, indicating that these configurations are unstable.

Example 8—Binding to TCR and BCMA

It was then investigated whether these proteins could bind either the T-cell receptor (TCR) on one end, and BCMA on the other end. Supernatant from 293T cells transfected was used to stain Jurkat T-cells and a Jurkat T-cell clone which has TCRαβ knocked out. This demonstrates the APRILiTE binds the TCR (FIG. 26b). SupT1 cells engineered to express BCMA and SupT1 cells engineered to express TACI were then stained with the above supernatant, using a secondary anti-APRIL biotin followed by streptavidin PE. The results are shown in FIG. 26a. It was found that APRILiTES 1, 3 and 6 bound BCMA, and TACI to a lesser extent.

Example 9—Stable APRILiTES Trigger IFNγ Release

Normal donor T-cells were cultivated 1:1 with different SupT1s. The SupT1s used were either non-transduced, engineered to express BCMA or engineered to express TACI. The results are shown in FIG. 27. It was found that T-cells only released IFNγ in the presence of either APRILiTE when exposed with SupT1-cells engineered with BCMA or TACI. The response to BCMA was greater than that with TACI.

Example 10—Stable APRILiTES Trigger T-Cell Mediated Killing of BCMA+ Targets T-cells were cultured 1:1 with wild-type SupT1 cells, SupT1 cells expressing BCMA and SupT1 cells expressing TACI in the absence of or in the presence of APRILiTEs 1, 3 and 6. The results are shown in FIG. 28. The remaining T-cells are shown as a proportion of SupT1 cells present in the condition with no APRILiTE added.

Example 11—Investigating BCMA Expression on Primary Myeloma Cells

Four different myeloma samples were stained with the rat anti-human BCMA mAb Vicky1. The results are shown in FIG. 29. In clinically and morphologically typical myelomas (panels 2 to 4) intermediate or dim staining is seen.

Example 12—Investigating the Effect of APRILiTEs on Primary Myeloma Cells

Left over material from a diagnostic bone-marrow aspirate from two patients with known multiple BCMA+ myeloma was used. A CD138 magnetic bead selection was performed to purify myeloma cells from the aspirate. These cells were rested in complete culture medium for 48 hours and staining for BCMA was performed to check that they were in fact BCMA positive. It was found that the myeloma cells express BCMA but at low levels (FIG. 31).

Next, normal donor peripheral mononuclear cells which had been stimulated using OKT3 and CD28.2 were CD56 depleted to remove NK cells. A 1:1 co-culture of CD56 depleted PBMCs and CD138 selected primary Myeloma cells were performed in the absence or presence of either APRILITE #03 and #06. Insufficient material was present to test APRILiTE #01. The co-cultures were observed by microscopy. Interferon gamma release into supernatant was measured by ELISA. Survival of myeloma cells was measured by Annexin V/PI staining and bead-count controlled flow-cytometry.

Figure 32:
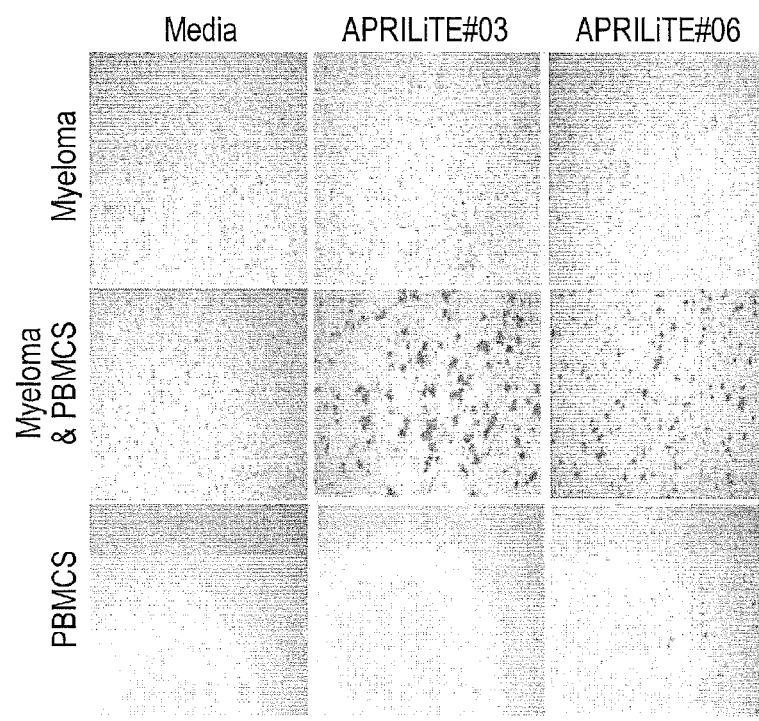

Clear clumping (a sign of T-cell activation) was seen upon co-culture (see FIG. 32). Interferon-gamma release was observed in conditions where PBMCs were cultured with Myeloma cells in the presence of the APRILiTES, albeit at less absolute amounts than when co-cultured with SupT1. BCMA cells (FIG. 33). Killing of Myeloma cells was also observed when PBMCs were present with APRILiTE after 6 days of co-culture (FIG. 34).

These findings demonstrate that APRILiTEs cause T cell activation in the presence of primary myeloma cells at a level sufficient to cause T-cell mediated killing of the myeloma cells.

Example 13—Testing the APRILiTES In Vivo

A huSCID model is used: NSG (nod-scid gamma, NOD-scid IL2Rgamma$^{null}$) mice are xenografted with a myeloma cell line which expresses typical levels of BCMA. These lines are engineered to express firefly Luciferase to measure disease by bioluminescence imaging. Normal donor PBMCs are administered via the tail vein during concomitant intraperitoneal administration of APRILiTEs. The following are sequentially measured (1) serum levels of APRILiTEs; (2) serum levels of human Interferon-gamma; (3) peripheral blood T-cell expansion, engraftment and activation by flow cytometry; (4) Bioluminescence measurement of tumour. At take-down, the following are measured: (1) tumour burden by marrow histology; (2) T-cell proliferation and engraftment by flow cytometry of marrow, spleen, blood and lymph nodes; and (3) the remaining tissues are examined grossly and immunohistochemically for any toxicity.

Example 14—Production of APRIL Mutants Particularly Suited to Targeting BCMA The aim was to generate APRIL mutants whose binding may be more suitable for CAR. Using crystallographic data described by Hymowitz et al, 2004, The Journal of biological chemistry: Volume 280; Issue 8; Pages 7218-27 and from RCSB deposits 1XU1 and 1XU2, several residues were selected which may alter binding to BCMA or may increase specificity to BCMA over TACI.

A strategy to identify mutations at these residues with useful properties is outlined in FIG. 31B. Using splicing by overlap PCR with oligonucleotides degenerate over codons for mutation, libraries of mutant APRILs were generated randomized over key mutants. These libraries were ligated into a scaffold shown in FIG. 31A which presents APRIL on a CD8 stalk and co-expresses CD34 with a foot-and-mouth 2A peptide. Typical expression from this construct is shown in FIGS. 9A-9C. These ligation products were transformed into competent bacteria, single colonies picked, individually expanded and the DNA was extracted and transfected into 293T cells.

The 293T cells were subsequently incubated separately with either recombinant human BCMA-Fc or TACI-Fc. Cells were then washed and secondarily stained with Jackson polyclonal anti-Fc Alexa fluor 488 and the marker gene stained with anti-CD34 APC. The APRIL mutants were screened in this manner in batches with wild-type APRIL and a CD34 only as controls in each batch. CD34 +ve events were split into 4 gates numbered as shown in FIG. 31. The Alexa fluor 488 median fluorescence index (MFI) was calculated for each gate and average gradient between MFI of various gates was calculated using the formula: [(MFI.1−MFI.2)+(MFI.2−MFI.3)+(MFI.3−MFI.4)]/3 (illustrated in FIG. 31C).

In this way, an average MFI gradient was calculated for binding to BCMA and TACI for each APRIL mutant. For each mutant, the average MFI gradient of BCMA and TACI binding was converted to a ratio of binding to APRIL WT control in each batch. Plasmids giving rise to potentially useful mutants were sequenced by capillary sequencing.

The results of this initial screening are summarized in Table 1 and illustrated in FIG. 10.

Classes of mutants were then combined together by a similar strategy to that outlined for single mutants, but mutant APRIL coding plasmid was used as template to introduce further mutations. The results of this work are summarized in Table 2 and illustrated in FIG. 11. It was possible to generate mutants with much higher affinity to BCMA than wild-type: for instance mutant D205R, R206G; we were able to generate mutants with BCMA binding equal to wild-type APRIL but no binding to TACI—for instance mutant T175A, S202P. We were also able to generate mutants with lower binding to BCMA than wild-type (which may paradoxically improve recognition of low-density antigen), but no binding of TACI—for instance mutant V174T, T175A, M200G, S202E.

Larger scale, higher quality plasmid DNA from the most promising mutants was generated and repeat transfection and expression data was performed. These data are shown in FIGS. 12A-12F.

Example 15—Secreted and Truncated APRIL Fused to an Fc Spacer Recognizes BCMA and TACI In order to investigate whether truncated APRIL in a CAR format (i.e. fused to a transmembrane domain and anchored to a cell membrane) could bind BCMA and TACI, a basic CAR was engineered in frame with the self-cleaving foot and mouth disease 2A peptide with truncated CD34, as a convenient marker gene. A stable SUPT1 cell line was established which expresses this construct. Secreted truncated BCMA and TACI fused to human (and other species, not shown) Ig Fc domain was also generated and recombinant protein produced. It was shown that both BCMA-Fc and TACI-Fc bind the engineered SUPT1 cell line. Only cells expressing the CD34 marker gene were found to bind BCMA-Fc and TACI-Fc (FIGS. 9A-9C).

Example 16—APRIL Based Chimeric Antigen Receptors are Stably Expressed on the Surface of T-Cells The CAR spacer domain can alter sensitivity and specificity. Three versions of an APRIL-based CAR were generated with three spacer domains: (i) a human IgG1 spacer altered to remove Fc binding motifs; (ii) a CD8 stalk; and (iii) the IgG1 hinge alone (FIG. 14B). Primary human T-cells were transduced with these different CARs and stained using a commercially available anti-APRIL mAb (FIG. 15).

Example 17—APRIL Based Chimeric Antigen Receptors are Active Against Cognate Target Expressing Cells T-cells from normal donors were transduced with the different APRIL CARs and tested against SupT1 cells either wild-type, or engineered to express BCMA and TACI. Several different assays were used to determine function. A classical chromium release assay was performed. Here, the target cells (the SupT1 cells) were labelled with $^{51}$Cr and mixed with effectors (the transduced T-cells) at different ratio. Lysis of target cells was determined by counting $^{51}$Cr in the co-culture supernatant (FIG. 16).

In addition, supernatant from T-cells cultured 1:1 with SupT1 cells was assayed by ELISA for Interferon-gamma (FIG. 17).

Measurement of T-cell expansion after one week of co-culture with SupT1 cells was also performed. T-cells were counted by flow-cytometry calibrated with counting beads. Initial data (not shown) appears to indicate that the CD8 stalk based construct results in more T-cell proliferation than the other constructs.

Example 18—Production of BCMA-Specific APRIL Mutants

APRIL mutants were generated using degenerate primers targeting specific codons. The codons were identified through in silico analysis of APRIL-BCMA and APRIL-TACI binding. From this analysis, residues that seemed involved in TACI binding but not BCMA binding were targeted.

Plasmids were produced encoding (i) cell surface expressed CD34 and (ii) the APRIL mutants. The plasmids were then transformed into bacteria, plated, single colonies picked, individually expanded and the DNA was extracted and transfected into 293T cells.

T cells expressing a single APRIL mutant and CD34 were each aliquoted into two and incubated separately with 0.1 µg RND human BCMA-hFc or TACI-hFc chimera. Cells were then washed and secondarily stained with Jackson polyclonal ahFc Alexa fluor 488 and BD aCD34 APC.

The APRIL mutants were screened in this manner in batches with wild-type APRIL as a control in each batch. CD34 +ve events were split into 4 gates numbered as shown in FIGS. 9A-9C. The Alexa fluor 488 median fluorescence index (MFI) was calculated for each gate and average gradient between MFI of various gates was calculated using the formula: [(MFI.1−MFI.2)+(MFI.2−MFI.3)+(MFI.3−MFI.4)]/3.

In this way, an average MFI gradient was calculated for binding to BCMA and TACI for each APRIL mutant. For each mutant, the average MFI gradient of BCMA and TACI binding was converted to a ratio of binding to APRIL WT control in the relevant screened batch. The mutants which showed a higher BCMA:TACI binding ratio than wild type were then sequenced.

The results are shown in FIGS. 20A-20W and the sequences of key mutants are shown in FIG. 21A-21B.

The effect of glycine substitution was then examined at the targeted residues. The results, which are shown in FIG. 22, show that residues S202, P201, M200, T175, V174, A125, H203, D205 and R206 on APRIL$_{wt}$ are comparatively more important for binding to TACI than BCMA.

Example 19—Demonstration of In Vivo Function of APRIL CAR T-Cells

In order to demonstrate APRIL CAR T-cell function in vivo, APRIL CAR T-cells were tested in a human/mouse chimeric model.

MM1.s (ATCC CRL-2974) is a human myeloma cell line which expresses intermediate levels of BCMA. The inventors engineered this cell line to express firefly Luciferase to derive the cell-line MM1.s.FLuc.

NOD scid gamma (NSG: NOD.Cg-Prkdc$^{scid}$ Il2rgtm1$^{Wjl/SzJ}$) mice are profoundly immunosuppressed mice capable of engrafting several human cell lines and human peripheral blood lymphocytes. Three month old female NSG mice received 1×10$^7$ MM1.s.FLuc cells vial tail-vein injection without any preparative therapy. Engraftment was determined by serial bioluminescence imaging (FIGS. 23A-23B). Robust and increasing intramedullary engraftment was observed in all mice. At day 13, 5×10$^6$ APRIL-HNG-CD28OXZ CAR T-cells were administered via tail vein injection. Serial bioluminescence was performed which showed rapid decrease in burden of MM1.s (FIGS. 23A-23B) in all treated mice to a complete remission. This response to CAR therapy was confirmed by flow-cytometry and immunohistochemistry.

Example 20—Testing Function of Various APRIL Mutants in a BiTE Format

Four normal donor PBMCs were incubated with SupT1 cells, SupT1 cells engineered to express BCMA, SupT1 cells engineered to express TACI or alone in the presence of different BiTES based on either WT APRIL or various mutants. Interferon-gamma levels were measured 24 hours later. The results are shown in FIG. 35. The mutant M200G shows significantly improved BCMA vs TACI specificity than wild-type.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A therapeutic agent which comprises a truncated proliferation-inducing ligand (APRIL) comprising the amino acid sequence shown in SEQ ID NO: 2 conjugated to a drug.

2. The therapeutic agent according to claim 1 wherein the drug is a cytotoxic drug.

3. The therapeutic agent according to claim 1, wherein the truncated APRIL comprises the BCMA-binding site of the sequence shown as SEQ ID NO: 1.

4. The therapeutic agent according to claim 1, wherein the truncated APRIL retains BCMA and TACI binding but lacks the capacity to bind proteoglycan.

5. The therapeutic agent according to claim 1, wherein the truncated APRIL lack the amino terminal 116 amino acids from SEQ ID NO: 1.

6. A pharmaceutical composition which comprises a therapeutic agent according to claim 1 and a pharmaceutically acceptable carrier, diluent or excipient.

7. A method for treating a plasma cell disorder which comprises the step of administering the pharmaceutical composition according to claim 6 to a subject.

8. The method according to claim 7, wherein the plasma cell disorder is selected from plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance and smoldering multiple myeloma.

9. The method according to claim 8, wherein the plasma cell disorder is multiple myeloma.

10. A pharmaceutical composition which comprises a therapeutic agent according to claim 4 and a pharmaceutically acceptable carrier, diluent or excipient.

11. A method for treating a plasma cell disorder which comprises the step of administering the pharmaceutical composition according to claim 10 to a subject, wherein the plasma cell disorder is selected from plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance and smoldering multiple myeloma.

12. The method according to claim 11, wherein the plasma cell disorder is multiple myeloma.

13. A pharmaceutical composition which comprises a therapeutic agent according to claim 5 and a pharmaceutically acceptable carrier, diluent or excipient.

14. A method for treating a plasma cell disorder which comprises the step of administering the pharmaceutical composition according to claim 13 to a subject, wherein the plasma cell disorder is selected from plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance and smoldering multiple myeloma.

15. The method according to claim 14, wherein the plasma cell disorder is multiple myeloma.

* * * * *